(12) United States Patent
Jorgensen et al.

(10) Patent No.: US 6,562,807 B2
(45) Date of Patent: May 13, 2003

(54) GLUCAGON ANTAGONISTS/INVERSE AGONISTS

(75) Inventors: Anker Steen Jorgensen, Copenhagen (DK); Inge Thoger Christensen, Lyngby (DK); Janos Tibor Kodra, Copenhagen (DK); Christian Sams, Frederiksberg (DK); Carsten Behrens, Copenhagen (DK); Peter Madsen, Bagsvaerd (DK); Jesper Lau, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/888,137

(22) Filed: Jun. 22, 2001

(65) Prior Publication Data

US 2002/0143186 A1 Oct. 3, 2002

Related U.S. Application Data

(60) Provisional application No. 60/215,059, filed on Jun. 29, 2000, and provisional application No. 60/252,320, filed on Nov. 20, 2000.

(30) Foreign Application Priority Data

Jun. 23, 2000 (DK) .................................. PA 2000 00984
Nov. 17, 2000 (DK) .................................. PA 2000 01734

(51) Int. Cl.$^7$ .................... A61K 31/555; A61K 31/195; C07C 817/00; C07C 323/00; C07D 319/06
(52) U.S. Cl. ...................... 514/186; 514/562; 514/563; 562/429; 562/432; 562/434; 562/435; 562/439; 548/469; 549/58; 549/373; 558/415
(58) Field of Search ................................ 562/434, 435, 562/429, 432, 439; 514/186, 562, 563; 558/415; 549/58, 373; 598/469

(56) References Cited

U.S. PATENT DOCUMENTS

| | | | |
|---|---|---|---|
| 4,359,474 A | 11/1982 | Anderson et al. | 424/273 |
| 4,374,130 A | 2/1983 | Barcza | 424/184 |
| 5,776,954 A | 7/1998 | de Laszlo et al. | 514/340 |
| 5,837,719 A | 11/1998 | de Laszlo et al. | 514/343 |
| 5,880,139 A | 3/1999 | Chang | 514/326 |
| 6,927,269 | * 10/2001 | Hulin et al. | |

FOREIGN PATENT DOCUMENTS

| | | |
|---|---|---|
| EP | 847992 | 6/1998 |
| WO | WO 94/14426 | 7/1994 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 98/24782 | 6/1998 |
| WO | WO 99/01423 | 1/1999 |
| WO | WO 99/24404 | 5/1999 |
| WO | WO 99/32448 | 7/1999 |
| WO | WO 00/32578 | 6/2000 |
| WO | WO 00/39088 | 7/2000 |
| WO | WO 00/69810 | 11/2000 |

OTHER PUBLICATIONS

C.L. Brand, et al., "Immunoneutralization of endogenous Glucagon with monoclonal glucagons antibody normalizes hyperglycaemia in moderately streptozotocin–diabetic rats" Diabetologia vol. 37., pp. 985–993 (1994).

C.L. Brand et al., "Role of glucagon in maintenance of euglycemia in Fed and fasted rats"., The American Physiological Society vol. 269., pp. E469–477 (1995).

C.L. Brand et al., Evidence for a Major Role for Glucagon in Regulation of Plasma Glucose in Conscious, Nondiabetic, and Alloxan–Induced Diabetic Rabbits. Diabetes., vol. 45., pp. 1076–1083 (1996).

L.J. Jelinek et al., "Expression Cloning and Signaling Properties of The Rat Glucagon Receptor"., Science., vol. 259., pp. 1614–1616 (1993).

C.G. Unson et al., "Biological Activities of des–His1[Glu9] Glucagon Amide, a Glucagon Antagonist1"., Peptides., vol. 10., Part 6, pp. 1171–1177 (1989).

S.R. Post et al., "Mechanism of action of des–His1–[Glu9] glucagon amide, a peptide antagonist of the glucagons receptor system"., Proc. Natl. Acad. Sci. vol. 90., pp. 1662–1666 (1993).

B.Y. Azizeh et al., "[des His1, des Phe6, Glu9] Glucagon Amide: A Newly Designed "Pure" Glucagon Antagonist" Bioorg Med Chem Lett., vol. 5, Part 16, pp. 1849–1852 (1995).

C.G. Unson et al., "Multiple–site Replacement Analogs of Glucagon"., The Journal of Biological Chemistry., vol. 269., No. 17, pp. 12548–12551 (1994).

Brand et al., "Evidence for a Major Rle of Glucagon in the Hyper–glycemia of Experimental Diabetes" Diabetes., vol. 43., Part 1, p. 172A (1994).

Brand et al., "Regulation of Insulin and Glucagon Secretion by Glucagon in Vivo", Diabetes, vol. 44, Part 1, p. 134A (1995).

J.L. Collins et al., "A Non–Peptide Glucagon Receptor Anatagoist"., Jour Med. Chem., vol. 2, Part 9., pp. 915–918 (1992).

P. Maden et al., Discovery and Structure—Activity Relationship of the First Non–peptide Competitive Human Glucagon Receptor Antagonists. J. Med. Chem. vol. 41., pp. 5150–5157 (1998).

* cited by examiner

Primary Examiner—Samuel Barts
Assistant Examiner—Paul A. Zucker
(74) Attorney, Agent, or Firm—Reza Green, Esq.; Richard Bork, Esq.; Marc Began, Esq.

(57) ABSTRACT

A novel class of compounds, which act to antagonize the action of the glucagon hormone on the glucagon receptor. Owing to their antagonizing effect of the glucagon receptor the compounds may be suitable for the treatment and/or prevention of any diseases and disorders, wherein a glucagon antagonistic action is beneficial, such as hyperglycemia, Type 1 diabetes, Type 2 diabetes, disorders of the lipid metabolism, such as dyslipidemia, and obesity.

70 Claims, No Drawings

GLUCAGON ANTAGONISTS/INVERSE AGONISTS

CROSS-REFERENCE TO RELATED APPLICATIONS

This application claims priority under 35 U.S.C. 119 of Danish application PA 2000 00984 filed Jun. 23, 2000, and PA 2000 01734 filed Nov. 17, 2000, and of U.S. Provisional application No. 60/215,059 filed Jun. 29, 2000, and No. 60/252,320 filed Nov. 20, 2000, the contents of which are fully incorporated herein by reference.

FIELD OF THE INVENTION

The present invention relates to agents that act to antagonize the action of the glucagon peptide hormone on the glucagon receptor. More particularly, it relates to glucagon antagonists or inverse agonists.

BACKGROUND OF THE INVENTION

Glucagon is a key hormonal agent that, in co-operation with insulin, mediates homeostatic regulation of the amount of glucose in the blood. Glucagon primarily acts by stimulating certain cells (mostly liver cells) to release glucose when blood glucose levels fall. The action of glucagon is opposite to that of insulin, which stimulates cells to take up and store glucose whenever blood glucose levels rise. Both glucagon and insulin are peptide hormones.

Glucagon is produced in the alpha islet cells of the pancreas and insulin in the beta islet cells. Diabetes mellitus is a common disorder of glucose metabolism. The disease is characterized by hyperglycemia and may be classified as Type 1 diabetes, the insulin-dependent form, or Type 2 diabetes, which is non-insulin-dependent in character. Subjects with Type 1 diabetes are hyperglycemic and hypoinsulinemic, and the conventional treatment for this form of the disease is to provide insulin. However, in some patients with Type 1 or Type 2 diabetes, absolute or relative elevated glucagon levels have been shown to contribute to the hyperglycemic state. Both in healthy control animals as well as in animal models of Type 1 and Type 2 diabetes, removal of circulating glucagon with selective and specific antibodies has resulted in reduction of the glycemic level (Brand et al., Diabetologia 37, 985 (1994); Diabetes 43, [suppl 1], 172A (1994); Am. J. Physiol. 269, E469–E477 (1995); Diabetes 44 [suppl 1], 134A (1995); Diabetes 45, 1076 (1996)). These studies suggest that glucagon suppression or an action that antagonizes glucagon could be a useful adjunct to conventional antihyperglycemia treatment of diabetes. The action of glucagon can be suppressed by providing an antagonist or an inverse agonist, ie substances that inhibit or prevent glucagon-induced responses. The antagonist can be peptidic or non-peptidic in nature.

Native glucagon is a 29 amino acid peptide having the sequence:

> His—Ser-Glu-Gly-Thr-Phe-Thr—Ser-Asp-Tyr—Ser-Lys-Tyr-Leu-Asp—Ser-Arg-Arg-Ala-Gln-Asp-Phe-Val-Gln-Trp-Leu-Met-Asn-Thr-NH$_2$.

Glucagon exerts its action by binding to and activating its receptor, which is part of the Glucagon-Secretin branch of the 7-transmembrane G-protein coupled receptor family (Jelinek et al., Science 259, 1614, (1993)). The receptor functions by activating the adenylyl cyclase second messenger system and the result is an increase in cAMP levels.

Several publications disclose peptides that are stated to act as glucagon antagonists. Probably, the most thoroughly characterized antagonist is DesHis$^1$[Glu$^9$]-glucagon amide (Unson et al., Peptides 10, 1171 (1989); Post et al., Proc. Natl. Acad. Sci. USA 90, 1662 (1993)). Other antagonists are DesHis$^1$, Phe$^6$[Glu$^9$]-glucagon amide (Azizh et al., Bioorganic & Medicinal Chem. Lett. 16, 1849 (1995)) and NLeu$^9$,Ala$^{11,16}$-glucagon amide (Unson et al., J. Biol. Chem. 269 (17), 12548 (1994)).

Peptide antagonists of peptide hormones are often quite potent. However, they are generally known not to be orally available because of degradation by physiological enzymes, and poor distribution in vivo. Therefore, orally available non-peptide antagonists of peptide hormones are generally preferred. Among the non-peptide glucagon antagonists, a quinoxaline derivative, (2-styryl-3-[3-(dimethylamino) propylmethylamino]-6,7-dichloroquinoxaline was found to displace glucagon from the rat liver receptor (Collins, J. L. et al., Bioorganic and Medicinal Chemistry Letters 2(9):915–918 (1992)). WO 94/14426 discloses use of skyrin, a natural product comprising a pair of linked 9,10-anthracenedione groups, and its synthetic analogues, as glucagon antagonists. U.S. Pat. No. 4,359,474 discloses the glucagon antagonistic properties of 1-phenyl pyrazole derivatives. U.S. Pat. No. 4,374,130 discloses substituted disilacyclohexanes as glucagon antagonists. WO 98/04528 (Bayer Corporation) discloses substituted pyridines and biphenyls as glucagon antagonists. U.S. Pat. No. 5,776,954 (Merck & Co., Inc.) discloses substituted pyridyl pyrroles as glucagon antagonists and WO 98/21957, WO 98/22108, WO 98/22109 and U.S. Pat. No. 5,880,139 (Merck & Co., Inc.) disclose 2,4-diaryl-5-pyridylimidazoles as glucagon antagonists. Furthermore, WO 97/16442 and U.S. Pat. No. 5,837,719 (Merck & Co., Inc.) disclose 2,5-substituted aryl pyrroles as glucagon antagonists. WO 98/24780, WO 98/24782, WO 99/24404 and WO 99/32448 (Amgen Inc.) disclose substituted pyrimidinone and pyridone compounds and substituted pyrimidine compounds, respectively, which are stated to possess glucagon antagonistic activity. Madsen et al. (J. Med. Chem. 1998 (41) 5151–7) discloses a series of 2-(benzimidazol-2-ylthio)-1-(3,4-dihydroxyphenyl)-1-ethanones as competitive human glucagon receptor antagonists. WO 99/01423 and WO 00/39088 (Novo Nordisk A/S) disclose different series of alkylidene hydrazides as glucagon antagonists/inverse agonists.

These known glucagon antagonists differ structurally from the present compounds.

DEFINITIONS

The following is a detailed definition of the terms used to describe the compounds of the invention:

"Halogen" designates an atom selected from the group consisting of F, Cl, Br and I.

The term "$C_{1-6}$-alkyl" as used herein represents a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{2-6}$-alkenyl" as used herein represents a branched or straight hydrocarbon group having from 2 to 6 carbon atoms and at least one double bond. Examples of such groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "$C_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadiynyl and the like.

The term "$C_{1-6}$-alkoxy" as used herein refers to the radical —O—$C_{1-6}$-alkyl, wherein $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{1-6}$-alkanoyl" as used herein denotes a group —C(O)H or —C(O)—$C_{1-5}$-alkyl. Representative examples are formyl, acetyl, propionyl, butyryl, valeyl, hexanoyl and the like.

The term "$C_{3-8}$-cycloalkyl" as used herein represents a saturated, carbocyclic group having from 3 to 8 carbon atoms. Representative examples are cyclopropyl, cyclobutyl, cyclopentyl, cyclohexyl, cycloheptyl, cyclooctyl and the like.

The term "$C_{4-8}$-cycloalkenyl" as used herein represents a non-aromatic, carbocyclic group having from 4 to 8 carbon atoms containing one or two double bonds. Representative examples are 1-cyclopentenyl, 2-cyclopentenyl, 3-cyclopentenyl, 1-cyclohexenyl, 2-cyclohexenyl, 3-cyclohexenyl, 2-cycloheptenyl, 3-cycloheptenyl, 2-cyclooctenyl, 1,4-cyclooctadienyl and the like.

The term "heterocyclyl" as used herein represents a non-aromatic 3 to 10 membered ring containing one or more heteroatoms selected from nitrogen, oxygen and sulfur and optionally containing one or two double bonds. Representative examples are pyrrolidinyl, piperidyl, piperazinyl, morpholinyl, thiomorpholinyl, aziridinyl, tetrahydrofuranyl and the like.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "arylene" as used herein is intended to include divalent carbocyclic aromatic ring systems such as phenylene, biphenylylene, naphthylene, anthracenylene, phenanthrenylene, fluorenylene, indenylene, pentalenylene, azulenylene and the like. Arylene is also intended to include the partially hydrogenated derivatives of the carbocyclic systems enumerated above. Non-limiting examples of such partially hydrogenated derivatives are 1,2,3,4-tetrahydronaphthylene, 1,4-dihydronaphthylene and the like.

The term "aryloxy" as used herein denotes a group —O-aryl, wherein aryl is as defined above.

The term "aroyl" as used herein denotes a group —C(O)-aryl, wherein aryl is as defined above.

The term "heteroaryl" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

"Aryl-$C_{1-6}$-alkyl", "heteroaryl-$C_{1-6}$-alkyl", "aryl-$C_{2-6}$-alkenyl" etc. mean $C_{1-6}$-alkyl or $C_{2-6}$-alkenyl as defined above, substituted by an aryl or heteroaryl as defined above, for example:

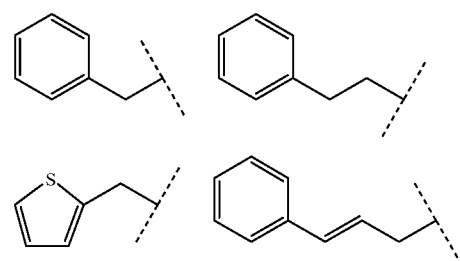

The term "optionally substituted" as used herein means that the groups in question are either unsubstituted or substituted with one or more of the substituents specified. When the groups in question are substituted with more than one substituent the substituents may be the same or different.

Certain of the above defined terms may occur more than once in the structural formulae, and upon such occurrence each term shall be defined independently of the other.

Furthermore, when using the terms "independently are" and "independently selected from" it should be understood that the groups in question may be the same or different.

DESCRIPTION OF THE INVENTION

The present invention is based on the unexpected observation that the compounds of the general formula (I) disclosed below antagonize the action of glucagon.

The compounds are advantageous by being selective towards the glucagon receptor and show a higher binding affinity for the glucagon receptor compared to the binding affinity for the structurally related GIP (Gastric Inhibitory Peptide) receptor and GIP-1 receptor.

Accordingly, the present inventions relate to compounds of the general formula (I):

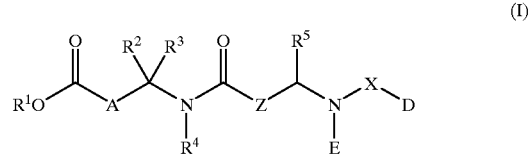

(I)

wherein
  $R^1$, $R^2$, $R^3$, $R^4$ and $R^5$ independently are hydrogen or $C_{1-6}$-alkyl, A is —C(O)—, —CH(OR⁶)— or —CHF—, wherein $R^8$ is hydrogen or $C_{1-6}$-alkyl, Z is arylene or a divalent radical derived from a 5 or 6 membered heteroaromatic ring containing 1 or 2 heteroatoms selected from nitrogen, oxygen and sulfur, which may optionally be substituted with one or two groups $R^7$ and $R^8$ selected from halogen, —CN, —CF₃, —OCF₃, —NO₂, —OR⁹, —NR⁹R¹⁰ and $C_{1-6}$-alkyl, wherein $R^9$ and $R^{10}$ independently are hydrogen or $C_{1-6}$-alkyl, X is

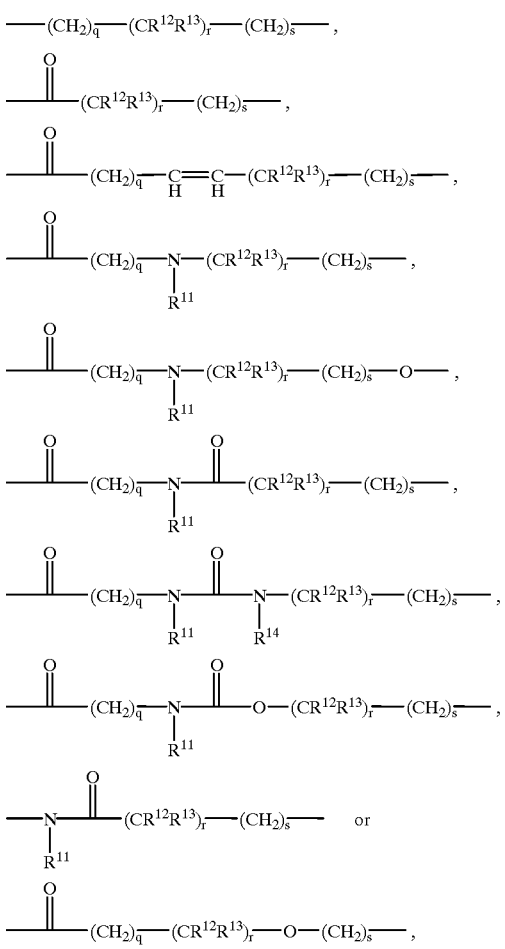

wherein r is 0 or 1, q and s independently are 0, 1, 2 or 3, $R^{11}$, $R^{12}$, $R^{13}$ and $R^{14}$ independently are hydrogen, $C_{1-6}$-alkyl or $C_{3-8}$-cycloalkyl, D is

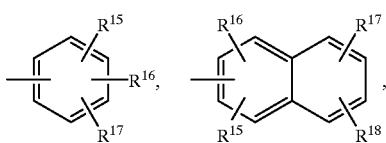

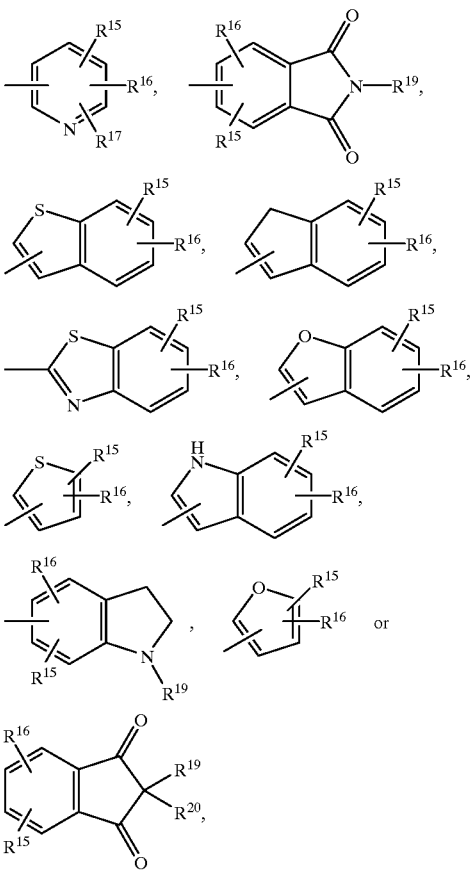

wherein $R^{15}$, $R^{16}$, $R^{17}$ and $R^{18}$ independently are hydrogen, halogen, —CN, —CHF₂, —CF₃, —OCF₃, —OCHF₂, —OCH₂CF₃, —OCF₂CHF₂, —S(O)₂CF₃, —SCF₃, —NO₂, —OR²¹, —NR²¹R²², —SR²¹, —N R²¹S(O)₂R²², —S(O)₂NR²¹R²², —S(O)NR²¹R²², —S(O)R²¹, —S(O)₂R²¹, —C(O)NR²¹R²², —OC(O)NR²¹R²², —NR²¹C(O)R²² —CH₂C(O)NR²¹R²², —OCH₂C(O)NR²¹R²², —C(O)R²¹, —C(O)R²¹ or —C(O)OR²¹, $C_{1-6}$-alkyl, $C_{2-6}$-alkenyl or $C_{2-6}$-alkynyl, which may optionally be substituted with one or more substituents selected from halogen, —CN, —CF₃, —OCF₃, —NO₂, —OR²¹, —NR²¹R²² and $C_{1-6}$-alkyl $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{1-6}$-alkoxy, $C_{3-8}$-cycloalkyloxy, $C_{3-8}$-cycloalkyl-$C_{1-6}$-alkylthio, $C_{3-8}$-cycloalkylthio, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aryloxycarbonyl, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl, of which the cyclic moieties optionally may be substituted with one or more sub-stituents selected from halogen, —C(O)OR²¹, —CN, —CF₃, —OCF₃, —NO₂, —OR²¹, —NR²¹R²² and $C_{1-6}$-alkyl, wherein $R^{21}$ and $R^{22}$ independently are hydrogen, $C_{1-6}$-alkyl, aryl-$C_{1-6}$-alkyl or aryl, or $R^{21}$ and $R^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{15}$ to $R^{18}$ when placed in adjacent positions together may form a bridge —$(CR^{23}R^{24})_a$—O$(CR^{25}R^{26})_c$—O—, wherein a is 0, 1 or 2, c is 1 or 2, $R^{23}$, $R^{24}$, $R^{25}$ and $R^{26}$ independently are hydrogen, $C_{1-6}$-alkyl or fluorine, $R^{19}$ and $R^{20}$ independently are hydrogen, $C_{1-6}$-alkyl, $C_{3-8}$-cycloalkyl or $C_{3-8}$-cyclo-alkyl-$C_{1-6}$-alkyl, E is

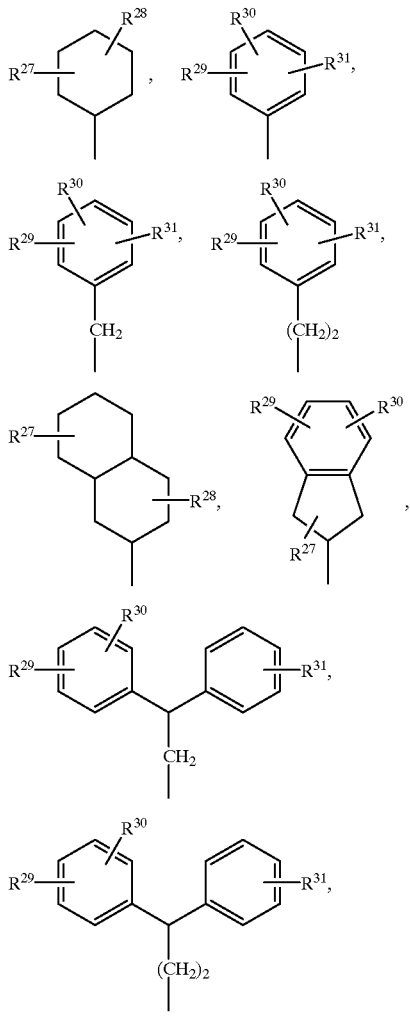

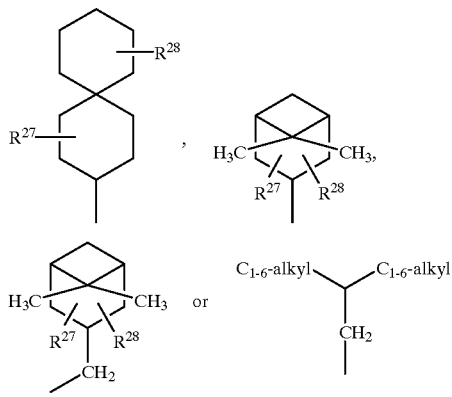

wherein $R^{27}$ and $R^{28}$ independently are hydrogen, halogen, —CN, —CF$_3$, —OR$^{32}$, —NR$^{32}$R$^{33}$, $C_{1-6}$-alkyl, $C_{3-8}$-cycloalkyl, $C_{4-8}$-cycloalkenyl or aryl, wherein the aryl group optionally may be substituted with one or more substituents selected from halogen, —CN, —CF$_3$, —NO$_2$, —OR$^{32}$, —NR$^{32}$R$^{33}$ and $C_{1-6}$-alkyl, wherein $R^{32}$ and $R^{33}$ independently are hydrogen or $C_{1-6}$-alkyl, or $R^{32}$ and $R^{33}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, $R^{29}$, $R^{30}$ and $R^{31}$ independently are hydrogen, halogen, —CHF$_2$, —CF$_3$, —OCF$_3$, —OCHF$_2$, —OCH$_2$CF$_3$, —OCF$_2$CHF$_2$, —SCF$_3$, —OR$^{34}$ —NR$^{34}$R$^{35}$—SR$^{34}$—S(O)R$^{34}$,—S(C)$_2$R$^{34}$R$^{35}$,—OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$, $C_{1-6}$-alkyl, $C_{2-6}$-alkenyl or $C_{2-6}$-alkynyl, which may optionally be substituted with one or more substituents selected from halogen, —CN, —CF$_3$,—OCF$_3$,—NO$_2$,—OR$^{34}$,—NR$^{34}$R$^{35}$ and $C_{1-6}$-alkyl, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cyclo-alkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cyclo-alkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, hetero-aryl-$C_{2-6}$-alkenyl or heteroaryl-$C_{2-6}$-alkynyl, of which the cyclic moieties optionally may be substituted with one or more substituents selected from halogen, —CN, —CF$_3$, —OCF$_3$, —NO$_2$, —OR$^{34}$, —NR$^{34}$R$^{35}$ and $C_{1-6}$-alkyl, wherein $R^{34}$ and $R^{35}$ independently are hydrogen, $C_{1-6}$-alkyl or aryl, or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{29}$, $R^{30}$ and $R^{31}$ when attached to the same ring carbon atom or different ring carbon atoms together may form a radical —O—(CH$_2$)$_t$—CR$^{36}$R$^{37}$—(CH$_2$)$_l$—O—, —(CH$_2$)$_t$—CR$^{36}$R$^{37}$—(CH$_2$)$_l$— or —S—(CH$_2$)$_t$—CR$^{36}$R$^{37}$—(CH$_2$)$_l$—S—, wherein t and l independently are 0, 1, 2, 3, 4 or 5, R$^{36}$ and R$^{37}$ independently are hydrogen or C$_{1-6}$-alkyl, as well as any optical or geometric isomer or tautomeric form thereof including mixtures of these or a pharmaceutically acceptable salt thereof.

In another aspect, the invention is concerned with compounds of the general formula (I')

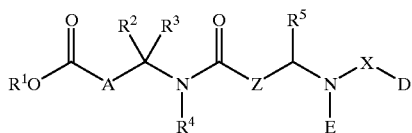
(I')

wherein

R$^1$, R$^2$, R$^3$, R$^4$ and R$^5$ independently are hydrogen or C$_{1-6}$-alkyl, A is —C(O)—, —CH(OR$^6$)— or —CHF—, wherein R$^6$ is hydrogen or C$_{1-6}$-alkyl, Z is arylene or a divalent radical derived from a 5 or 6 membered heteroaromatic ring containing 1 or 2 heteroatoms selected from nitrogen, oxygen and sulfur, which may optionally be substituted with one or two groups R$^7$ and R$^8$ selected from halogen, —CN, —CF$_3$, —OCF$_3$, —NO$_2$, —OR$^9$, —NR$^9$R$^{10}$ and C$_{1-6}$-alkyl, wherein R$^9$ and R$^{10}$ independently are hydrogen or C$_{1-6}$-alkyl, X is

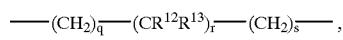,

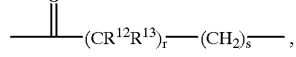,

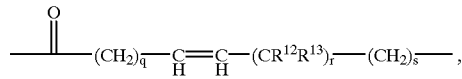,

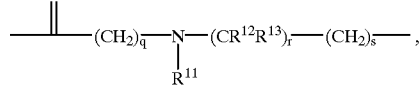,

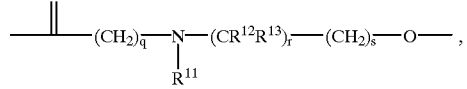,

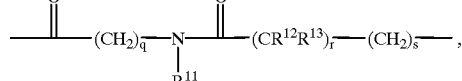,

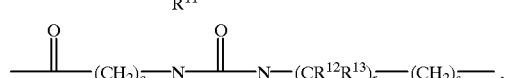,

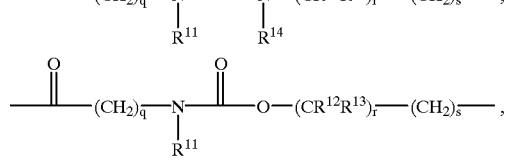

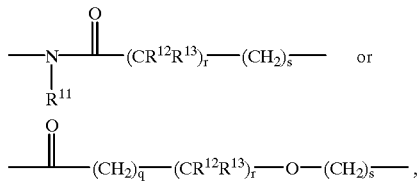 or wherein r is 0 or 1, q and s independently are 0, 1, 2 or 3,

R$^{11}$, R$^{12}$, R$^{13}$ and R$^{14}$ independently are hydrogen, C$_{1-6}$-alkyl or C$_{3-8}$-cycloalkyl, D is

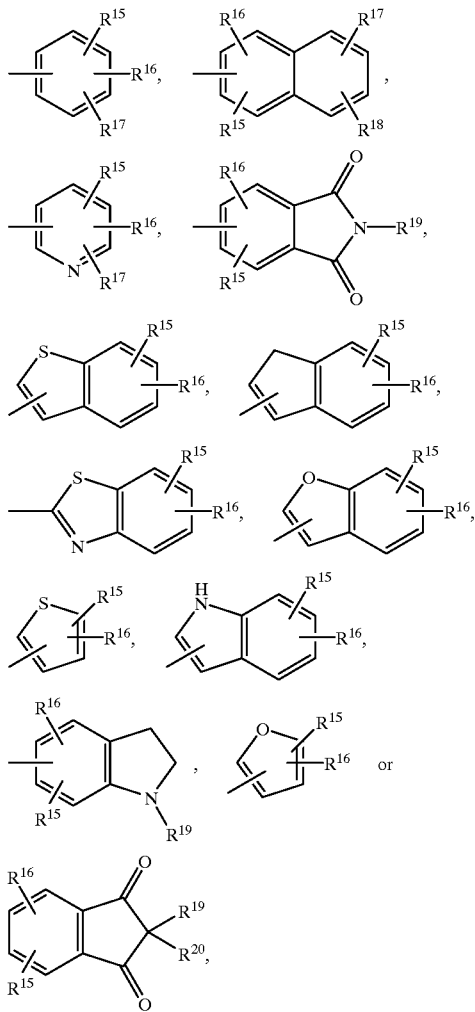

wherein

R$^{15}$, R$^{16}$, R$^{17}$ and R$^{18}$ independently are hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —NO$_2$, —OR$^{21}$ —NR$^{21}$R$^{22}$, —SR$^2$, NR$^{21}$S(O)$_2$ R$^{22}$ —S(O)$_2$ NR$^{21}$R$^{22}$, —S(O)NR$^{21}$R$^{22}$, —S(O)$_2$ R$^{21}$, —OC(O)NR$^{21}$R$^{22}$, —OC(O)NR$^{21}$R$^{22}$, —NR$^{21}$C (O)R$^{22}$ —CH$_2$C(O)NR$^{21}$ R$^{22}$, —OCH$_2$C(O) NR$^{21}$R$^{22}$, —CH$_2$OR$^{21}$, —CH$_2$NR R$^2$, —OC(O) R$^2$,—C(O)R$^{21}$ or —C(O)OR$^{21}$, $C_{1-6}$-alkyl, $C_{2-6}$-alkenyl or $C_{2-6}$-alkynyl,
  which may optionally be substituted with one or more substituents selected from halogen, —CN, —CF$_3$, —OCF$_3$, —NO$_2$, —OR$^{21}$, —NR$^{21}$R$^{22}$ and $C_{1-6}$-alkyl,
$C_{3-8}$-cycloalkyl, $C_{4-8}$-cycloalkenyl, heterocyclyl, $C_{3-8}$cycloalkyl-$C_{1-6}$-alkyl, $C_{3-8}$-cyclo-alkyl-$C_{1-6}$-alkoxy, $C_{3-8}$-cycloalkyloxy, $C_{3-8}$-cycloalkyl-$C_{1-6}$-alkylthio, $C_{3-8}$-cycloalkylthio,
$C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aryloxycarbonyl, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl,
  of which the cyclic moieties optionally may be substituted with one or more substituents selected from halogen, —C(O)OR$^{21}$, —CN, —CF$_3$, —OCF$_3$, —NO$_2$, —OR$^{21}$, —NR$^{21}$R$^{22}$ and $C_{1-6}$-alkyl,
  wherein R$^{21}$ and R$^{22}$ independently are hydrogen, $C_{1-6}$-alkyl, aryl-$C_{1-6}$-alkyl or aryl,
  or R$^{21}$ and R$^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
or two of the groups R$^{15}$ to R$^{18}$ when placed in adjacent positions together may form a bridge —(CR$^{23}$R$^{24}$)$_a$—(CR$^{25}$R$^{26}$)$_c$—O—,
wherein
  a is 0, 1 or 2,
  c is 1 or 2,
  R$^{23}$, R$^{24}$, R$^{25}$ and R$^{26}$ independently are hydrogen, $C_{1-6}$-alkyl or fluorine,
  R$^{19}$ and R$^{20}$ independently are hydrogen, $C_{1-6}$-alkyl, $C_{3-8}$-cycloalkyl or $C_{3-8}$-cycloalkyl-$C_{1-6}$-alkyl,
  E is

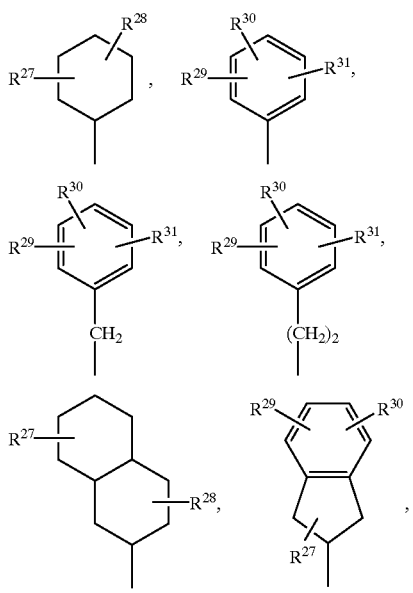

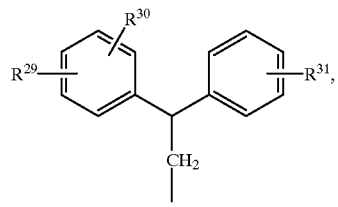

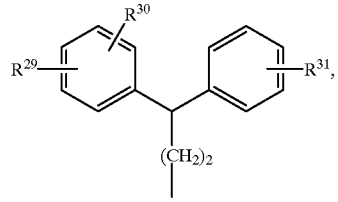

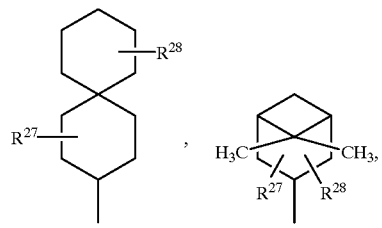

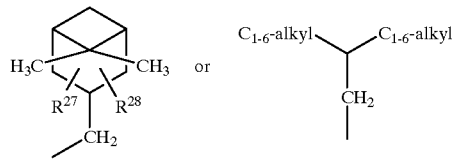

wherein
  R$^{27}$ and R$^{28}$ independently are
    hydrogen, halogen, —CN, —CF$_3$, —OR$^{32}$, —NR$^{32}$R$^{33}$, $C_{1-6}$-alkyl, $C_{3-8}$-cycloalkyl, $C_{4-8}$-cycloalkenyl or aryl,
    wherein the aryl group optionally may be substituted with one or more substituents selected from halogen, —CN, —CF$_3$, —NO$_2$ R$^{32}$ —NR$^{32}$R$^{33}$ and $C_{1-6}$-alkyl
    wherein R$^{32}$ and R$^{33}$ independently are hydrogen or $C_{1-6}$-alkyl, or
    R$^{32}$ and R$^{33}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
  R$^{29}$, R$^{30}$ and R$^{31}$ independently are
    hydrogen, halogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)N R$^{34}$R$^{35}$, —C(O)R$^{34}$ or —C(O)OR$^{34}$,
    $C_{1-6}$-alkyl, $C_{2-6}$-alkenyl or $C_{2-6}$-alkynyl,
      which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$- alkynyl, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl, of which the cyclic moieties optionally may be substituted with one or more substituents selected from halogen, —CN, —$CF_3$, —$OCF_3$, —$NO_2$, —$OR^{34}$, —$NR^{34}R^{35}$ and $C_{1-6}$-alkyl, wherein $R^{34}$ and $R^{35}$ independently are hydrogen, $C_{1-6}$-alkyl or aryl, or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{29}$, $R^{30}$ and $R^{31}$ when attached to the same ring carbon atom or different ring carbon atoms together may form a radical —O—$(CH_2)_t$—$CR^{36}R^{37}$—$(CH_2)_l$—O—, —$(CH_2)_t$—$CR^{36}R^{37}$-$(CH_2)_l$— or —S—$(CH_2)_t$—$CR^{36}R^{37}$—$(CH_2)_l$—S—, wherein t and I independently are 0, 1, 2, 3, 4 or 5, $R^{36}$ and $R^{37}$ independently are hydrogen or $C_{1-6}$-alkyl, as well as any optical or geometric isomer or tautomeric form thereof including mixtures of these or a pharmaceutically acceptable salt thereof.

In another aspect, the invention is concerned with compounds of the general formula (I"):

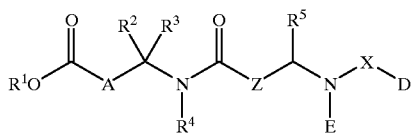

(I")

wherein $R^1$, $R^2$, $R^3$, $R^4$ and $R^5$ independently are hydrogen or $C_{1-6}$-alkyl, A is —C(O)—, —CH($O^6$)— or —CHF—, wherein R is hydrogen, $C_{1-6}$-alkyl or halogen, Z is arylene or a divalent radical derived from a 5 or 6 membered heteroaromatic ring containing 1 or 2 heteroatoms selected from nitrogen, oxygen and sulfur, which may optionally be substituted with one or two groups $R^7$ and R" selected from halogen, —CN, —$CF_3$, —$OCF_3$, —$NO_2$, —$OR^9$, —$NR^9R^{10}$ and $C_{1-6}$-alkyl, wherein $R^9$ and $R^{10}$ independently are hydrogen or $C_{1-6}$-alkyl, X is

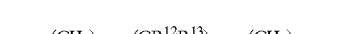

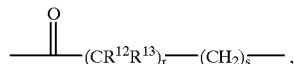

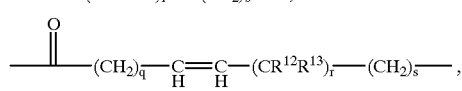

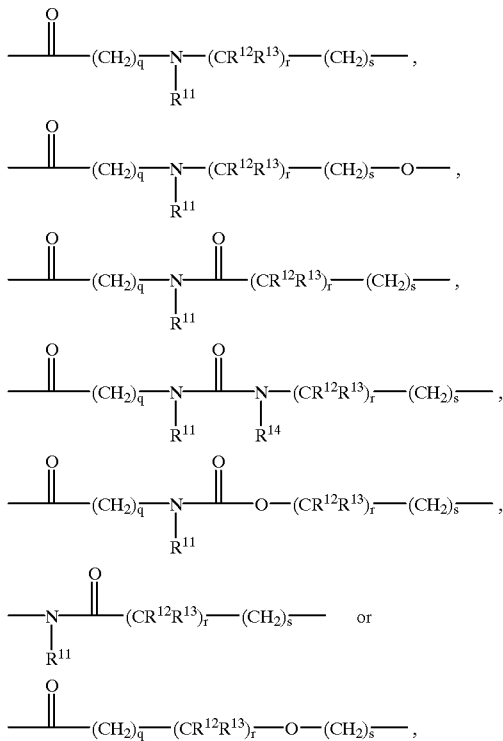

wherein r is 0 or 1, q and s independently are 0, 1, 2 or 3, $R^{11}$, $R^{12}$, $R^{13}$ and $R^{14}$ independently are hydrogen or $C_{1-6}$-alkyl, D is

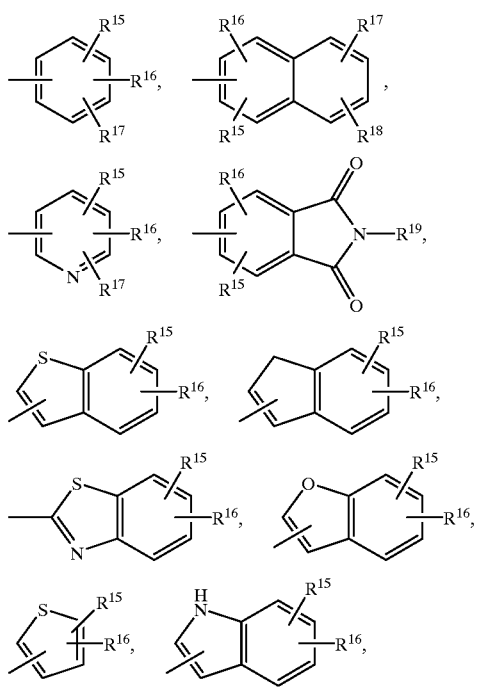

-continued

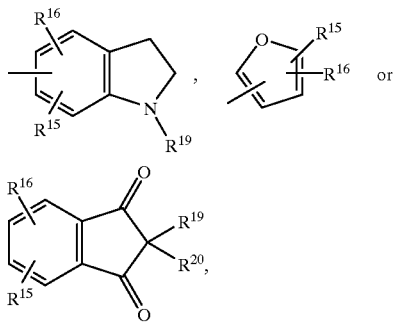

wherein $R^{15}$, $R^{16}$, $R^{17}$ and $R^{18}$ independently are hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^2$, —NR$^{21}$R$^{22}$, —SR$^{21}$, —NR$^{21}$ S(Q)$_2$R$^{22}$ —S(O)$_2$NR$^{21}$R$^{22}$, —S(O)NR$^2$R$^{22}$, —S(O)R$^{21}$, —S(OS(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$R$^2$NR$^{21}$R$^{22}$, —OC(O)R$^{21}$, —C(O)R$^{21}$ or —C(O)OR, C$_{1-6}$-alkyl, C$_{2-6}$-alkenyl or C$_{2-6}$-alkynyl, which may optionally be substituted with one or more substituents selected from halogen, —CN, —CF$_3$, —OCF$_3$, —NO$_2$, —OR$^{21}$, —NR$^{21}$R$^{22}$ and C$_{1-6}$-alkyl, C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{1-6}$-alkoxy, C$_{3-8}$-cycloalkyloxy, C$_{3-8}$-cycloalkyl-C$_{1-6}$-alkylthio, C$_{3-8}$-cycloalkylthio, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aryloxycarbonyl, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl, of which the cyclic moieties optionally may be substituted with one or more substituents selected from halogen, —CN, —CF$_3$, —OCF$_3$, —NO$_2$, —OR$^{21}$, —NR$^{21}$R$^{22}$ and C$_{1-6}$-alkyl, wherein $R^{21}$ and $R^{22}$ independently are hydrogen, C$_{1-6}$-alkyl or aryl, or $R^{21}$ and $R^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{15}$ to $R^{18}$ when placed in adjacent positions together may form a bridge —(CR$^{23}$R$^{24}$)$_a$—O—(CR$^{25}$R$^{26}$)$_c$—O—, wherein a is 0, 1 or 2, c is 1 or 2, $R^{23}$, $R^{24}$, $R^{25}$ and $R^{26}$ independently are hydrogen, C$_{1-6}$-alkyl or fluorine, $R^{19}$ and $R^{20}$ independently are hydrogen, C$_{1-6}$-alkyl, C$_{3-8}$-cycloalkyl or C$_{3-8}$-cycloalkyl-C$_{1-6}$-alkyl, E is

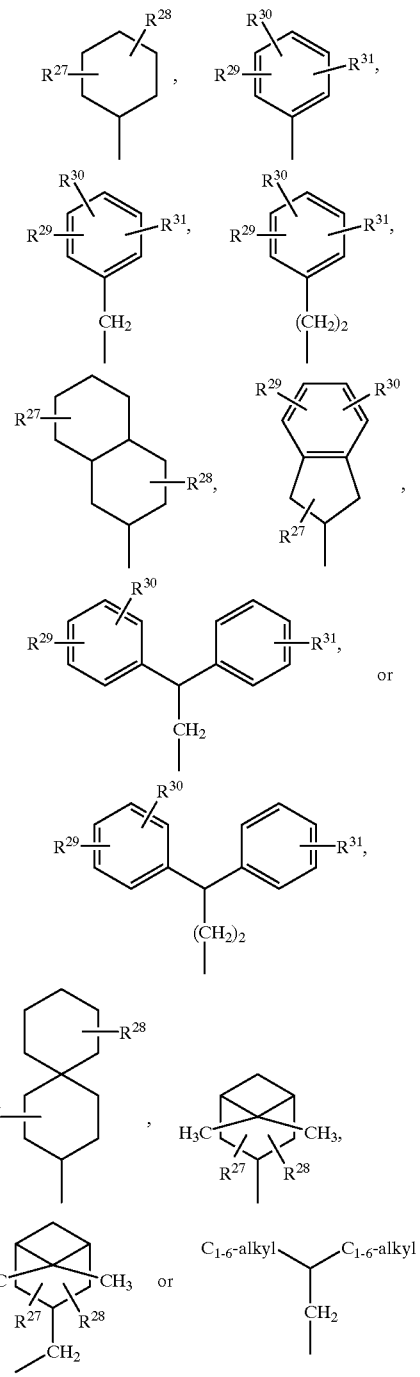

wherein $R^{27}$ and $R^{28}$ independently are hydrogen, halogen, —CN, —CF$_3$, —OR$^{32}$, —NR$^{32}$R$^{33}$, C$_{1-6}$-alkyl, C$_{3-8}$-cycloalkyl, C$_{4-8}$-cycloalkenyl or aryl, wherein the aryl group optionally may be substituted with one or more substituents selected from halogen, —CN, —CF$_3$, —NO$_2$, —OR$^{32}$, —NR$^{32}$R$^{33}$ and C$_{1-6}$-alkyl, wherein $R^{32}$ and $R^{33}$ independently are hydrogen or C$_{1-6}$-alkyl, or $R^{32}$ and $R^{33}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, $R^{29}$, $R^{30}$ and $R^{31}$ independently are hydrogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R34 or —C(O)OR$^{34}$, C$_{1-6}$-alkyl, C$_{2-6}$-alkenyl or C$_{2-6}$-alkynyl, which may optionally be substituted with one or more substituents selected from halogen, —CN, —CF$_3$, —OCF$_3$, —NO$_2$, —OR$^{34}$, —NR$^{34}$R$^{35}$ and C$_{1-6}$-alkyl, C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl, of which the cyclic moieties optionally may be substituted with one or more substituents selected from halogen, —CN, —CF$_3$, —OCF$_3$, —NO$_2$, —OR$^{34}$, —NR$^{34}$R$^{35}$ and C$_{1-6}$-alkyl, wherein R$^{34}$ and R$^{35}$ independently are hydrogen, C$_{1-6}$-alkyl or aryl, or R$^{34}$ and R$^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups R$^{29}$, R$^{30}$ and R$^{31}$ when attached to the same ring carbon atom or different ring carbon atoms together may form a radical —O—(CH$_2$)$_t$—CR$^{36}$R$^{37}$—(CH$_2$)$_l$—O—, —(CH$_2$)$_t$—CR$^{36}$R$^{37}$—(CH$_2$)$_l$— or —S—(CH$_2$)$_t$—CR$^{36}$R$^{37}$—(CH$_2$)$_l$—S—, wherein t and l independently are 0, 1, 2, 3, 4 or 5, R$^{36}$ and R$^{37}$ independently are hydrogen or C$_{1-6}$-alkyl, as well as any optical or geometric isomer or tautomeric form thereof including mixtures of these or a pharmaceutically acceptable salt thereof.

In one embodiment, R$^1$, R$^2$, R$^3$, R$^4$ and R$^5$ are hydrogen.

In one embodiment, A is —CHF—.

In another embodiment, A is —CH(OR$^6$)—, wherein R$^6$ is as defined for formula (I), such as —CH(OH)—.

In one embodiment, Z is

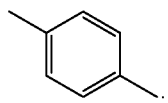

wherein R$^7$ and R$^8$ are as defined for formula (I), such as

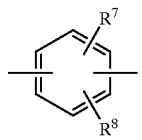

In one embodiment, X is

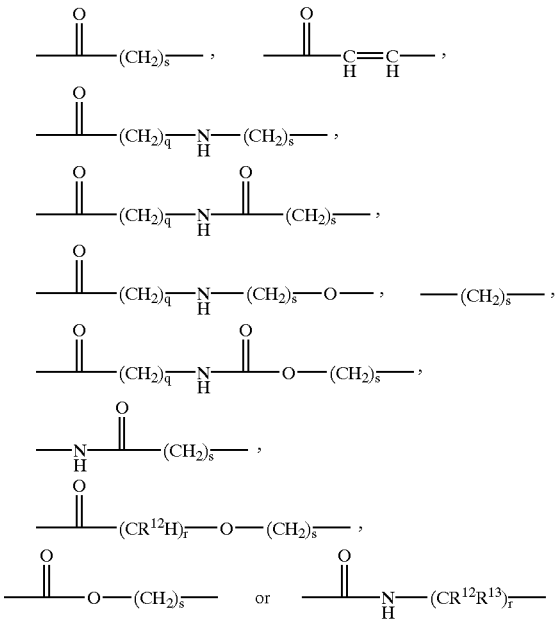

wherein q is 0 or 1, r is 0 or 1, s is 0, 1 or 2, and R$^{12}$ and R$^{13}$ independently are hydrogen or C$_{1-6}$-alkyl.

In another embodiment, X is —C(O)NH—, —C(O)NHCH$_2$—, —C(O)NHCH(CH$_3$)—, —C(O)NHC(CH$_3$)$_2$—, —C(O)NHCH$_2$CH$_2$—, —C(O)CH$_2$—, —C(O)CH$_2$CH$_2$—, —C(O)CH=CH—, —(CH$_2$)$_s$—, —C(O)—, —C(O)O— or —NHC(O)—, wherein s is 0 or 1.

In yet another embodiment, X is —C(O)NH—, —C(O)NHCH$_2$—, —C(O)NHCH(CH$_3$)—, —C(O)NHCH$_2$CH$_2$—, —C(O)CH$_2$—, —C(O)CH=CH—, —(CH$_2$)$_s$—, —C(O)—, —C(O)O— or —NHC(O)—, wherein s is 0 or 1.

In still another embodiment, X is —C(O)NH—, —C(O)NHCH$_2$—, —C(O)NHCH(CH$_3$)—, —C(O)NHCH$_2$CH$_2$—, —C(O)CH$_2$—, —CH$_2$—, —C(O)— or —NHC(O)—. In still a further embodiment, X is —C(O)NH—, —C(O)NHCH$_2$—, —C(O)NHCH(CH$_3$)—, —C(O)CH$_2$— or —C(O)—, such as —C(O)NH—.

In one embodiment, D is

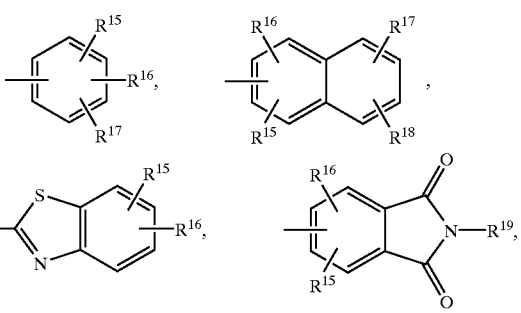

-continued

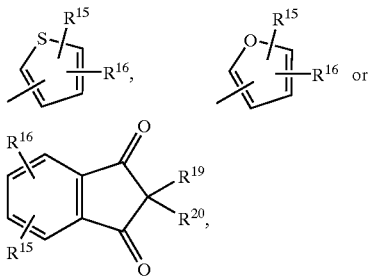

wherein $R^{15}$, $R^{16}$, $R^{17}$, $R^{18}$, $R^{19}$ and $R^{20}$ are as defined for formula (I).

In another embodiment, D is

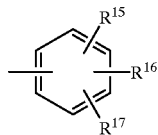

wherein $R^{15}$, $R^{16}$ and $R^{17}$ are as defined for formula (I).

In one embodiment, $R^{15}$, $R^{13}$ and $R^{17}$ are independently hydrogen, halogen, —CN, —NO$_2$, —CF$_3$, —OCF$_3$, —SCF$_3$, C$_{1-6}$-alkyl, C$_{1-6}$-alkoxy, —S-C$_{1-6}$-alkyl, —C(O)OR$^{21}$, —C(O)R$^{21}$, —CH$_2$OR$^{21}$, —C(O)NR$^{21}$R$^{22}$, —S(O)R$^{21}$, —S(O)$_2$R$^2$, —S(O)$_2$CF$_3$, —S(O)$_2$NR$^{21}$R$^{22}$, C$_{3-8}$-cycloalkyl, C$_{3-8}$-cycloalkyl-C$_{1-6}$-alkoxy or C$_{3-8}$-cycloalkyl-C$_{1-6}$-thioalkyl, or aryl, heteroaryl or aryloxy, which may optionally be substituted with —CF$_3$, —OCF$_3$, C$_{1-6}$-alkyl, halogen or —C(O)OR$^{21}$, or two of the groups $R^{15}$, $R^{16}$ and $R^{17}$ when placed in adjacent positions together form a bridge —(CR$^{23}$R$^{24}$)$_a$—O—(CR$^{25}$R$^{26}$)$_c$—O—, wherein $R^{21}$ and $R^{22}$ independently are hydrogen or C$_{1-6}$-alkyl, and a, c, $R^{23}$, $R^{24}$, $R^{25}$ and $R^{26}$ are as defined for formula (I).

In another embodiment, $R^{15}$, $R^{16}$ and $R^{17}$ are independently hydrogen, halogen, —CN, —CF$_3$, —OCF$_3$ or C$_{1-6}$alkoxy or wherein $R^{15}$ and $R^{16}$ together form a bridge —CF$_2$—O—CF$_2$—O— and $R^{17}$ is hydrogen.

In yet another embodiment, $R^{15}$, $R^{16}$ and $R^{17}$ independently are hydrogen, halogen, —CN, —CF$_3$, —OCF$_3$ or C$_{1-6}$-alkoxy.

In another embodiment, D is

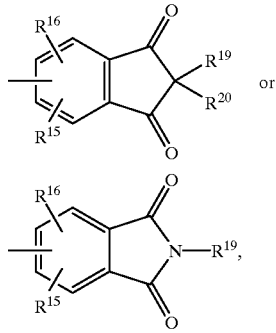

wherein $R^{15}$, $R^{16}$, $R^{19}$ and $R^{20}$ are as defined for formula (I).

In yet another embodiment, D is

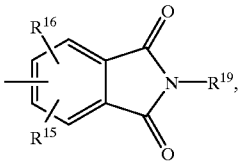

wherein $R^{15}$ and $R^{16}$ are both hydrogen and $R^{19}$ is C$_{1-6}$-alkyl, C$_{3-8}$-cycloalkyl or C$_{3-8}$-cycloalkyl-C$_{1-6}$-alkyl.

In still another embodiment, D is

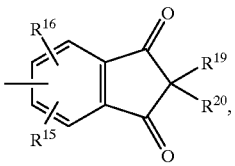

wherein $R^{15}$ and $R^{16}$ are both hydrogen and $R^{19}$ and $R^{20}$ are both C$_{1-6}$-alkyl.

In one embodiment, E is

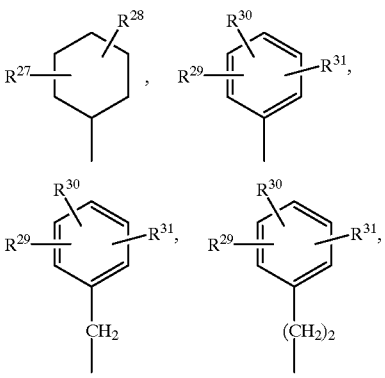

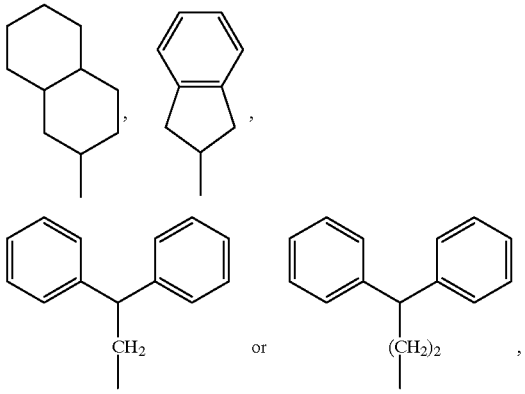

wherein $R^{27}$ $R^{28}$ $R^{29}$ $R^{30}$ and $R^{31}$ are as defined for formula (I).

In another embodiment, E is

[structure: cyclohexyl with R27 and R28 substituents]

wherein $R^{27}$ and $R^{28}$ are as defined for formula (I).

In still another embodiment, E is

[structure: cyclohexyl with R27 and R28 on same carbon]

wherein $R^{27}$ and $R^{28}$ are as defined for formula (I).

In one embodiment, $R^{27}$ and $R^{28}$ are independently hydrogen, $C_{1-6}$-alkyl, $C_{3-8}$-cycloalkyl, $C_{4-8}$-cycloalkenyl or phenyl, wherein the phenyl group is optionally substituted as defined for formula (I).

In another embodiment, $R^{27}$ and $R^{2-3}$ are independently hydrogen, $C_{1-6}$-alkyl, $C_{3-8}$-cycloalkyl or $C_{4-8}$-cycloalkenyl.

In still another embodiment, $R^{27}$ is hydrogen and $R^{28}$ is $C_{1-6}$-alkyl or $C_{3-8}$-cycloalkyl, such as tert-butyl, cyclohexyl or cyclohexenyl.

In another embodiment, E is

[structure: phenyl with R29, R30, R31 substituents]

wherein $R^{29}$, $R^{30}$ and $R^{31}$ are as defined for formula (I).

In yet another embodiment, E is

[structure: phenyl with R29, R30, R31 substituents, para]

wherein $R^{29}$, $R^{30}$ and $R^{31}$ are as defined for formula (I).

In one embodiment, $R^{29}$, $R^{30}$ and $R^{31}$ are independently
hydrogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$,
$C_{1-6}$-alkyl, $C_{2-6}$-alkenyl or $C_{2-6}$-alkynyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl
$C_{3-8}$-cycloalkyl or $C_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl,
wherein $R^{34}$ and $R^{35}$ independently are hydrogen, $C_{1-6}$-alkyl or aryl, or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In yet another embodiment, $R^{29}$, $R^{30}$ and $R^{31}$ are independently
hydrogen, $C_{1-6}$-alkoxy, halogen, —CF$_3$, OCF$_3$ or —NR$^{34}$R$^{35}$, wherein $R^{34}$ and $R^{35}$ are as defined for formula (I), or
$C_{1-6}$-alkyl, $C_{3-8}$cycloalkyl or $C_{4-8}$-cycloalkenyl, which are optionally substituted as defined for formula (I).

In still another embodiment, $R^{29}$ $R^{30}$ and $R^3$ are independently
hydrogen or
$C_{1-6}$-alkyl, $C_{3-8}$-cycloalkyl or $C_{4-8}$-cycloalkenyl, which are optionally substituted as defined for formula (I).

In yet another embodiment, R29, $R^{30}$ and $R^{31}$ are independently
hydrogen or
$C_{1-6}$-alkyl, $C_{3-8}$-cycloalkyl or $C_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl,
wherein $R^{34}$ and $R^{35}$ independently are hydrogen, $C_{1-6}$-alkyl or aryl,
or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In another embodiment, $R^{29}$ and $R^{31}$ are both hydrogen, and $R^{30}$ is different from hydrogen.

In still another embodiment, $R^{29}$ and $R^{31}$ are both hydrogen, and $R^{30}$ is $C_{3-8}$-cycloalkyl or $C_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl,
wherein $R^{34}$ and $R^{35}$ independently are hydrogen, $C_{1-6}$-alkyl or aryl,
or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In yet a further embodiment, $R^{29}$ and $R^{31}$ are both hydrogen, and $R^{30}$ is $C_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl,
wherein $R^{34}$ and $R^{35}$ independently are hydrogen, $C_{1-6}$-alkyl or aryl,
or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In still a further embodiment $R^{29}$ and $R^{31}$ are both hydrogen, and $R^{30}$ is cyclohexenyl, which may optionally be substituted with one or more substituents selected from halogen, —CN, —CF$_3$, —OCF$_3$, —NO$_2$, —OR$^{34}$, —NR$^{34}$R$^{35}$ and C$_{1-6}$-alkyl, wherein $R^{34}$ and $R^{35}$ independently are hydrogen, C$_{1-6}$-alkyl or aryl, or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In another embodiment, $R^{30}$ is substituted with one C$_{1-6}$-alkyl substituent, such as tert-butyl or methyl.

In still another embodiment, $R^{29}$, $R^{30}$ and $R^{31}$ are independently hydrogen, C$_{1-6}$-alkyl, C$_{3-8}$-cycloalkyl or C$_{4-8}$-cycloalkenyl.

In yet another embodiment, $R^{29}$ and $R^{31}$ are both hydrogen and $R^{30}$ is C$_{1-6}$-alkyl, C$_{3-8}$-cycloalkyl or C$_{4-8}$-cycloalkenyl, such as tert-butyl, cyclohexyl or cyclohexenyl.

In one embodiment, the invention relates to a compound of the general formula (I$_1$):

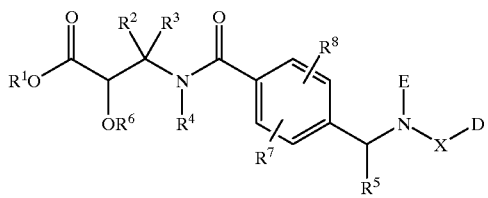

(I$_1$)

wherein $R^1$, $R^2$, $R^3$, $R^4$, $R^5$, $R^6$, $R^7$, $R^8$, X, D and E are as defined for formula (I) or in any one of the preceding embodiments.

In one embodiment, the invention relates to a compound of the general formula (I$_2$):

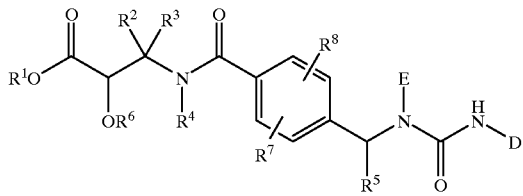

(I$_2$)

wherein $R^1$, $R^2$, $R^3$, $R^4$, $R^5$, $R^6$, $R^7$, $R^8$, D and E are as defined for formula (I) or in any one of the preceding embodiments.

In one embodiment, the invention relates to a compound of the general formula (I$_3$):

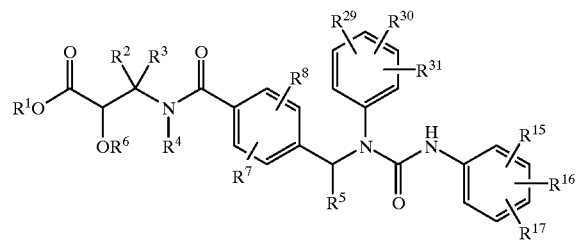

(I$_3$)

wherein $R^1$, $R^2$, $R^3$, $R^4$, $R^5$, $R^6$, $R^7$, $R^8$, $R^{15}$, $R^{16}$, $R^{17}$, $R^{29}$, $R^{30}$, and $R^{31}$ are as defined for formula (I) or in any one of the preceding embodiments.

In one embodiment of the formulae (I$_1$), (I$_2$) and (I$_3$), $R^1$, $R^2$, $R^3$, $R^4$, $R^5$, $R^6$, $R^7$ and $R^8$ are hydrogen.

In one embodiment, the invention relates to a compound of the general formula (I$_4$):

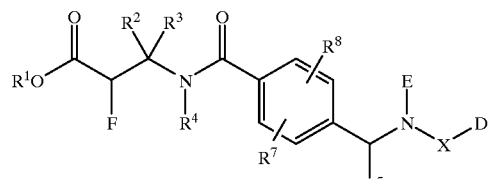

(I$_4$)

wherein $R^1$, $R^2$, $R^3$, $R^4$, $R^5$, $R^7$, $R^8$, X, D and E are as defined for formula (I) or in any one of the preceding embodiments.

In one embodiment, the invention relates to a compound of the general formula (I$_5$):

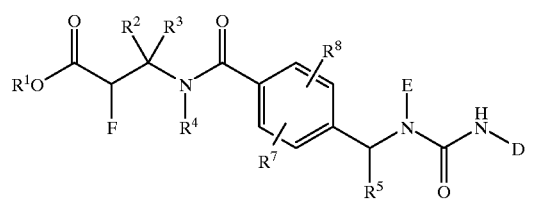

(I$_5$)

wherein $R^1$, $R^2$, $R^3$, $R^4$, $R^5$, $R^7$, $R^8$, D and E are as defined for formula (I) or in any one of the preceding embodiments.

In one embodiment of the formulae (I$_4$) and (I$_5$), $R^1$, $R^2$, $R^3$, $R^4$, $R^5$, $R^7$ and $R^8$ are hydrogen.

The compounds of the present invention may have one or more asymmetric centres and it is intended that any optical isomers, as separated, pure or partially purified optical isomers or racemic mixtures thereof are included within the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methane-sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Also intended as pharmaceutically acceptable acid addition salts are the hydrates, which the present compounds, are able to form.

Furthermore, the pharmaceutically acceptable salts comprise basic amino acid salts such as lysine, arginine and ornithine.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula (I), which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the present invention act to antagonize the action of glucagon and are accordingly useful for the treatment and/or prevention of disorders and diseases in which such an antagonism is beneficial.

Accordingly, the present compounds may be applicable for the treatment and/or prevention of hyperglycemia, IGT (impaired glucose tolerance), insulin resistance syndromes, syndrome X, Type 1 diabetes, Type 2 diabetes, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

Furthermore, they may be applicable as diagnostic agents for identifying patients having a defect in the glucagon receptor, as a therapy to increase gastric acid secretions and to reverse intestinal hypomobility due to glucagon administration.

Accordingly, in a further aspect the invention relates to a compound according to the invention for use as a medicament.

The invention also relates to pharmaceutical compositions comprising, as an active ingredient, at least one compound according to the invention together with one or more pharmaceutically acceptable carriers or excipients.

The pharmaceutical composition is preferably in unit dosage form comprising from about 0.05 mg to about 1000 mg, preferably from about 0.1 mg to about 500 mg and especially preferred from about 0.5 mg to about 200 mg of the compound according to the invention.

Furthermore, the invention relates to the use of a compound according to the invention for the preparation of a pharmaceutical composition for the treatment and/or prevention of a disorder or disease, wherein a glucagon antagonistic action is beneficial.

The invention also relates to a method for the treatment and/or prevention of disorders or diseases, wherein a glucagon antagonistic action is beneficial the method comprising administering to a subject in need thereof an effective amount of a compound according to the invention.

In a preferred embodiment of the invention the present compounds are used for the preparation of a medicament for the treatment and/or prevention of any glucagon-mediated conditions and diseases.

In a preferred embodiment of the invention the present compounds are used for the preparation of a medicament for the treatment and/or prevention of hyperglycemia.

In yet a preferred embodiment of the invention the present compounds are used for the preparation of a medicament for lowering blood glucose in a mammal.

In another preferred embodiment of the invention the present compounds are used for the preparation of a pharmaceutical composition for the treatment and/or prevention of IGT.

In still another preferred embodiment of the invention the present compounds are used for the preparation of a pharmaceutical composition for the treatment and/or prevention of Type 2 diabetes.

In yet another preferred embodiment of the invention the present compounds are used for the preparation of a pharmaceutical composition for the delaying or prevention of the progression from IGT to Type 2 diabetes.

In yet another preferred embodiment of the invention the present compounds are used for the preparation of a pharmaceutical composition for the delaying or prevention of the progression from non-insulin requiring Type 2 diabetes to insulin requiring Type 2 diabetes.

In a further preferred embodiment of the invention the present compounds are used for the preparation of a pharmaceutical composition for the treatment and/or prevention of Type 1 diabetes. Such treatment and/or prevention is normally accompanied by insulin therapy.

In a further preferred embodiment of the invention the present compounds are used for the preparation of a pharmaceutical composition for the treatment and/or prevention of obesity.

In yet a further preferred embodiment of the invention the present compounds are used for the preparation of a pharmaceutical composition for the treatment and/or prevention of disorders of the lipid metabolism, such as dyslipidemia.

In still a further embodiment of the invention the present compounds are used for the preparation of a pharmaceutical composition for the treatment and/or prevention of an appetite regulation or energy expenditure disorder.

In a further aspect of the invention the present compounds are combined with diet and/or exercise.

In yet a further aspect of the invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents comprise insulin, insulin analogues and derivatives such as those disclosed in EP 792 290 (Novo Nordisk A/S), eg $N^{\epsilon B29}$-tetradecanoyl des (B30) human insulin, EP 214 826 and EP 705 275 (Novo Nordisk A/S), eg $Asp^{B28}$ human insulin, U.S. Pat. No. 5,504,188 (Eli Lilly), eg $Ly_{B28}Pro^{B29}$ human insulin, EP 368 187 (Aventis), eg Lantus, which are all incorporated herein by reference, GLP-1 derivatives such as those disclosed in WO 98/08871 (Novo Nordisk A/S), which is incorporated herein by reference, as well as orally active hypoglycaemic agents.

The orally active hypoglycaemic agents preferably comprise imidazolines, sulphonylureas, biguanides, meglitinides, oxadiazolidinediones, thiazolidinediones, glucosidase inhibitors, glucagon antagonists, GLP-1 agonists, agents acting on the ATP-dependent potassium channel of the 3-cells eg potassium channel openers such as those disclosed in WO 97/26265, WO 99/03861 and WO 00137474 (Novo Nordisk A/S) which are incorporated herein by reference, or nateglinide or potassium channel blockers such as BTS-67582, insulin sensitizers, DPP-IV (dipeptidyl peptidase-IV) inhibitors, PTPase inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, PPAR (peroxisome proliferator-activated receptor) and RXR (retinoid X receptor) agonists such as ALRT-268, LG-1268 or LG-1069.

In one embodiment of the invention the present compounds are administered in combination with insulin or an insulin analogue or derivative, such as $N^{B29}$-tetradecanoyl des (B30) human insulin, $Asp^{B28}$ human insulin, $Lys^{B28}$ $Pro^{B29}$ human insulin, Lantus, or a mix-preparation comprising one or more of these.

In a further embodiment of the invention the present compounds are administered in combination with a sulphonylurea eg tolbutamide, chlorpropamide, tolazamide, glibenclamide, glyburide, glipizide or glicazide.

In another embodiment of the invention the present compounds are administered in combination with a biguanide eg metformin.

In yet another embodiment of the invention the present compounds are administered in combination with a meglitinide eg repaglinide or nateglinide.

In still another embodiment of the invention the present compounds are administered in combination with a thiazolidinedione insulin sensitizer eg troglitazone, ciglitazone, pioglitazone, rosiglitazone, isaglitazone, darglitazone, englitazone, CS-011/Cl-1037 or T174 or the compounds disclosed in WO 97/41097, WO 97/41119, WO 97/41120, WO 00/41121 and WO 98/45292 (Dr. Reddy's Research Foundation).

In still another embodiment of the invention the present compounds may be administered in combination with an insulin sensitizer such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S).

In a further embodiment of the invention the present compounds are administered in combination with an α-glucosidase inhibitor eg voglibose, emiglitate, miglitol or acarbose.

In another embodiment of the invention the present compounds are administered in combination with an agent acting on the ATP-dependent potassium channel of the β-cells eg tolbutamide, chlorpropamide, tolazamide, glibenclamide, glyburide, glipizide, glicazide, BTS-67582, repaglinide or nateglinide.

In still another embodiment of the invention the present compounds are administered in combination with an antihyperlipidemic agent or antilipidemic agent eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds eg in combination with metformin and a sulphonylurea such as glibenclamide or glyburide; a sulphonylurea and acarbose; metformin and a meglitinide such as repaglinide; acarbose and metformin; a sulfonylurea, metformin and troglitazone; a sulfonylurea, metformin and pioglitazone; a sulfonylurea, metformin and an insulin sensitizer such as disclosed in WO 00/63189 or WO 97/41097; a meglitinide such as repaglinide, metformin and troglitazone; a meglitinide such as repaglinide, metformin and pioglitazone; a meglitinide such as repaglinide, metformin and an insulin sensitizer such as disclosed in WO 00/63189 or WO 97/41097; insulin and a sulfonylurea; insulin and a meglitinide such as repaglinide; insulin and metformin; insulin, metformin and a meglitinide such as repaglinide; insulin, metformin and a sulfonylurea; insulin and troglitazone; insulin and pioglitazone; insulin and an insulin sensitizer such as such as disclosed in WO 00/63189 or WO 97/41097; insulin and lovastatin; an insulin analogue or derivative, metformin and a meglitinide such as repaglinide; an insulin analogue or derivative, metformin and a sulfonylurea; an insulin analogue or derivative and troglitazone; an insulin analogue or derivative and pioglitazone; an insulin analogue or derivative and an insulin sensitizer such as disclosed in WO 00/63189 or WO 97/41097; an insulin analogue or derivative and lovastatin; etc.

Furthermore, the compounds according to the invention may be administered in combination with one or more antiobesity agents or appetite regulating agents.

Such agents may be selected from the group consisting of CART (cocaine amphetamine regulated transcript) agonists, NPY (neuropeptide γ) antagonists, MC4 (melanocortin 4) agonists, orexin antagonists, TNF (tumor necrosis factor) modulators, CRF (corticotropin releasing factor) agonists, CRF BP (corticotropin releasing factor binding protein)

antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline reuptake inhibitors, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators or TR β agonists.

In one embodiment of the invention the antiobesity agent is leptin.

In another embodiment of the invention the antiobesity agent is dexamphetamine or amphetamine.

In another embodiment of the invention the antiobesity agent is fenfluramine or dexfenfluramine.

In still another embodiment of the invention the antiobesity agent is sibutramine.

In a further embodiment of the invention the antiobesity agent is orlistat.

In another embodiment of the invention the antiobesity agent is mazindol or phentermine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and cc-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

PHARMACEUTICAL COMPOSITIONS

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. One example is a base addition salt of a compound having the utility of a free acid. When a compound of the formula (I) contains a free acid such salts are prepared in a conventional manner by treating a solution or suspension of a free acid of the formula (I) with a chemical equivalent of a pharmaceutically acceptable base. Representative examples are mentioned above.

For parenteral administration, solutions of the novel compounds of the formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho-lipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | | |
|---|---|---|
| Active compound (as free compound or salt thereof) | | 5.0 mg |
| Lactosum Ph. Eur. | | 67.8 mg |
| Cellulose, microcryst. (Avicel) | | 31.4 mg |
| Amberlite ® IRP88* | | 1.0 mg |
| Magnesii stearas Ph. Eur. | | q.s. |
| Coating: | | |
| Hydroxypropyl methylcellulose | approx. | 9 mg |
| Mywacett 9-40 T** | approx. | 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of the glucagon antagonists of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

Some of the NMR data shown in the following examples are only selected data.

In the examples and pharmacological methods the following terms are intended to have the following meanings:

| | |
|---|---|
| DCM: | dichloromethane |
| DMF: | N,N-dimethylformamide |
| DMSO: | dimethyl sulphoxide |
| M.p.: | melting point |
| TFA: | trifluoroacetic acid |
| THF: | tetrahydrofuran |
| EDAC: | 1-ethyl-3-(3-dimethylaminopropyl)carbodiimide hydrochloride |
| HOBt: | 1-hydroxybenzotriazole |
| HOAt: | 3-hydroxy-3H-[1,2,3]triazolo[4,5-b]pyridine, also denoted 1-hydroxy-7-azabenzotriazole |
| EGTA: | ethylene glycol bis(β-aminoethyl ether) N,N,N',N'-tetracetic acid |
| BSA: | N,O-bis(trimethylsilyl)acetimidate |
| IBMX: | isobutylmethylxanthine |

HPLC-MS (Method A)

The following instrumentation was used:
Sciex API 100 Single quadropole mass spectrometer
Perkin Elmer Series 200 Quard pump
Perkin Elmer Series 200 autosampler
Applied Biosystems 785A UV detector
Sedex 55 evaporative light scattering detector
A Valco column switch with a Valco actuator controlled by timed events from the pump.

The Sciex Sample control software running on a Macintosh PowerPC 7200 computer was used for the instrument control and data acquisition.

The HPLC pump was connected to four eluent reservoirs containing:

| | |
|---|---|
| A: | acetonitrile |
| B: | water |
| C: | 0.5% TFA in water |
| D: | 0.02 M ammonium acetate |

The requirements for samples are that they contain approximately 500 μg/mL of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis was performed at room temperature by injecting 20 μL of the sample solution on the column, which was eluted with a gradient of acetonitrile in either 0.05% TFA or 0.002 M ammonium acetate. Depending on the analysis method varying elution conditions were used.

The eluate from the column was passed through a flow splitting T-connector, which passed approximately 20 μL/min through approx. 1 m. 75μ fused silica capillary to the API interface of API 100 spectrometer.

The remaining 1.48 mL/min was passed through the UV detector and to the ELS detector.

During the LC-analysis the detection data were acquired concurrently from the mass spectrometer, the UV detector and the ELS detector.

The LC conditions, detector settings and mass spectrometer settings used for the different methods are given in the following table.

| | |
|---|---|
| Column | YMC ODS-A 120Å s-5μ 3 mm × 5 mm id |
| Gradient | 5%–90% acetonitrile in 0.05% TFA linearly during 7.5 min at 1.5 mL/min |
| Detection | UV: 214 nm  ELS: 40° C. |
| MS | Experiment: Start: 100 amu Stop: 800 amu Step: 0.2 amu |
| | Dwell: 0.571 msec |
| | Method: Scan 284 times = 9.5 min |

HPLC-MS (Method B)

The following instrumentation was used:

Hewlett Packard series 1100 G1312A Bin Pump

Hewlett Packard series 1100 Column compartment

Hewlett Packard series 1100 G1315A DAD diode array detector

Hewlett Packard series 1100 MSD

The instrument was controlled by HP Chemstation software.

The HPLC pump was connected to two eluent reservoirs containing:

| | |
|---|---|
| A: | 0.01% TFA in water |
| B: | 0.01% TFA in acetonitrile |

The analysis was performed at 40° C. by injecting an appropriate volume of the sample (preferably 1 μL) onto the column, which was eluted with a gradient of acetonitrile.

The HPLC conditions, detector settings and mass spectrometer settings used are given in the following table.

| | |
|---|---|
| Column | Waters Xterra MS C-18 × 3 mm id |
| Gradient | 10%–100% acetonitrile linearly during 7.5 min at 1.0 mL/min |
| Detection | UV: 210 nm (analog output from DAD) |
| MS | Ionisation mode: API-ES |
| | Scan 100–1000 amu step 0.1 amu |

HPLC-MS (Method C)

The following instrumentation was used:

Hewlett Packard series 1100 G1312A Bin Pump

Hewlett Packard series 1100 G 1315A DAD diode array detector

Sciex 300 triplequadropole mass spectrometer

Gilson 215 micro injector

Sedex 55 evaporative light scattering detector

Pumps and detectors were controlled by MassChrom 1.1.1 software running on a Macintosh G3 computer. Gilson Unipoint Version 1.90 controls the auto-injector.

The HPLC pump was connected to two eluent reservoirs containing:

| | |
|---|---|
| A: | 0.01% TFA in water |
| B: | 0.01% TFA in acetonitrile |

The analysis was performed at room temperature by injecting an appropriate volume of the sample (preferably 1 μL) onto the column that was eluted with a gradient of acetonitrile.

The HPLC conditions, detector settings and mass spectrometer settings are given in the following table.

| | |
|---|---|
| Column | YMC ODS-A 120Å s-5μ 3 mm × 50 mm id |
| Gradient | 5%–90% acetonitrile linearly during 7.5 min at 1.5 mL/min |
| Detection | 210 nm (analog output from DAD) |
| MS | Ionisation mode: API-ES |
| | Scan 100–1000 amu step 0.1 amu |

Preparation of Building Blocks Used in the Following Examples

Building block 1: (RS)-Isoserine Ethyl Ester Hydrochloride

Dry ethanol (40 mL) was cooled on an ice bath and thionyl chloride (4 mL) was added dropwise maintaining the temperature below 5° C. To this cold solution was added (RS)-isoserine (2.5 g, 23.79 mmol) and stirring was continued until a homogeneous solution was obtained. The ice bath was removed and stirring was continued for 17 hours at room temperature. The solution was concentrated in vacuo to afford 4.0 g (100%) of (RS)-isoserine ethyl ester hydrochloride as an oil.

$^1$H-NMR (DMSO-$d_6$): δ 1.22 (t, 3H), 3.00 (dm, 2H), 4.15 (q, 2H), 4.40 (dd, 1H), 6.30 (br s, 1H), 8.32 (br s, 2H). $^{13}$C-NMR (DMSO-$d_6$): δ 14.7 (q), 42.4 (t), 61.7 (t), 67.7 (d), 171 (s).

Building Block 2: (R)-Isoserine Ethyl Ester Hydrochloride

Step A: (R)-(2,2-Dimethyl-5-oxo-[1,3]dioxolan-4-yl)acetic Acid

To a suspension of D-(+)-malic acid (15.0 g, 0.1119 mol) in dry toluene (150 mL) was added 2,2-dimethoxypropane (50 mL, 0.392 mmol). The mixture was refluxed at 100° C. for 2 hours and evaporated in vacuo. The residue was dissolved in diethyl ether (150 mL) and subjected to flash column chromatography using diethyl ether as eluent (200 mL). The pure fractions were pooled and evaporated in vacuo and the residue was stirred in n-hexane. The precipitate was collected, washed with n-hexane and dried to afford 15.7 g (81%) of (R)-(2,2-di-methyl-5-oxo-[1,3]dioxolan-4-yl)acetic acid as a solid.

$^1$H-NMR (Acetone-$d_6$): δ 1.57 (ds, 6H), 2.85 (m, 2H), 4.80 (dd, 1H), 11.0 (br s, 1H). $^{13}$C-NMR (Acetone-$d_6$): δ 25.9 (q), 26.8 (q), 36.2 (t), 71.5 (d), 111.2 (s), 170.7 (s), 172.7 (s).

Microanalysis: Calculated for $C_7H_{10}O_5$:
C, 48.28%; H, 5.79%. Found:
C, 48.31%; H, 6.09%.

Step B: (R)-(2,2-Dimethyl-5-oxo-[1,3]dioxolan-4-ylmethyl)carbamic Acid Benzyl Ester A mixture of (R)-(2,2-dimethyl-5-oxo-[1,3]dioxolan-4-yl)acetic acid (10.0 g, 57.41 mmol), triethylamine (10 mL, 68.89 mmol) and diphenylphosphoryl azide (14 mL, 63.15 mmol) in dry toluene (100 mL) was heated and stirred at 85° C. When the gas evolution had ceased stirring was continued for an additional hour. Dry benzyl alcohol (6.3 mL, 63.15 mmol) was added and heating was continued for 17 hours. After evaporation in vacuo, the residue was partitioned between dichloromethane, water and brine. The aqueous phase was further extracted twice with dichloromethane. The combined organic phases were washed twice with saturated sodium hydrogen carbonate. After drying (magnesium sulphate), filtration, and concentration in vacuo of the organic phase, the residue was subjected to flash column chromatography with dichloromethane as eluent. This afforded 6.4 g (40%) of (R)-(2,2-dimethyl-5-oxo-[1,3] dioxolan-4-ylmethyl)carbamic acid benzyl ester as an oil.

$^1$H-NMR (Acetone-d$_6$): δ 1.56 (s, 6H), 3.61 (m, 2H), 4.64 (dd, 1H), 5.08 (dd, 2H), 6.51 (br s, 1H), 7.29–7.38 (m, 5H).

Step C: (R)-3-Benzyloxycarbonylamino-2-hydroxypropionic Acid

To a solution of (R)-(2,2-dimethyl-5-oxo-[1,3]dioxolan-4-ylmethyl)carbamic Acid Benzyl Ester (6.0 g, 25.08 mmol) in acetonitrile (100 mL) was added hydrochloric acid, (1 N, 100 mL). The mixture was stirred for 3 hours at 40° C. and concentrated in vacuo to half the original volume. The solid was collected by filtration and washed with water. The crude product was stirred for 5 min in acetone (100 mL) and filtered. Toluene was added to the clear and colorless filtrate and the whole was concentrated in vacuo until a precipitate was obtained. The precipitate was collected by filtration and dried to afford 4.45 g (87%) of (R)-3-benzyloxy-carbonylamino-2-hydroxypropionic acid.

$^1$H-NMR(Acetone-d$_6$): δ 3.45 (ddd, 1H), 3.58 (ddd,1H), 4.29 (dd, 1H), 5.08 (s, 2H), 6.41 (br s, 1H), 7.29–7.38 (m, 5H). $^{13}$C-NMR (Acetone-d$_6$): δ 45.1 (t), 66.4 (t), 70.4 (d), 128.3 (d), 128.9 (d), 138.0 (d), 157.2 (s), 173.8 (s); HPLC-MS (Method C): m/z=262 (M+Na$^+$); R$_t$=2.20 min.

M.p. 131–132° C.
Microanalysis: Calculated for C$_{11}$H$_{13}$NO$_5$:
C, 55.23%; H, 5.48%; N, 5.85%. Found:
C, 55.35%; H, 5.72%; N, 5.82%.

Step D: (R)-Isoserine (R)-3-Benzyloxycarbonylamino-2-hydroxypropionic acid (4.4 g, 18.39 mmol) was dissolved in absolute ethanol (150 mL). Under a nitrogen atmosphere palladium on activated carbon (10%, 0.5 g) was added, and the mixture was hydrogenated at 1 atmosphere for 17 hours. The catalyst was filtered off and washed with water. The combined filtrate and washings were concentrated to about 20 mL by evaporation in vacuo. A precipitate was obtained by drop-wise addition of methanol (100 mL). The precipitate was filtered off, washed with methanol and dried to afford 1.78 g (92%) of (R)-isoserine as a solid.

$^1$H-NMR (D$_2$O): δ 3.07 (dd, 1H), 3.30 (dd, 1H), 4.19 (dd, 1H). $^{13}$C-NMR (D$_2$O): 643.0(t), 68.9 (d), 177.5 (s). M.p. 200–201° C.

Step E: (R)-Isoserine Ethyl Ester Hydrochloride

The compound was prepared in analogy with the method outlined above for (RS)-isoserine ethyl ester hydrochloride.
$^1$H-NMR (DMSO-d$_6$): δ 1.22 (t, 3H), 2.88 (dd, 1H), 3.10 (dd, 1H), 4.14 (q, 2H), 4.40 (m, 1H), 6.32 (d, 1H), 8.28 (br s, 2H). $^{13}$C-NMR (DMSO-d$_6$): δ 13.9 (q), 41.4 (t), 60.7 (t), 66.9 (d), 170.9 (s).

Building block 3: (S)-2,2-Dimethyl-5-oxo-[1,3] dioxolan-4-ylmethylammonium Trifluoroacetate

Step A: (S)-(2,2-Dimethyl-5-oxo-[1,3]-dioxolan-4-yl)acetic Acid

To a suspension of L-malic acid (3 g, 22.4 mmol) in toluene (25 mL) was added 2,2-dimethoxypropane (8.5 g, 81 mmol). The suspension was heated to reflux for 20 min. The solvent was removed by evaporation in vacuo to afford (S)-(2,2-dimethyl-5-oxo [1,3]-4-yl)-acetic acid.
$^1$H-NMR (DMSO-d$_6$): δ 1.52 (6H, d), 2.75 (2H, t), 4.78 (1H, t), 12.52 (1H, brs).

Step B: (S)-(2,2-Dimethyl-5-oxo-[1,3]dioxolan-4-ylmethyl)carbamic Acid Benzyl Ester To (S)-(2,2-dimethyl-5-oxo-[1,3]dioxolan-4-yl)acetic acid (1 g, 5.7 mmol) and triethylamine (0.66 g, 6.5 mmol) in toluene (20 mL) was added phosphorazidic acid diphenyl ester (1.7 g, 6.2 mmol). The solution was heated to reflux for 1 hour. Benzyl alcohol (0.54 g, 5 mmol) was added and reflux was maintained for additional 6 hours. After cooling, the solution was partitioned between ethyl acetate (2×50 mL) and aqueous sodium hydrogen carbonate (10%, 2×50 mL). The organic layers were collected, dried (sodium sulphate) and the solvent removed by evaporation in vacuo to afford 976 mg of crude (S)-(2,2-dimethyl-5-oxo-[1,3] dioxolan-4-ylmethyl)carbamic acid benzyl ester as an oil.
$^1$H-NMR (DMSO-d$_6$): δ 1.53 (6H, d), 3.34 (1H, m), 3.50 (1H, m), 4.50 (1H, d), 4.64 (1H, t), 5.03 (2H, d), 7.32 (5H, m)

Step C: (S)-2,2-Dimethyl-5-oxo-[1.3]dioxolan-4-ylmethylammonium Trifluoroacetate The crude (S)-(2,2-dimethyl-5-oxo-[1,3]dioxolan-4-ylmethyl)carbamic acid benzyl ester (976 mg, 3.5 mmol) was dissolved in ethanol (14 mL), and palladium (10% on activated charcoal, 300 mg) and 1,3-cyclohexadiene (2.8 g, 35 mmol) were added and the reaction was stirred for 1 hour at room temperature, and heated to 40° C. for 10 min. After filtration, TFA (0.4 g, 3.5 mmol) was added and the solvent was removed by evaporation to afford crude (S)-2,2-dimethyl-5-oxo-[1,3]dioxolan-4-ylmethylammonium trifluoroacetate as an oil.
$^1$H-NMR (CDCl$_3$): δ 1.46 (6H, d), 3.40–3.70 (2H, m), 4.38 (1H, m), 7.25 (>4H, brs); HPLC-MS (Method B): m/z=146 (M+); R$_t$=0.38 min.

Building block 4: 3-Amino-2-fluoropropionic Acid Methyl Ester

Dry methanol (5.3 mL) was cooled to −15° C. on an ice bath and thionyl chloride (2.5 mL) was added dropwise maintaining the temperature below 5° C. To this cold solution was added (RS)-3-amino-2-fluoropropionic acid (0.27 g, 2.52 mmol) and stirring was continued until a homogeneous solution was obtained. The ice bath was removed and stirring was continued for 17 hours at room temperature. The solution was concentrated in vacuo and further co-evaporated three times with dry methanol. The residue was filtered off, washed with DCM and dried to afford 0.13 g (33%) of 3-amino-2-fluoropropionic acid methyl ester hydrochloride as a solid.
$^1$H-NMR (DMSO-d$_6$): δ 3.36 (m, 2H), 3.76 (s, 3H), 5.51(d, 2H), 8.59 (brs, 3H).

Building block 5: 3-Amino-2(R)-methoxypropionic Acid Methyl Ester Hydrochloride

Step (A): (R)-2-Hydroxysuccinic Acid Dimethyl Ester

To an ice cooled solution of methanol (250 mL) was added acetyl chloride (12.5 mL), and the solution was stirred for 1 hour at 0° C. (R)-Malic acid (20.0 g) was added, and the solution was stirred for 16 hours at room temperature.

Solvent was removed by evaporation in vacuo leaving a quantitative yield of (R)-2-hydroxysuccinic acid dimethyl ester as an oil.
$^1$H-NMR (CDCl$_3$): δ 4.52 (dd, 1H), 3.80 (s, 3H), 3.71 (s, 3H), 3.55 (bs, 1H), 2.88 (dd, 1H), 2.80 (dd, 1H).

Step (B): (R)-2-Methoxysuccinic Acid Dimethyl Ester

The above (R)-2-hydroxysuccinic acid dimethyl ester was re-dissolved in methyl iodide (100 mL), freshly prepared silver oxide (30.2 g) was added and the mixture was stirred for 24 hours at room temperature. The reaction mixture was diluted with acetonitrile (200 mL), and filtered through celite to remove silver salts and excess silver hydroxide. The filtrate was taken to dryness to leave (R)-2-methoxysuccinic acid dimethyl ester as an oil (23.2 g, 88%).
$^1$H-NMR (CDCl$_3$): δ4.20 (dd, 1H), 3.78 (s, 3H), 3.71 (s, 3H), 3.48 (s, 3H), 2.80 (dd, 2H).

Step (C): (R)-2-Methoxysuccinic Acid 1-methyl Ester

The above (R)-2-methoxysuccinic acid dimethyl ester was suspended in 2 N aqueous hydrochloric acid, and heated to reflux for 30 min to give a clear solution. Upon evaporation of solvent in vacuo a quantitative yield of 2(R)-methoxysuccinic acid was obtained as an oil. The oil was redissolved in acetic anhydride (120 mL) and heated to 110° C. for 2 hours. Solvent was removed by rotary evaporation to leave an oil. Ice cooled methanol (150 mL) was added, and the mixture was stirred for 3 hours at 0° C. followed by 16 hours at room temperature. The solvent was removed to leave (R)-2-methoxysuccinic acid 1-methyl ester.
$^1$H-NMR (CDCl$_3$): δ 10.30 (bs, 1H), 4.19 (dd, 1H), 3.80 (s, 3H), 3.50 (s, 3H), 2.86 (dd, 1H), 2.78 (dd, 1H).

Step (D): 3-tert-Butoxycarbonylamino-2(R)-methoxypropionic Acid Methyl Ester Without further purification, the above (R)-2-methoxysuccinic acid 1-methyl ester (5.0 g, 30.8 mmol) was dissolved in thionyl chloride (16 mL), and heated to reflux for 2 hours Thionyl chloride and traces thereof was removed by rotary evaporation followed by co-evaporation with acetonitrile.
$^1$H-NMR (CDCl$_3$): δ 3.27 (dd, 1H), 3.48 (dd, 1H), 3.51 (s, 3H), 3.80 (s, 3H), 4.22 (dd, 1H).

The neat acid chloride was dissolved in toluene (50 mL). Trimethylsilylazide (5.0 mL, 38.2 mmol) was added and the mixture was heated to 100° C. overnight. Then tert-butanol (30 mL) was added, and heating was continued for an additional 16 hours. The reaction mixture was cooled and insoluble material was removed by filtration. The organic phase was washed with water (100 mL), saturated sodium hydrogen carbonate solution (100 mL), 10% citric acid solution (100 mL), water (100 mL) and saturated sodium chloride solution (100 mL), then dried over anhydrous sodium sulphate. Solvent was removed by rotary evaporation. The residual oil was further purified by column chromatography using 20% ethyl acetate/heptane as eluent. Pure fractions (TLC plates were stained with ammonium molybdate/cerium sulphate/sulphuric acid) were pooled and taken to dryness. The final yield of 3-tert-butoxycarbonylamino-2(R)-methoxypropionic acid methyl ester was 600 mg (9%).

$^1$H-NMR (CDCl$_3$): δ6.93 (t, 1H), 3.83 (t, 1H), 3.64 (s, 3H), 3.25 (s, 3H), 3.18 (dd, 2H), 1.36 (s, 9H).

Step (E): 3-Amino-2(R)-methoxypropionic Acid Methyl Ester Hydrochloride 3-tert-Butoxycarbonylamino-2-methoxypropionic acid methyl ester (500 mg, 2 mmol) was dissolved in 10% TFA in DCM (20 mL), and the reaction mixture was stirred at 30 min at ambient temperature. Solvent was removed and the residue co-evaporated twice from 30 mL of 1 N hydrochloric acid in ether. Yield: 320 mg (88%).
$^1$H-NMR (CDCl$_3$): δ8.25 (s, 3H), 4.21 (dd, 1H), 3.71 (s, 3H), 3.40 (s, 3H), 3.15 (m, 1H), 2.98 (m, 1H).

Building block 6: (R)-3-(9H-Fluoren-9-ylmethoxycarbonylamino)-2-hydroxypropionic Acid ((R)-Fmoc-isoserine To (R)-(2,2-dimethyl-5-oxo[1,3]dioxolan-4-yl)acetic acid (5.88 g, 33.8 mmol) was added toluene (100 mL), triethylamine (4.7 mL, 33.8 mmol) and diphenoxyphosphoryl azide (8.0 mL, 37.2 mmol). The reaction mixture was heated to a 100° C and stirred under nitrogen at this temperature for 1.5 hour. 9-Fluorenemethanol (5.1 g, 26 mmol) was added and the reaction mixture was refluxed for 6 hours. After cooling to room temperature the mixture was transferred to a separatory funnel and washed with water (2×50 mL). The solvent was removed in vacuo and co-evaporated with acetonitrile (100 mL). The remaining light brown oil was dissolved in DCM (20 mL) and purified on silica gel column with DCM as eluent. The DCM was removed by evaporation to yield a light yellow oil, which was redissolved in acetonitrile (150 mL) and aqueous hydrochloric acid was added (1 N, 75 mL). The yellow reaction mixture was stirred for 3 hours at room temperature. The solvent was removed in vacuo, toluene (100 mL) was added and the suspension was heated to reflux and allowed to cool to room temperature. (R)-Fmoc-isoserine (3.1 g, 28%) was isolated as a powder by filtration. Mp: 165–166° C.
$^1$H-NMR (DMSO-d$_6$): δ 12.5 (brs, 1H), 7.90 (m, 2H), 7.70 (m, 2H), 7.50–7.30 (m, 4H), 5.45 (br s, 1H), 4.23 (m, 3H), 4.05 (m, 1H), 3.17 (m, 1H); HPLC-MS (Method B): m/z= 350 (M+Na); R$_t$=3.20 min.

Building block 7: 3-(tert-Butyldimethylsilanyloxymethyl)-4-trifluoromethoxyphenyl Amine

Step A: 5-Nitro-2-trifluoromethoxybenzoic Acid Methyl Ester

In a three-necked round bottom flask, equipped with a thermometer and a separatory funnel, HNO$_3$ (5 mL fuming, 100%) was cooled in an ice bath. Methyl 2-(trifluoromethoxy)benzoate (5 g, 22.7 mmol) was slowly added to the cooled HNO$_3$ within 0.5 hour while keeping the temperature below 15° C. The reaction was then stirred at 60° C. for 1 hour and 2 hours at room temperature. The mixture was added to ice water and an oil separated. The oily residue was added water (50 mL), neutralised with an aqueous solution of sodium hydrogen carbonate and then extracted with ethyl acetate (25 mL). The aqueous phase was extracted with ethyl acetate (15 mL) once more. The combined organic phases were washed with saturated sodium chloride (2×15 mL), dried (magnesium sulphate), and concentrated in vacuo to give 5.69 g of 5-nitro-2-trifluoromethoxybenzoic acid methyl ester.
$^1$H-NMR (DMSO-d$_6$): δ3.93 (3H, s), 7.82 (1H, d), 8.58 (1H, d), 8.67 (1H, s).

Step B: 5-Amino-2-trifluoromethoxybenzoic Acid Methyl Ester

5-Nitro-2-trifluoromethoxybenzoic acid methyl ester (5.69 g, 21.5 mmol) was dissolved in ethanol 99.9% (80 mL) and added stannous(II)chloride dihydrate (24.2 g, 107 mmol). The suspension was stirred at 75° C. for 2 hours and then concentrated in vacuo. The residue was added ethyl acetate (100 mL) and water (50 mL) and pH was adjusted to pH 8 with 4 N sodium hydroxide (50 mL). The liquid was decanted from the fine precipitation, which occurred, and the precipitate was washed with ethyl acetate and decanted twice. The combine organic phases were washed with water-:saturated sodium chloride (1:1) solution (2×100 mL), dried (magnesium sulphate) and concentrated in vacuo. The residue was purified by column chromatography (120 g silica) using ethyl acetate:heptane (1:1) as eluent to give 3.8 g of 5-amino-2-trifluoromethoxybenzoic acid methyl ester.
$^1$H-NMR (DMSO-d$_6$): δ 3.82 (3H, s), 5.63 (2H, s), 6.79 (1H, d), 7.07 (1H, s), 7.11 (1H, d).

Step C: (5-Amino-2-trifluoromethoxyphenyl)methanol

5-Amino-2-trifluoromethoxybenzoic acid methyl ester (3.0 g, 12.8 mmol) was dissolved under nitrogen in THF (20 mL) in a three-necked flask equipped with a thermometer and a separatory funnel. With stirring and ice-cooling lithium aluminium hydride (1 M in THF, 15 mL) was added dropwise over 10 min. Stirring was continued at room temperature for 1 hour, and the reaction mixture was concentrated in vacuo. The residue was suspended in DCM (150 mL) and water (50 mL), and filtered through celite. The filtrate was partitioned between DCM and water. The combined organic phases were washed with water (2×20 mL), dried (magnesium sulphate) and concentrated in vacuo to give 2.47 g of (5-amino-2-trifluoromethoxy-phenyl)methanol
$^1$H-NMR (DMSO-d$_6$): δ 3.92 (2H, d), 5.18 (1H, t), 5.28 (2H, s), 6.45 (1H, d), 6.91 (1H, d).

Step (D): 3-(tert-Butyldimethylsilanyloxymethyl)-4-trifluoromethoxyphenylaniline (5-Amino-2-trifluoromethoxyphenyl)methanol (1.2 g, 5.8 mmol) was dissolved in DMF (5 mL) and imidazole (0.48 g, 7.1 mmol) and tert-butyldimethylsilylchloride (0.99 g, 6.6 mmol) were added and the mixture was stirred for 16 hours. The reaction mixture was extracted with ethyl acetate (50 mL) and water (20 mL). The aqueous phase was extracted once more with ethyl acetate (20 mL). The combined organic phases were washed with water (10 mL), aqueous citric acid (10 mL, 10%) and water (2×10 mL), dried (magnesium sulphate) and concentrated in vacuo. The residue was purified by column chromatography (110 g, silica gel) using ethyl acetate and heptane (1:3) as eluent to give 1.2 g of 3-(tert-butyldimethylsilanyloxymethyl)-4-trifluoromethoxyphenylaniline.

$^1$H-NMR (DMSO-d$_6$): δ 0.82 (9H, s), 3.25 (6H, s), 4.52 (2H, s), 5.23 (2H, s), 6.41 (1H, d), 6.61 (1H, s), 6.86 (1H, d).

Building block 8: 4-Cyclohex-1-enylaniline

This compound was prepared similarly as described in J. v. Braun et al., *J. Liebigs Ann. Chem.*, 472 (1929), 1–89, from refluxing aniline (2 equivalents), cyclohexanone (1 equivalent) in ethanol and 37% hydrochloric acid for 4–5 days, followed by addition of ethyl acetate, water, and sodium hydroxide, neutralisation with 85% phosphoric acid, phase separation, and distillation of the organic phase. The residue was added a catalytic amount of sulfuric acid and distilled (180° C., 5–7 mbar). The distillate was redistilled (120° C., 3 mbar) to afford (in the residue) the desired 4-cyclohex-1-enylaniline.
$^1$H NMR (DMSO-d$_6$): δ1.50–1.60 (m, 2H), 1.60–1.70 (m, 2H), 2.10–2.15 (m, 2H), 2.20–2.30 (brd s, 2H), 5.00 (s, 2H), 5.90 (t, 1H), 6.50 (d, 2H), 7.10 (d, 2H).

Building block 9: 4-Cyclohexylaniline

This compound is commercially available (e.g. from Lancaster or Avocado).

Building block 10: 4-Cyclohexylcyclohexylamine

The preparation of this compound is described in the literature, see H. Booth et al., J. Chem. Soc. (B), 1971, 1047–1050.

Building block 11: 4-(2-Methylcyclohex-1-enyl) aniline and (R,S)-4-(6-methylcyclohex-1-enyl) aniline

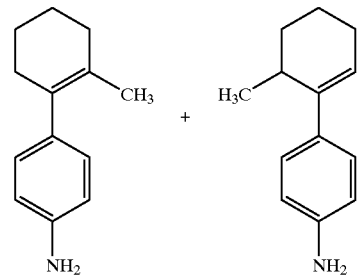

A mixture of 2-methyl-cyclohexanone (112 g, 1,0 mol), aniline (186 g, 2 mol) and ethanol (26 mL) was stirred at room temperature and 12 M hydrochloric acid (167 mL) was added during 30 min. The dark yellow solution was refluxed at 85° C. for seven days. The solution was cooled and diluted with ethyl acetate. The mixture was stirred in an ice bath and made alkaline (pH=9) with a 27% sodium hydroxide solution, keeping the temperature below 30° C.

The organic layer was separated and washed with brine (3 x), dried over magnesium sulphate, and concentrated to give a brown oil (131 g). Excess of aniline was removed under reduced pressure. A catalytic amount of 12 M hydrochloric acid (1 mL) was added, and the residue was fractionated under high vacuum. The fraction distilling at 145–175° C. (0,2 mmHg) was collected and subjected to column chromatography (silica gel) and eluated with 30% ethyl acetate/toluene to afford a 9:1 mixture (8.7 g) of 4-(2-methylcyclohex-1-enyl)aniline and (R, S)-4-(6-methylcyclohex-1-enyl)aniline, respectively.

4-(2-Methylcyclohex-1-enyl)aniline:

$^1$H NMR (DMSO-$d_6$): δ1.53 (s, 3H), 1.61 (m, 4H), 2.00 (bs, 2H), 2.13 (bs, 2H), 4.92 (s, 2H), 6.50 (d, 2H), 6.79 (d, 2H); HPLC-MS (Method B): m/z=188 (M+); $R_t$=2.96 min.

(R,S)-4-(6-Methylcyclohex-1-enyl)aniline:

$^1$H NMR (DMSO-$d_6$): δ0.88 (d, 3H), 1.61 (m, 4H), 2.00 (bs, 2H), 2.13 (bs, 2H), 2.74 (m, 1H), 4,92 (s, 2H), 5.68 (t, 1H), 6.50 (d, 2H), 6.79 (d, 2H).

Building block 12: 4-(4-tert-Butylcyclohex-1-enyl)aniline

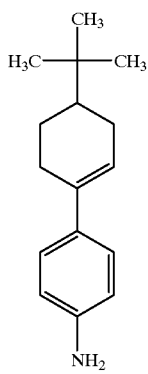

4-(4-tert-Butylcyclohex-1-enyl)aniline was prepared in analogy to procedure for preparation of building block 11 using 4-tert-butylcyclohexanone (0.59 mol) and aniline.

$^1$H NMR (DMSO-$d_6$): δ0.88 (s, 9H), 1..21 (m, 2H), 1.90 (m, 2H), 2.10–2.50 (m, 3H), 4.97 (s, 2H), 5.90 (m, 1H), 6.50 (d, 2H), 7.06 (d, 2H); HPLC-MS (Method B): m/z=230 (M+); $R_t$=4.07 min.

Building block 13: (R,S)-4-(5-Methylcyclohex-1-enyl)aniline and (R,S)-4-(3-methylcyclohex-1-enyl)aniline

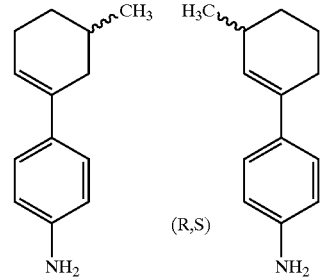

A mixture of (R,S)-3-methylcyclohexanone (123 mL, 1.0 mol), aniline (182 mL, 2.0 mol), 12 M hydrochloric acid (167 mL, 2.0 mol), and ethanol (26 mL) was refluxed at 90° C. for ten days. The solution was cooled and diluted with ethyl acetate. The aqueous layer was made alkaline (pH=10) with a 6 M sodium hydroxide solution. The organic layer was separated and washed with brine (3 x), dried over magnesium sulphate, and concentrated to give a brown oil. Excess of aniline was removed under reduced pressure. A catalytic amount of 12 M hydrochloric acid (1 mL) was added, and the residue was fractionated under high vacuum. The fraction distilling at 123–128° C. (0.15–0.20 mmHg) was collected to afford 21.0 g of an oil. $^1$H-NMR showed presence of a 3:2 mixture of (R,S)-4-(5-methylcyclohex-1-enyl)aniline and (R,S)-4-(3-methylcyclohex-1-enyl)aniline, respectively.

(R,S)-4-(5-Methylcyclohex-1-enyl)aniline:
$^1$H NMR (DMSO-$d_6$): δ1.00 (d, 3H), 1.45–1.95 (m, 3H), 2.10–2.45 (m, 3H), 5.04 (s, 2H), 5.86 (t, 1H), 6.48 (d, 2H), 7.06 (d, 2H).

(R,S)-4-(3-Methylcyclohex-1-enyl)aniline:
$^1$H NMR (DMSO-$d_6$): δ 1.00 (d, 3H), 1.45–1.95 (m, 3H), 2.10–2.45 (m, 3H), 5.04 (s, 2H), 5.75 (d, 1H), 6.48 (d, 2H), 7.06 (d, 2H).

General procedure (A) for Solution Phase Synthesis of Compounds of the General Formulae (Ia) and (Ib):

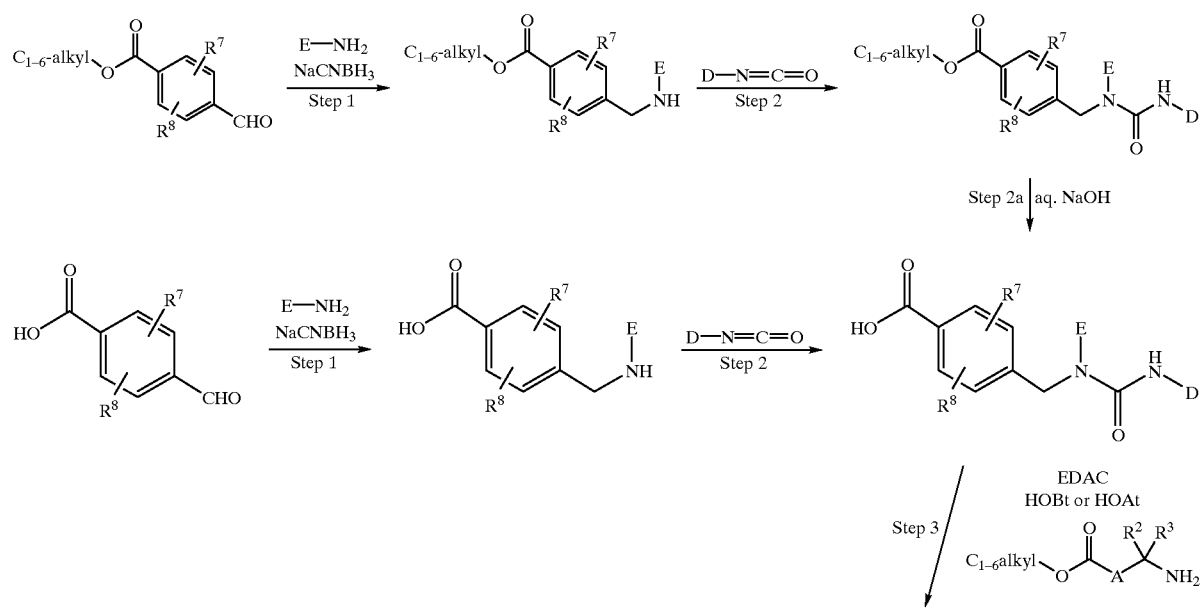

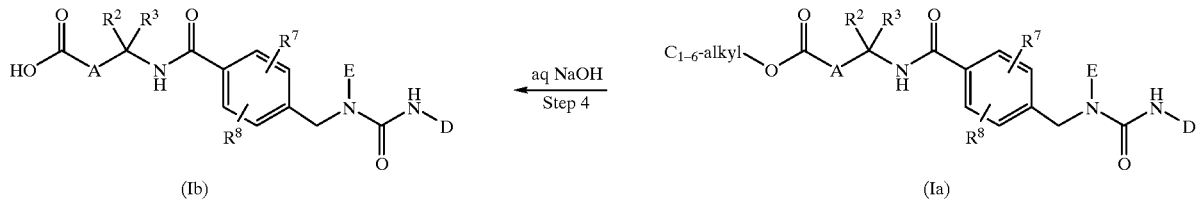

(Ib) ⇌ aq NaOH Step 4 ⇌ (Ia)

wherein $R^2$, $R^3$, $R^7$, $R^8$, A, E and D are as defined for formula (I).

Compounds made according to this general procedure (A) can either be prepared via the ester route or the carboxylic acid route. The only difference between these two routes is the protection of the benzoic acid as an ester. The deprotection of the ester (step 2a) provides intermediates identical with those of the carboxylic acid route.

This procedure according to the ester route is illustrated in examples 1 and 2 and according to the carboxylic acid route in example 3.

Example 1

(General Procedure (A)

(R)-3-{4-[1-(4-Cyclohexylphenyl)-3-(3-methoxy-5-trifluoromethylphenyl)ureidomethyl]benzoylamino}-2-hydroxypropionic Acid

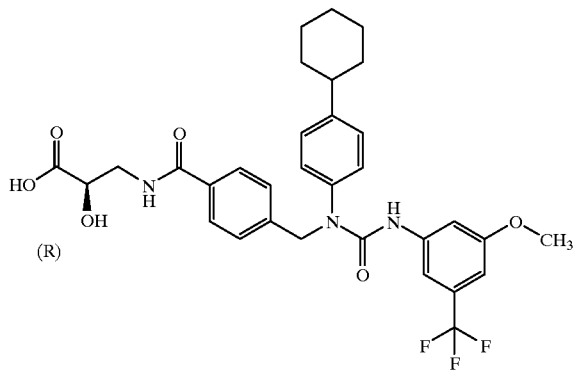

Step 1: 4-((4-Cyclohexylphenylamino)methyl) benzoic Acid Methyl Ester

4-Formylbenzoic acid methyl ester (6.65 g, 40.5 mmol) was dissolved in hot methanol (175 mL). To this mixture, 4-cyclohexylaniline (7.1 g, 40.5 mmol) was added. To the resulting suspension, more methanol (75 mL) was added and the mixture was heated at reflux for 1 hour. After cooling to 0° C., the mixture was filtered and the solid was washed with ice-cold methanol and dried in vacuo at 40° C. for 16 hours to afford 10.95 g of 4-[(4-cyclohexylphenylimino)-methyl] benzoic acid methyl ester. This compound (10.93 g, 34 mmol) was suspended in methanol (200 mL) and glacial acetic acid (27 mL) was added followed by sodium cyano borohydride (1.9 g, 30 mmol) in small portions. The mixture was stirred at room temperature for 1 hour and concentrated in vacuo. The residue was dissolved in DCM (200 mL) and washed with 5% aqueous sodium carbonate (5×80 mL), dried (magnesium sulphate) and concentrated in vacuo. The residue was added ethyl acetate (100 mL) and n-heptane (200 mL) and concentrated in vacuo to half the original volume. The solid was filtered, washed with n-heptane and dried in vacuo at 40° C. for 16 hours to afford 9.52 g (87%) of 4-((4-cyclo-hexylphenylamino)methyl)benzoic acid methyl ester.
$^1$H-NMR (DMSO-$d_6$): δ 1.2–1.4 (5H, m), 1.65 (5H, m), 2.30 (1H, t), 3.84 (3H, s), 4.30 (2H, d), 6.18 (1H, t), 6.50 (2H, d), 6.87 (2H, d), 7.49 (2H, d), 7.92 (2H, d); HPLC-MS (Method B): m/z=324 (M+1); $R_t$=7.18 min.

Step 2: 4-[1-(Cyclohexylphenyl)-3-(3-methoxy-5-trifluoromethylphenyl)ureidomethyl]benzoic Acid Methyl Ester 5-Methoxy-3-(trifluoromethyl)aniline (2.0 g, 10.5 mmol) was dissolved in ethyl acetate (10 mL), and dry HCl in ethyl acetate (15 mL) was added and the solvent was removed in vacuo.

The solid was co-evaporated with toluene (3×15 mL). Toluene (75 mL) and diphosgene (13 mL) were added and the reaction mixture was refluxed under a nitrogen atmosphere for 2.5 hours. Excess diphosgene was removed in vacuo and the clear oil was co-evaporated with toluene. The obtained isocyanate was used without further purification.

The above isocyanate was dissolved in DCM (75 mL) and 4-((4-cyclohexylphenylamino)-methyl)benzoic acid methyl ester (2.3 g, 7.1 mmol) was added. The reaction mixture was stirred overnight at room temperature, the solvent was removed in vacuo and the residual oil was purified by column chromatography on silica gel, eluting with a mixture of heptane and ethyl acetate (7:3). This afforded 3 g of 4-[1-(cyclohexylphenyl)-3-(3-methoxy-5-trifluoromethylphenyl)ureidomethyl]benzoic acid methyl ester as an oil.
$^1$H-NMR (DMSO-$d_6$): δ 1.22 (broad, 1H), 1.37 (broad, 4H), 1.7 (broad, 1H), 1.79 (broad, 4H), 3.77 (s, 3H), 3.83 (s, 3H), 4.98 (s, 2H), 6.81 (s, 1H), 7.18 (d, 2H), 7.23 (d, 2H), 7.42 (m, 3H), 7.51 (s, 1H), 7.90 (d, 2H), 8.53 (s, 1H), 10.01 (s, 1H); HPLC-MS (Method A): m/z=541 (M+1); $R_t$=8.98 min.

Step 2a: 4-[1-(Cyclohexylphenyl)-3-(3-methoxy-5-trifluoromethylphenyl)ureidomethyl]benzoic acid 4-[1-(Cyclohexylphenyl)-3-(3-methoxy-5-trifluoromethylphenyl)ureidomethyl]benzoic acid methyl ester (3.0 g) was dissolved in absolute ethanol (50 mL), sodium hydroxide (4 N, 15 mL) was added and the reaction mixture was stirred at room temperature for 16 hours. The organic solvent was removed in vacuo, and additional water (50 mL) was added, pH was adjusted with hydrochloric acid (4 N) to acidic reaction and then ethyl acetate (200 mL) was added. The organic phase was washed with water (5×50 mL), dried (magnesium sulphate), filtered and evaporated in vacuo. The residue was recrystallised from acetonitrile (25 mL) to afford 4-[1-(cyclohexylphenyl)-3-(3-methoxy-5-trifluoromethylphenyl)ureidomethyl]benzoic acid (1.83 g) as crystals.

¹H-NMR (DMSO-d₆): δ 1.22 (m, 1H), 1.37 (m, 4H), 1.70 (m, 1H), 1.79 (m, 4H), 3.77 (s, 3H), 4.95 (s, 2H), 6.81 (s, 1H), 7.18 (d, 2H), 7.23 (d, 2H), 7.40 (d, 2H), 7.42 (s, 1H), 7.51 (s, 1H), 7.89 (d, 2H), 8.55 (s, 1H), 12.90 (s, 1H); HPLC-MS (Method A): m/z=527 (M+1); R_t=8.23 min; M.p. 148–150° C.

Microanalysis: Calculated for C₂₉H₂₉N₂F₃O₄:
C, 66.15%; H 5.55%; N 5.32%. Found:
C, 66.65%; H 5.70%; N 5.33%.

Step 3: (R)-3-{4-[1-(4-Cyclohexylphenyl)-3-(3-methoxy-5-trifluoromethylphenyl)ureidomethyl]-benzoylamino}-2-hydroxypropionic acid ethyl ester 4-[1-(Cyclohexylphenyl)-3-(3-methoxy-5-trifluoromethylphenyl)ureidomethyl]benzoic acid (420 mg, 0.8 mmol) was dissolved in DMF (10 mL), and then HOBt (160 mg, 1.2 mmol) and EDAC (230 mg, 1.2 mmol) were added. The reaction mixture was allowed to stand for 30 min, then (R)-isoserine ethyl ester (260 mg, 1.2 mmol) and diisopropylethylamine (210 mL, 1.2 mmol) dissolved in DMF (5 mL) were added and the reaction mixture was stirred at room temperature for 16 hours. Water (50 mL) and ethyl acetate (100 mL) were added and the organic phase was washed with water (5×50 mL), dried (magnesium sulphate), filtered and evaporated in vacuo. The residue was purified by column chromatography on silica gel, eluting with a mixture of heptane and ethyl acetate (1:3) to afford 510 mg of (R)-3-{4-[1-(4-cyclohexylphenyl)-3-(3-methoxy-5-trifluoromethylphenyl)ureidomethyl]benzoylamino)}-2-hydroxypropionic acid ethyl ester as an amorphous solid.

¹H-NMR (DMSO-d₆): δ 1.12 (t, 3H), 1.22 (m, 1H), 1.37 (m, 4H), 1.70 (m, 1H), 1.79 (broad, 4H), 3.41 (m, 1H), 3.52 (m, 1H), 3.77 (s, 3H), 4.06 (q, 2H), 4.21 (q, 1H), 4.95 (s, 2H), 5.68 (d, 1H), 6.81 (s, 1H), 7.18 (d, 2H), 7.23 (d, 2H), 7.33 (d, 2H), 7.42 (s, 1H), 7.51 (s, 1H), 7.77 (d, 2H), 8.47 (t, 1H), 8.53 (s, 1H); HPLC-MS (Method A): m/z=658 (M+1); R_t=8.17 min.

Step 4

(R)-3-{4-[1-(4-Cyclohexylphenyl)-3-(3-methoxy-5-trifluoromethylphenyl)ureidomethyl]benzoyl-amino}-2-hydroxypropionic acid ethyl ester was dissolved in ethanol (15 mL) and sodium hydroxide (2 N, 2 mL) was added. The reaction mixture was stirred at room temperature for 60 min. Then ethanol was removed in vacuo, water (50 mL) was added and pH was adjusted with 4 N hydrochloric acid to acidic reaction. Filtration and washing with water (5×5 mL) and drying in vacuo afforded 460 mg of the title compound as a crystalline solid.

¹H-NMR (DMSO-d₆): δ 1.22 (m, 1H), 1.37 (m, 4H), 1.70 (m, 1H), 1.79 (broad, 4H), 3.37 (m, 1H), 3.51 (m, 1H), 3.77 (s, 3H), 4.09 (t, 1H), 4.95 (s, 2H), 6.80 (s, 1H), 7.18 (d, 2H), 7.23 (d, 2H), 7.33 (d, 2H), 7.42 (s, 1H), 7.51 (s, 1H), 7.77 (d, 2H), 8.47 (t, 1H), 8.53 (s, 1H); HPLC-MS (Method A): m/z=614 (M+1); R_t=7.67 min.

Microanalysis: Calculated for C₃₂H₃₄N₃F₃O₆ (+1.25 H₂O):
C, 60.42%; H, 5.78%; N, 6.61%. Found:
C, 60.25%; H, 5.55%; N, 6.50%.

Example 2

General Procedure (A)

(R)-3-{4-[3-(3,5-Bis(trifluoromethyl)phenyl)-1-(4-cyclohexylphenyl)ureidomethyl]benzoyl-amino}-2-hydroxypropionic acid

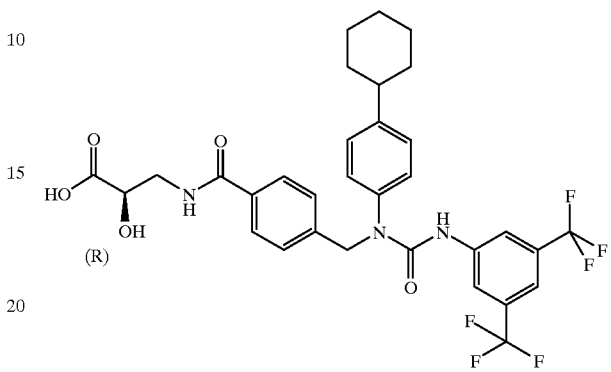

Step 2: 4-[3-(3,5-Bis(trifluoromethyl)phenyl)-1-(4-cyclohexylphenyl)ureidomethyl]benzoic Acid Methyl Ester 4-((4-Cyclohexylphenylamino)methyl)benzoic acid methyl ester (2.38 g, 7.36 mmol) was dissolved in DCM (150 mL) and 3,5-bis(trifluoromethyl)phenyl isocyanate (1.36 mL, 8.10 mmol) was added and the mixture was stirred at room temperature for 16 hours. The reaction mixture was washed with water (3×15 mL), dried (magnesium sulphate) and concentrated in vacuo to afford 4.3 g of 4-[3-(3,5-bis(trifluoromethyl)phenyl)-1-(4-cyclohexylphenyl)ureidomethyl]benzoic acid methyl ester.

¹H-NMR (DMSO-d₆): δ 1.17–1.44 (m, 5H), 1.66–1.82 (m, 5H), 3.83 (s, 3H), 4.98 (s, 2H, 7.20-7.28 (m, 4H), 7.44 (d, 2H), 7.62 (s, 1H), 7.93 (d, 2H), 8.24 (s, 2H), 8.94 (s, 1H); HPLC-MS (Method A): m/z=579 (M+1); R_t=9.50 min.

Step 2a: 4-[3-(3,5-Bis(trifluoromethyl)phenyl)-1-(4-cyclohexyyphenyl)ureidomethyl]benzoic Acid 4-[3-(3,5-Bis(trifluoromethyl)phenyl)-1-(4-cyclohexylphenyl)ureidomethyl]benzoic acid methyl ester (4.2 g, 7.36 mmol) was suspended in ethanol (80 mL) and added sodium hydroxide (4 N, 11 mL) and stirred at room temperature for 16 hours. The reaction mixture was concentrated to dryness in vacuo, and the residue was added water (50 mL) and acidified with hydrochloric acid (4 N, 12 mL). The aqueous phase was extracted twice with ethyl acetate (75 mL and 25 mL) and the combined organic phases were washed with water (3×15 mL), dried (magnesium sulphate) and concentrated in vacuo to afford 4-[3-(3,5-bis(trifluoromethyl)-phenyl)-1-(4-cyclohexylphenyl)ureidomethyl]benzoic acid.

¹H-NMR (DMSO-d₆): δ 1.32–1.43 (m, 5H), 1.7 (m, 1H), 1.75–1.85 (5H), 4.98 (s, 2H), 7.20–7.28 (m, 4H), 7.4 (d, 2H), 7.61 (d, 1H), 7.88 (d, 2H), 8.25 (s, 2H), 8.93 (s, 1H), 12.90 (s, 1H); HPLC-MS (Method B): m/z=565 (M+1); R_t=8.65 min; M.p. 148.5–149.5° C.

Microanalysis: Calculated for C₂₉H₂₆F₆N₂O₃:
C, 61.70%; H, 4.64%; N, 4.96%. Found:
C, 61.54%; H, 4.71%; N, 4.92%.

Step 3: (R)-3-{4-[3-(3,5-Bis(trifluoromethyl)phenyl)-1-(4-cyclohexylphenyl)ureidomethyl]-benzoylamino}-2-hydroxyrropionic Acid Ethyl Ester 4-[3-(3,5-Bis(trifluoromethyl)phenyl)-1-(4-cyclohexylphenyl)ureidomethyl]benzoic acid (0.22 g, 0.39 mmol) was dissolved in DMF (3 mL) and 1-hydroxy-7-azabenzotriazole (0.06 g, 0.47 mmol) and EDAC (0.09 g, 1.2 mmol) were added. The mixture was stirred for 1.5 hour, and (R)-isoserine ethyl ester (0.10 g, 0.59 mmol) and diisopropylethylamine (0.10 mL, 0.59 mmol) in DMF (2 mL) were added. The mixture was stirred at room temperature for 16 hours. The reaction mixture was diluted with water (10 mL) and extracted with ethyl acetate (25 mL). The aqueous phase was extracted with ethyl acetate (10 mL). The combined organic phases were washed with hydrochloric acid (0.2 N, 3×10 mL) and water:saturated sodium chloride (1:1), dried (magnesium sulphate) and concentrated in vacuo. The residue was purified by column chromatography (35 g silica gel) using ethyl acetate and n-heptane (6:4) as eluent to afford 0.27 g of (R)-3-{4-[3-(3,5-bis(trifluoromethyl)phenyl)-1-(4-cyclohexylphenyl)ureidomethyl]benzoylamino}-2-hydroxypropionic acid ethyl ester.

$^1$H-NMR (DMSO-d$_6$): δ 1.14 (t, 3H), 1.19–1.42 (m, 5H), 1.67–1.85 (m, 5H), 3.38–3.48 (m, 1H), 3.49–3.57 (m, 1H), 4.08 (q, 2H), 4.20 (m, 1H), 4.97 (s, 2H), 5.67 (d, 1H), 7.20–7.27 (m, 4H), 7.36 (d, 2H), 7.62 (s, 1H), 7.75 (d, 2H), 8.24 (s, 2H), 8.48 (t, 1H), 8.90 (s, 1H); HPLC-MS (Method A): m/z=680 (M+1); R$_t$=8.42 min.

Step 4

(R)-3-{4-[3-(3,5-Bis(trifluoromethyl)phenyl)-1-(4-cyclohexylphenyl)ureidomethyl] benzoyl-amino}-2-hydroxypropionic acid ethyl ester (0.26 g, 0.38 mmol) was dissolved in ethanol (96%, 15 mL) and added sodium hydroxide (4 N, 0.57 mL, 2.3 mmol). After stirring at 25 OC for 1 hour the mixture was evaporated in vacuo, and the residue was added water (30 mL) and acidified with hydrochloric acid (4 N, 0.62 mL). The aqueous phase was extracted twice with ethyl acetate (25 mL and 10 mL) and the combined organic phases were washed with saturated sodium chloride:water (1:1), dried (magnesium sulphate) and concentrated in vacuo to afford 0.21 g of the title compound.

$^1$H-NMR (DMSO-d$_6$): δ 1.21–1.45 (m, 5H), 1.66–1.86 (m, 5H), 3.37–3.44 (m, 1H), 3.53–3.60 (m, 1H), 4.18 (t, 1H), 4.95 (s, 2H), 7.18–7.27 (m, 4H), 7.45 (d, 2H), 7.60 (s, 1H), 7.78 (d, 2H), 8.24 (s, 2H), 8.44 (t, 1H), 8.90 (s, 1H); HPLC-MS (Method B): m/z=652 (M+1); R$_t$=7.93 min.

Example 3

General Procedure (A)

(R)-3{-4-[3-(3-Bromophenyl)-1-(4-cyclohexylphenyl)ureidomethyl]benzoylamino}-2-hydroxypropionic acid

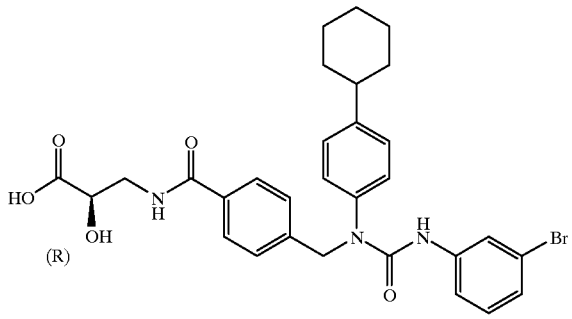

Step 1: 4-[(4-Cyclohexylphenylamino)methyl]benzoic acid

4-Cyclohexylaniline (8.0 g, 53 mmol) was dissolved in methanol (200 mL) and a suspension of 4-formylbenzoic acid (9.4 g, 53 mmol) in glacial acetic acid (12 mL) was added in portions and the resulting mixture was heated at reflux temperature for 1.5 hour. After cooling to room temperature a mixture of sodium cyano borohydride (5.0 g, 80 mmol) in methanol (100 mL) was added in portions, and the resulting mixture was stirred at room temperature for 16 hours. The mixture was filtered and washed thoroughly with water and dried in vacuo at 50° C. for 3 days to afford 12.8 g (78%) of 4-[(4-cyclohexylphenylamino)methyl]benzoic acid.

$^1$H-NMR (DMSO-d6): δ 1.1–1.35 (5H, m), 1.65–1.75 (5H, m), 2.29 (1H, m), 4.31 (2H, s), 6.15 (1H, bs), 6.45 (2H, d), 6.89 (2H, d), 7.46 (2H, d), 7.88 (2H, d).

Step 2: 4-[3-(3-Bromophenyl)-1-(4-cyclohexylphenyl)ureidomethyl]benzoic Acid

3-Bromoaniline (1.4 g, 8.1 mmol) was dissolved in diethyl ether (50 mL) and 3.5 M dry HCl in ethyl acetate (2.3 mL) was added. The mixture was concentrated in vacuo. The residue was added toluene (100 mL) and concentrated in vacuo. The residue was added toluene (100 mL) and diphosgene (8.1 g, 41 mmol) and the resulting mixture was refluxed for 1.5 hour. After cooling, the mixture was concentrated in vacuo. The residue was dissolved in toluene (100 mL) and concentrated in vacuo. The residue was dissolved in DMF (30 mL) and 4-[(4-cyclohexylphenylamino)methyl]benzoic acid (1.3 g, 4.1 mmol) was added. The mixture was stirred at room temperature for 16 hours. The mixture was added ethyl acetate (150 mL) and washed with water:brine (1:1) (2×100 mL). The organic phase was dried with sodium sulphate and concentrated in vacuo. The residue was purified by column chromatography on silica gel eluting first with a mixture of ethyl acetate:n-heptane:triethylamine (7:2:1), then with ethyl acetate and finally with methanol to afford 1.95 g (94%) of 4-[3-(3-bromophenyl)-1-(4-cyclohexylphenyl)ureidomethyl]benzoic acid.

$^1$H-NMR (CDCl$_3$): δ 1.2–1.4 (5H, m), 1.7–1.8 (5H, m), 4.94 (2H, s), 7.1–7.25 (6H, m), 7.30 (2H, d), 7.44 (1H, d), 7.78 (1H, t), 7.83 (2H, d), 8.38 (1H, s); HPLC-MS (Method B): m/z=507 (M+1); R$_t$=5.52 min.

Step 3: (R)-3-{4-[3-(3-Bromophenyl)-1-(4-cyclohexylphenyl)ureidomethyl]benzoylamino}-2-hydroxypropionic Acid Ethyl Ester 4-[3-(3-Bromophenyl)-1-(4-cyclohexylphenyl) ureidomethyl]benzoic acid (0.20 g, 0.39 mmol) was dissolved in DMF (2.5 mL) and EDAC (0.12 g, 0.6 mmol) and HOBt (0.089 mg, 0.6 mmol) were added and the mixture was stirred at room temperature for 10 min. (R)-isoserine ethyl ester hydrochloride (0.10 g, 0.6 mmol) and N,N-diisopropylethylamine (130 μL) dissolved in DMF (2.5 mL) were added and the resulting mixture was stirred at room temperature for 16 hours. The mixture was added ethyl acetate (70 mL) and washed with water (2×100 mL), the organic phase was dried with sodium sulphate and concentrated in vacuo. The residue was purified by column chromatography on silica gel eluting with a mixture of ethyl acetate:n-heptane (1:2) containing 10% acetic acid. This afforded 100 mg of (R)-3-{4-[3-(3-bromophenyl)-1-(4-cyclohexylphenyl)ureidomethyl]benzoylamino}-2-hydroxypropionic acid ethyl ester.

HPLC-MS (Method B): m/z=624 (M+1); $R_t$=5.33 min.

Step 4: (R)-3-[4-[3-(3-Bromophenyl)-1-(4-cyclohexylphenyl)ureidomethy]benzoylamino]-2-hydroxypropionic Acid (R)-3-{4-[3-(3-Bromophenyl)-1-(4-cyclohexylphenyl) ureidomethyl]benzoylamino}-2-hydroxypropionic acid ethyl ester (100 mg) was dissolved in ethanol (10 mL), 1 N sodium hydroxide (480 μL) was added and the resulting mixture was stirred at room temperature for 1 hour. 1 N Hydrochloric acid (480 μL) was added and the mixture was concentrated in vacuo. The residue was suspended in water (50 mL) and filtered to afford 38 mg of the title compound.
$^1$H-NMR (CDCl$_3$): δ 1.2–1.4 (5H, m), 1.7–1.85 (5H, m). 2.45 (1H, s), 3.7 (2H, m), 4.30 (1H, m), 4.78 (2H, s), 6.23 (1H, s), 6.95–7.3 (8H, m), 7.42 (1H, s), 7.60 (2H, d); HPLC-MS (Method A): m/z=595 (M+1); $R_t$=7.48 min.

Example 4

General Procedure (A)

(R)-3{-4-[1-(4-Cyclohexylphenyl)-3-(4-trifluoromethoxyphenyl)ureidomethyl] benzoylamino}-2-hydroxypropionic Acid

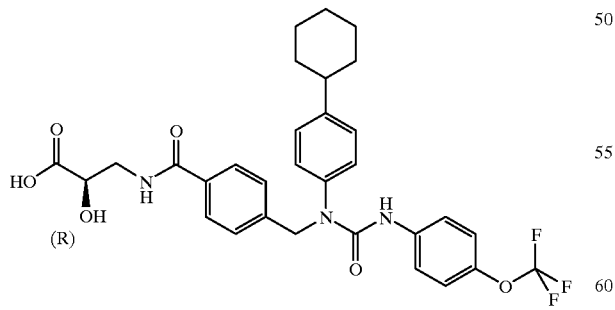

$^1$H-NMR (DMSO-d$_6$): δ 1.2–1.4 (5H, m), 1.7–1.8 (5H, m), 3.40 (1H, m), 3.56 (1H, dt), 4.18 (1H, t), 4.97 (2H, s), 5.5 (1H, brd) 7.14–7.25, (6H, m), 7.34 (2H, d), 7.55 (2H, d), 7.79 (2H, d), 8.38 (1H, s), 8.44 (1H, t); HPLC-MS (Method A): m/z=600 (M+1); $R_t$=7.38 min.

Example 5

General Procedure (A)

(R)-3-{4-[1-(4-Cyclohexylphenyl)-3-(3-trifluoromethylphenyl)ureidomethyl]benzoylamino}-2-hydroxypropionic Acid

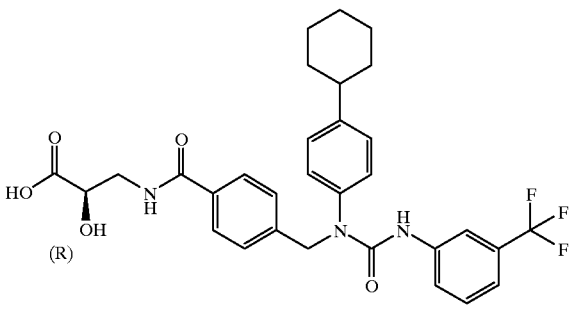

$^1$H-NMR (400 MHz, DMSO-d$_6$): δ 1.15–1.45 (m, 5H), 1.60–1.90 (m, 5H), 4.95 (s, 2H), 7.12 (d, 2H), 7.19 (d, 2H), 7.24 (d, 1H), 7.45 (t, 1H), 7.72 (d, 2H), 7.75 (s br, 1H), 7.90 (s, 1H), 8.55 (s, 1H), 8.58 (s br, 1H); HPLC-MS (Method B): m/z=584 (M+1); $R_t$=4.99 min.

Example 6

General Procedure (A)

(R)-3-{4-[1-(4-Cyclohexylphenyl)-3-(3-fluoro-5-trifluoromethylphenyl)ureidomethyl]benzoylamino}-2-hydroxypropionic acid

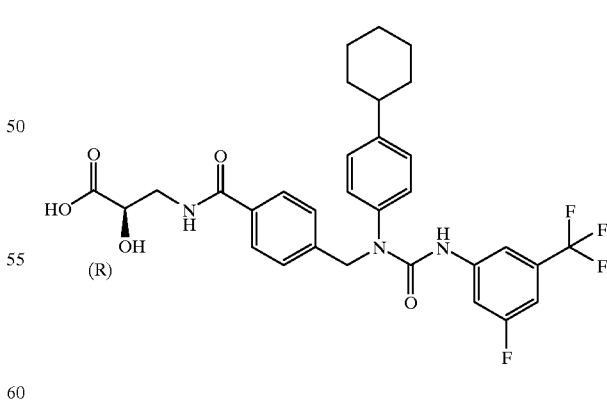

$^1$H-NMR (200 MHz, DMSO-d$_6$): δ 1.15–1.45 (m, 5H), 1.60–1.85 (m, 5H), 3.25–3.65 (m, 3H), 4.13 (t, 1H), 4.95 (s, 2H), 7.10–7.22 (m, 5H), 7.30 (d, 2H), 7.75 (m, 3H), 8.45 (t, 1H), 8.78 (s, 1H); HPLC-MS (Method A): m/z=602 (M+1); $R_t$=7.83 min.

Example 7

General Procedure (A)

(R)-3-{4[-3-(3-Cyano-5-trifluoromethylphenyl)-1-(4-cyclohex-1-enylphenyl)ureidomethyl]-benzoylamino}-2-hydroxypropionic Acid

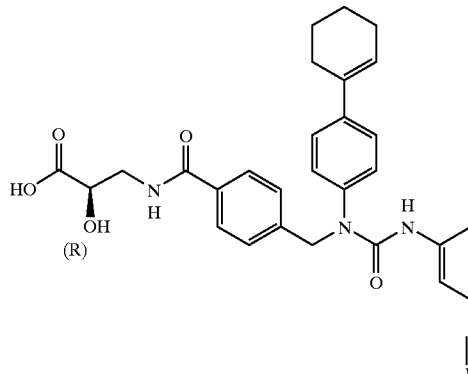

$^1$H-NMR (200 MHz, DMSO-d$_6$): S1.15–1.70 (m, 4H), 2.12 (s, 2H), 2.35 (s, 2H), 5.00 (s, 2H), 6.15 (s, 1H), 7.10–7.40 (m, 6H), 7.78 (m, 3H), 8.20 (d, 2H), 8.90 (s, 1H); HPLC-MS (Method A): m/z=607 (M+1); R$_t$=7.42 min.

Example 8

General Procedure (A)

(R)-3{-4-[3-(3-Cyano-5-trifluoromethylphenyl)-1-(4-cyclohexylphenyl)ureidomethyl]benzoyl-amino}-2-hydroxypropionic Acid

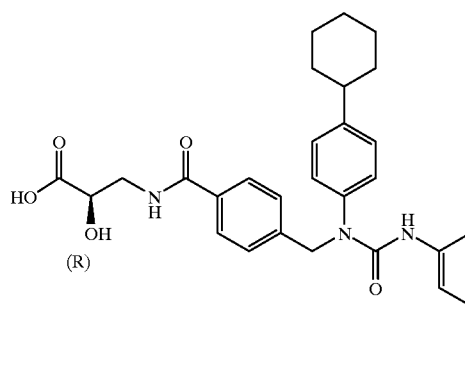

$^1$H-NMR (400 MHz, DMSO-d$_6$): δ 1.15–1.45 (m, 5H), 1.60–1.85 (m, 5), 3.45–3.60 (m, 3H), 4.15 (t, 1H) 4.95 (s, 2H), 7.20 (dd, 4H), 7.35 (d, 2H), 7.76 (d, 2H), 7.88 (s, 1H), 8.18 (s, 1H), 8.21 (s, 1H), 8.45 (t, 1H), 8.95 (s, 1H); HPLC-MS (Method A): m/z=609 (M+1); R$_t$=7.58 min.

Example 9

General Procedure (A)

(R)-3{-4-[3-(3-Bromo-5-trifluoromethylphenyl)-1-(4-cyclohex-1-enylphenyl)ureidomethyl]-benzoylamino}-2-hydroxypropionic acid

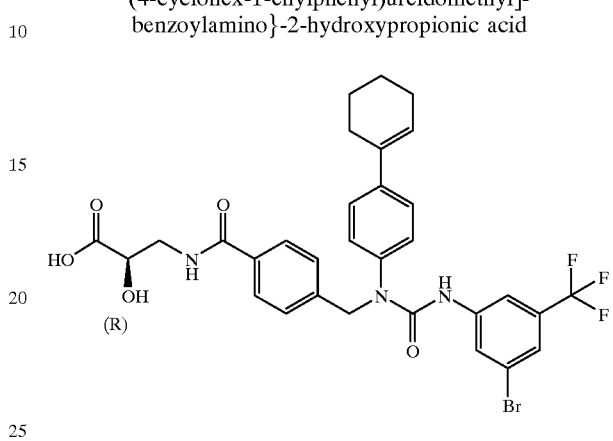

$^1$H-NMR (DMSO-d$_6$): δ 1.50–1.76 (m, 4H), 2.15 (m, 2H), 2.33 (m, 2H), 3.37 (m, 2H), 3.54 (m, 1H), 4.14 (dd, 1H), 4.95 (s, 2H), 6.17 (t, 1H), 7.17 (d, 2H), 7.33 (d, 2H), 7.40 (d, 2H), 7.46 (s, 1H), 7.75 (d, 2H), 7.91 (s, 1H), 8.07 (s, 1H), 8.44 (t, 1H), 8.66 (s, 1H).

Example 10

General Procedure (A)

(R)-3-[4-[1-(4-Cyclohex-1-enylphenyl)-3-(3-methoxy-5-trifluoromethylphenyl)ureidomethyl]-benzoylamino]-2-hydroxypropionic Acid

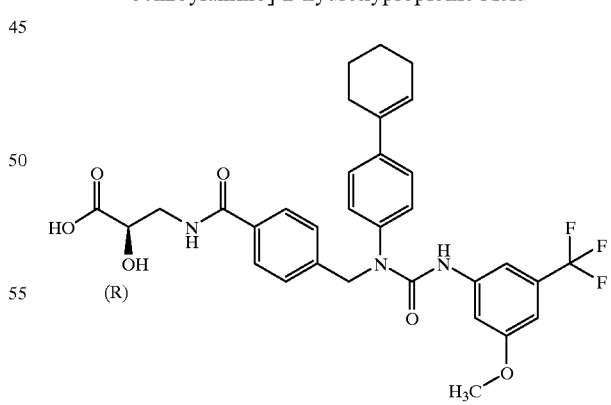

$^1$H-NMR (DMSO-d$_6$): δ 1.51–1.76 (m, 4H), 2.15 (m, 2H), 2.34 (m, 2H), 3.37 (m, 2H), 3.54 (m, 1H), 3.75 (s, 3H), 4.14 (dd, 1H), 4.95 (s, 2H), 6.16 (t, 3H), 6.78 (s, 1H), 7.16 (d, 2H), 7.32 (d, 2H), 7.38 (d, 2H), 7.43 (s, 1H), 7.76 (d, 2H), 8.44 (t, 1H), 8.51 (s, 1H).

Example 11

(General Procedure (A))

(R)-3-[4-[3-(3-Bromophenyl)-1-(4-cyclohex-1-enylphenyl)ureidomethyl]benzoylamino]-2-hydroxypropionic Acid

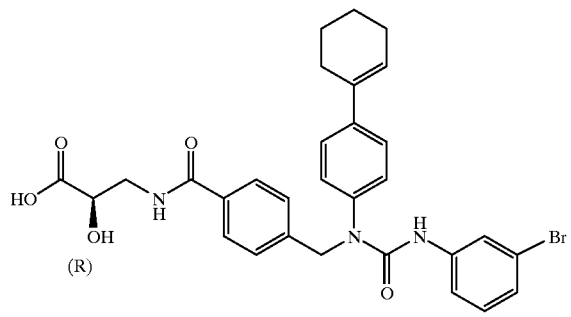

The title compound was prepared according to general procedure (A) modifying step 2 as follows:

Step 2: 4-[3-(3-Bromophenyl)-1-(4-cyclohex-1-enylphenyl)ureidomethyl]benzoic Acid Methyl Ester To 3-bromobenzoic acid (1.2 g, 5.7 mmol) in toluene (20 mL) was added triethylamine (0.91 mL, 6.5 mmol) and diphenoxyphosphoryl azide (1.3 mL, 6.2 mmol) and the mixture was heated to 100° C. while stirring. After 1 hour 4-[(4-cyclohex-1-enylphenylamino)methyl]-benzoic acid methyl ester (prepared similarly as described in example 1, step 1) (1.6 g, 5 mmol) was added and heating was continued for additional 1.5 hour. After cooling to room temperature the mixture was transferred with ethyl acetate (50 mL) to a separatory funnel. The organic mixture was washed with saturated aqueous sodium hydrogen carbonate (2×50 mL), backwash with ethyl acetate (50 mL). The organic phases were collected, dried (sodium sulphate) and the solvent removed in vacuo to yield a brown oil that was purified on silica column eluted with DCM to afford 700 mg of 4-[3-(3-bromophenyl)-1-(4-cyclohex-1-enylphenyl)ureidomethyl]benzoic acid methyl ester.

HPLC-MS (Method B): m/z=521 (M+1); $R_t$=6.1 min.

Data for the Title Compound $^1$H-NMR (CDCl$_3$): δ 1.54 (s, 2H), 1.65 (s, 2H), 2.15 (s, 2H), 2.36 (s, 2H), 3.56 (br s, 2H), 4.19 (br s, 1H), 4.71 (s, 2H), 6.09 (s, 1H), 6.42 (s, 1H), 6.90–7.18 (m, 6H), 7.30.7.70 (m, 6H); HPLC-MS (Method B): m/z=592.5 (M+1); $R_t$=4.73 min.

Example 12

General Procedure (A)

(R)-3-{4-[3-(3-Bromo-5-trifluoromethylphenyl)-1-(4-cyclohexylphenyl)ureidomethyl]benzoyl-amino}-2-hydroxypropionic acid

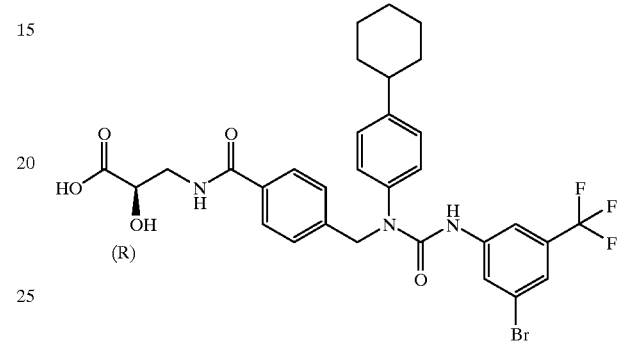

$^1$H-NMR (DMSO-d$_6$): δ 1.14–1.43 (m, 5H), 1.64–1.83 (m, 5H), 3.40–3.45 (m, 1H), 3.45–3.53 (m, 1H), 4.00 (t, 1H), 4.95 (s, 2H), 7.13–7.27 (m, 4H), 7.33 (d, 2H), 7.48 (s, 1H), 7.77 (d, 2H), 7.92 (s, 1H), 8.07 (s, 1H), 8.43 (t, 1H), 8.71 (s, 1H); HPLC-MS (Method A): m/z=662 (M+1); $R_t$=8.17 min.

Example 13

General Procedure (A)

(S)-Trans-3{-4-[3-(3,5-Bis(trifluoromethyl)phenyl)-1-(4-tert-butylcyclohexyl)ureidomethyl]-benzoylamino}-2-hydroxypropionic Acid

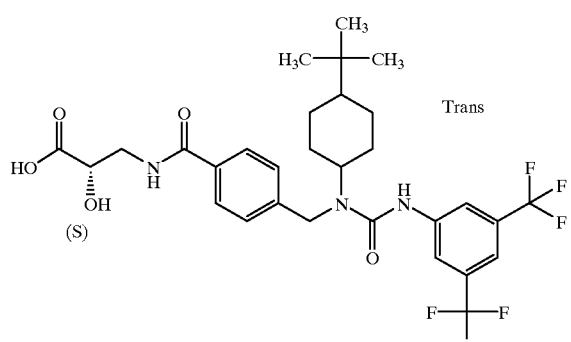

Step 1: trans-4-[(4-tert-butylcyclohexylamino)methyl]benzoic Acid Methyl Ester

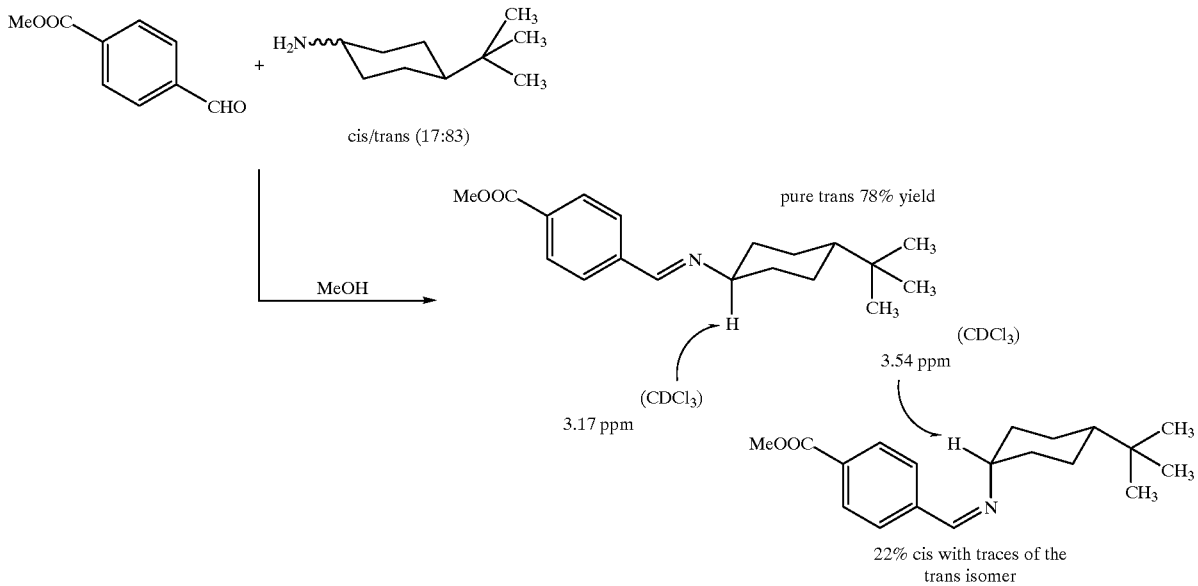

cis/trans (17:83)

pure trans 78% yield

22% cis with traces of the trans isomer

4-Formylbenzoic acid methyl ester (10.6 g, 64.4 mmol) was dissolved in methanol (200 mL). A 17:83 cis/trans mixture of 4-tert-butylcyclohexylamine (10.0 g, 64.4 mmol, Aldrich) was added, leading to immediate precipitation of white crystals. The mixture was heated to reflux for 30 min to complete imine formation, then cooled to 0° C. on an ice bath. The crystalline pure trans-4-[(4-tert-butylcyclohexylimino)methyl]benzoic acid methyl ester was then collected by filtration, and dried overnight in vacuo. Yield: 15.3 g (78%).

$^1$H NMR (CDCl$_3$), 300 MHz: δ 8.37 (s, 1H); 8.06 (d, 2H); 7.77 (d, 2H); 3.92 (s, 3H); 3.17 (m, 1H); 1.83 (m, 4H); 1.60 (m, 2H), 1.09 (m, 3H); 0.87 (s, 9H).

Microanalysis: Calculated for C$_{19}$H$_{27}$NO$_2$
C, 75.71%; H, 9.03%; N, 4.65%. Found:
C, 75.60%; H, 9.37%; N, 4.68%.

The mother liquid was taken to dryness to leave 4.2 g (22%) white solid, which according to NMR consisted mainly of the imino cis isomer.

$^1$H NMR (CDCl$_3$), 300 MHz: δ 8.36 (s, 1H); 8.07 (d, 2H); 7.81 (d, 2H); 3.92 (s, 3H); 3.54 (m, 1H); 1.55–1.92 (m, 8H); 1.14 (m, 1H); 0.90 (s, 9H).

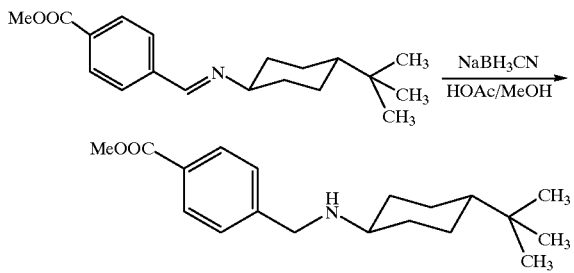

trans-4-[(4-tert-Butylcyclohexylimino)methyl]benzoic acid methyl ester (21.0 g, 69.2 mmol) was suspended in methanol (300 mL), and acetic acid (50 mL) was added. To the resulting clear solution was added sodium cyanoborohydride (3.5 g, 55.5 mmol), and the mixture was stirred at ambient temperature for 30 min. The reaction volume was then reduced to one third by rotary evaporation, and ethyl acetate (500 mL) was added. The organic phase was washed with sodium carbonate solution (5%, 500 mL), and dried with sodium sulphate. The solvent was removed by rotary evaporation to leave the title material as a white crystalline solid sufficiently pure for further reactions. Yield: 21.1 g (100%).

$^1$H NMR (CDCl$_3$), 300 MHz: δ 7.98 (d, 2H); 7.38 (d, 2H); 3.90 (s, 3H); 3.86 (s, 2H); 2.39 (m, 1H); 2.01 (m, 2H); 1.77 (m, 2H);1.51 (bs, 1H); 0.93–1.18 (m, 5H); 0.82 (s, 9H); HPLC-MS (Method B: R$_t$=4.87 m/z=304 (M+1).

Step 2: Trans-4-[1-(35-bis(trifluoromethyl)phenyl)-3-(4-tert-butylcyclohexyl)ureidomethyl]-benzoic Acid Methyl Ester Trans-4-[(4-tert-butylcyclohexylamino)methyl]benzoic acid methyl ester (1.0 g, 3.3 mmol) was dissolved in acetonitrile (40 mL), 3,5-bis(trifluoromethyl)phenylisocyanate (0.9 g, 3.6 mmol) was added and the reaction mixture was stirred at room temperature overnight. The solvent was concentrated in vacuo to 5–10 mL and the crystals were isolated by filtration to afford 1.45 g (81%) of trans-4-[1-(3,5-bis(trifluoromethyl)phenyl)-3-(4-tert-butylcyclohexyl)ureidomethyl]benzoic acid methyl ester:

$^1$H-NMR (DMSO-d$_6$): δ 9.08 (s, 1H); 8.25 (s, 2H); 7.91 (d, 2H); 7.60 (s, 1H); 7.40 (d, 2H); 4.65 (s, 2H); 4.07 (broad, 1H); 3.83 (s, 3H); 1.71 (broad, 4H); 1.42 (broad, 2H); 1.11 (broad, 2H); 0.93 (broad, 1H); HPLC-MS (Method B): m/z=559 (M+1); R$_t$=9.40 min; M.p. 188–190° C. (CH$_3$CN). Microanalysis: Calculated for C$_{28}$H$_{32}$N$_2$F$_6$O$_3$:
C, 60.21%; H, 5.77%; N, 5.02%. Found:
C, 60.46%; H, 5.94%; N, 5.00%.

Step 2a: Trans-4[-1-(3,5-bis(trifluoromethyl)phenyl)-3-(4-tert-butylcyclohexyl)ureidomethyl]-benzoic Acid Trans-4-[1-(3,5-bis(trifluoromethyl)phenyl)-3-(4-tert-butylcyclohexyl)ureidomethyl]benzoic acid methyl ester (1.4 g) was suspended in absolute ethanol (20 mL), sodium hydroxide (2N, 11 mL) was added and the reaction mixture was gently refluxed for 2 hours. The ethanol was removed in vacuo, additional water (40 mL) was added, pH was adjusted with hydrochloride (4 N) to acidic reaction and then ethyl acetate (200 mL) was added. The organic phase was isolated, washed with water (4×50 mL), dried with magnesium sulphate, filtered and evaporated in vacuo, affording 1.1 g (85%) trans-4-[1-(3,5-bis(trifluoromethyl)phenyl)-3-(4-tert-butylcyclohexyl)ureidomethyl]benzoic acid as a solid.

$^1$H-NMR (DMSO-$d_6$): δ 12.85 (s, 1H); 9.08 (s, 1H); 8.25 (s, 2H); 7.89 (d, 2H); 7.61 (s, 1H); 7.38 (d, 2H); 4.65 (s, 2H); 4.07 (m, 1H); 1.73 (m, 4H); 1.43 (m, 2H); 1.11 (m, 2H); 0.93 (m, 1H); 0.82 (s, 9H); M.p. 239–241° C (MeCN).

Microanalysis: Calculated for $C_{27}H_{30}N_2F_6O_3$:
C, 59.55%; H, 5.55%; N, 5.14%. Found:
C, 59.58%; H, 5.65%; N, 5.11%.

Following steps 3 and 4 afforded the title compound.

$^1$H-NMR (DMSO-$d_6$): δ 0.83 (s, 9H), 0.90–0.99 (m, 1H), 1.06–1.15 (m, 2H), 1.37–1.50 (m, 2H), 1.64–1.80 (m, 4H), 3.35–3.43 (m, 1H), 3.52–3.61 (m, 1H), 4.01–4.11 (m, 1H), 4.18 (t, 1H), 4.63 (s, 2H), 7.35 (d, 2H), 7.61 (s, 1H), 7.81 (d, 2H), 8.27 (s, 2H), 8.43 (t, 1H), 9.07 (s, 1H), 12.46 (broad, 1H); HPLC-MS (Method A): m/z=632 (M+1); $R_t$=8.00 min; M.p. 185–187° C.

Microanalysis: Calculated for $C_{30}H_{35}F_6N_3O_5$:
C, 57.05%; H, 5.59%; N, 6.65%. Found:
C, 57.32%; H, 5.70%; N, 6.27%.

Example 14 (General Procedure (A))

(R)-Trans-3{-4[-3-(3,5-bis(trifluoromethyl)phenyl)-1-(4-tert-butylcyclohexyl)ureidomethyl]-benzoylamino}-2-hydroxypropionic Acid

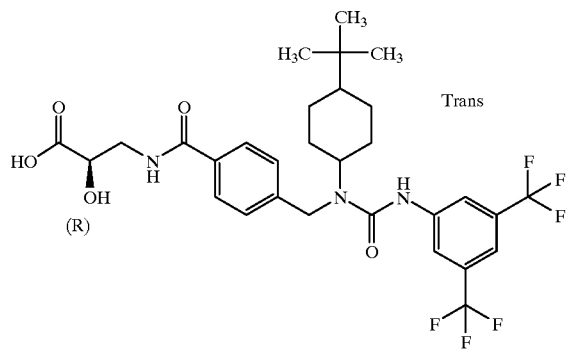

$^1$H-NMR (DMSO-$d_6$): δ 0.82 (s, 9H), 0.93 (m, 1H), 1.11 (m, 2H), 1.43 (m, 2H), 1.71 (m, 4H), 3.38 (m, 1H), 3.56 (m, 1H), 4.05 (m, 1H), 4.16 (t, 1H), 4.63 (s, 2H), 7.33 (d, 2H), 7.61 (s, 1H), 7.80 (d, 2H), 8.26 (s, 2H), 8.43 (t, 1H); HPLC-MS (Method A): m/z=632 (M+1); $R_t$=8.17 min; M.p. 184–187° C.

Microanalysis: Calculated for $C_{30}H_{35}N_3F_6O_5$ (+0.5 ethyl acetate):
C, 56.88%; H, 5.82%; N, 6.22%. Found:
C, 56.63%; H, 5.66%; N, 6.47%.

Example 15

General Procedure (A)

Trans-(R)-3{-4-[3-(3-methyl-5-trifluoromethylphenyl)-1-(4-tert-butylcyclohexyl)ureidomethyl]-benzoylamino}-2-hydroxypropionic Acid

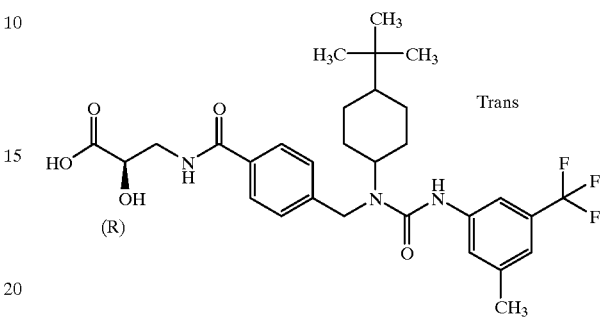

$^1$H-NMR (DMSO-$d_6$): δ 0.82 (s, 9H), 0.93 (m, 1H), 1.11 (m, 2H), 1.43 (m, 2H), 1.71 (m, 4H), 2.33 (s, 3H), 3.38 (m, 1H), 3.56 (m, 1H), 4.05 (m, 1H), 4.16 (t, 1H), 4.63 (s, 2H), 7.10 (s, 1H), 7.33 (d, 2H), 7.73 (s, 1H), 7.80 (d, 2H), 8.43 (t, 1H), 8.62 (s, 1H); HPLC-MS (Method A): m/z=578 (M+1); $R_t$=7.45 min.

Example 16

General Procedure (A)

(RS)-3-[4-[1-(4-tert-Butylphenyl)-3-(4-trifluoromethoxyphenyl)ureidomethyl]benzoylamino}-2-hydroxypropionic Acid

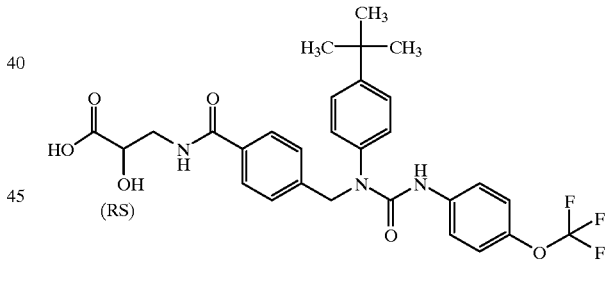

Step 1: 4-[1-(4-tert-Butylphenyl)-3-(4-trifluoromethoxyphenyl)ureidomethyl]benzoic Acid 4-Formylbenzoic acid methyl ester (10.6 g, 64 mmol) was dissolved in methanol (200 mL). 4-tert-Butylaniline (9.61 g, 64 mmol) was added and the resulting suspension was refluxed for 15 min. After cooling to room temperature, TFA (5.18 mL, 68 mmol) was added followed by portion wise addition of sodium cyanoborohydride (3.26 g, 52 mmol). The resulting mixture was stirred at room temperature for 2 hours and concentrated in vacuo. The residue was partitioned between ethyl acetate (200 mL) and 1 N aqueous sodium hydroxide (150 and 100 mL). The organic phase was dried (magnesium sulphate) and evaporated in vacuo to afford 19.0 g (99%) of 4-[(4-tert-butylphenylamino)methyl] benzoic acid methyl ester as a solid.

$^1$H-NMR (CDCl$_3$): δ 1.28 (9H, s), 3.92 (3H, s), 4.39 (2H, s), 6.57 (2H, d), 7.20 (2H, d), 7.44 (2H, d), 8.00 (2H, d).

Step 2

The above benzoic acid methyl ester (0.73 g, 2.44 mmol) was dissolved in acetonitrile (7 mL) and 4-trifluoromethoxyphenylisocyanate (405 μL, 2.68 mmol) was added. The resulting mixture was stirred at room temperature for 3 hours and then refluxed for 1.5 hour. After cooling and concentration in vacuo, the residue was purified by column chromatography on silica gel, eluting first with a mixture of ethyl acetate and heptane (1:6), then with a mixture of ethyl acetate and heptane (1:3) to afford 1.14 g (94%) of 4-[1-(4-tert-butylphenyl)-3-(4-trifluoromethoxyphenyl)ureidomethyl]benzoic acid methyl ester as an oil.

$^1$H-NMR (CDCl$_3$): δ 1.35 (9H, s), 3.91 (3H, s), 4.97 (2H, s), 6.30 (1H, s), 7.1 (4H, m), 7.32–7.43 (6H, m), 7.96 (2H, d). TLC: Rf=0.11 (SiO$_2$; ethyl acetate/heptane (1:6)); HPLC-MS (Method B): m/z=501 (M+1); R$_t$=9.05 min.

Step 2a

The above ureidomethylbenzoic acid methyl ester (1.14 g, 2.28 mmol) was dissolved in 1,4-dioxane (25 mL) and added 1 N aqueous sodium hydroxide (5 mL). The resulting mixture was stirred at room temperature for 1 hour. Ethanol (15 mL) and 1 N aqueous sodium hydroxide (5 mL) were added and the resulting mixture was stirred at room temperature for 16 hours. The mixture was concentrated in vacuo and partitioned between 1 N hydrochloric acid (100 mL) and ethyl acetate (2×50 mL). The combined organic phases were dried (magnesium sulphate) and concentrated in vacuo to afford 847 mg (76%) of 4-[1-(4-tert-butylphenyl)-3-(4-trifluoromethoxyphenyl)ureidomethyl]benzoic acid as a solid.

$^1$H-NMR (CDCl$_3$): δ 1.33 (9H, s), 3.91 (3H, s), 4.97 (2H, s), 6.30 (1H, s), 7.1 (4H, m), 7.33 (2H, d), 7.43 (4H, m), 8.03 (2H, d).

Step 3: (RS)-3-{4-[1-(4-tert-Butylphenyl)-3-(4-trifluoromethoxyphenyl)ureidomethyl]benzoyl-amino}-2-hydroxypropionic Acid Ethyl Ester To a solution of [1-(4-tert-butylphenyl)-3-(4-trifluoromethoxyphenyl)ureidomethyl]benzoic acid (1.0 g, 2.06 mmol) in DMF (1 mL) and DCM (10 mL) was added 1-hydroxy-7-azabenzo-triazole (0.33 g, 2.47 mmol). After stirring for 1 hour at room temperature, EDAC (0.47 g, 2.47 mmol), (RS)-isoserine ethyl ester hydrochloride (0.52 g, 3.09 mmol) and diisopropylethylamine (1.1 mL, 6.18 mmol) were added, successively. After stirring for 17 hours at ambient temperature the reaction mixture was partitioned between water, brine and ethyl acetate. The aqueous phase was further extracted with ethyl acetate. The combined organic phases were washed with water and brine. After drying (magnesium sulphate) and filtration, the organic phase was evaporated in vacuo. The residue was purified by column chromatography on silica gel eluting with a mixture of toluene and ethyl acetate (6:4). This afforded 1.2 g (97%) of (RS)-3-{4-[1-(4-tert-butylphenyl)-3-(4-trifluoromethoxyphenyl)ureidomethyl]-benzoylamino}-2-hydroxypropionic acid ethyl ester as an oil.

$^1$H-NMR (DMSO-d$_6$): δ 1.12 (t, 3H), 1.27 (s, 9H), 3.45 (m, 2H), 4.05 (q, 2H), 4.21 (dd, 1H), 4.98 (s, 2H), 5.67 (d, 1H), 7.20 (dd, 4H), 7.35 (dd, 4H), 7.55 (d, 2H), 5.77 (d, 2H), 8.42 (s, 1H), 8.48 (t, 1H); HPLC-MS (Method B): m/z=602 (M+1); R$_t$=3.38 min.

Step 4

A solution of 3-{4-[1-(4-tert-butylphenyl)-3-(4-trifluoromethoxyphenyl)ureidomethyl]benzoyl-amino}-2-hydroxypropionic acid ethyl ester was stirred in absolute ethanol (20 mL) and 1 M sodium hydroxide (6 mL) was added. Stirring was continued for 17 hours and the solution was acidified with aqueous hydrochloric acid. The solvent was decanted and the remaining oil was dissolved in acetonitrile (20 mL) by heating. Water (20 mL) was added dropwise under vigorous stirring and the mixture was allowed to cool to room temperature. The precipitate was filtered off, washed with water and dried to afford 0.51 g (43%) of the title compound as a solid.

$^1$H-NMR (DMSO-d$_6$): δ 1.25 (s, 9H), 3.50 (ddd, 2H), 4.18 (dd, 1H), 4.95 (s, 2H), 7.20 (dd, 4H), 7.39 (dd, 4H), 7.52 (d, 2H), 7.78 (d, 2H), 8.32 (s, 1H), 8.46 (t, 1H); HPLC-MS (Method B): m/z=574 (M+1); R$_t$=3.07 min.

Microanalysis: Calculated for C$_{29}$H$_{30}$F$_3$N$_3$O$_6$:
C, 60.73%; H, 5.27%; N, 7.33%. Found:
C, 60.77%; H, 5.37; N%, 7.26%.

Example 17

General Procedure (A)

(RS)-3-{4-[1-(4-Cyclohex-1-enylphenyl)-3-(3,5-dichlorophenyl)ureidomethyl]benzoylamino}-2-hydroxypropionic Acid

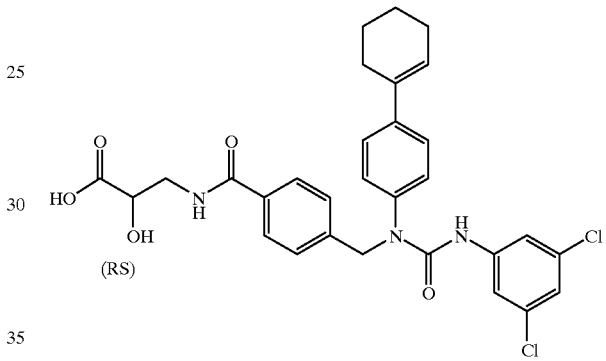

Step 3: (RS)-3-{4{-1-(4-Cyclohex-1-enylphenyl)-3-(3,5-dichlorophenyl)ureidomethyl]benzoyl-amino}-2-hydroxypropionic Acid Ethyl Ester Yield: 0.33 g (89%).

$^1$H-NMR (CDCl$_3$): δ 1.30 (t, 3H), 1.68 (m, 2H), 1.79 (m, 2H), 2.23 (m, 2H), 2.38 (m, 2H), 3.41 (d, 1H), 3.83 (m, 2H), 4.27 (q, 2H), 4.37 (dd, 1H), 4.92 (s, 2H), 6.20 (m, 1H), 6.27 (s, 1H), 6.51 (t, 1H), 6.98 (s, 1H), 7.04 (d, 2H), 7.18 (d, 2H), 7.33 (d, 2H), 7.42 (d, 2H), 7.68 (d, 2H).

Step 4: (RS)-3-{4-[1-(4-Cyclohex-1-enylphenyl)-3-(3,5-dichlorophenyl)ureidomethyl]benzoyl-amino}-2-hydroxypropionic Acid A solution of (RS)-3-{4-[1-(4-cyclohex-1-enylphenyl)-3-(3,5-dichlorophenyl)ureidomethyl]-benzoylamino}-2-hydroxypropionic acid ethyl ester (0.99 g, 1.61 mmol) in ethanol (15 mL) and THF (15 mL) was stirred and 1 M sodium hydroxide (6 mL) was added. The mixture was stirred at 40° C. for 4 hours and acidified with 1 N hydrochloric acid. After evaporation in vacuo the residue was purified on semipreparative HPLC (Gilson system). The pure fractions were combined and evaporated in vacuo to afford 0.749 (79%) of the title compound as a solid.

$^1$H-NMR (DMSO-d$_6$): δ 1.56 (m, 2H), 1.70 (m, 2H), 2.17 (s, 2H), 2.33 (s, 2H), 3.35 (m, 2H), 3.55 (m, 2H), 4.15 (dd, 1H), 4.95 (s, 2H), 6.20 (s. 1H), 7.12 (s, 1H), 7.18 (d, 2H), 7.33 (d, 2H), 7.40 (d, 2H), 7.62 (d, 2H), 7.76 (d, 2H), 8.43 (t, 1H), 8.55 (s, 1H); HPLC-MS (Method B): m/z=582 (M+1); R$_t$=5.13 min.

Microanalysis: Calculated for C$_{29}$H$_{30}$Cl$_2$N$_3$O$_5$:
C, 61.86%; H, 5.02%; N, 7.21%. Found:
C, 61.10%; H, 5.05%; N, 7.03%.

Example 18

(S)-3-{-4-[1-(4-Cyclohex-1-enylphenyl)-3-(3,5-dichlorophenyl)ureidomethyl]benzoylamino}-2-hydroxypropionic Acid

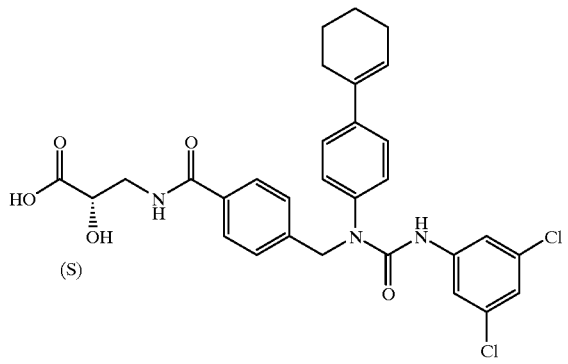

4-[1-(4-Cyclohex-1-enylphenyl)-3-(3,5-dichlorophenyl)ureidomethyl]benzoic acid (130 mg, 0.26 mmol) was dissolved in DMF (2 mL), then EDAC (50 mg, 0.26 mmol) and HOBt (43 mg, 0.32 mmol) were added and the reaction mixture was stirred at room temperature for 1 hour. The above crude (S)-2,2-dimethyl-5-oxo-[1,3]dioxolan-4-ylmethylammonium trifluoroacetate was dissolved in DMF (1 mL) and added to the reaction mixture together with diisopropylethylamine (450 mg, 3.5 mmol). The mixture was stirred at room temperature for 16 hours.

The reaction mixture was transferred to a silica gel column and eluted with DCM to afford crude (S)-4-[1-(4-cyclohex-1-enylphenyl)-3-(3,5-dichlorophenyl)ureidomethyl]-N-(2,2-dimethyl-5-oxo-[1,3]dioxolan-4-ylmethyl)benzamide as an oil after evaporation. The oil was redissolved in acetonitrile (5 mL), hydrochloric acid (1 N, 5 mL) was added and the mixture was stirred at room temperature for 1.5 hour. The solvent was removed by evaporation and the crude product was purified on semipreparative HPLC (acetonitrile/water gradient) to afford the title compound.

HPLC-MS (Method B): m/z=582 (M+1); $R_t$=5.10 min.

Example 19

General Procedure (A)

(R)-3{-4-[1-(4-Cyclohex-1-enylphenyl)-3-(3,5-dichlorophenyl)ureidomethy]benzoylamino}-2-hydroxyiropionic Acid

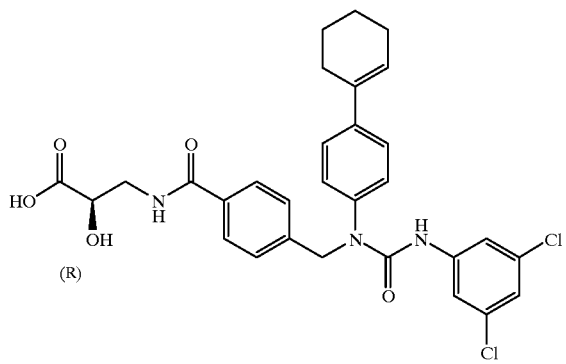

Step 3: (R)-3-{4-[1-(4-Cyclohex-1-enylphenyl)-3-(3,5-dichlorophenyl)ureidomethyl]benzoyl-amino}-2-hydroxypropionic Acid Ethyl Ester $^1$H-NMR (Acetone-d$_6$): δ 1.20 (t, 3H), 1.70 (dm, 4H), 2.31 (dm, 4H), 3.70 (m, 2H), 4.15 (q, 2H), 4.35 (dd, 1H), 5.02 (s, 2H), 6.22 (m, 1H), 7.00 (s, 1H), 7.20 (d, 2H), 7.40 (dd, 4H), 7.61 (ds, 2H), 7.80 (d, 3H), 7.89 (s, 1H).

Step 4

A solution of (R)-3-{4-[1-(4-cyclohex-1-enylphenyl)-3-(3,5-dichlorophenyl)ureidomethyl]-benzoylamino}-2-hydroxypropionic acid ethyl ester (0.60 g, 0.98 mmol) in ethanol (5 mL) and THF (5 mL) was stirred and 4 N sodium hydroxide (0.76 mL, 2.94 mmol) was added. The solution was stirred for 3 hours at room temperature and then acidified with 1 N hydrochloric acid. Evaporation in vacuo afforded an oil, which was partitioned between ethyl acetate, water and brine. The aqueous phase was extracted twice with ethyl acetate and the combined organic phases were washed with water and brine. Drying (magnesium sulphate), filtration, and evaporation in vacuo afforded 0.43 g (73%) of the title compound as a solid. 5.11 min.

Example 20

General Procedure (A)

(R)-3{4-[3-(3-Chlorophenyl)-1-(4-cyclohex-1-enylphenyl)ureidomethyl]benzoylamino}-2-hydroxyprpoionic acid

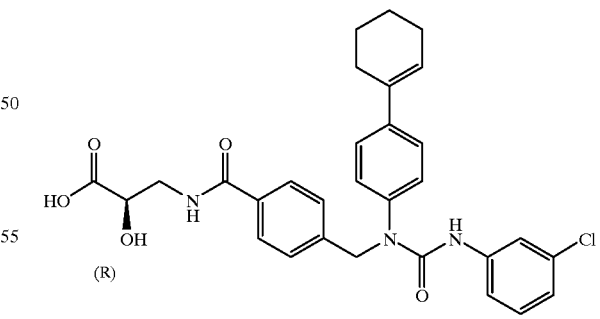

$^1$H-NMR (DMSO-d$_6$): δ 1.56–1.71 (m, 4H), 1.15–2.33 (m, 4H), 3.37–3.51 (m, 2H), 4.14–4.17 (m, 1H), 4.96 (s, 1H), 6.17 (t, 1H)(.7.12 (d, 1H), 7.27–7.41 (m, 8H), 7.62 (t, 1H). 7.87 (d, 2H), 8.38–8.43 (m, 3H), HPLC-MS (Method B): m/z=548 (M+1); $R_t$=4.69 min.

Example 21

General Procedure (A)

(R)-3-{4-[1-(4-Cyclohex-1-enylphenyl)-3-phenylureidomethyl]benzoylamino)-2-hydroxypropionic Acid

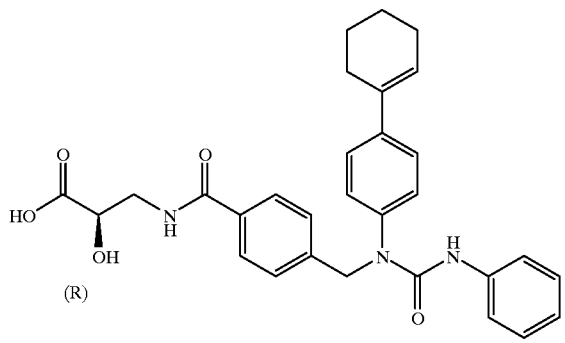

¹H-NMR (DMSO-d₆): δ 1.56–1.71 (m, 4H), 2.15–2.40 (m4H m), 3.30–3.51 (m, 2H), 4.14–4.19 (m, mH), 4.97 (s, mH), 6.16 (t, tH), 6.98 (t, 1H), 7.12–7.48 (m, 1O H), 7.79 (d, 2H), 8.15 (s, 1H), 8.43 (t, 1H).

Example 22

General Procedure (A)

(R)-3-{4-[3-Benzyl-1-(4-cyclohex-1-enylphenyl)ureidomethyl]benzoylamino}-2-hydroxypropionic Acid

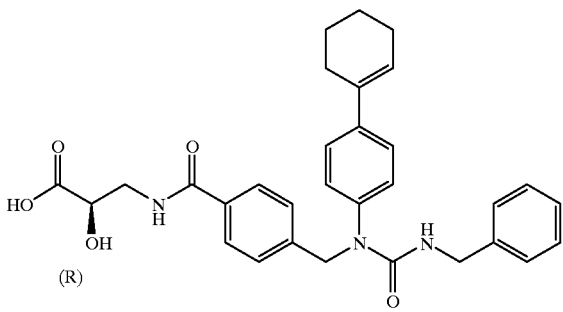

¹H-NMR (DMSO-d₆): δ 1.50–1.75 (m, 4H), 1.86 (s, 2H), 2.08 (s, 2H), 3.30–3.60 (m, 2H), 4.13–4.20 (m, 1H), 4.25 (d, 2H) 4.87 (s, 2H), 6.18 (t, 1H) 6.55 (t, 1H), 7.08–7.42 (m, 11H), 7.77 (d, 2H), 8.48 (t, 1H).

Example 23

General Procedure (A)

(RS)-3{-4-[1-(4-Cyclohex-1-enylphenyl)3-(3,5-dichlorophenyl)ureidomethyl]benzoylamino}-2-fluoropropionic Acid

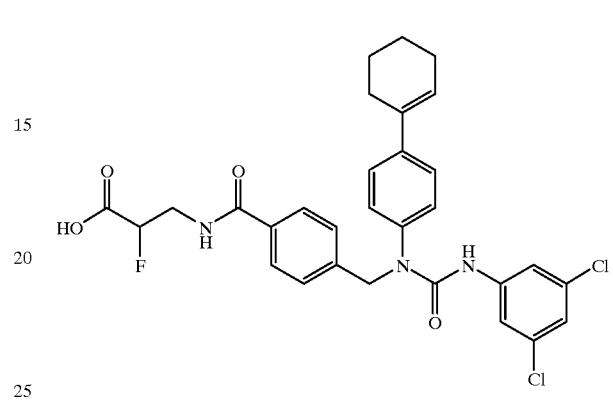

Steps 1 and 2: 4-[1-(4-Cyclohex-1-enyl phenyl)-3-(3,5-dichlorophenyl)ureidomethyl-1-benzoic Acid ¹H-NMR (DMSQ-d₆): δ 1.52–1.77 (m, 4H), 2.10–2.23 (m, 2H), 2.26–2.38 (m, 2H), 4.95 (s, 2H), 6.18 (t, 1H), 7.14 (t, 1H), 7.17 (d, 2H), 7.34 (d, 2H), 7.40 (d, 2H), 7.64 (dd, 2H), 7.85 (d, 2H), 8.55 (s, 1H).

Microanalysis: Calculated for $C_{27}H_{24}N_2O_3Cl_2$:

C, 65.46%; H, 4.88%; N, 5.65%. Found:

C, 65.43%; H, 5.10%; N, 5.66%.

Step 3: (RS)-3-4-[1-(4-Cyclohex-1-enylphenyl)-3-(3,5-dichlorophenyl)ureidomethyl]benzoyl-amino}-2-fluoropropionic Acid Methyl Ester ¹H-NMR (DMSQ-d₆): δ 1.52–1.75 (m, 4H), 2.10–2.40 (m, 4H), 3.60–3.81 (m, 5H), 4.95 (s, 2H), 5.04–5.35 (m, 1H), 6.18 (m, 1H), 7.10–7.80 (m, 1H), 8.55 (s, 1H), 8.75 (t, 1H), 13.45 (br s, 1H).

Step 4

Hydrolysis of (RS)-3-{4-[1-(4-cyclohex-1-enylphenyl)-3-(3,5-dichlorophenyl)ureidomethyl]-benzoylamino}-2-fluoropropionic acid methyl ester in a mixture of THF and methanol afforded the title compound.

¹H-NMR (DMSO-d₆): δ 1.59–1.72 (m, 4H), 2.15–2.33 (m, 4H), 3.58–3.81 (m, 2H), 4.96 (s, 2H), 5.17–5.23 (m, 1H), 6.18 (m, 1H), 7.13–7.80 (m, 1H), 8.54 (s, 1H), 8.73 (t, 1H), 13.45 (br s, 1H).

Example 24

General Procedure (A)

(R)-3{-4-[1-(4-Cyclohexylphenyl)-3-(4-trifluoromethylsulfanylphenylureidomethyl]benzoyl-amino}-2-hydroxypropionic acid

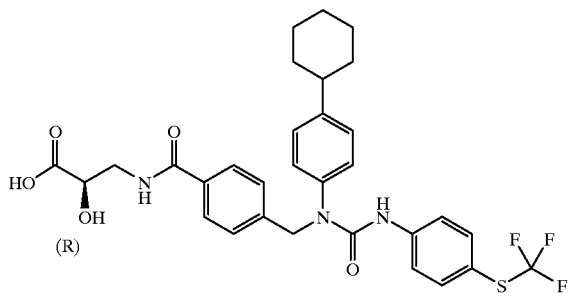

Step 2: 4-[1-(4-Cyclohexylphenyl)-3-(4-trifluoromethylsulfanylphenyl)ureidomethyl]benzoic Acid Methyl Ester 4-((4-Cyclohexylphenylamino)methyl)benzoic acid methyl ester (0.32 g, 1 mmol) was suspended in acetonitrile (5 mL) and 4-(trifluoromethylthio)phenyl isocyanate (0.24 g, 1.1 mmol) was added. Additional amounts (0.05 g) of the isocyanate was added after the first day and again after the second day (0.05 g). The reaction was stopped on the third day and concentrated in vacuo. The residue was purified by column chromatography on silica gel (30 g) using ethyl acetate: n-heptane (400 mL 1:4 and 100 mL 1:1) as eluent to afford 0.53 g of 4-[1-(4-cyclohexylphenyl)-3-(4-trifluoromethylsulfanylphenyl)ureidomethyl]benzoic acid methyl ester.
$^1$H-NMR (DMSO-$d_6$): δ 1.16–1.43 (m, 5H), 1.65–1.82 (m, 5H), 3.84 (s, 3H), 4.99 (s, 2H), 8.62 (s, 1H); HPLC-MS (Method B): m/z=543 (M+1); $R_t$=9.35 min.

Step 2a: 4-[1-(4-Cyclohexylphenyl)-3-(4-trifluoromethylsulfanylphenyl)ureidomethyl]benzoic Acid 4-[1-(4-Cyclohexylphenyl)-3-(4-trifluoromethylsulfanylphenyl)ureidomethyl]benzoic acid methyl ester (0.53 g, 0.98 mmol) was dissolved in ethanol (96%, 11 mL) and sodium hydroxide (4 N, 1.47 mL) was added. The mixture was stirred overnight. The reaction was concentrated to dryness and added water (15 mL) and acidified with hydrochloric acid (4 N, 1.6 mL) to pH 2–3 and extracted with ethyl acetate (25 mL). The aqueous phase was extracted once more with ethyl acetate (15 mL) and the combined organic phases were washed 3 times with water (10 mL), dried over magnesium sulphate, filtered and concentrated in vacuo. Crystallisation from ethyl acetate:n-heptane gave 0.34 g of 4-[1-(4-cyclohexylphenyl)-3-(4-trifluoromethylsulfanylphenyl)ureidomethyl]benzoic acid.
$^1$H-NMR (DMSO-$d_6$): δ 1.5–1.42 (m, 5H), 1.67–1.83 (m, 5H), 2.45 (m, 1H), 5.00 (s, 2H), 7.15–7.25 (dd, 4H), 7.40 (d, 2H), 7.54–7.63 (dd, 4H), 7.88 (d, 2H), 7.62 (s, 1H), 12.90 (broad, 1H), HPLC-MS (Method B): m/z=529 (M+1); $R_t$=8.55 min; M.p. 162.0–164.0° C.
Microanalysis: Calculated for $C_{28}H_{27}F_3N_2O_3S$: C, 63.62%; H, 5.15%; N, 5.30%. Found: C, 63.97%; H, 5.28%; N, 5.26%.

Step 3: (R)-3-{4-[1-(4-Cyclohexylphenyl)-3-(4-trifluoromethylsulfanylphenyl)ureidomethyl]-benzoylamino}-2-hydroxypropionic Acid Methyl Ester 4-[1-(4-Cyclohexylphenyl)-3-(4-trifluoromethylsulfanylphenyl)ureidomethyl]benzoic acid (0.32 g, 0.606 mmol) was dissolved in DMF (7 mL) and HOAt (0.10 g, 0.727 mmol) and EDAC (0.14 g, 0.727 mmol) were added. The mixture was stirred for 30 min. Then (R)-3-amino-2-hydroxypropionic acid methyl ester hydrochloride (0.14 g) and diisopropylethylamine (0.16 mL, 0.909 mmol) were added. The reaction was stirred overnight. The reaction mixture was transferred to a separatory funnel with ethyl acetate (30 mL) and water (15 mL) and extracted. The aqueous phase was extracted once more with ethyl acetate (15 mL) and the combined organic phases were washed with hydrochloric acid (0.2 N, 3×10 mL) and an aqueous solution of saturated sodium chloride (3×10 mL), dried over magnesium sulphate, filtered and concentrated in vacuo. The residue was purified on a column (silica gel, 30 g) using a mixture of ethyl acetate and n-heptane (200 mL, 40:60 and 450 mL 1:1) as eluent to afford 0.33 g of (R)-3-{4-[1-(4-cyclohexylphenyl)-3-(4-trifluoromethylsulfanylphenyl)ureidomethyl] benzoylamino}-2-hydroxypropionic acid methyl ester.
$^1$H-NMR (DMSO-$d_6$): δ 1.16–1.43 (m, 5H), 1.66–1.81 (m, 5H), 2.47 (m, 1H), 3.4 (m, 1H), 3.51 (m, 1H), 3.63 (s, 3H), 4.22 (q, 1H), 4.97 (s, 2H), 5.73 (d, 1H), 7.2 (dd, (4H), 7.35 (d, 2H), 7.60 (dd, 4H), 7.76 (d, 2H), 8.50 (t, 1H), 8.60 (s, 1H), HPLC-MS (Method B): m/z=630 (M+1); $R_t$=8.07 min.

Step 4

(R)-3-{4-[1-(4-Cyclohexylphenyl)-3-(4-trifluoromethylsulfanylphenyl)ureidomethyl]benzoyl-amino}-2-hydroxypropionic acid methyl ester (0.32 g, 0.508 mmol) was dissolved in ethanol (15 mL) and sodium hydroxide (4 N, 0.76 mL, 3.05 mmol) was added. The reaction mixture was stirred for 1.5 hour. The reaction was evaporated and added water (15 mL) and acidified with hydrochloric acid (4 N, 0.8 mL). The mixture was extracted with ethyl acetate (20 mL). The aqueous phase was extracted once more with ethyl acetate (15 mL) and the combined organic phases were washed with water (3×10 mL), dried over magnesium sulphate, filtered and concentrated to give the title compound (0.3 g).
$^1$H-NMR (DMSO-$d_6$): δ 1.12–1.42 (m, 5H), 1.66–1.82 (m, 5H), 2.45 (m, 1H), 3.38 (m, 1H), 3.54 (m, 1H), 4.17 (q, 1H), 4.96 (s, 2H), 5.45 (broad, 1H), 7.20 (dd, 4H), 7.34 (d, 2H), 7.60 (dd, 4H), 7.78 (d, 2H), 8.45 (t, 1H), 8.60 (s, 1H), 12.53 (broad, 1H), HPLC-MS (Method B): m/z=616 (M+1); $R_t$=7.68 min.
Microanalysis: Calculated for $C_{31}H_{32}F_3N_3O_5S$: C, 60.48%; H, 5.24%; N, 6.83%. Found: C, 60.25%; H, 5.52%; N, 6.53%.

Example 25 (General Procedure (A))

(R)-3-[4-[1-(4-Cyclohexen-1-ylphenyl)-3-(3-methanesulfonyl-4-trifluoromethoxyphenyl)ureido-methyl]benzoylamino}-2-hydroxypropionic Acid

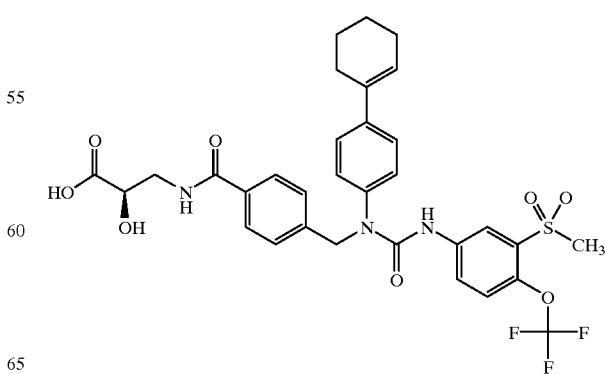

Preparation of 3-methylsulfonyl-4-trifluoromethoxyphenyl isocyanate, intermediate D-N=C=O used in step 2

To a solution of methyl iodide (59.0 g, 0.41 mol) in DMF (150 mL) was added potassium carbonate (23.0 g, 0.16 mol). 2-(Trifluoromethoxy)thiophenol (16.0 g, 0.08 mol) was added in portions during 30 min. The reaction mixture was then stirred vigorously overnight. Water (250 mL) was added. The reaction mixture was extracted with ethyl acetate (2×150 mL). The combined organic phases were washed with a 50% saturated aqueous solution of sodium chloride (4×100 mL), dried (magnesium sulphate), and concentrated in vacuo to give 15.0 g of 1-methylsulfanyl-2-trifluoromethoxybenzene.

1-Methylsulfanyl-2-trifluoromethoxybenzene (15.0 g, 72 mmol) was dissolved in DCM (200 mL) and m-chloroperoxybenzoic acid (39.0 g, 216 mmol) was added in small portions during 30 min. The reaction mixture was then allowed to stand overnight. DCM (200 mL) was added followed by slow addition of sodium hydroxide (2 N, 200 mL). The organic phase was separated and washed with sodium hydroxide (2 N, 3×150 mL), dried (magnesium sulphate) and concentrated in vacuo to give 15.8 g of 1-methylsulfonyl-2-trifluoromethoxybenzene
$^1$H-NMR (400 MHz, CDCl$_3$): δ 8.11 (d, 1H), 7.71 (t, 1H), 7.48 (m, 2H) 3.23(s 1H); M.p. 44–46 C.
Microanalysis: Calculated for C$_8$H$_7$F$_3$O$_3$S:
C, 40.00%; H, 2.94%. Found:
C, 40.22%; H, 2.92%.

1-Methylsulfonyl-2-trifluoromethoxybenzene (15.7 g, 65 mmol) was dissolved in concentrated sulfuric acid (27 mL) and the solution was heated to 40° C. Nitric acid (100%, 27 mL) was added dropwise over 45 min. The reaction mixture was allowed to stand overnight at 60° C., cooled, and then poured on crushed ice (300 mL). The precipitated product was isolated by filtration, washed with water (10×50 mL) and dried (magnesium sulphate), affording 17.5 g of 3-methylsulfonyl-4-trifluoromethoxynitrobenzene.
$^1$H-NMR (400 MHz, DMSO-d$_6$): δ 8.69 (d, 1H), 8.64 (d, 1H), 7.95 (d, 1H) 3.45 (s 3H); M.p. 102–104° C.
Microanalysis: Calculated for C$_8$H$_6$F$_3$NO$_5$S:
C, 33.69%; H, 2.12%; N, 4.91%. Found:
C, 33.91%; H, 2.08%; N, 4.92%.

3-Methylsulfonyl-4-trifluoromethoxynitrobenzene (17.5 g) was dissolved in methanol (400 mL) followed by addition of palladium on carbon (10%, 50% water, 3.2 g). The reaction mixture was hydrogenated for 17 hours at 1 atm of hydrogen, filtered and concentrated in vacuo to give 14.3 g of 3-methylsulfonyl-4-trifluoromethoxyaniline.
$^1$H-NMR (400 MHz, DMSO-d$_6$): δ 7.26 (d, 1H), 7.14 (d, 1H), 6.85 (dd, 1H) 5.89(s, 2H) 3.21(s, 3H); M.p. 106–109° C.
Microanalysis: Calculated for C$_8$H$_8$F$_3$NO$_3$S:
37.65% C, 3.16% H, 5.49% N. Found:
37.65% C, 3.14% H, 5.45% N.

To 3-methylsulfonyl-4-trifluoromethoxyaniline (2.0 mmol, 500 mg) dissolved in ethyl acetate (6 mL) was added 3 N hydrochloric acid in ethyl acetate (5 mL) followed by concentration in vacuo. The residue was treated with toluene (3×5 mL) and each time concentrated in vacuo. To the residue was added toluene (10 mL) and diphosgene (6 mmol, 0.73 mL) under a nitrogen atmosphere and the suspension was gently refluxed for 2 hours. Additional diphosgene (6 mmol, 0.73 mL) was added and refluxing was continued overnight. The reaction mixture was concentrated in vacuo to afford 3-methylsulfonyl-4-trifluoromethoxyphenyl isocyanate.

Step 3: (R)-3-{4-[1-(4-cyclohexen-1-ylphenyl)-3-(3-methanesulfonyl-4-trifluoromethoxy-phenyl)ureidomethyl]benzoylamino}-2-hydroxypropionic Acid Methyl Ester This intermediate was prepared using general procedure (A) (steps 1, 2, 2a, and 3).
$^1$H-NMR (DMSO-d$_6$): δ 1.60 (m, 2H), 1.72 (m, 2H), 2.18 (m, 2H), 2.36 (m, 2H), 3.27 (s, 3H), 3.41 (m, 1H), 3.51 (m, 1H), 3.61 (s, 3H), 4.23 (q, 1H), 4.96 (s, 2H), 5.70 (d, 1H), 6.18 (m, 1H), 7.19 (d, 2H), 7.33 (d, 2H), 7.39 (d, 2H), 7.53 (d, 1H), 7.75 (d, 2H), 8.00 (d, 1H), 8.18 (s, 1H), 8.50 (t, 1H), 8.85 (s, 1H); HPLC-MS (Method B): m/z=690 (M+1); R$_t$=6.92 min.

Step 4

Hydrolysis of (R)-3-{4-[1-(4-cyclohexen-1-ylphenyl)-3-(3-methanesulfonyl-4-trifluoromethoxy-phenyl)ureidomethyl]benzoylamino}-2-hydroxypropionic acid methyl afforded the title compound.
$^1$H-NMR (DMSO-d$_6$): δ 1.60 (m, 2H), 1.72 (m, 2H), 2.18 (m, 2H), 2.36 (m, 2H), 3.27 (s, 3H), 3.41 (m, 1H), 3.51 (m, 1H), 4.17 (t, 1H), 4.96 (s, 2H), 5.50 (broad, 1H), 6.18 (m, 1H), 7.19 (d, 2H), 7.33 (d, 2H), 7.39 (d, 2H), 7.53 (d, 1H), 7.75 (d, 2H), 8.00 (d, 1H), 8.18 (s, 1H), 8.50 (t, 1H), 8.85 (s, 1H), 12.55 (broad, 1H); HPLC-MS (Method B): m/z=676 (M+1); R$_t$=6.50 min.

Example 26

(General Procedure (A)

Trans-(R)-3-{4-[-3-(3,5-bis(methyl)phenyl)-1-(4-tert-butylcyclohexyl)ureidomethyl]benzoylamino}-2-hydroxypropionic Acid

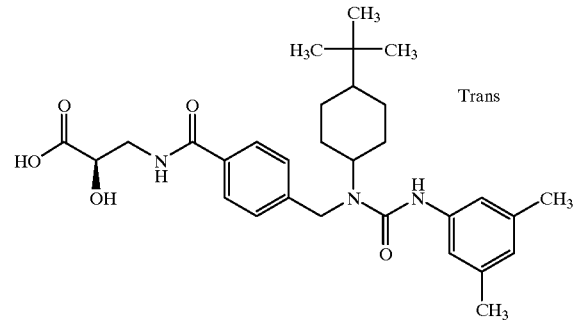

Steps 1 and 2: Trans-4-[3-(3,5-bis(methyl)phenyl)-1-(tert-butylcyclohexyl)ureidomethyl]-benzoic Acid Methyl Ester $^1$H-NMR (DMSO-d$_6$): δ 0.82 (s, 9H), 0.93 (m, 1H), 1.11 (m, 2H), 1.41 (m, 2H), 1.71 (m, 4H), 2.23 (s, 6H), 3.83 (s, 3H), 4.09 (m, 1H), 4.61 (s, 2H), 6.60 (s, 1H), 7.08 (s, 2H), 7.38 (d, 2H), 7.90 (d, 2H), 8.20 (s, 1H); HPLC-MS (Method B): m/z=451 (M+1); R$_t$=8.93 min.

Step 2a: Trans-4-[3-(3,5-bis(methyl)phenyl)-1-(tert-butylcyclohexyl)ureidomethyl]benzoic Acid The compound was prepared by hydrolysis of trans-4-[3-(3,5-bis(methyl)phenyl)-1-(tert-butyl-cyclohexyl)ureidomethyl]benzoic acid methyl ester.
$^1$H-NMR (DMSO-d$_6$): δ 0.82 (s, 9H), 0.93 (m, 1H), 1.11 (m, 2H), 1.41 (m, 2H), 1.71 (m, 4H), 2.23 (s, 6H), 4.09 (m, 1H), 4.61 (s, 2H), 6.60 (s, 1H), 7.08 (s, 2H), 7.38 (d, 2H), 7.90 (d, 2H), 8.20 (s, 1H), 12.82 (s, 1H); HPLC-MS (Method B): m/z=437 (M+1); $R_t$=8.00 min.
Microanalysis: Calculated for $C_{27}H_{36}N_2O_3$:
C, 74.28%; H, 8.31%; N, 6.42%. Found:
C, 74.31%; H, 8.40%; N, 6.35%.

Step 3: Trans-(R)-3{-4-[-3-(3,5-bis(methyl)phenyl)-1-(4-tert-butylcyclohexyl)ureidomethyl]-benzoylamino}-2-hydroxypropionic Acid Methyl Ester:

This compound was prepared from trans-4-[3-(3,5-bis(methyl)phenyl)-1-(tert-butylcyclohexyl)ureidomethyl] benzoic acid.
$^1$H-NMR (DMSO-$d_6$): δ 0.82 (s, 9H), 0.93 (m, 1H), 1.11 (m, 2H), 1.43 (m, 2H), 1.71 (m, 4H), 2.23 (s, 6H), 3.42 (m, 1H), 3.52 (m, 1H), 3.63 (s, 3H), 4.05 (m, 1H), 4.23 (q, 1H), 4.59 (s, 2H), 5.70 (d, 1H), 6.58 (s, 1H), 7.08 (s, 2H), 7.30 (d, 2H), 7.78 (d, 2H), 8.18 (s, 1H), 8.47 (t, 1H); HPLC-MS (Method B): m/z=538 (M+1); $R_t$=7.43 min; M.p. 159–160° C.
Microanalysis: Calculated for $C_3H_{43}N_3O_5$:
C, 69.25%; H. 8.06%; N, 7.81%. Found:
C, 69.03%; H, 8.15%; N, 7.79%.

Step 4

Hydrolysis of trans-(R)-3-{4-[-3-(3,5-bis(methyl)phenyl)-1-(4-tert-butylcyclohexyl)ureido-methyl]benzoylamino}-2-hydroxypropionic acid methyl ester afforded the title compound.
$^1$H-NMR (DMSO-$d_6$): δ 0.82 (s, 9H), 0.93 (m, 1H), 1.11 (m, 2H), 1.43 (m, 2H), 1.71 (m, 4H), 2.23 (s, 6H), 3.40 (m, 1H), 3.55 (m, 1H), 4.05 (m, 1H), 4.18 (t, 1H), 4.59 (s, 2H), 6.58 (s, 1H), 7.08 (s, 2H), 7.30 (d, 2H), 7.78 (d, 2H), 8.18 (s, 1H), 8.47 (t, 1H); HPLC-MS (Method B): m/z=524 (M+1); $R_t$=7.08 min.
Microanalysis: Calculated for $C_{30}H_{41}N_3O_5$, 1½$H_2O$:
C, 65.43%; H, 8.05%; N, 7.63%. Found:
C, 65.54%; H, 7.93%; N, 7.44%.

Example 27

General Procedure (A)

(R)-3-{4-[1-(4-Cyclohexylphenyl)-3-(3,5-dichlorophenyl)ureidomethyl]benzoylamino}-2-hydroxypropionic acid

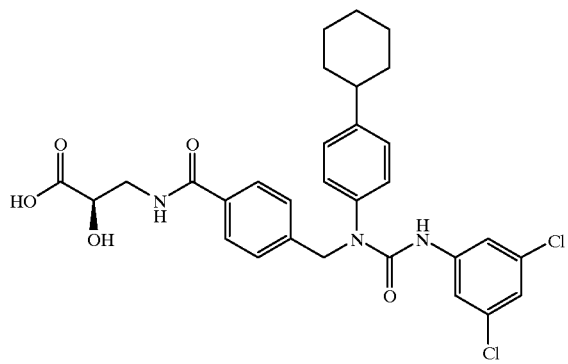

$^1$H-NMR (CDCl$_3$): δ 7.64 (d, 2H), 7.49 (brs, 1H), 7.25–7.15 (m, 6H), 7.03 (d, 2H), 6.90 (m, 1H), 6.40 (s, 1H), 4.75 (s, 2H), 4.30 (br s, 1H), 3.80–3.60 (m, 2H), 2.49 (m, 1H), 1.90–1.65 (m 5H), 1.45–1.25 (m, 5H); HPLC-MS (Method B): m/z=584 (M+1); $R_t$=5.28 min.

Example 28

General Procedure (A)

(R)-(3{-4-[1-(4-Cyclohex-1-enylphenyl)-3-(3-fluoro-5-trifluoromethylphenyl)ureidomethyl]-benzoylamino}-2-hydroxypropionic acid

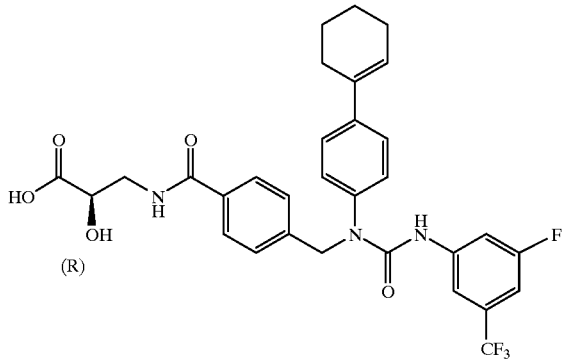

$^1$H-NMR (DMSO-$d_6$): δ 8.75 (s, 1H), 8.42 (t, 1H), 7.75 (d, 4H), 7.45–7.30 (m, 4H), 7.20 (d, 3H), 6.20 (s, 1H), 4.96 (s, 2H), 4.15 (dd, 1H), 3.55 (m, 1H), 3.40 (m, 1H), 2.35 (brs, 2H), 2.15 (br s, 2H). 1.75–1.55 (m, 4H); HPLC-MS (Method B): m/z=600 (M+1); $R_t$=5.01 min.

Example 29

General Procedure (A)

(R)-3-{4-[1-(4-Cyclohexylphenyl)-3-(3-methylsulfanylphenyl)ureidomethyl]benzoylamino}-2-hydroxypropionic Acid

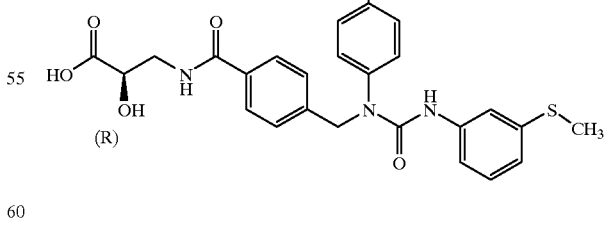

$^1$H-NMR (DMSO-$d_6$): δ 12.2 (brs, 1H), 8.44 (t, 1H), 8.20 (s, 1H), 7.78 (m, 2H), 7.40 (s, 1H), 7.33 (m, 2H), 7.25–7.10 (m, 6H), 6.84 (d, 1H), 4.95 (s, 1H), 4.15 (dd, 1H), 3.55 (m, 1H), 3.38 (m, 1H). 2.42 (s, 3H) 1.85–1.65 (m, 5H), 1.40–1.15 (m, 5H); HPLC-MS (Method B): m/z=562 (M+1); $R_t$=4.77 min.

Example 30

General Procedure (A)

(R)-3{-4-[1]-(4-Cyclohex-1-enylphenyl)-3-(2,2,4,4-tetrafluoro-4H-benzo[1,3]dioxin-6-yl)ureidomethyl]benzoylamino}-2-hydroxypropionic Acid

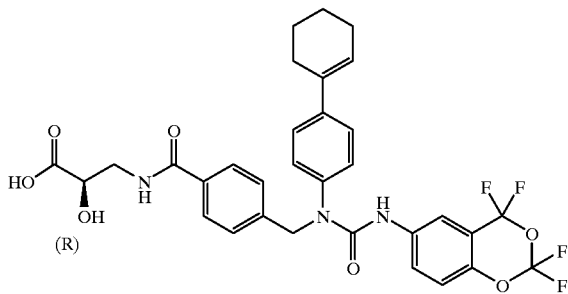

$^1$H-N MR (CDCl$_3$): δ 7.70–7.50 (m, 3H), 7.45–7.30 (m, 4H), 7.25–6.85 (m, 6H), 6.12 (s, 1H), 4.80 (s, 2H), 4.28 (m, 1H), 3.70 (m, 2H), 2.40–2.00 (m, 4H), 1.70–1.55 (m, 4H); HPLC-MS (Method B): m/z=644 (M+1); R$_t$=5.13 min.

Example 31

General Procedure (A)

3-{4-[1-(4-Cyclohex-1-enylphenyl)-3-(3,5-dichlorophenyl)ureidomethyl]benzoylamino}-2(R)-methoxypropionic Acid

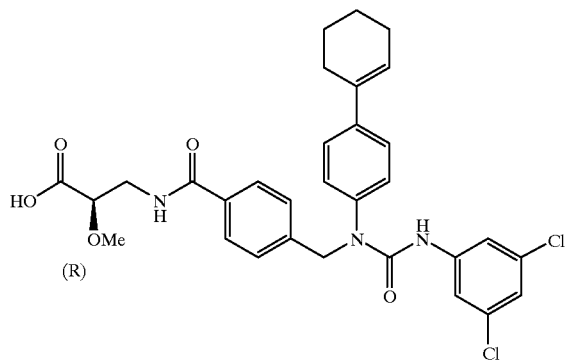

Step 3

4-[1-(4-Cyclohex-1-enylphenyl)-3-(3,5-dichloro-phenyl)ureidomethyl]benzoic acid (500 mg, 1.0 mmol), HOBt (184 mg, 1.2 mmol) and EDAC (232 mg; 1.2 mmol) was dissolved in a mixture of DCM (4.0 mL) and DMF (1.0 mL). The clear solution was stirred at ambient temperature for 1 hour. A solution of 3-amino-2(R)-methoxypropionic acid methyl ester hydrochloride (257 mg, 1.5 mmol) in DCM (2.0 mL) and DMF (0.2 mL) was added followed by diisopropylethylamine (515 μL). The mixture was stirred at room temperature overnight, then diluted with DCM (40 mL) and washed once with a mixture of saturated sodium chloride/water (1:2). The organic phase was dried with anhydrous sodium sulphate and taken to dryness in vacuo.

Step 4

The oil was dissolved in a mixture of THF (4.0 mL) and methanol (4.0 mL). 4 N Aqueous sodium hydroxide was added (625 μL, 2.5 mmol) and the mixture was stirred at room temperature for 2 hours. The pH was adjusted to 3.0 with 1 N hydrochloric acid, then solvent was removed. The product was re-dissolved in ethyl acetate (20 mL) and washed once with water (20 mL). The water phase was back-extracted once with ethyl acetate (10 mL) and the combined organic extracts were washed with sodium chloride (2×20 mL) and dried over anhydrous sodium sulphate. After removal of solvent, 230 mg (67%) of pure title compound was obtained.

$^1$H-NMR (DMSO-d$_6$): δ 12.90 (bs, 1H), 8.55 (s, 1H), 8.54 (t, 1H), 7.76 (d, 2H), 7.63 (s, 2H), 7.41 (d, 2H), 7.34 (d, 2H), 7.20 (d, 2H), 7.15 (s, 1H), 6.18 (s, 1H), 4.95 (s, 2H), 3.90 (dd, 1H), 3.57 (m, 1H), 3.42 (m, 1H), 3.29 (s, 3H), 2.34 (m, 2H), 2.16 (m, 2H), 1.70 (m, 2H), 1.59 (m, 2H); HPLC-MS (method B): m/z=596.2 (M+1); R$_t$=5.93 min.

Example 32

General Procedure (A)

3-(4-{3-(3,5-Dichlorophenyl)-1-[4-(2-methylcyclohex-1-enyl)phenyl]ureidomethylbenzoyl-amino)-2-(R)-hydroxypropionic acid and (R S)-3-(4-{3-(3,5-dichlorophenyl)-1-[4-(6-methylcyclohex-1-enyl)phenyl]ureidomethyl}benzoylamino)-2-(R)-hydroxypropionic Acid

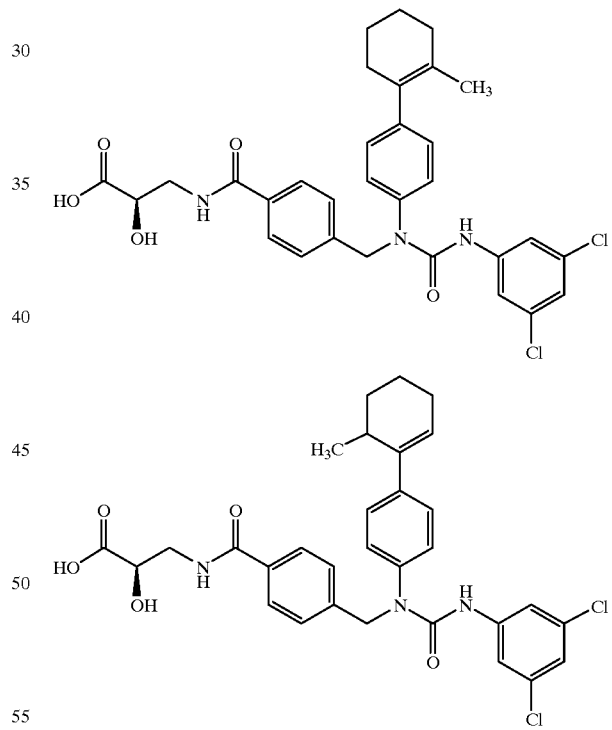

Using the mixture of 4-(2-methylcyclohex-1-enyl)aniline and (R,S)-4-(6-methylcyclohex-1-enyl)aniline (building block 11) and (R)-3-amino-2-hydroxypropionic acid methyl ester (building block 5) according to the general procedure (A) the title compounds was obtained.

(R,S)-3-(4-{3-(3,5-Dichlorophenyl)-1-[4-(6-methylcyclohex-1-enyl)phenyl]ureidomethyl}-benzoylamino)-2(R)-hydroxypropionic acid:

$^1$H-NMR (DMSO-d$_6$): δ 1.55 (s, 3H), 1.63 (bs, 4H), 2.03 (bs, 2H), 2.19 (bs, 2H), 3.47 (dm, 2H), 4.16 (m, 1H), 4.96

(s, 2H), 5.49 (bs, 1H), 7.15 (m, 5H), 7.33 (d, 2H), 7.61 (s, 2H), 7.78 (d, 2H), 8.45 (t, 1H), 8.65 (s, 1H), 12.53 (bs, 1H); M.p.: 105–107° C; HPLC-MS (Method B): m/z=596 (M+); R,=5.34 min.

3-(4-{3-(3,5-Dichlorophenyl)-1-[4-(6-methylcyclohex-1-enyl)phenyl]ureidomethyl}benzoyl-amino)-2(R)-hydroxypropionic acid:

$^1$H-NMR (DMSO-d$_6$): δ 0,90 (ds, 3H), 1.63 (bs, 4H), 2.03 (bs, 2H), 2.19 (bs, 2H), 3.47 (dm, 2H), 4.16 (m, 1H), 4.96 (s, 2H), 5.49 (bs, 1H), 5.93 (t, 1H), 7.15 (m, 5H), 7.33 (d, 2H), 7.61 (s, 2H), 7.78 (d, 2H), 8.45 (t, 1H), 8.62 (s, 1H), 12.53 (bs, 1H).

Example 33

General Procedure (A)

3-}4-[1-[4-(4-tert-Butylcyclohex-1-enyl)phenyl]-3-(3,5-dichlorophenyl)ureidomethyl]benzoyl-amino}-2-(R)-hydroxypropionic Acid

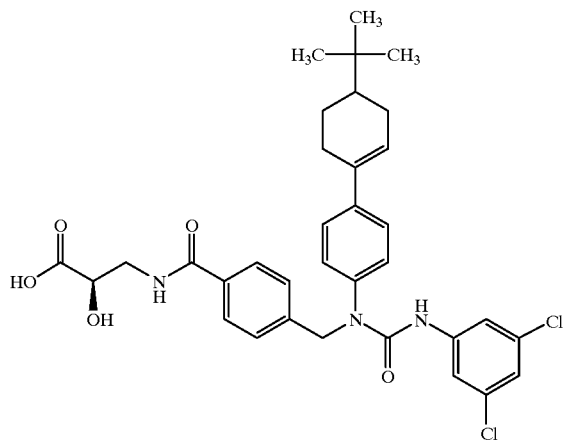

Using 4-(4-tert-butylcyclohex-1-enyl)aniline (building block 12) and (R)-3-amino-2-hydroxypropionic acid methyl ester (building block 5) according to the general procedure (A) the title compound was obtained.

$^1$H-NMR (DMSO-d$_6$): δ 0,88 (s, 9H), 1.23 (m, 2H), 1.93(m, 2H), 2.27 (m, 3H), 3.47 (dm, 2H), 4.16 (dd, 1H), 4.95 (s, 2H), 6.19 (m, 1H), 7.13 (m1H), 7.18 (d, 2H), 7.33 (d, 2H), 7.39 (d, 2H), 7.62 (s, 2H), 7.77 (d, 2H), 8.44 (t, 1H), 8.55 (s, 1H), 12.53 (bs, 1H); M.p.: 151–155° C.; HPLC-MS (Method B): m/z=638 (M$^+$); R$_t$=6,04 min.

Example 34

General Procedure (A)

(R,S)-3-(4-(3-(3,5-Dichlorophenyl)-1-(4-(5-methylcyclohex-1-enyl)phenyl)ureidomethyl)-benzoylamino)-2-hydroxypropionic acid and (R,S)-3-(4-(3-(3,5-dichlorophenyl)-1-(4-(3-methylcyclohex-1-enyl)phenyl)ureidomethyl) benzoylamino)-2-hydroxypropionic Acid

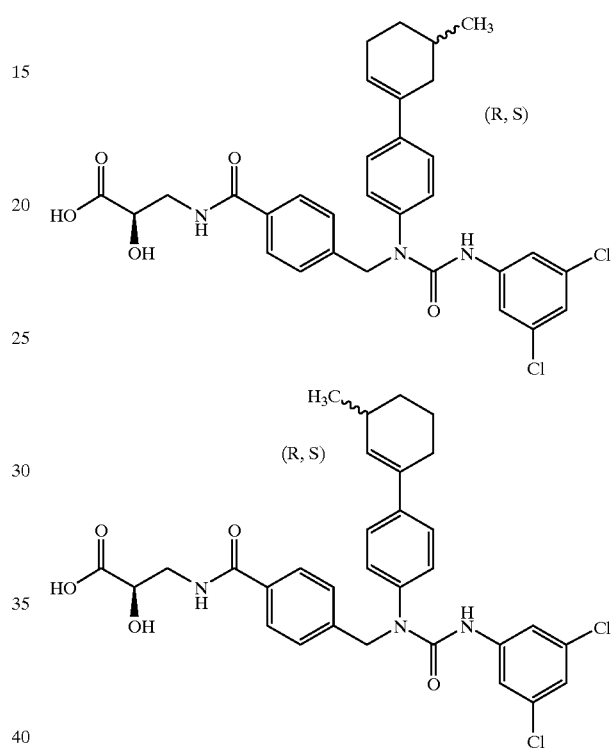

Using the mixture of (R,S)-4-(5-methylcyclohex-1-enyl) aniline and (R,S)-4-(3-methylcyclohex-1-enyl)aniline (building block 13) according to the general procedure (A) gave a mixture (6:4) of the title compounds.

(R,S)-3-(4-(3-(3,5-Dichlorophenyl)-1-(4-(5-methylcyclohex-1-enyl)phenyl)ureidomethyl)-benzoylamino)-2-hydroxypropionic acid:

$^1$H-NMR (200 MHz, DMSO-d$_6$): δ 1.02 (d, 3H), 1.15–1.24 (m, 1H), 1.61–1.96 (m, 3H), 2.14–2.44 (m, 3H), 3.40 (t, 2H), 3.47–3.62 (m, 1H), 4.10–4.19 (m, 1H), 4.95 (s, 2H), 6.16 (t, 1H), 7.14 (t, 1H), 7.17 (d, 2H), 7.34 (d, 2H), 7.39 (d, 2H), 7.61 (d, 2H), 7.76 (d, 2H), 8.44 (t, 1H), 8.56 (s, 1H), 12.08 (s br, 1H).

(R,S)-3-(4-(3-(3,5-Dichlorophenyl)-1-(4-(3-methylcyclohex-1-enyl)phenyl)ureidomethyl)-benzoylamino)-2-hydroxypropionic acid:

$^1$H-NMR (200 MHz, DMSO-d$_6$): δ1.02 (d, 3H), 1.15–1.24 (m, 1H), 1.61–1.96 (m, 3H), 2.14–2.44 (m, 3H), 3.40 (t, 2H), 3.47–3.62 (m, 1H), 4.10–4.19 (m, 1H), 4.95 (s, 2H), 6.04 (d, 1H), 7.14 (t, 1H), 7.17 (d, 2H), 7.34 (d, 2H), 7.39 (d, 2H), 7.61 (d, 2H), 7.76 (d, 2H), 8.44 (t, 1H), 8.53 (s, 1H), 12.08 (s br, 1H).

Example 35

3-{4-[3-[1(S)-(4-Chlorophenyl)ethyl]-1-(4-cyclohexylphenyl)ureidomethyl]benzoylamino}-2(R)-hydroxypropionic Acid

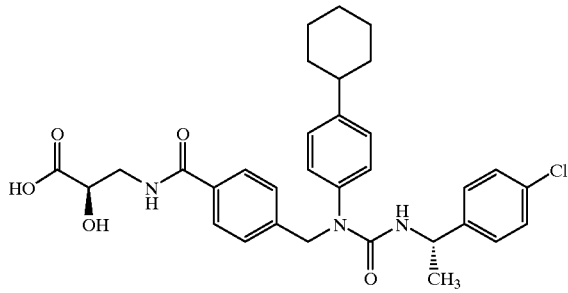

4-[(4-Cyclohexylphenylamino)methyl]benzoic acid methyl ester

Methyl 4-formylbenzoate (47 g, 285 mmol) was dissolved in methanol (400 mL) and a solution of 4-cyclohexylaniline (50 g, 0.285 mmol) in methanol (200 mL) is slowly added with mechanical stirring. More methanol (1 L) was added and the suspension was stirred at room temperature for 3 days. Filtration, washing and drying in vacuo afforded 90.7 g (99%) of 4-[(4-cyclohexylphenylimino)methyl]benzoic acid methyl ester. This was dissolved in N-methylpyrrolidone (855 mL) and methanol (45 mL). With mechanical stirring sodium borohydride pellets (42.4 g, 1.12 mol) was added in portions keeping the temperature below 40° C. The mixture was then stirred at room temperature for 2 hours and at 40° C. for 16 hours. The mixture was cooled to 5° C. and water (2 L) was slowly added. Then acetone (350 mL) was added and the mixture was stirred at 5° C. for 1 hour. Filtration, washing with water (2×500 mL) and drying in vacuo afforded 78 g (86%) of 4-[(4-cyclohexylphenylamino)-methyl]benzoic acid methyl ester as a solid.

$^1$H-NMR (CDCl$_3$): δ 1.2–1.4 (5H, m), 1.7–1.85 (5H, m), 2.39 (1H, m), 3.97 (3H, s), 4.04 (1H, bs), 4.39 (2H, s), 6.55 (2H, d), 7.01 (2H, d), 7.44 (2H, d), 8.00 (2H, d).

N-Chlorocarbamoyl-4-[(4-cyclohexylphenylamino)methyl]benzoic Acid Methyl Ester

4-[(4-Cyclohexylphenylamino)methyl]benzoic acid methyl ester (75 g, 0.23 mol) was dissolved in THF (750 mL). Diisopropylethylamine (56.0 mL, 0.32 mmol) and 4-dimethylaminopyridine (1.0 g; 8.1 mmol) were added. The solution was cooled to 5° C. Bis(trichloromethyl)-carbonate (28.0 g, 0.093 mol) was added in small portions while maintaining the internal reaction temperature below 10° C. The mixture was stirred for a further 2 hours at 10° C., and then transferred to a separatory funnel. Ethyl acetate (800 mL) and water (1000 mL) were added. After mixing, the organic layer was separated, dried with anhydrous sodium sulfate, and concentrated to dryness by rotary evaporation in vacuo. The product was obtained quantitatively as a stable hard crystalline material.

$^1$H-NMR (CDCl$_3$): δ 7.92 (d, 2H); 7.40 (d, 2H); 7.25 (d, 2H); 7.17 (d, 2H); 4.98 (s, 2H); 3.83 (s, 3H); 2.5 (m, 1H); 1.65–1.80 (m, 5H); 1.15–1.40 (m, 5H).

N-Chlorocarbamoyl-4-[(4-cyclohexylphenylamino)methyl]benzoic Acid Methyl Ester

4-[(4-Cyclohexylphenylamino)methyl]benzoic acid methyl ester (75 g, 0.23 mol) was dissolved in THF (750 mL). Diisopropylethylamine (56.0 mL, 0.32 mmol) and 4-dimethylamino-pyridine (1.0 g, 8.1 mmol) were added. The solution was cooled to 5° C. Bis(trichloromethyl)-carbonate (28.0 g, 0.093 mol) was added in small portions while maintaining the internal reaction temperature below 10° C. The mixture was stirred for a further 2 hours at 10° C., and then transferred to a separatory funnel. Ethyl acetate (800 mL) and water (1000 mL) were added. After mixing, the organic layer was separated, dried with anhydrous sodium sulphate, and concentrated to dryness by rotary evaporation in vacuo. The product was obtained quantitatively as a stable hard crystalline material.

$^1$H-NMR (CDCl$_3$): δ 7.92 (d, 2H), 7.40 (d, 2H), 7.25 (d, 2H), 7.17 (d, 2H), 4.98 (s, 2H), 3.83 (s, 3H), 2.5 (m, 1H), 1.65–1.80 (m, 5H), 1.15–1.40 (m, 5H).

4-[3-[1(S)-(4-Chlorophenyl)ethyl]-1-(4-cyclohexylphenyl)ureidomethyl]benzoic acid methyl ester A 2 L reaction flask equipped with mechanical stirring was charged with N-chlorocarbamoyl-4-[(4-cyclohexylphenylamino)methyl]benzoic acid methyl ester (94 g, 0.244 mol), N-methyl-2-pyrrolidinone (1.0 L) and triethylamine (68 mL, 0.487 mol). To the clear solution was added drop wise (S)-1-(4-chlorophenyl)ethylamine (38.0 g, 0.244 mol), keeping the internal reaction temperature below 30° C. Stirring was continued for 2 hours, then the reaction mixture was partitioned between water (1.0 L) and ethyl acetate (1.0 L). After extensive mixing, the organic layer was separated, and washed with a 5% aqueous solution of citric acid (500 mL), and saturated ammonium chloride (500 mL), before drying with anhydrous sodium sulphate. Solvent was removed, and the residual oil was evaporated once from acetonitrile. This product was sufficiently pure for further synthesis. Yield: 103 g (84%).

$^1$H-NMR (DMSO-d$_6$): δ 7.88 (d, 2H), 7.32 (d, 2H), 7.30 (d, 4H), 7.19 (d, 2H), 7.08 (d, 2H), 6.28 (d, 1H), 4.88 (dd, 2H), 4.76 (m, 1H), 3.81 (s, 3H), 2.44 (m, 1H), 1.65–1.80 (m, 5H), 1.15–1.40 (m, 5H); HPLC-MS (method B): m/z=505 (M+1); R$_t$=6.17 min.

4-[3-[1(S)-(4-Chlorophenyl)ethyl]-1-(4-cyclohexylphenyl)ureidomethyl benzoic Acid 4-[3-[1(S)-(4-Chlorophenyl)ethyl]-1-(4-cyclohexylphenyl)ureidomethyl]benzoic acid methyl ester (35.0 g, 69.3 mmol) was dissolved in ethanol (400 mL). 4 N aqueous sodium hydroxide (100 mL) was added and the clear solution was stirred at room temperature for 3 hours. The solution was neutralised with 4 N hydrochloric acid (100 mL), and placed upon an ice bath to initiate crystallization. The crystals were collected, washed extensively with water, and dried in vacuo overnight. Yield: 34.25 g (100%).

$^1$H-NMR (DMSO-d$_6$): δ 12.85 (bs, 1H), 7.85 (d, 2H), 7.32 (d, 2H), 7.30 (d, 4H), 7.19 (d, 2H), 7.08 (d, 2H), 6.27 (d, 1H), 4.85 (m, 3H), 2.45 (m, 1H), 1.65–1.80 (m, 5H), 1.15–1.40 (m, 5H); HPLC-MS (method B): m/z=491 (M+1); R$_t$=5.50 min.

3-{4-[3-[1(S)-(4-Chlorophenyl)ethyl]-1-(4-cyclohexylphenyl)ureidomethyl]benzoylamino}-2(R)-hydroxypropionic Acid Methyl Ester 4-[3-[1(S)-(4-Chlorophenyl)ethyl]-1-(4-cyclohexylphenyl)ureidomethyl]benzoic acid (200 mg, 0.4 mmol), HOBt (75 mg, 0.5 mmol), and EDAC (94 mg, 0.5 mmol) were dissolved in a mixture of DMF (200 µL) and DCM (2 mL). The clear solution was stirred at room temperature for 90 min. A solution of R-isoserine methyl ester hydrochloride (95 mg, 0.6 mmol) in a mixture of DCM (1.0 mL) and DMF (0.4 mL) was added, and the reaction mixture was left stirring at ambient temperature overnight.

The reaction mixture was partitioned between DCM (20 mL) and water (20 mL). The organic phase was separated and washed with a mixture of brine and water (1:2), dried with anhydrous sodium sulphate and evaporated to dryness. The residue was subsequently evaporated from acetonitrile, to give a quantitative yield of title material.
$^1$H-NMR (DMSO-d$_6$): δ 8.48 (t, 1H), 7.73 (d, 2H), 7.34 (d, 2H), 7.30 (d, 2H), 7.24 (d, 2H), 7.18 (d, 2H), 7.08 (d, 2H), 6.27 (d, 1H), 5.70 (d, 1H), 4.34 (m, 1H), 4.32 (d, 2H), 4.22 (q, 1H), 3.62 (s, 3H), 3.52 (m, 1H), 3.40 (m, 1H), 1.65–1.80 (m, 5H), 1.10–1.40 (m, 9H).

3-{4-[3-[1(S)-(4-Chlorophenyl)ethyl]-1-(4-cyclohexylphenyl)ureidomethyl]benzoylamino}-2 (R)-hydroxypropionic acid 3-{4-[3-[1(S)-(4-Chlorophenyl)ethyl]-1-(4-cyclohexylphenyl)ureidomethyl]benzoylamino}-2(R)-hydroxypropionic acid methyl ester (280 mg, 0.473 mmol) was dissolved in a mixture of THF (2.5 mL) and methanol (2.5 mL) and 4 N aqueous sodium hydroxide (0.355 mL) was added. The reaction mixture was stirred at room temperature for 2 hours. The pH was adjusted to 3.0 by addition of 1 N hydrochloric acid. Solvent was removed by rotary evaporation in vacuo and the residue re-dissolved in ethyl acetate (10 mL). The organic phase was washed twice with water and once with brine, and then concentrated to dryness in vacuo leaving the title compound as a powder. Yield: 168 mg (89%).
$^1$H-NMR (DMSO-d$_6$): δ 8.46 (t, 1H), 7.75 (d, 2H), 7.35 (d, 2H), 7.31 (d, 2H), 7.25 (d, 2H), 7.19 (d, 2H), 7.08 (d, 2H), 6.28 (d, 2H), 4.85 (m, 1H), 4.80 (d, 2H), 4.15 (m, 1H), 3.55 (m, 1H), 3.40 (m, 1H), 1.65–1.80 (m, 5H), 1.10–1.40 (m, 9H); HPLC-MS (method B): m/z=579 (M+1); R$_t$=5.27 min.

Example 36

3-{4-[3-Biphenyl-2-ylmethyl-1-(4-cyclohexylphenyl)ureidomethyl]benzoylamino}-2 (R)-hydroxypropionic Acid

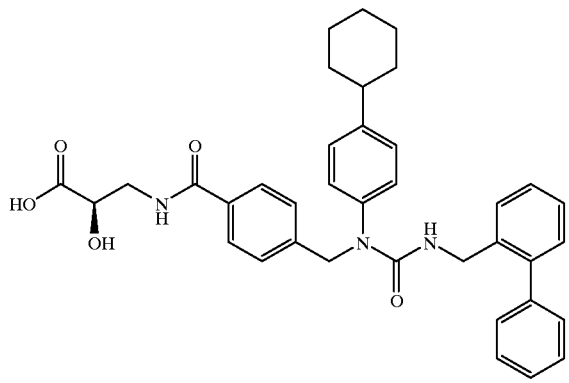

This compound was prepared similarly as described in example 35 from N-chlorocarbamoyl-4-[(4-cyclohexylphenylamino)methyl]benzoic acid methyl ester and biphenyl-2-ylmethylamine followed by hydrolysis of the benzoic acid methyl ester, coupling with (R)-isoserine ethyl ester hydrochloride. Hydrolysis afforded the title compound.
$^1$H-NMR (DMSO-d$_6$): δ 12.6 (s, 1H), 8.45 (t, 1H), 7.78 (d, 2H), 7.45–7.20 (m, 14H), 7.05 (d, 2H), 6.10 (t, 1H), 5.50 (bs, 1H), 4.85 (s, 2H), 4.2 (m, 3H), 3.55 (m, 1H), 2.45 (m, 1H), 1.85–1.70 (m, 5H), 1.40–1.20 (m, 6H); HPLC-MS (method B): m/z=606 (M+1); R$_t$=5.08 min.

General procedure (B) for Solution Phase Synthesis of Compounds of the General Formulae (Ia) and (Ib):

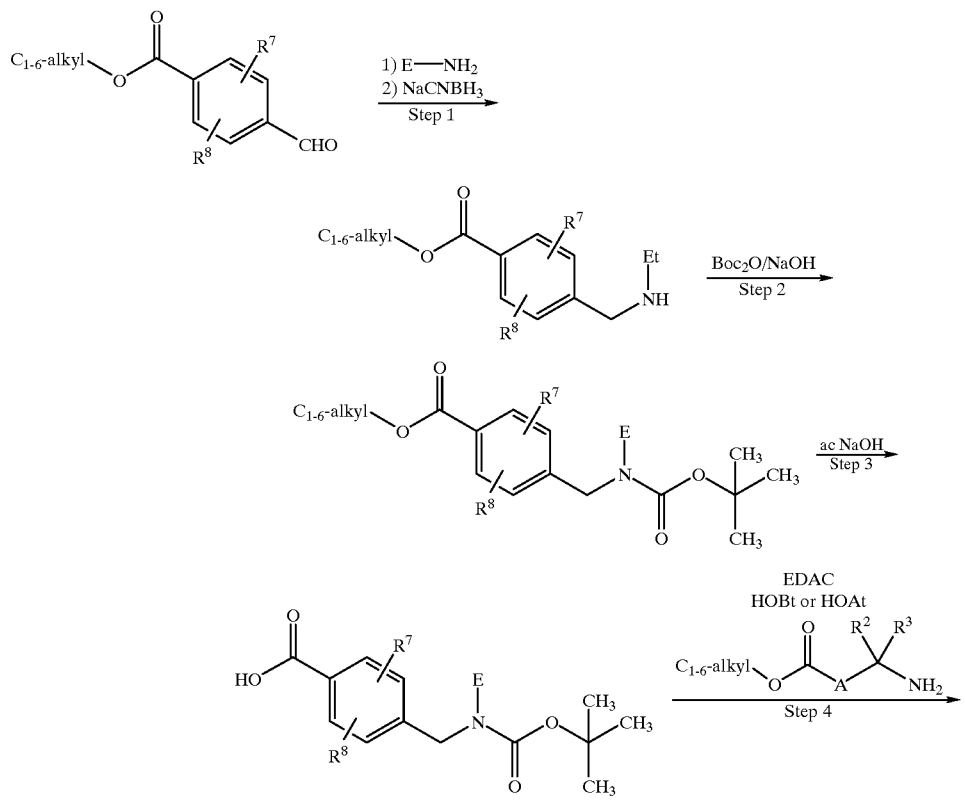

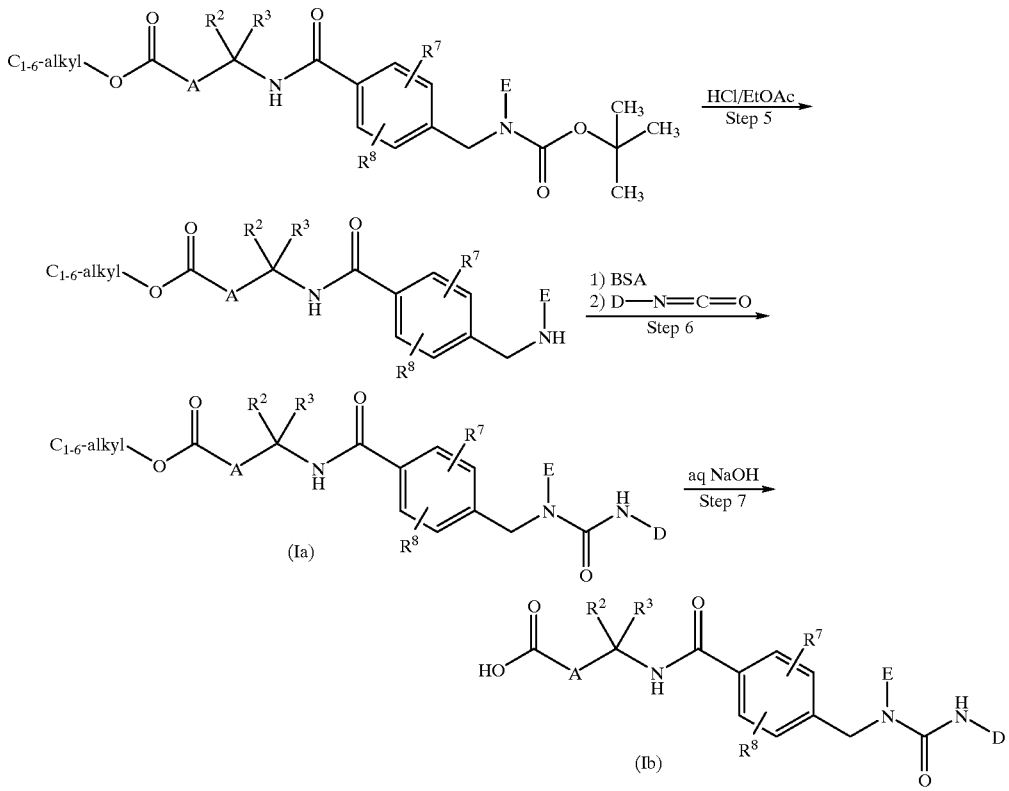

wherein R², R³, R⁷, R⁸, A, E and D are as defined for formula (I).

When A is —CHOH— step 6 is performed using 1) BSA and 2) D—N=C=O. Otherwise, step 6 is performed using only D—N=C=O.

The procedure is illustrated further in the following examples.

Example 37

General Procedure (B)

(R)-3-{4-[3-(4-Cyano-3-trifluoromethylphenyl)-1-(4-cyclohexylphenyl)ureidomethyl]benzoyl-amino}-2-hydroxypropionic acid

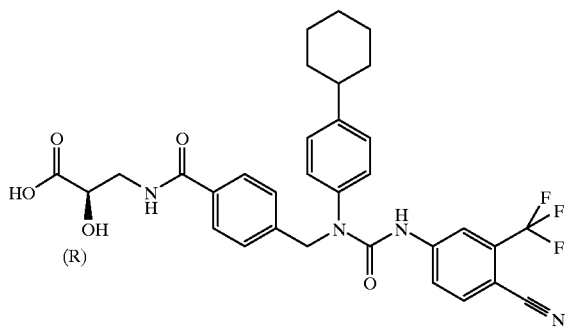

Step 1 is performed using the same method as in general procedure (A).

Step 2: 4-{[tert-Butoxycarbonyl-(4-cyclohexylphenyl)amino}methyl]benzoic acid methyl ester 4-((4-Cyclohexylphenylamino)methyl)benzoic acid methyl ester (2.0 g, 6.18 mmol) was suspended in sodium hydroxide (1 N, 6.18 mL) and a solution of di-tert-butyldicarbonate (1.67 g, 7.42 mmol) in THF (10 mL) was added dropwise. The reaction mixture was stirred overnight and was concentrated in vacuo to a solid residue, which was redissolved in diethyl ether (50 mL) and washed with water (25 mL) added sodium hydroxide (1.3 mL, 1 N). The aqueous phase was extracted again with diethyl ether (25 mL) at pH 11–12. The combined organic phases were washed with sodium hydrogen sulphate (30 mL, 10%) and water (3×20 mL), dried with magnesium sulphate and concentrated in vacuo. Crystallisation from ethyl acetate and n-heptane afforded 1.98 g of 4-{[tert-butoxycarbonyl-(4-cyclohexylphenyl)amino]methyl}-benzoic acid methyl ester.

$^1$H-NMR (DMSO-$d_6$): δ 1.13–1.44 (m, 14H), 1.63–1.81 (m, 5H), 2.46 (m, 1H), 3.83 (s, 3H), 4.88 (s, 2H), 7.12 (m, 4H), 7.48 (d, 2H), 7.92 (d, 2H); HPLC-MS (Method B): m/z=424 (M+1); $R_t$=9.10 min; M.p. 99.5–101.0° C.

Microanalysis: Calculated for $C_{26}H_{33}NO_4$:
C, 73.73%; H, 7.85%; N, 3.31%. Found:
C, 73.30%; H, 8.07%; N, 3.26%.

Step 3: 4-{[tert-Butoxycarbonyl-(4-cyclohexylphenyl)amino}methyl]benzoic acid

4-{[tert-Butoxycarbonyl-(4-cyclohexylphenyl)amino]methyl}benzoic acid methyl ester was suspended in ethanol (30 mL) and sodium hydroxide (4 N, 8.1 mL) was added. The reaction mixture was stirred overnight. The mixture was concentrated to dryness, suspended in water (100 mL), acidified with hydrochloric acid (8.5 mL, 4 N) and extracted with ethyl acetate (100 mL). The aqueous phase was extracted once more with ethyl acetate (30 mL) and the combined organic phases were washed with water (3×50 mL), dried with magnesium sulphate and concentrated in vacua. The residue was crystallised from a mixture of ethyl acetate and n-heptane to afford 1.75 g of 4-{[tert-butoxycarbonyl-(4-cyclohexylphenyl)amino]methyl}-benzoic acid.
$^1$H-NMR (CDCl$_3$-d$_6$): δ 1.18–1.42 (m, 14H), 1.68–1.87 (m, 5H), 2.46 (m, 1H), 4.88 (s, 2H), 7.10 (m, 4H), 7.47 (d, 2H), 8.07 (d, 2H); HPLC-MS (Method B): m/z=410 (M+1); R$_t$=8.15 min; M.p. 192.5–194.5° C.
Microanalysis: Calculated for C$_{25}$H$_{31}$NO$_4$:
C, 73.32%; H, 7.63%; N, 3.42%. Found:
C, 73.03%; H, 7.86%; N, 3.36%.

Step 4: (R)-3-(4-{[tert-Butoxycarbonyl-(4-cyclohexylphenyl)amino}methyl]benzoylamino)-2-hydroxypropionic Acid Methyl Ester 4-{[tert-Butoxycarbonyl-(4-cyclohexylphenyl)amino]methyl}benzoic acid was dissolved in DMF (10 mL) and HOBt (0.40 g, 2.93 mmol) and EDAC (0.52 g, 2.73 mmol) were added. The reaction mixture was stirred for 45 min. Then a solution of (R)-3-amino-2-hydroxypropionic acid methyl ester in DMF (8 mL) and diisopropylethylamine (0.46 mL) were added. The mixture was stirred overnight. The reaction mixture was diluted with water (40 mL) and extracted with ethyl acetate (75 mL). The aqueous phase was extracted with ethyl acetate (30 mL). The combined organic phases were washed with hydrochloric acid (0.2 N, 3×30 mL), water: saturated sodium chloride (3×30 mL), dried with magnesium sulphate and concentrated in vacua. The residue was purified by column chromatography on silica gel (100 g) using mixtures of ethyl acetate and n-heptane (1 L (1:1) and 0.5 L (7:3)) as eluents to afford 0.77 g (R)-3-(4-{[tert-butoxycarbonyl-(4-cyclohexylphenyl)amino]methyl}benzoylamino)-2-hydroxypropionic acid methyl ester.
$^1$H-NMR (DMSO-d$_6$): δ 1.16–1.41 (m, 14H), 1.63–1.81 (m, 5H), 2.46 (m, 1H), 3.42 (m, 1H), 3.54 (m, 1H), 3.62 (s, 3H), 4.24 (m, 1H), 4.84 (s, 2H), 5.70 (d, 1H), 7.12 (m, 4H), 7.28 (d, 2H), 7.78 (d, 2H), 8.51 (t, 1H); HPLC-MS (Method B): m/z=511 (M+1); R$_t$=7.63 min.

Step 5: (R)-3-{4-[(4-Cyclohexylphenylamino)methyl]benzoylamino}-2-hydroxypropionic Acid Methyl Ester (R)-3-(4-{[tert-Butoxycarbonyl-(4-cyclohexylphenyl)amino]methyl}benzoylamino)-2-hydroxypropionic acid methyl ester was dissolved in ethyl acetate (10 mL) and dry hydrogen chloride in ethyl acetate (3 M, 10 mL) was added. The mixture was stirred at room temperature for 2 hours and concentrated in vacuo. The residue was suspended in ethyl acetate (15 mL) and concentrated. This was repeated twice. The residue was then suspended in ethyl acetate (10 mL) and placed at 5° C. overnight. The precipitate was filtered and washed with ice-cooled ethyl acetate and dried in vacuo to afford 0.62 g of (R)-3-{4-[(4-cyclohexylphenylamino)-methyl]benzoylamino}-2-hydroxypropionic acid methyl ester.
$^1$H-NMR (DMSO-d$_6$): δ 1.12–1.43 (m, 5H), 1.63–1.82 (m, 5H), 2.45 (m, 1H), 3.42 (m, 1H), 3.53 (m, 1H), 3.60 (s, 3H), 4.25 (t, 1H), 4.48 (s, 2H), 7.18 (m, 4H), 7.57 (d, 2H), 7.82 (d, 2H), 8.58 (t, 1H); HPLC-MS (Method B): m/z=411 (M+1); R$_t$=4.93 min.

Step 6: (R)-3{-4-[3-(4-Cyano-3-trifluoromethylphenyl)-1-(4-cyclohexylphenyl)ureidomethyl]-benzoylamino}-2-hydroxypropionic Acid Methyl Ester 5-Amino-2-cyanobenzotrifluoride (0.07 g, 0.36 mmol) was dissolved in ethyl acetate (2 mL) and dry hydrogen chloride in ethyl acetate (3.5 M, 5.5 mL) was added. After 15 min the solution was concentrated to dryness and co-evaporated three times from toluene (3×5 mL). The residue was added toluene (2.5 mL) and flushed with nitrogen for about 10 min, before diphosgene (0.43 mL) was added. Then the mixture was gently refluxed for 1 hour under a nitrogen atmosphere. The mixture was cooled and concentrated to dryness in vacuo and then co-evaporated twice from toluene to remove excessive diphosgene to afford 4-cyano-3-trifluoromethylphenyl isocyanate.

(R)-3-{4-[(4-Cyclohexylphenylamino)methyl]benzoylamino}-2-hydroxypropionic acid methyl ester, hydrochloride (0.13 g, 0.3 mmol) was dissolved in DCM (5 mL) and BSA (0.22 mL, 0.9 mmol) added. The mixture was stirred for 0.5 hour, and diisopropylethylamine (0.052 mL, 0.3 mmol) was added. The reaction mixture was added to the isocyanate above and the reaction mixture stirred overnight. The reaction mixture was transferred to a separatory funnel and washed twice with water (10 mL), dried with magnesium sulphate and concentrated in vacuo.

The residue was purified by column chromatography (30 g) using ethyl acetate/n-heptane (4:6) (400 mL) and then ethyl acetate (200 mL) as eluents to afford 0.085 g of (R)-3-{4-[3-(4-cyano-3-trifluoromethylphenyl)-1-(4-cyclohexylphenyl)ureidomethyl]benzoylamino}-2-hydroxypropionic acid methyl ester.

$^1$H-NMR (DMSO-d$_6$): δ 1.12–1.44 (m, 6H), 1.66–1.82 (m, 5H), 3.41 (m, 1H), 3.53 (m, 1H), 3.60 (s, 3H), 4.22 (m, 1H), 4.47 (s, 2H), 5.69 (s, 1H), 7.21 (m, 4H), 7.33 (d, 2H), 7.76 (d, 2H), 7.98 (s, 2H), 8.14 (s, 1H), 8.48 (t, 1H), 9.1 (s, 1H); HPLC-MS (Method B): m/z=623 (M+1); R$_t$=6.02 min.

Step 7

(R)-3-{4-[3-(4-Cyano-3-trifluoromethylphenyl)-1-(4-cyclohexylphenyl)ureidomethyl]benzoyl-amino}-2-hydroxypropionic acid methyl ester (0.07 g, 0.124 mmol) was suspended in ethanol (3 mL) and sodium hydroxide (4 N, 0.19 mL, 0.742 mmol) was added. The reaction mixture was stirred for 1.5 hour, and concentrated to remove the ethanol. The residue was diluted with water (10 mL) and acidified with hydrochloric acid (4 N, 0.21 mL). The mixture was extracted with ethyl acetate (2×10 mL) and the combined organic phases were washed with water (3×10 mL), dried with magnesium sulphate and concentrated in vacuo to afford the title compound (0.68 g).

$^1$H-NMR (DMSO-d$_6$), δ 1.16–1.42 (m, 6H), 1.66–1.82 (m, 5H), 3.40 (m, 1H), 3.54 (m, 1H), 4.16 (m, 1H), 4.48 (s, 2H), 7.20 (m, 4H), 7.34 (d, 2H), 7.78 (d, 2H), 7.99 (s, 2H), 8.16 (s, 1H), 8.44 (t, 1H), 9.1 (s, 1H); HPLC-MS (Method B): m/z=609 (M+1); R$_t$=7.27 min.

Example 38

General Procedure (B)

(R)-3{-4[-3-(3-tert-Butylphenyl)-1-(4-cyclohexylphenyl)ureidomethyl]benzoylamino}-2-hydroxypropionic Acid

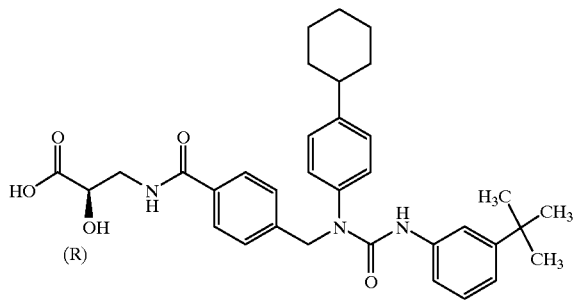

Step 6: (R)-3{-4-[3-(3-tert-Butylphenyl)-1-(4-cyclohexylphenyl)ureidomethyl]benzoylamino}-2-hydroxypropionic Acid Methyl Ester 3-(tert-Butyl)aniline (0.054 g, 0.36 mmol) was dissolved in ethyl acetate (2 mL) and added dry hydrogen chloride in ethyl acetate twice (3.5 M, 3 mL+2.5 mL). After 15 min the mixture was concentrated to dryness and co-evaporated three times from toluene (3×5 mL). The residue was added toluene (2.5 mL) and flushed with nitrogen for about 10 min, before diphosgene (0.43 mL) was added. Then the mixture was gently refluxed for 1 hour under a nitrogen atmosphere. The mixture was cooled and concentrated in vacuo. This was repeated twice to remove excess of diphosgene. The mixture was concentrated to dryness and coevaporated three times from toluene (5 mL each time). The residue was concentrated to dryness and co-evaporated twice from toluene. Then it was redissolved in toluene (2.5 mL) and flushed with nitrogen for about 10 min, before diphosgene (0.43 mL) was added. The mixture was gently refluxed under nitrogen for 1 hour. After cooling, the mixture was concentrated and co-evaporated twice from toluene to remove excess diphosgene to afford 3-tert-butyl-phenyl isocyanate.

(R)-3-{4-[(4-Cyclohexylphenylamino)methyl]benzoylamino}-2-hydroxypropionic acid methyl ester, hydrochloride (0.13 g, 0.3 mmol) was dissolved in DCM (5 mL) and BSA (0.22 mL, 0.9 mmol) was added. The mixture was stirred for 0.5 hour, and diisopropylethylamine (0.052 mL, 0.3 mmol) was added. The reaction mixture was added to the isocyanate above and stirred overnight. The reaction was transferred to a separatory funnel and washed twice with water (10 mL), dried with magnesium sulphate and concentrated in vacuo. The residue was purified by column chromatography on silica gel (30 g) using ethyl acetate and n-heptane (6:4) (400 mL) and then ethyl acetate (100 mL) as eluent to afford 0.12 g of (R)-3-{4-[3-(3-tert-butylphenyl)-1-(4-cyclohexylphenyl)ureidomethyl]benzoylamino}-2-hydroxypropionic acid methyl ester.

$^1$H-NMR (DMSO-d$_6$): δ 1.23 (s, 11H), 1.28–1.42 (m, 3H), 1.65–1.80 (m, 5H), 2.47 (m, 1H), 3.40 (m, 1H), 3.51 (m, 1H), 4.22 (m, 1H), 4.94 (s, 2H), 5.71 (d, 1H), 6.99 (d, 1H), 7.12–7.24 (m, 5H), 7.28 (d, 1H), 7.36 (d, 2H), 7.42 (s, 1H), 7.77 (d, 2H), 8.08 (s, 1H), 8.50 (t, 1H); HPLC-MS (Method B): m/z=(585+1); R$_t$=8.30 min.

Step 7

(R)-3-{4-[3-(3-tert-Butylphenyl)-1-(4-cyclohexylphenyl)ureidomethyl]benzoylamino}-2-hydroxypropionic acid methyl ester (0.11 g, 0.188 mmol) was dissolved in ethanol (4 mL) and sodium hydroxide (4 N, 0.28 mL, 1.128 mmol) was added. The reaction was stirred for 1.5 hour and concentrated in vacuo to remove the ethanol. The residue was diluted with water (10 mL), acidified with hydrochloric acid (4 N, 0.3 mL) and extracted with ethyl acetate (2×10 mL). The combined organic phases were washed with water (3×10 mL) and dried with magnesium sulphate and concentrated in vacuo to afford the title compound (0.10 g).

$^1$H-NMR (DMSO-d$_6$): δ 1.23 (s, 9H), 1.28–1.42 (m, 4H), 1.65–1.81 (m, 5H), 2.47 (m, 1H), 3.38 (m, 1H), 3.55 (m, 1H), 4.16 (m, 1H), 4.94 (s, 2H), 7.00 (d, 1H), 7.11–7.24 (m, 6H), 7.28 (d, 1H), 7.35 (d, 1H), 7.41 (s, 1H), 7.80 (d, 2H), 8.10 (s, 1H), 8.46 (t, 1H); HPLC-MS (Method B): m/z=572 (M+1); R$_t$=7.78 min.

Example 39

General Procedure (B)

(R)-3-{4-[1-(4-Cyclohexylphenyl)-3-(3-hydroxymethyl-4-trifluoromethoxyphenyl)ureidomethyl]-benzoylamino}-2-hydroxypropionic Acid

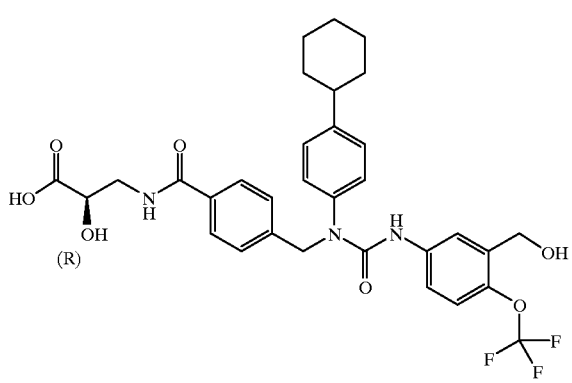

Preparation of 3-(tert-butyldimethylsilanyloxymethyl)-4-trifluoromethoxyaniline to be Used in Step 6:

Fuming nitric acid (5 mL) was cooled on an ice bath. Methyl 2-(trifluoromethoxy)benzoate (5 g, 22.7 mmol) was slowly added within 30 min keeping the temperature below 15° C. The reaction was then stirred at 60° C. for 1 hour and 2 hours at room temperature. The mixture was poured on ice water whereupon an oil separated. The aqueous supernatant was decanted and additional water (50 mL) was added to the oil. After neutralisation with sodium hydrogen carbonate, the mixture was extracted with ethyl acetate (25 mL). The aqueous phase was extracted with ethyl acetate (15 mL) once more. The combined organic phases were washed with saturated sodium chloride (2×15 mL), dried (magnesium sulphate), and concentrated in vacuo to give 5.69 g of 5-nitro-2-trifluoromethoxybenzoic acid methyl ester.

$^1$H NMR (DMSO-d$_6$): δ 3.93 (3H, s), 7.82 (1H, d), 8.58 (1H, d), 8.67 (1H, s); HPLC-MS (method B): m/z: 266; R$_t$=6.0 min.

5-Nitro-2-trifluoromethoxybenzoic acid methyl ester (5.69 g, 21.5 mmol) was dissolved in ethanol 99.9% (80 mL) and stannous (II) chloride dihydrate (24.2 g, 107 mmol) was added. The suspension was stirred on an oil-bath at 75° C for 2 hours and concentrated in vacuo. Ethyl acetate (100 mL) and water (50 mL) was added and pH was adjusted to pH 8 with 4 N sodium hydroxide (50 mL). The liquid was decanted from the precipitation. The precipitate was washed twice with ethyl acetate. The aqueous phase was extracted twice with ethyl acetate (60 mL). The combined organic phases were washed with a saturated sodium chloride solution (2×100 mL), dried (magnesium sulphate) and concentrated in vacuo. Purification by column chromatography (120 g silica) using ethyl acetate and heptane (1:1) as eluent afforded 3.8 g of 5-amino-2-trifluoromethoxybenzoic acid methyl ester.

$^1$H NMR (DMSO-d$_6$): δ 3.82 (3H, s), 5.63 (2H, s), 6.79 (1H, d), 7.07 (1H, s), 7.11 (1H, d); HPLC-MS (method B): m/z: 236, R$_t$=4.6 min.

5-Amino-2-trifluoromethoxybenzoic acid methyl ester (3.0 g, 12.8 mmol) was dissolved in THF (20 mL) in a three-necked flask equipped with a thermometer and an addition funnel under nitrogen. Under stirring and ice-cooling lithium aluminum hydride (1 M in THF, 15 mL) was added dropwise within 10 minutes. Stirring was continued at room temperature for 1 hr, and the reaction was concentrated in vacuo. The residue was suspended in DCM (150 mL) and water (50 mL), then filtered through celite, washed with DCM and water. The filtrate was separated, and the water phase was extracted once more with DCM (30 mL). The combined organic phases were washed with water (2×20 mL), dried (magnesium sulphate) and concentrated in vacuo to give 2.47 g of (5-amino-2-trifluoromethoxyphenyl)methanol.

$^1$H NMR (DMSO-d$_6$): δ 3.92 (2H, d), 5.18 (1H, t), 5.28 (2H, s), 6.45 (1H, d), 6.91 (1H, d); HPLC-MS (method B): m/z: 208, R$_t$=7.2 min.

5-Amino-2-trifluoromethoxyphenyl)methanol (1.2 g, 5.8 mmol) was dissolved in DMF (5 mL) and imidazole (0.48 g, 7.1 mmol) and tert-butyldimethylsilyl chloride (0.99 g, 6.6 mmol) were added. The reaction mixture was stirred for 16 hours and water (20 mL) was added. The mixture was extracted with ethyl acetate (2×50 mL) and the combined organic phases were washed with water (10 mL), citric acid (10 mL, 10%) and water (2×10 mL), dried (magnesium sulphate) and concentrated in vacuo. The residue was purified by column chromatography (110 g, silica) using ethyl acetate and heptane (1:3) as eluent to give 1.2 g of 3-(tert-butyldimethylsilanyloxymethyl)-4-trifluoromethoxyaniline.

$^1$H NMR (DMSO-d$_6$): δ 0.82 (9H, s), 3.25 (6H, s), 4.52 (2H, s), 5.23 (2H, s), 6.41 (1H, d), 6.61 (1H, s), 6.86 (1H, d); HPLC-MS (method B): m/z: 322; R$_t$=7.17 min.

Step 6: (R)-3-{4-[3-[3-(tert-Butyldimethylsilanyloxymeth(l)-4-trifluoromethoxyphenyl-(4-cyclohexylphenyl]ureidomethyl]benzoylamino}-2-hydroxypropionic Acid Methyl Ester Bis(trichloromethyl)carbonate (triphosgene) (0.09 g, 0.31 mmol) was dissolved in DCM (2 mL) and cooled in an ice-bath under nitrogen. 3-(tert-Butyldimethylsilanyloxymethyl)-4-trifluoromethoxyaniline (0.3 g, 0.93 mmol) was evaporated twice from toluene to remove any moisture and then dissolved in DCM (2 mL) and diisopropylethylamine (0.32 mL) was added. This solution was added to the cooled triphosgene solution and the mixture was stirred at 20° C. for 2.5 hours. (R)-3-{4-[(4-Cyclohexylphenylamino)methyl]benzoylamino}-2-hydroxypropionic acid methyl ester hydrochloride (0.37 g, 0.83 mmol) was evaporated twice from toluene and dissolved in DMF (3 mL) and diisopropylethylamine (0.141 mL, 0.83 mmol) was added. The solution was added to the isocyanate above and, with stirring, heated at 80° C under nitrogen for 2 hours. The reaction mixture was evaporated in vacuo and the residue was extracted with DCM (80 mL), aqueous citric acid (10%, 25 mL). The aqueous phase was extracted with DCM (30 mL). The combined organic phases were washed with aqueous citric acid (10%, 3×25 mL), dried with magnesium sulphate and evaporated in vacuo. The residue was purified by column chromatography on silica gel (58 g) using ethyl acetate and n-heptane (940 mL, 1:1 and 300 mL ethyl acetate) as eluent to afford 0.03 g of (R)-3-{4-[3-[3-(tert-butyldimethylsilanyloxymethyl)-4-trifluoromethoxyphenyl]-1-(4-cyclohexylphenyl)ureidomethyl]benzoylamino}-2-hydroxypropionic acid methyl ester.

HPLC-MS (Method B): m/z=758 (M+1); R$_t$=9.57 min.

Step 7

(R)-3-{4-[3-[3-(tert-butyldimethylsilanyloxymethyl)-4-trifluoromethoxyphenyl]-1-(4-cyclohexyl-phenyl)ureidomethyl]benzoylamino}-2-hydroxypropionic acid methyl ester (24 mg, 0.032 mmol) was dissolved in ethanol (1 mL) and sodium hydroxide (0.05 mL, 019 mmol) was added. The reaction mixture was stirred for 2 hours and concentrated to remove the ethanol. The residue was diluted with water (10 mL), acidified with hydrochloric acid (4 N, 0.3 mL) and extracted with ethyl acetate (2×10 mL). The combined organic phases were washed with water (3×10 mL) and dried with magnesium sulphate and concentrated in vacuo to give 17 mg of (R)-3-{4-[3-[3-(tert-butyldimethylsilanyloxymethyl)-4-trifluoromethoxyphenyl]-1-(4-cyclohexylphenyl)ureidomethyl]benzoylamino}-2-hydroxypropionic acid.

HPLC-MS (Method B): m/z=744 (M+1); R$_t$=9.35 min.

(R)-3-{4-[3-[3-(tert-Butyldimethylsilanyloxymethyl)-4-trifluoromethoxyphenyl]-1-(4-cyclohexyl-phenyl)ureidomethyl]benzoylamino}-2-hydroxypropionic acid (17 mg, 0.023 mmol) was dissolved in acetonitrile:water (9:1) (2 mL) and caesium fluoride (35 mg, 0.35 mmol) added. The reaction mixture was stirred at 80° C. for 6 hours and additional amounts of caesium fluoride (35 mg) added. The mixture was stirred at 60° C. overnight, concentrated in vacuo and diluted with ethyl acetate (10 mL) and water (5 mL). The organic phase was washed with water (3×5 mL) and dried with magnesium sulphate and concentrated in vacua. The residue was purified by preparative HPLC affording the title compound.

$^1$H-NMR (DMSO-d$_6$): δ 1.35 (m, 5H), 1.79 (m, 5H), 4.49 (s, 2H), 4.95 (s, 2H), 5.29 (s, 1H), 7.12–7.26 (m, 6H), 7.34 (d, 2H), 7.49 (dd, 1H), 7.63 (d, 1H), 7.77 (d, 2H), 8.42 (t, 1H); HPLC-MS (Method B): m/z=630 (M+1); R$_t$=6.62 min.

General Procedure (C) for Solid Phase Synthesis of Compounds of the General Formula (Ic):

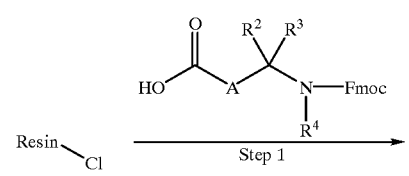

-continued

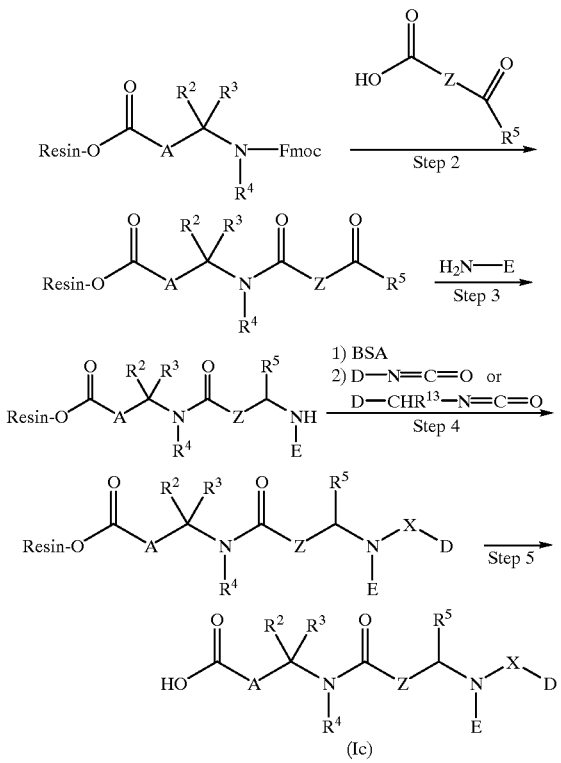

wherein
$R^2$, $R^3$, $R^4$, $R^5$, A, Z, D and E are as defined for formula (I),
X is —C(O)NH— or —C(O)NHCR$^{12}$R$^{13}$— wherein R$^{12}$ and R$^{13}$ are as defined for formula (I), and
Resin is a polystyrene resin loaded with a 2-chlorotrityl linker.
When A is —CHOH— step 4 is performed using 1) BSA and 2) D—N=C=O or D—CHR$^{13}$—N=C=O. Otherwise, step 4 is performed using only D-N=C=O or D—CHR$^{13}$-N=C=O.
The procedure is illustrated in the following examples.

Example 40

General Procedure (C)

(R)-3-{4-[1-(4-tert-Butylphenyl)-3-(3,4-dichlorophenyl)ureidomethyl]benzoylamino}-2-hydroxypropionic acid

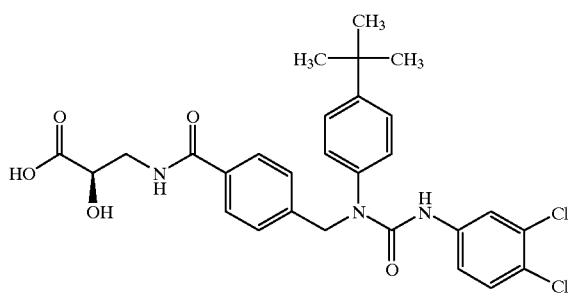

Step 1: Resin Bound (R)-Fmoc-isoserine 50 mg polystyrene resin functionalized with a 2-chlorotrityl chloride linker was vortexed with N-methyl-2-pyrrolidinone (500 µL) and 1,2-dichloropropane (500 µL) for 1 hour. The resin was filtered and washed with N-methyl-2-pyrrolidinone:1,2-dichloropropane (1:1, 2×1 mL). N-methyl-2-pyrrolidinone (500 µL) and 1,2-dichloropropane (500 µL) were added followed by 150 µmol (R)-Fmoc-isoserine and 100 µL diisopropylethylamine. After shaking the suspension for 4 hours at 25° C., the resin was isolated by filtration and washed with DCM: methanol-:diisopropylethylamine 17:2:1 (2×1 mL) and N-methyl-2-pyrrolidinone (2×1 mL).

Step 2: Resin Bound (R)-3-(4-Formylbenzoylamino)-2-hydroxypropionic Acid

To the above resin bound (R)-Fmoc-isoserine was added 500 µL of a 20% solution of piperidine in DMF. Upon shaking for 30 min, the resin was drained and washed with N-methyl-2-pyrrolidinone (6×1 mL). Then 200 µmol 4-formylbenzoic acid (30 mg) and 200 µmol HOBt (31 mg) were dissolved in N-methyl-2-pyrrolidinone (500 µL) and added to the resin followed by 200 µmol diisopropyl carbodiimide (25.2 mg) dissolved in acetonitrile (500 µL). The mixture was shaken for 4 hours at 25° C. followed by filtration and washing of the resin with N-methyl-2-pyrrolidinone (3×1 mL).

Step 3: Resin Bound (R)-3-{4-[(4-tert-butylphenylamino)methyl]benzoylamino}-2-hydroxypropionic Acid The above resin bound (R)-3-(4-formylbenzoylamino)-2-hydroxypropionic acid was treated with a 0.5 M solution of 4-tert-butylaniline (0.25 mmol) in a mixture of N-methyl-2-pyrrolidinone and trimethylorthoformate (1:1, 0.5 mL) and glacial acetic acid (50 µL) for 1 hour at 25° C. Sodium cyanoborohydride (250 µmol, 16 mg) dissolved in a mixture of N-methyl-2-pyrrolidinone and methanol (1:1, 0.25 mL) was added and the mixture was vortexed at 25° C. for 4 hours followed by filtration and washing with a mixture of N-methyl-2-pyrrolidinone and methanol (1:1, 2×1 mL) 3×1 mL N-methyl-2-pyrrolidinone (3×1 mL) and a mixture of 1,2-dichloropropane and diisopropylethylamine (7:1, 2×0.75 mL).

Step 4: Resin Bound (R)-3-{4-[1-(4-tert-butylphenyl)-3-(3,4-dichlorophenyl)ureidomethyl]benzoylamino}-2-hydroxypropionic Acid The above resin bound (R)-3-{4-[(4-tert-butylphenylamino)methyl]benzoylamino}-2-hydroxypropionic acid was added 1,2-dichloropropane (500 µL) and BSA (100 µL) and the mixture was vortexed at 25° C. for 1 hour. 200 µmol 3,4-Dichlorophenylisocyanate was added and shaking the mixture 5 hours at 25° C. followed by filtration and washing of the resin with 2×1 mL DCM, 4×1 mL N-methyl-2-pyrrolidinone, 2×1 mL H$_2$O, 3×1 mL THF and 5×1 mL DCM afforded the resin bound title compound.

Step 5: (R)-3-{4-[1-(4-tert-butylphenyl)-3-(3,4-dichlorophenyl)ureidomethyl]benzoylamino}-2-hydroxypropionic Acid The above resin bound (R)-3-{4-[1-(4-tert-butylphenyl)-3-(3,4-dichlorophenyl)ureidomethyl]-benzoylamino}-2-hydroxypropionic acid was treated with 1 mL 20% TFA in DCM for 1 hour at 25° C. The product was filtered off and the resin was washed with 1 mL DCM. The combined extracts were concentrated in vacuo to afford the title compound.

¹H-NMR (CDCl₃): δ 7.65 (d, 2H), 7.45–7.40 (m, 4H), 7.35–7.20 (m, 3H), 7.10–7.00 (m, 3H), 6.30 (s, 1H), 4.90 (s, 2H), 4.40 (m, 1H), 3.83 (m, 2H), 1.32 (s, 9H); HPLC-MS (Method B): m/z=558 (M+1); $R_t$=4.71 min.

The following examples were made as described above.

Example 41

General Procedure (C)

(R)-3{-4-[1-(4-tert-Butylcyclohexyl)-3-(3,4-dichlorophenyl)ureidomethyl]benzolamino}-2-hydroxypropionic acid

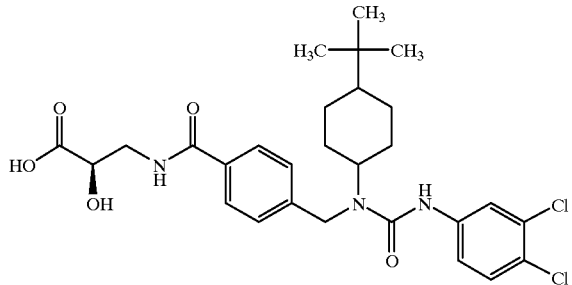

HPLC-MS (Method B): m/z=564 (M+1); $R_t$=4.92 min/ 5.02 min.

Example 42

General Procedure (C)

(R)-3{-4-[1-(4-Cyclohexylphenyl)-3-(3,4-dichlorophenyl)ureidomethyl]benzoylamino}-2-hydroxypropionic acid

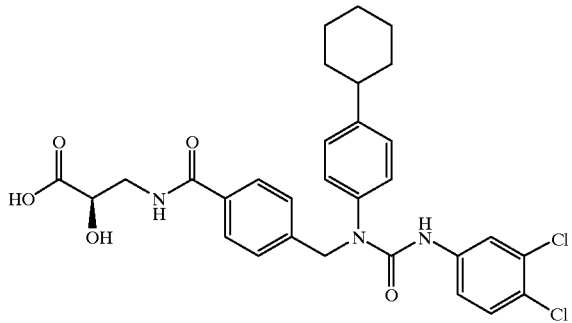

HPLC-MS (Method B): m/z=584 (M+1); $R_t$=5.12 min.

Example 43

General Procedure (C)

(R)-3{-4[-1-(4-Cyclohexylphenyl)-3-(2,2,4,4-tetrafluoro-4H-benzo[1,3]dioxin-6-yl)ureido-methyl]benzoylamino}-2-hydroxypropionic Acid

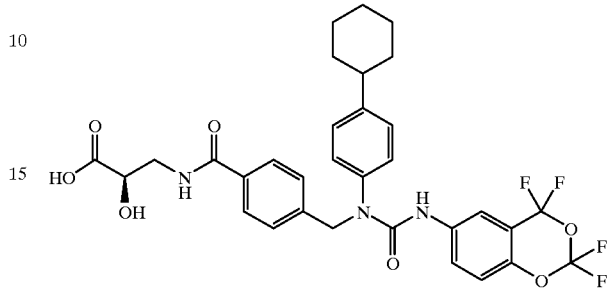

HPLC-MS (Method B): m/z=646 (M+1); $R_t$=5.24 min.

Example 44

General Procedure (C)

(R)-3-{4-[1-(4-tert-Butylphenyl)-3-(2,2,4,4-tetrafluoro-4H-benzo[1,3]dioxin-6-yl)ureidomethyl]-benzoylamino}-2-hydroxypropionic Acid

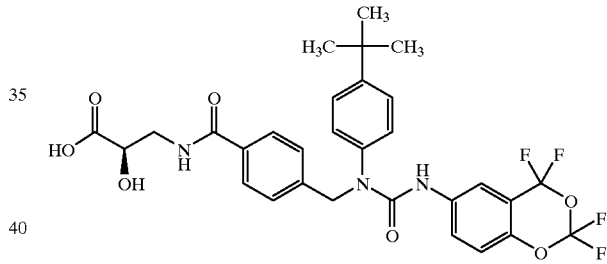

HPLC-MS (Method B): m/z=620 (M+1); $R_t$=4.88 min.

Example 45

General Procedure (C)

(R)-3-{-4-[1-(4-tert-Butylcyclohexyl)-3-(2,2,4,4-tetrafluoro-4H-benzo[1,3]dioxin-6-yl)ureido-methyl]benzoylamino}-2-hydroxypropionic Acid

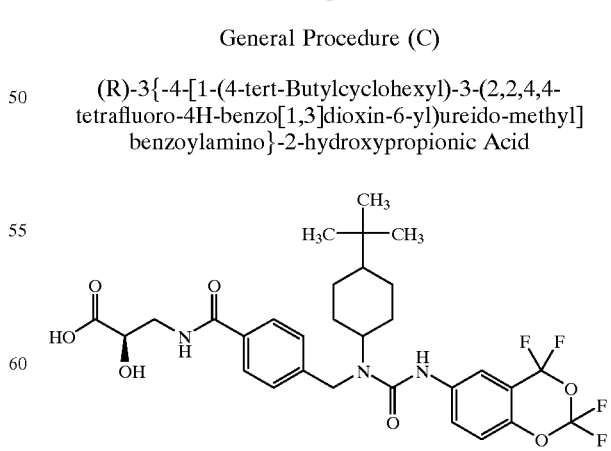

HPLC-MS (Method B): m/z=606 (M+1); $R_t$=5.11 min/ 5.20 min.

Example 46

General Procedure (C)

(R)-3-{4-[1-(4-tert-Butylphenyl)-3-(3,4-difluorophenyl)ureidomethyl]benzoylamino}-2-hydroxypropionic Acid

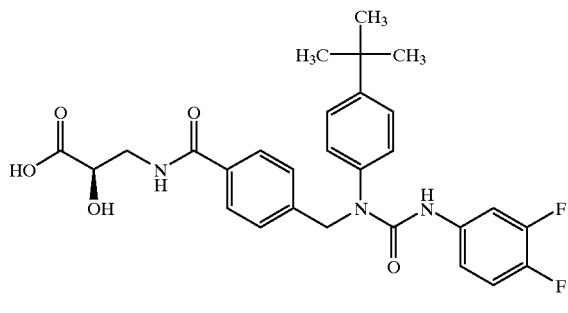

HPLC-MS (Method B): m/z=526 (M+1); $R_t$=4.24 min.

Example 47

General Procedure (C)

(R)-3-{4-[1-(4-Cyclohexylphenyl)-3-(3,4-difluorophenyl)ureidomethyl]benzoylamino}-2-hydroxypropionic Acid

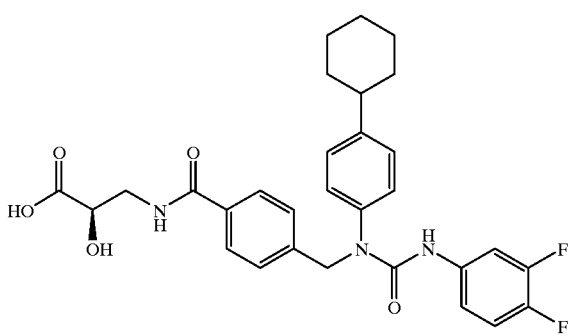

HPLC-MS (Method B): m/z=552 (M+1); $R_t$=4.65 min.

Example 48

General Procedure (C)

(R)-3-{4-[1-(4-Cyclohex-1-enylphenyl)-3-(3,4-difluorophenyl)ureidomethyl]benzoylamino}-2-hydroxypropionic Acid

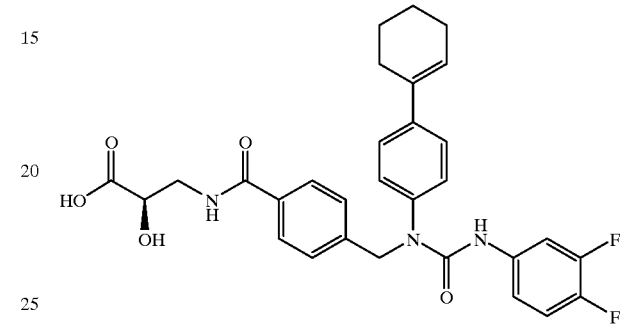

HPLC-MS (Method A): m/z=550 (M+1); $R_t$=6.77 min.

Example 49

General Procedure (C)

(R)-3-{4-[3-(4-Chloro-3-trifluoromethylphenyl)-1-(4-cyclohexylphenyl)ureidomethyl]benzoyl-amino}-2-hydroxypropionic Acid

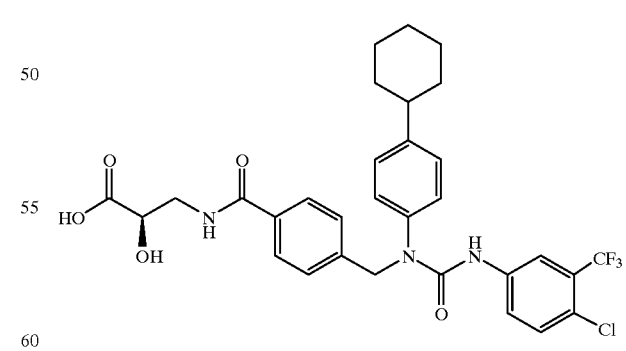

HPLC-MS (Method A): m/z=618 (M+1); $R_t$=7.58 min.

Example 50

General Procedure (C)

(R)-3{-4-[1-(4-Cyclohexylphenyl)-3-(4-fluoro-3-nitrophenyl)ureidomethyl]benzoylamino}-2-hydroxypropionic acid

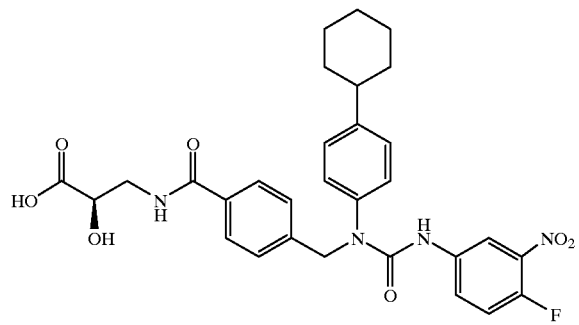

HPLC-MS (Method A): m/z=579 (M+1); $R_t$=6.85 min.

Example 51

General Procedure (C)

(R)-3{-4-[1-(4-Cyclohexylphenyl)-3-(4-isopropylphenyl)ureidomethyl]benzoylamino}-2-hydroxypropionic acid

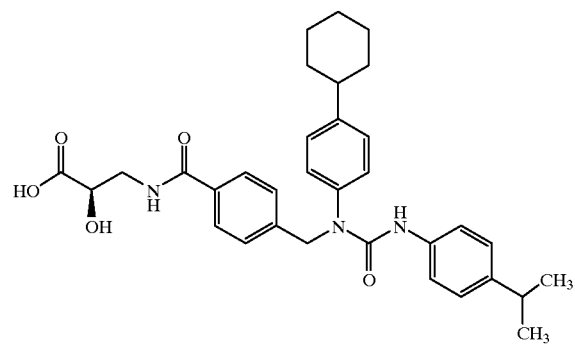

HPLC-MS (Method A): m/z=558 (M+1); $R_t$=7.73 min.

Example 52

General Procedure (C)

(R)-3{-4-[1-(4-Cyclohex-1-enylphenyl)-3-(3,4-dichlorophenyl)ureidomethyl]benzoylamino}-2-hydroxypropionic acid

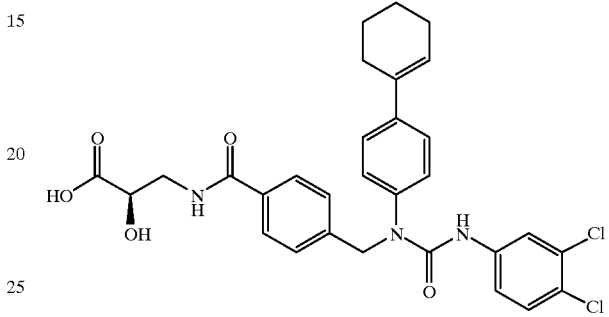

HPLC-MS (Method B): m/z=582 (M+1); $R_t$=4.99 min.

Example 53

General Procedure (C)

(R)-3{-4-[3-(4-Acetylphenyl)-1-(4-cyclohexylphenyl)ureidomethyl]benzoylamino}-2-hydroxypropionic acid

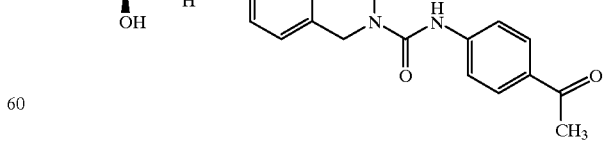

HPLC-MS (Method A): m/z=558 (M+1); $R_t$=6.42 min.

Example 54

General Procedure (C)

3-{4-[3-[1 (RS)-(4-Bromophenyl)ethyl]-1-(4-cyclohexylphenyl)ureidomethyl]benzoylamino}-2 (R)-hydroxypropionic acid

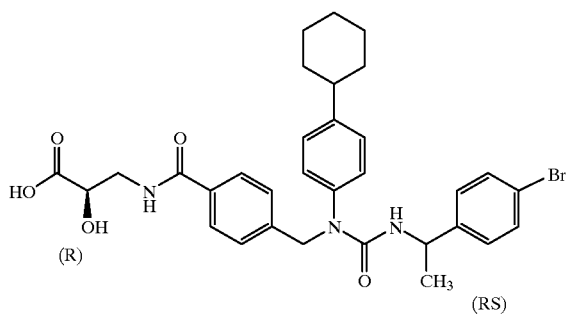

HPLC-MS (Method A): m/z=624 (M+1); $R_t$=7.45 min.

Example 55

General Procedure (C)

(R)-3-{4-[1-(4-Cyclohexylphenyl)-3-(3,5-difluorophenyl)ureidomethyl]benzoylamino}-2-5 hydroxypropionic acid

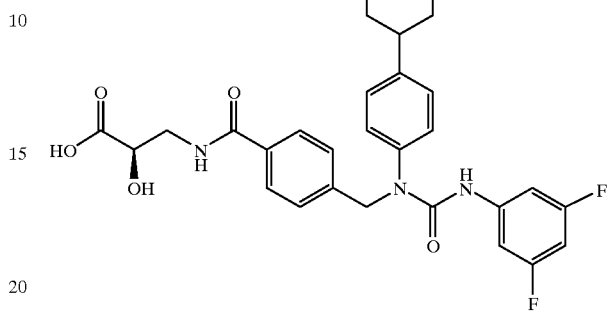

HPLC-MS (Method B): m/z=552 (M+1); $R_t$=4.76 min.

General Procedure (D) for Solid Phase Synthesis of Compounds of the General Formula

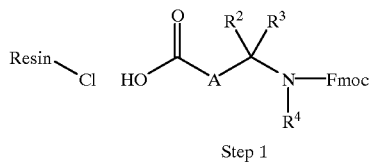

Step 1

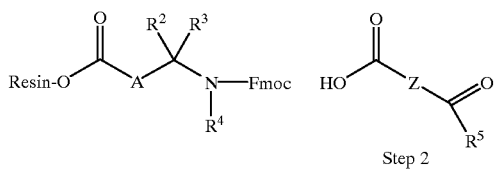

Step 2

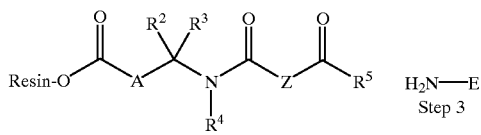

Step 3

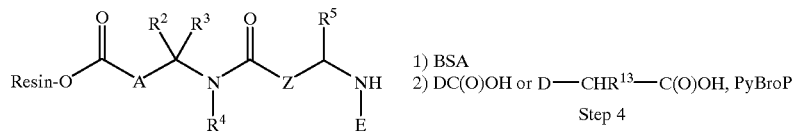

1) BSA
2) DC(O)OH or D—CHR$^{13}$—C(O)OH, PyBroP

Step 4

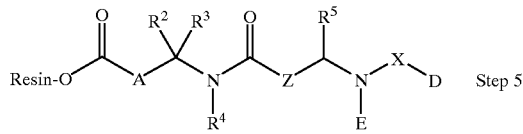

Step 5

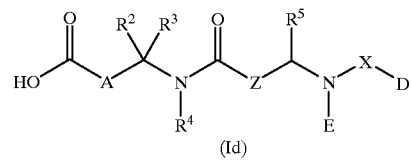

(Id)

wherein
- $R^2$, $R^3$, $R^4$, $R^5$, A, Z, D and E are as defined for formula (I),
- X is —C(O)—$(CR^{12}R^{13})_r$—$(CH_2)_s$— wherein r, s, $R^{12}$ and $R^{13}$ are as defined for formula (I), and
- Resin is a polystyrene resin loaded with a 2-chlorotrityl linker.
- When A is —CHOH— step 4 is performed using 1) BSA and 2) D—C(O)OH or D—$CHR^{13}$—C(O)OH. Otherwise, step 4 is performed using only D—C(O)OH or D—$CHR^{13}$—C(O)OH.

Example 56

General Procedure (D)

(R)-3-[4-({(4-tert-Butylcyclohexyl)-[2-(4-trifluoromethoxyphenyl)acetyl]amino}methyl)benzoyl-amino]-2-hydroxypropionic acid

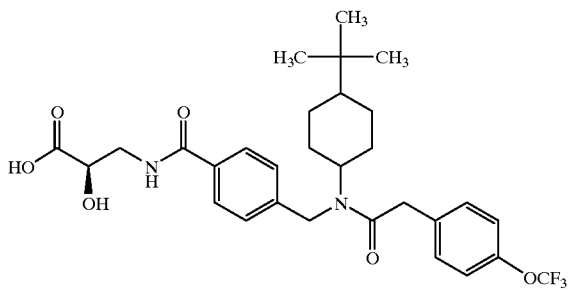

Step 1: Resin Bound (R)-Fmoc-isoserine 50 mg polystyrene resin functionalized with a 2-chlorotrityl chloride linker was vortexed with N-methyl-2-pyrrolidinone (500 μL) and 1,2-dichloropropane (500 μL) for 1 hour. The resin was filtered and washed with N-methyl-2-pyrrolidinone/1,2-dichloropropane (1:1, 2×1 mL). N-methyl-2-pyrrolidinone (500 μL) and 1,2-dichloropropane (500 μL) was added followed by 150 μmol (R)-Fmoc-isoserine and 100 μL diisopropylethylamine. After shaking the suspension for 4 hours at 25° C., the resin was isolated by filtration and washed with DCM:methanol:diisopropylethylamine (17:2:1) (2×1 mL) and N-methyl-2-pyrrolidinone (2×1 mL).

Step 2: Resin Bound (R)-3-(4-formylbenzoylamino)-2-hydroxypropionic Acid

To the above resin bound (R)-Fmoc-isoserine was added 500 μL of a 20% solution of piperidine in DMF. Upon shaking for 30 min, the resin was drained and washed with N-methyl-2-pyrrolidinone (6×1 mL). Then, 200 μmol 4-formylbenzoic acid (30 mg) and 200 μmol HOBt (31 mg) was dissolved in N-methyl-2-pyrrolidinone (500 μL) and added to the resin followed by 200 μmol diisopropyl carbodiimide (25.2 mg) dissolved in acetonitrile (500 μL). The mixture was shaken for 4 hours at 25° C. followed by filtration and washing of the resin with N-methyl-2-pyrrolidinone (3×1 mL).

Step 3: Resin Bound (R)-3{-4-[(4-tert-butylcyclohexylamino)methyl]benzoylamino}-2-hydroxypropionic acid The above resin bound (R)-3-(4-formylbenzoylamino)-2-hydroxypropionic acid was treated with a 0.5 M solution of 4-tert-butylcyclohexylamine (0.25 mmol) in a mixture of N-methyl-2-pyrrolidinone and trimethylorthoformate (1:1, 0.5 mL) and glacial acetic acid (50 μL) for 1 hour at 25° C. Sodium cyanoborohydride (250 μmol, 16 mg) dissolved in a mixture of N-methyl-2-pyrrolidinone and methanol (1:1, 0.25 mL) was added and the mixture was vortexed at 25° C. for 4 hours followed by filtration and washing with a mixture of N-methyl-2-pyrrolidinone and methanol (1:1, 2×1 mL) 3×1 mL N-methyl-2-pyrrolidinone (3×1 mL) and a mixture of 1,2-dichloropropane and diisopropylethylamine (7:1, 2×0.75 mL).

Step 4: Resin Bound (R)-3-[4-({(4-tert-butylcyclohexyl)-[2-(4-trifluoromethoxyphenyl)acetyl]-amino}methyl)benzoylamino]-2-hydroxypropionic Acid The above resin bound (R)-3-{4-[(4-tert-butylcyclohexylamino)methyl]benzoylamino}-2-hydroxypropionic acid was added 1,2-dichloropropane (500 μL) and BSA (100 μL) and the mixture was vortexed at 25° C. for 1 hour followed by filtration. To the resin was added a solution of 4-(trifluoromethoxy)phenylacetic acid (400 umol) in a mixture of N-methyl-2-pyrrolidinone, 1,2-dichloropropane and diisopropylethylamine (4.5:4.5:1, 1 mL) was added followed by a solution of bromo-tris(pyrrolidino)phosphonium hexafluorophosphate (400 μmol) in 1,2-dichloropropane (500 μL). The mixture was allowed to react for 3 hours at 50° C. and the resin was allowed to cool to 25° C. while washed with N-methyl-2-pyrrolidinone (4×1 mL), and DCM (10×1 mL) afforded the resin bound title compound.

Step 5: (R)-3-[4-({(4-tert-Butylcyclohexyl)-[2-(4-trifluoromethoxyphenyl)acetyl]amino}methyl)-benzoylamino]-2-hydroxypropionic acid The above resin bound (R)-3-{4-[1-(4-tert-butylcyclohexyl)-3-(4-trifluoromethoxyphenyl)-ureidomethyl]benzoylamino}-2-hydroxypropionic acid was treated with 1 mL 20% TFA in DCM for 1 hour at 25° C. The product was filtered off and the resin was washed with 1 mL DCM. The combined extracts were concentrated in vacuo to afford the title compound.

HPLC-MS (Method A): m/z=579 (M+1); $R_t$=7.20 min.

The following examples were made as described above.

Example 57

General Procedure (D)

(R)-3-[4-({(4-tert-Butylcyclohexyl)-[2-(3-fluoro-5-trifluoromethylphenyl)acetyl]amino}methyl)-benzoylamino]-2-hydroxypropionic Acid

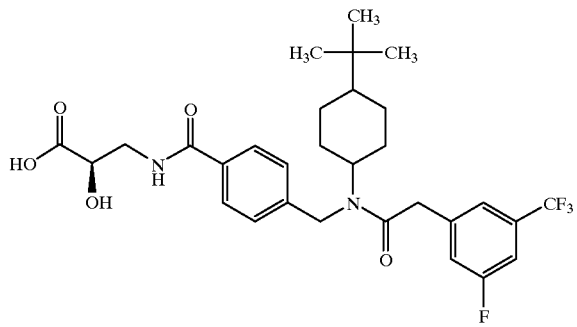

HPLC-MS (Method A): m/z=581 (M+1); $R_t$=7.22 min.

Example 58

General Procedure (D)

(R)-3-[4-({(2,2-Diphenylethyl)-[2-(3-fluoro-5-trifluoromethyl phenyl)acetyl]amino}methyl)-benzoylamino]-2-hydroxypropionic Acid

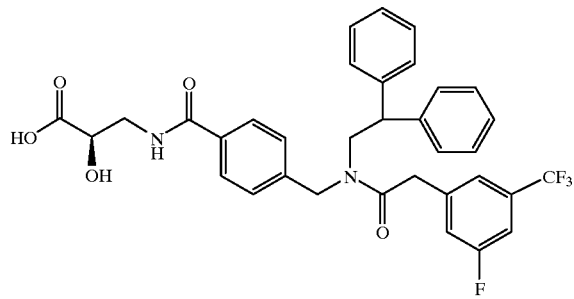

HPLC-MS (Method A): m/z=623 (M+1); $R_t$=6.87 min.

Example 59

General Procedure (D)

(R)-3-(4-{[(5-Chlorobenzo[b]thiophene-3-carbonyl)-(2,2-diphenylethyl)amino}methyl]benzol-amino)-2-hydroxypropionic Acid

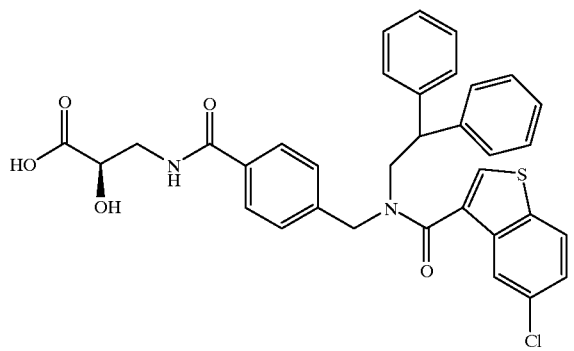

HPLC-MS (Method A): m/z=613 (M+1); $R_t$=6.50 min.

Example 60

General Procedure (D)

(R)-3-[4-({(2,2-Diphenylethyl)-[2-(4-trifluoromethoxyphenyl)acetyl]amino}methyl)benzoyl-amino]-2-hydroxypropionic acid

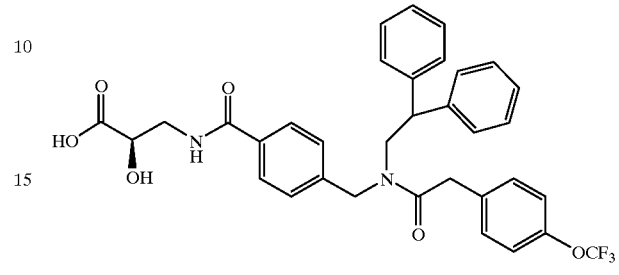

HPLC-MS (Method A): m/z=621 (M+1); $R_t$=6.90 min.

Example 61

General Procedure (D)

(R)-3-(4-{[(4-tert-Butylcyclohexyl)-(5-chlorobenzo[b]thiophene-3-carbonyl)amino}methyl]-benzoylamino)-2-hydroxypropionic Acid

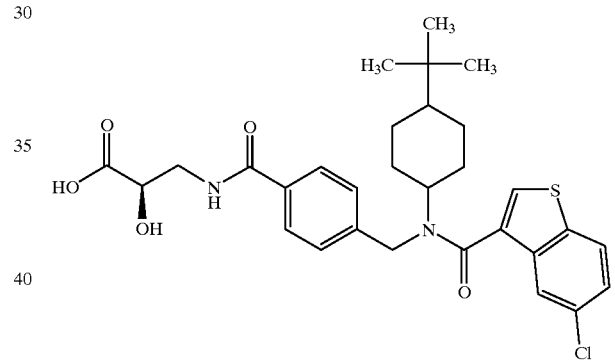

HPLC-MS (Method A): m/z=571 (M+1); $R_t$=7.15 min.

Example 62

General Procedure (D)

(R)-3-(4-{[(2,2-Diphenylethyl)-(5-trifluoromethoxy-1H-indole-2-carbonyl)amino]methyl}-benzoylamino)-2-hydroxypropionic Acid

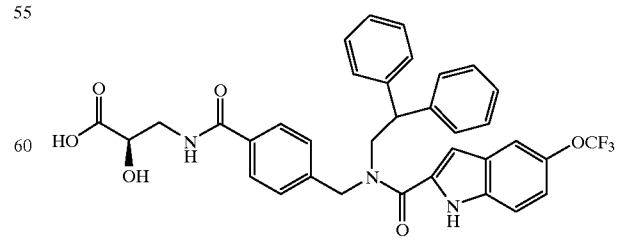

HPLC-MS (Method A): m/z=646 (M+1); $R_t$=6.93 min.

Example 63

General Procedure (D)

(R)-3-[4-({(4-Cyclohexylphenyl)-[(4-trifluoromethoxyphenyl)acetyl]amino}methyl)benzoyl-amino]-2-hydroxypropionic Acid

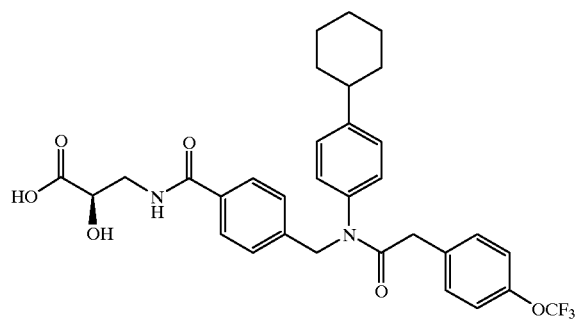

HPLC-MS (Method B): m/z=599 (M+1); $R_t$=5.19 min.

Example 64

General Procedure (D)

(R)-3-[4-({(4-Cyclohexylphenyl)-[(3-trifluoromethoxyphenyl)acetyl]amino}methyl)benzoyl-amino]-2-hydroxypropionic Acid

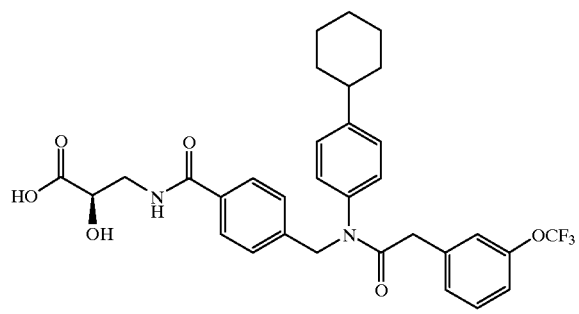

HPLC-MS (Method B): m/z=599 (M+1); $R_t$=5.17 min.

Example 65

General Procedure (D)

(R)-3-[4-({(4-Cyclohexylphenyl)-[(3-fluoro-5-trifluoromethylphenyl)acetyl]amino}methyl)-benzoylamino]-2-hydroxypropionic Acid

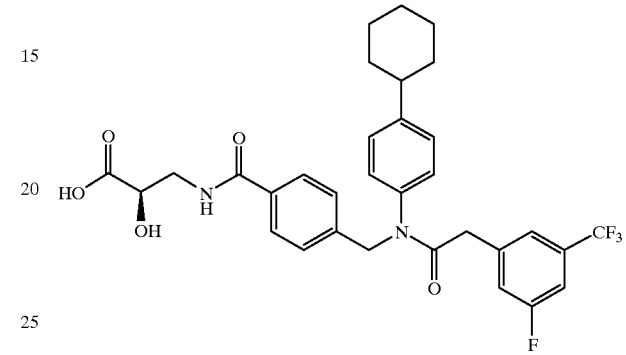

HPLC-MS (Method B): m/z=601 (M+1); $R_t$=5.19 min.

Example 66

General Procedure (D)

(R)-3-(4-{([(3,5-Bis(trifluoromethyl)phenyl)acetyl]-(4-cyclohexylphenyl)amino)methyl}benzoyl-amino)-2-hydroxypropionic Acid

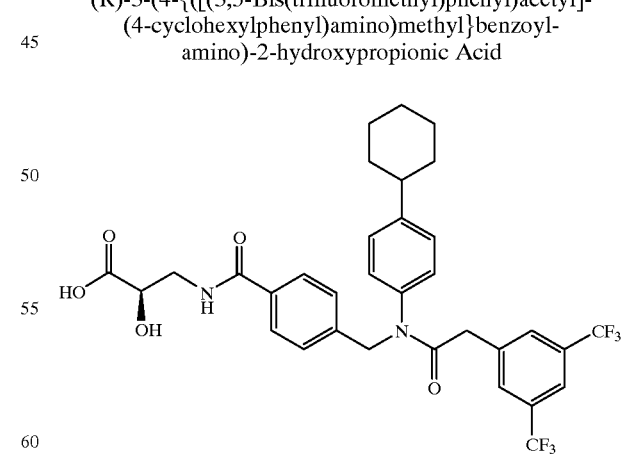

HPLC-MS (Method B): m/z=651 (M+1); $R_t$=5.50 min.

Example 67

General Procedure (D)

(R)-3-[4-({(4-Cyclohexylphenyl)-[(3-trifluoromethylphenyl)acetyl]amino}methyl)benzoylamino]-2-hydroxypropionic Acid

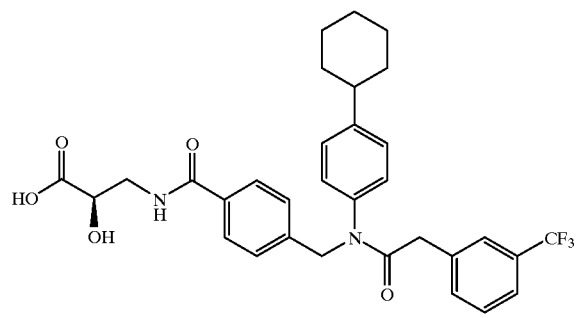

HPLC-MS (Method B): m/z=583 (M+1); $R_t$=5.08 min.

Example 68

General Procedure (D)

(R)-3-[4-({(4-Cyclohexylphenyl)-[(3,4-dichlorophenyl)acetyl]amino}methyl)benzoylamino]-2-hydroxypropionic Acid

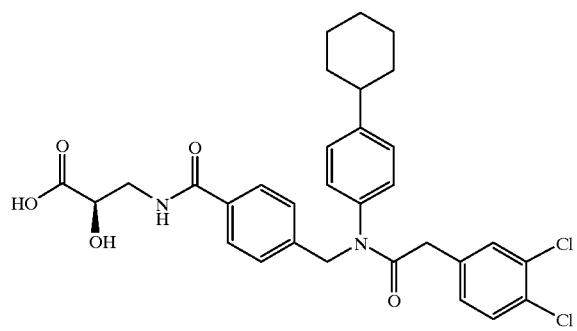

HPLC-MS (Method B): m/z=583 (M+1); $R_t$=5.26 min.

Example 69

General Procedure (D)

(R)-3-(4-{[[(3-Bromophenyl)acetyl]-(4-cyclohexylphenyl)amino}methyl]benzoylamino)-2-hydroxypropionic Acid

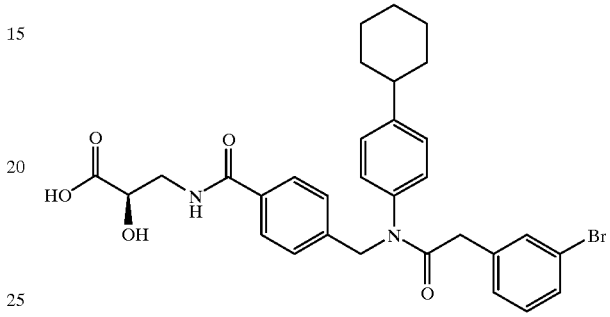

HPLC-MS (Method B): m/z=595 (M+1); $R_t$=5.01 min.

Example 70

General Procedure (D)

(R)-3-(4{[(Biphenyl-4-ylacetyl)-(4-cyclohexylphenyl)amino}methyl]benzoylamino)-2-hydroxypropionic Acid

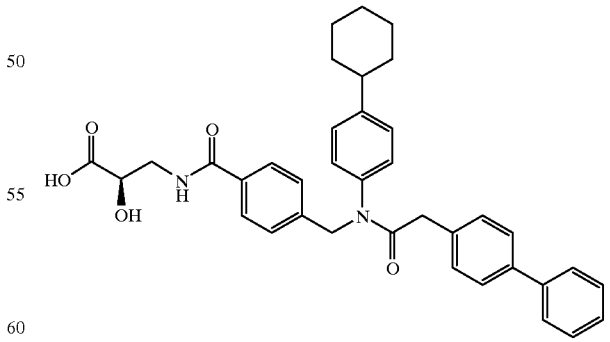

HPLC-MS (Method B): m/z=591 (M+1); $R_t$=5.38 min.

Example 71

General Procedure (D)

(R)-3-(4-{[(4-Cyclohexylphenyl)-(2-naphthylacetyl)amino]methyl]benzoylamino)-2-hydroxypropionic Acid

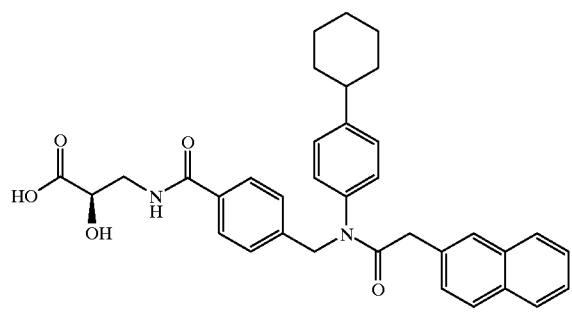

HPLC-MS (Method B): m/z=565 (M+1); R$_t$=5.10 min.

Example 72

General Procedure (D)

(R)-3-(4-{[(3-(3,5-Bis(trifluoromethyl)phenyl)propionyl)-(4-cyclohexylphenyl)amino]methyl]-benzoylamino)-2-hydroxypropionic Acid

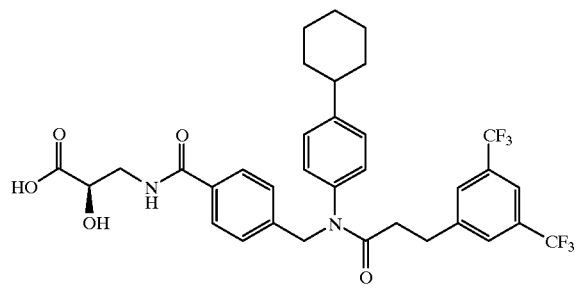

HPLC-MS (Method B): m/z=665 (M+1); R$_t$=5.51 min.

Example 73

General Procedure (D)

(R)-3-[4-({(4-Cyclohexylphenyl)-[3-(3-nitrophenyl)propionyl]amino}methyl)benzoylamino]-2-hydroxypropionic Acid

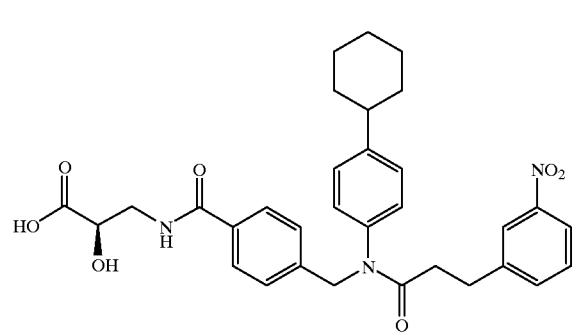

HPLC-MS (Method B): m/z=665 (M+1); R$_t$=5.51 min.

The following preferred compounds are within the scope of the invention and may be prepared according to the procedures disclosed herein. Other preferred compounds are:

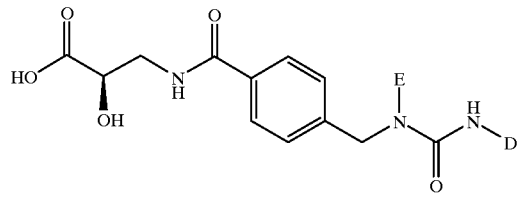

wherein

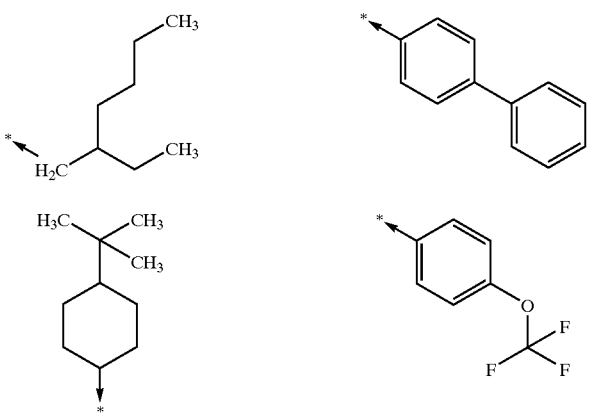

| E | D |
|---|---|

-continued
| E | D |
|---|---|
| 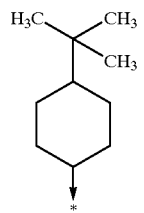 | 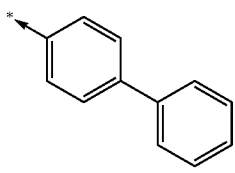 |
| 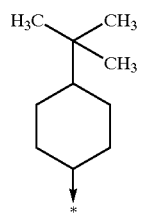 |  |
| 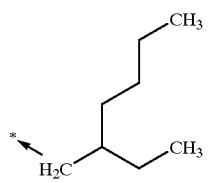 | 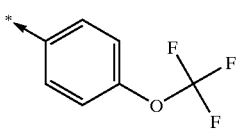 |
| 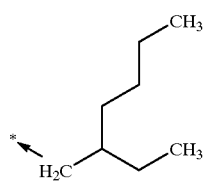 | 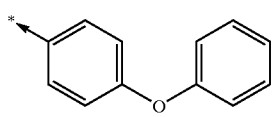 |
| 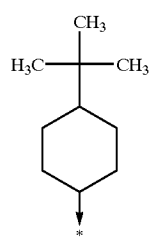 | 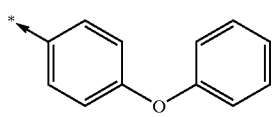 |
| 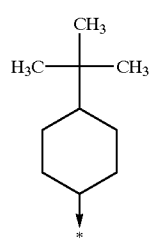 | 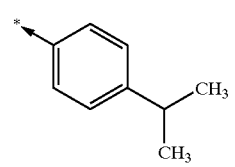 |
| 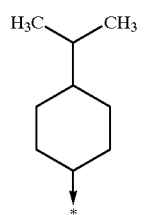 | 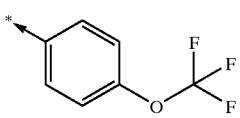 |

-continued
| E | D |
|---|---|
| 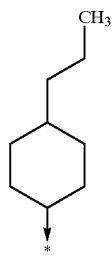 | 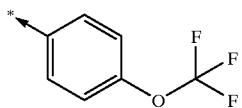 |
| 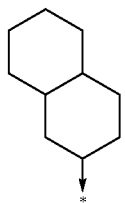 | 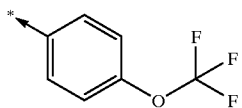 |
| 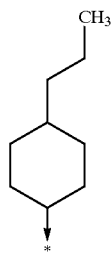 | 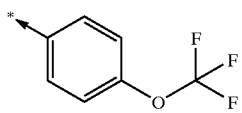 |
| 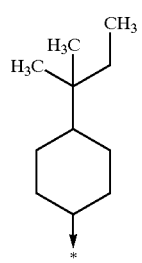 | 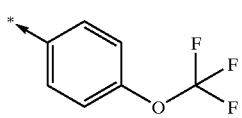 |
| 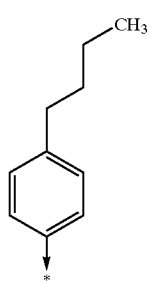 | 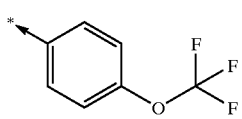 |

-continued
| E | D |
|---|---|
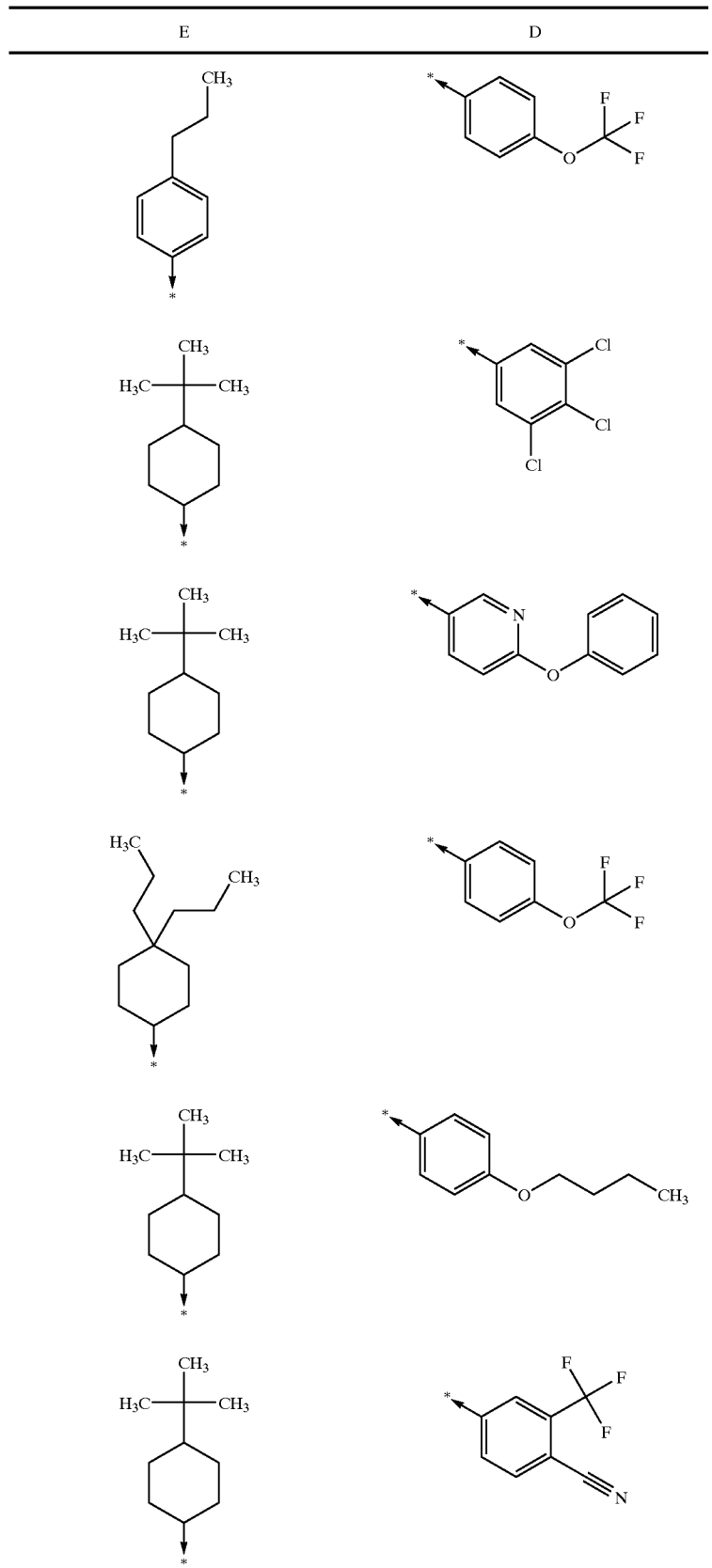

-continued
| E | D |
|---|---|
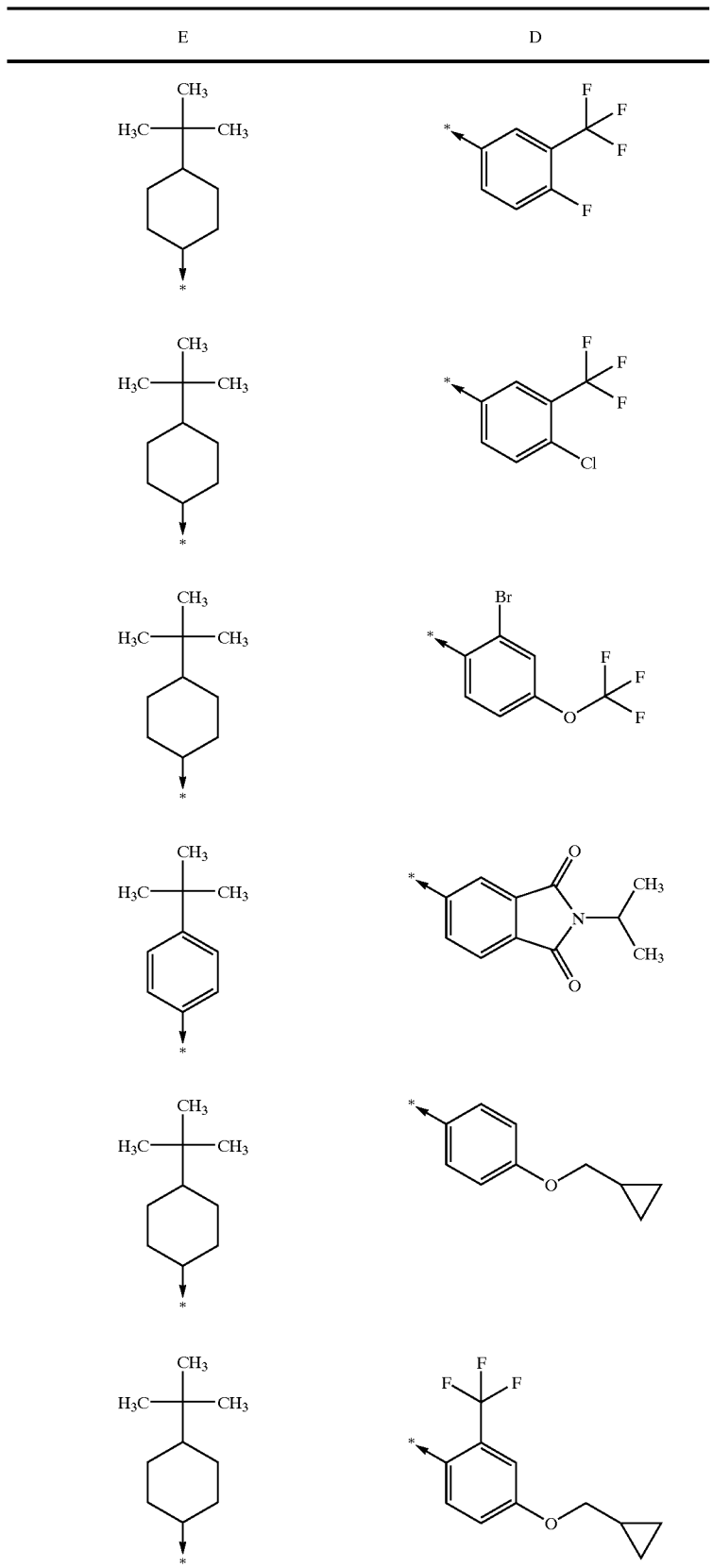

-continued
| E | D |
|---|---|
| 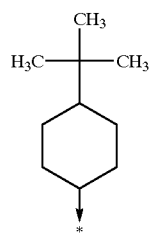 | 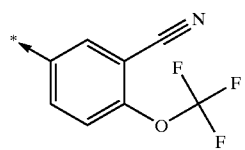 |
| 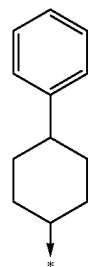 | 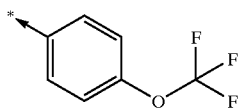 |
| 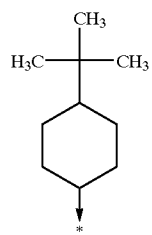 | 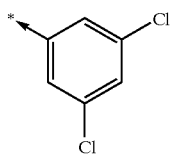 |
| 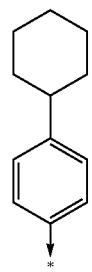 | 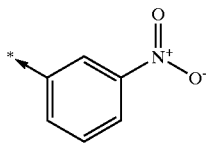 |
| 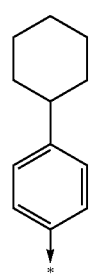 | 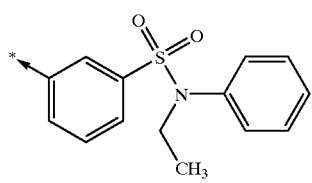 |

-continued
| E | D |
|---|---|
| 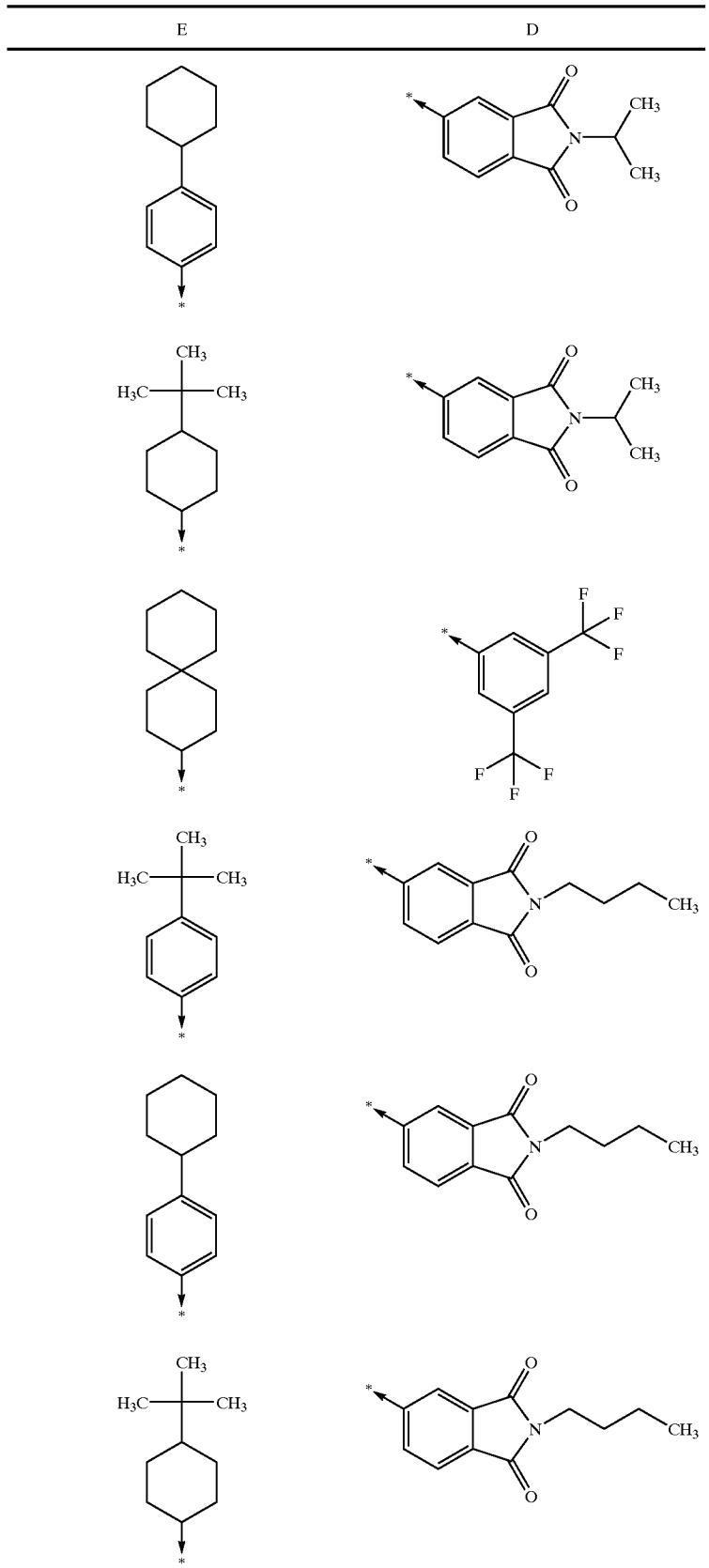 | |

-continued
| E | D |
|---|---|
| 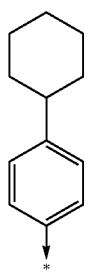 | 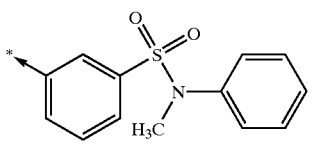 |
| 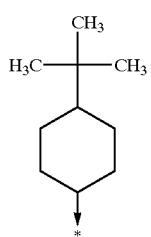 | 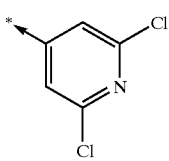 |
| 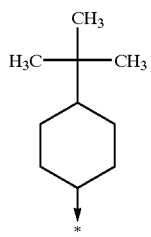 | 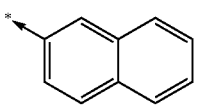 |
| 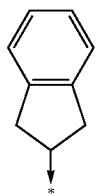 | 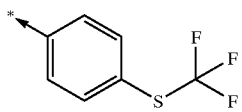 |
|  | 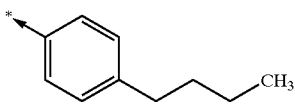 |
| 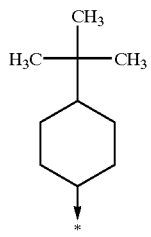 | 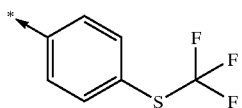 |

-continued
| E | D |
|---|---|
| | |
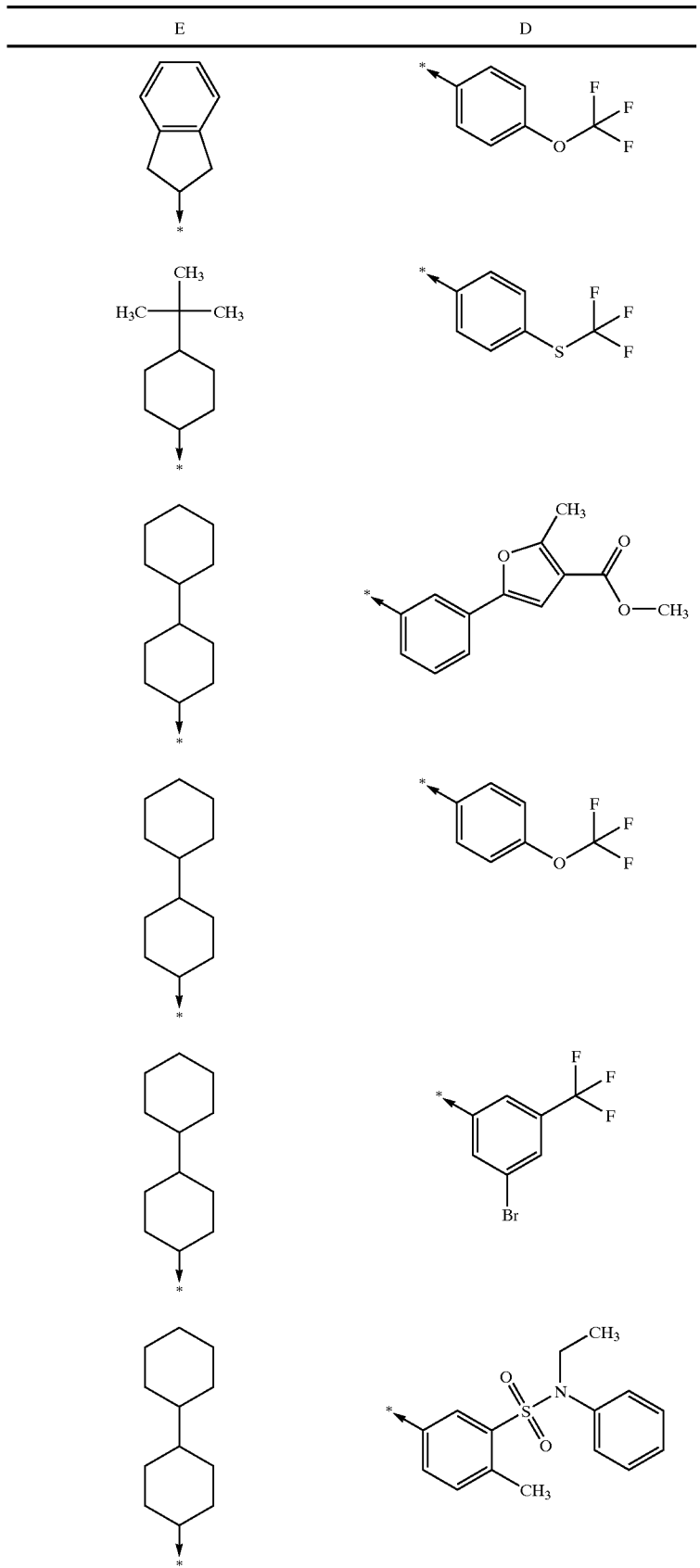

-continued
| E | D |
|---|---|
| 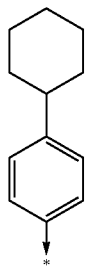 | 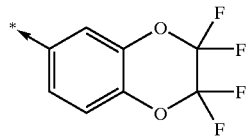 |
| 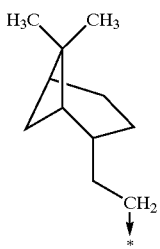 | 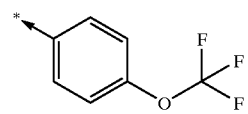 |
| 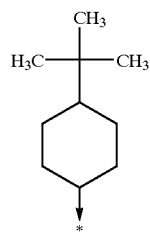 | 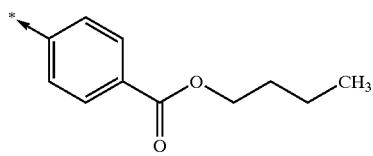 |
| 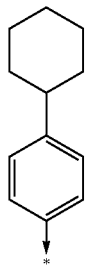 | 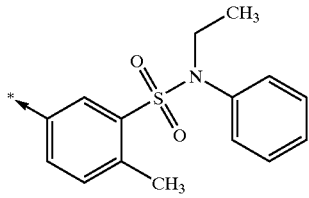 |
| 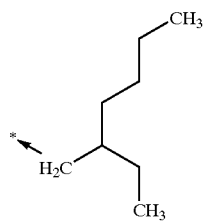 | 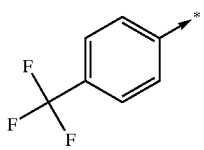 |
| 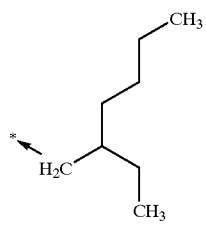 | 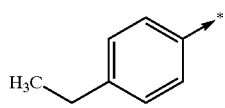 |

-continued
| E | D |
|---|---|
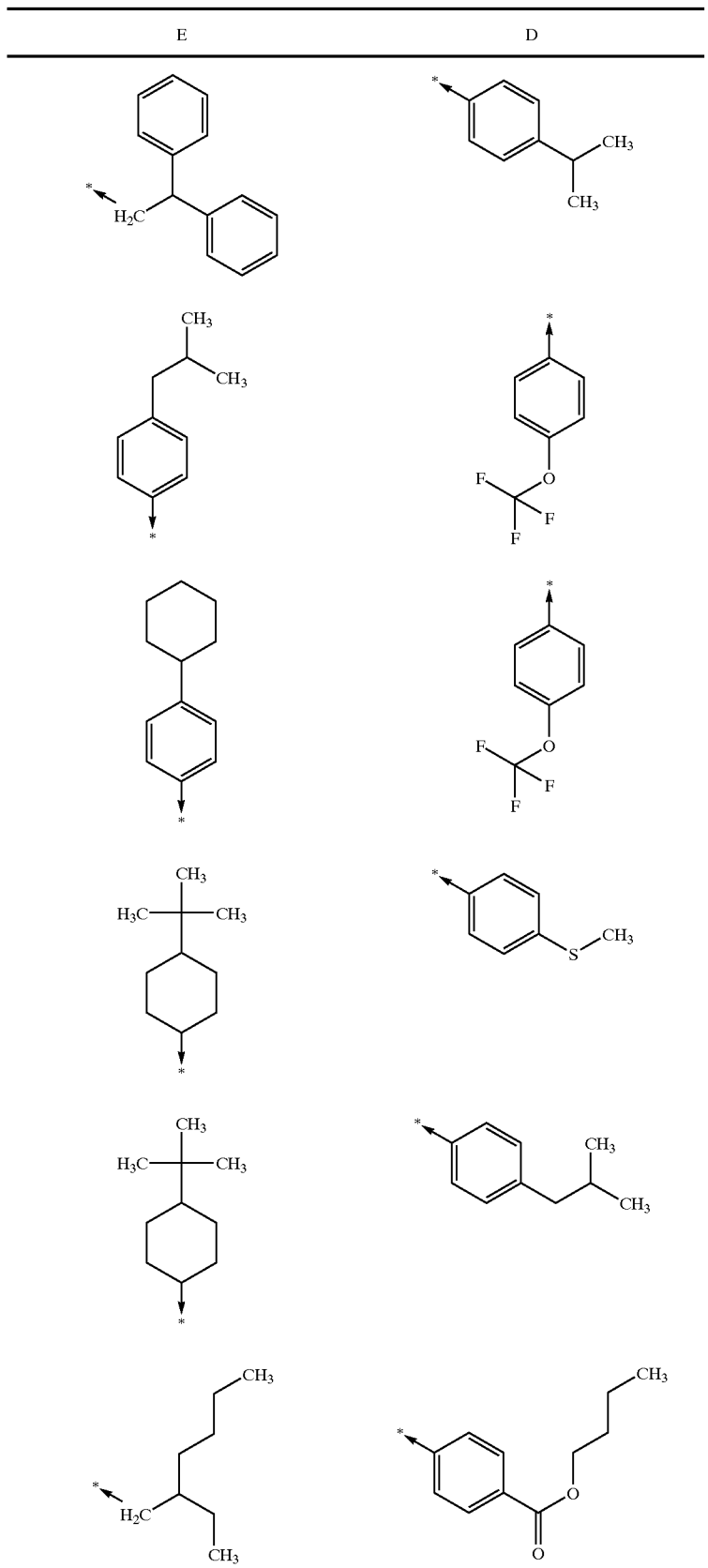

-continued
| E | D |
|---|---|
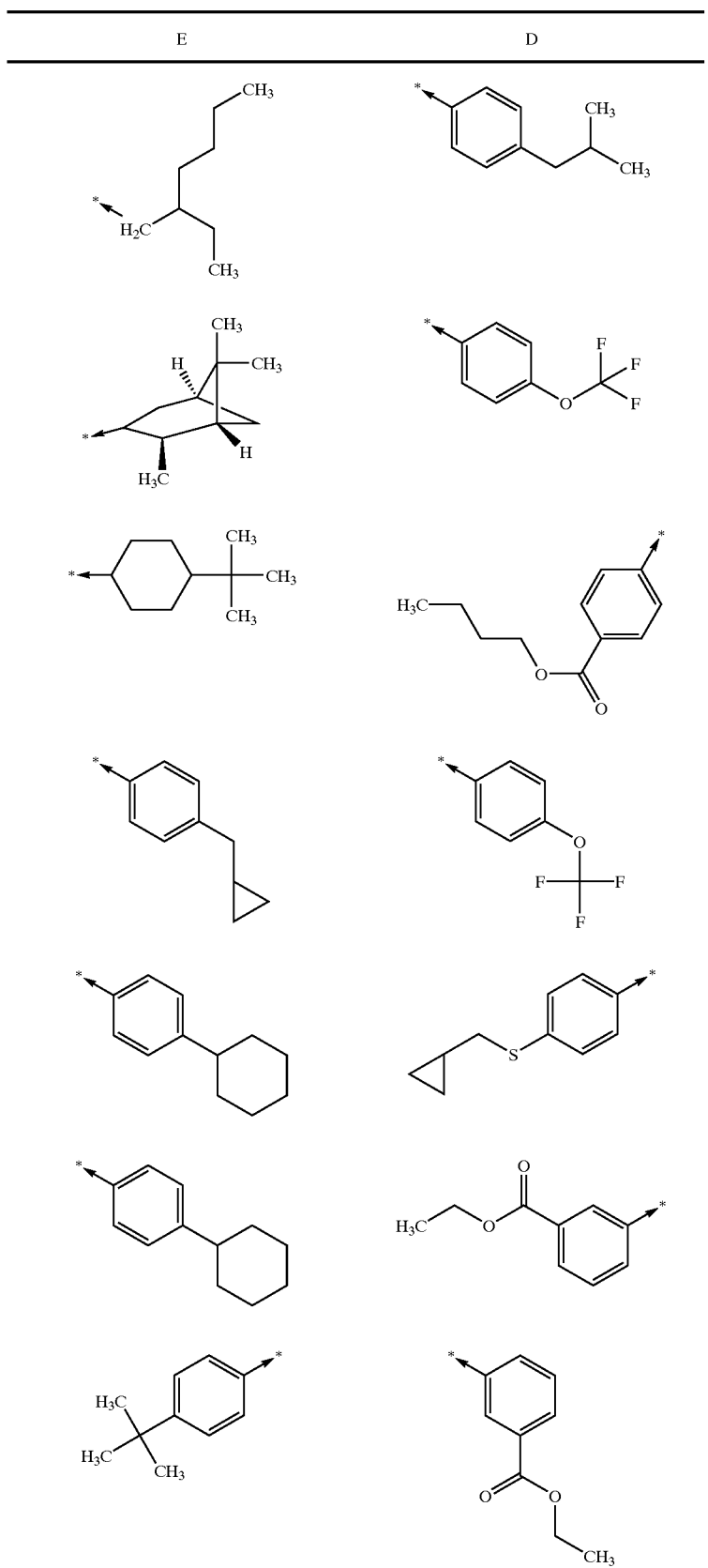

-continued
| E | D |
|---|---|
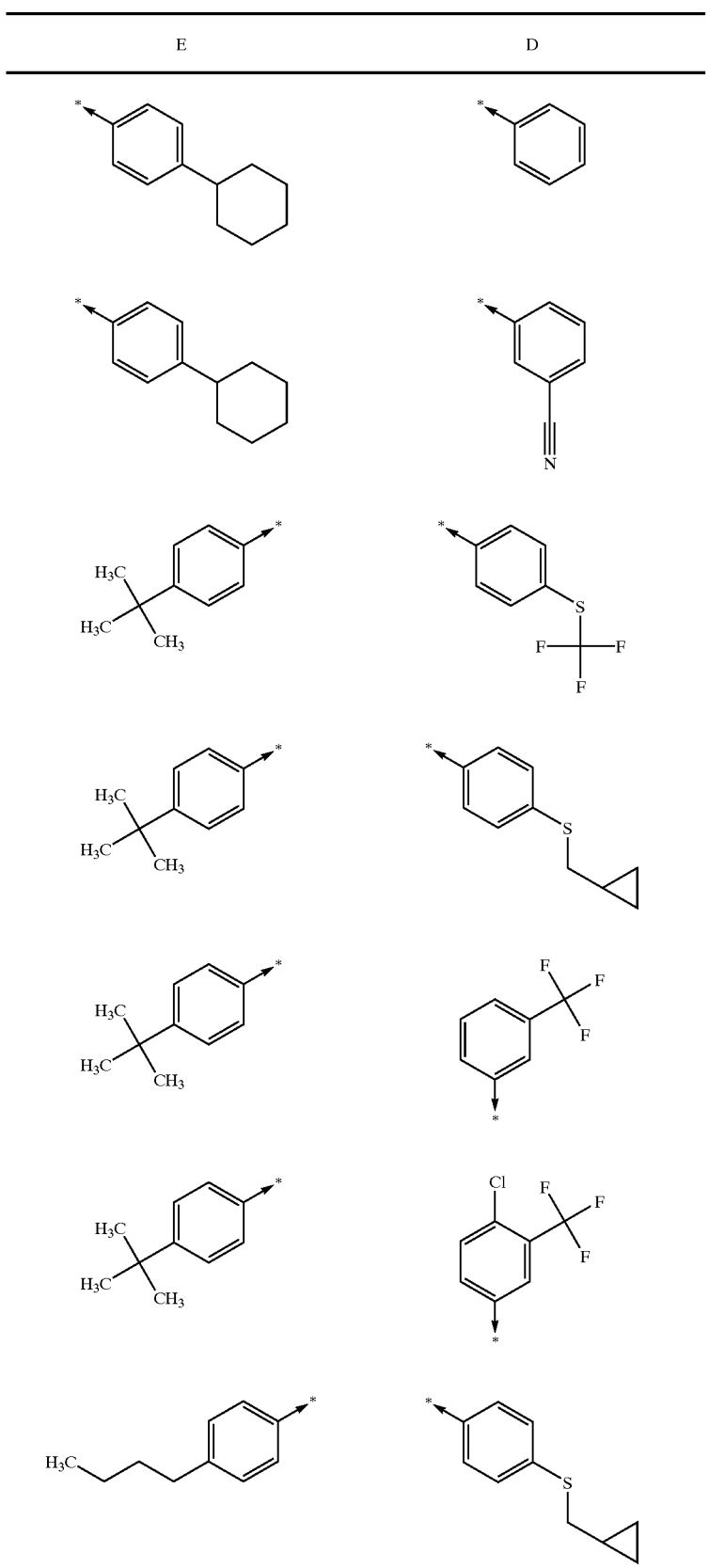

-continued
| E | D |
|---|---|
| | |
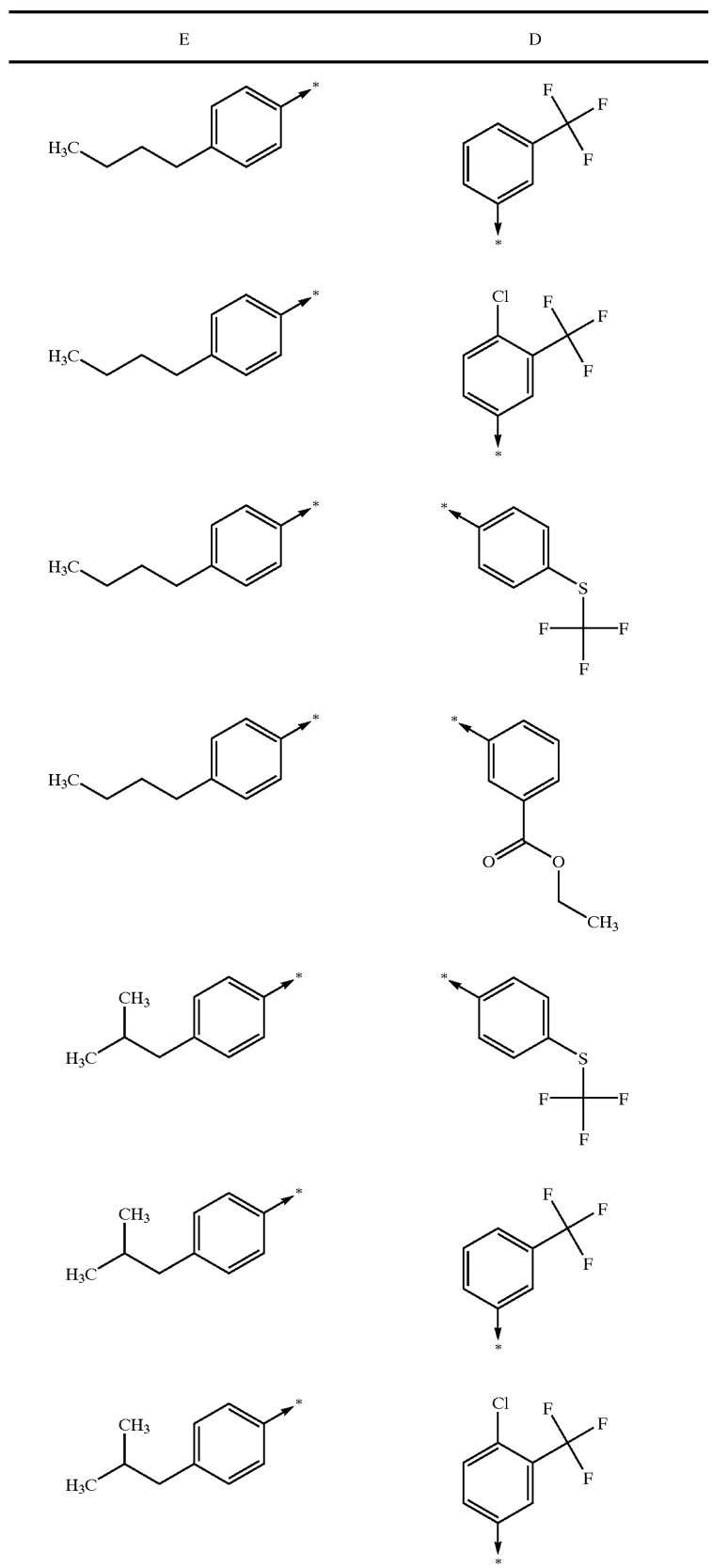

| E | D |
|---|---|
| 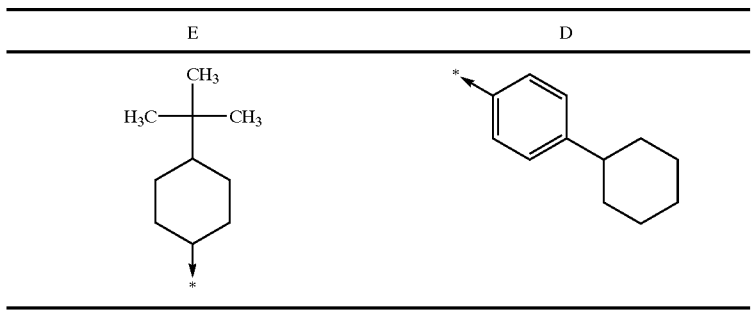 | |
Furthermore, the following compounds are within the scope of the present invention and may be prepared according to the procedures disclosed herein:
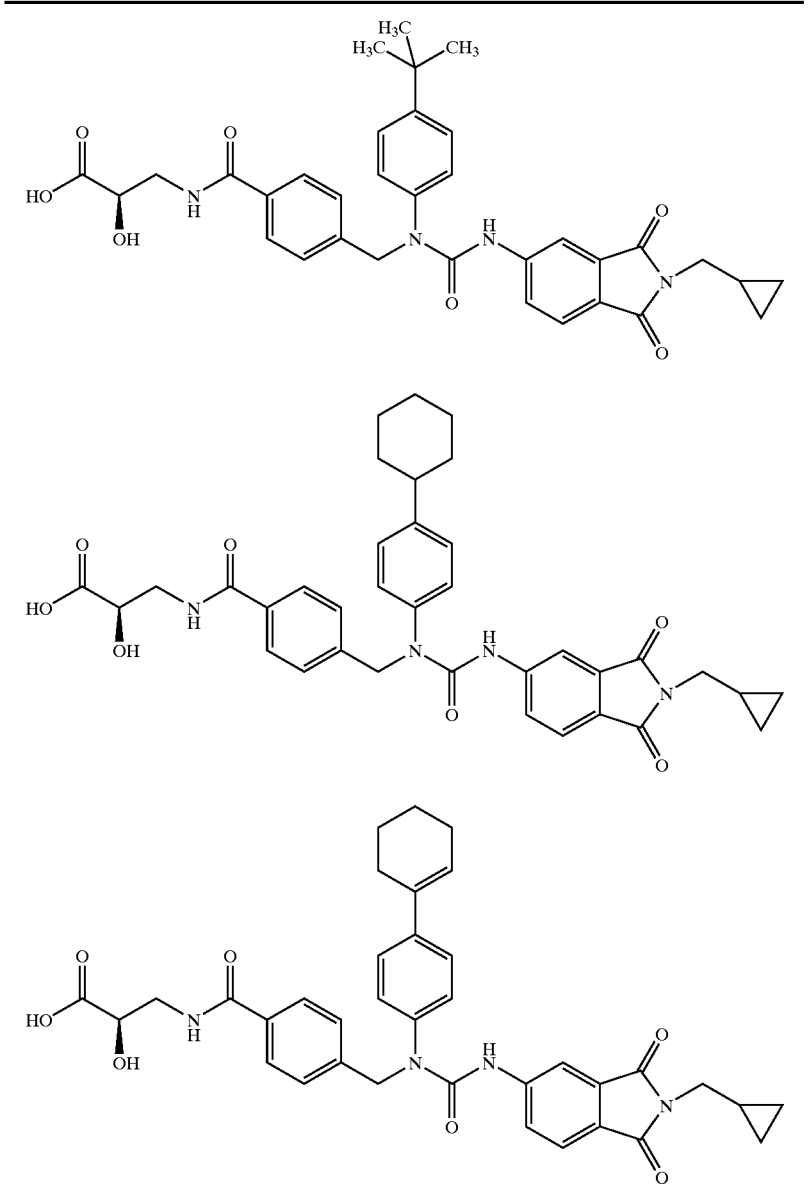

-continued
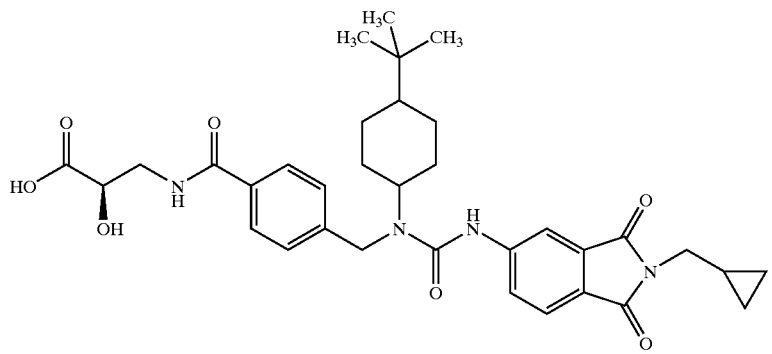
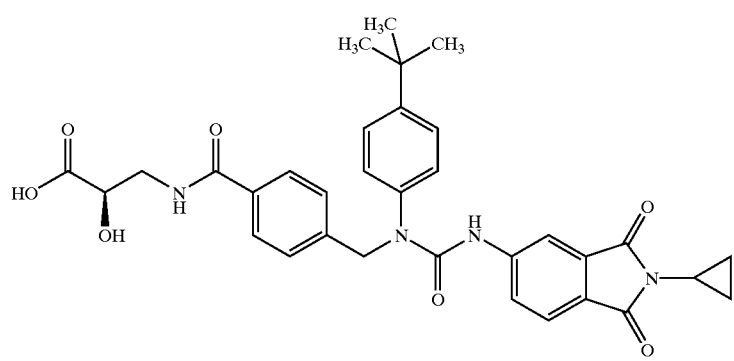
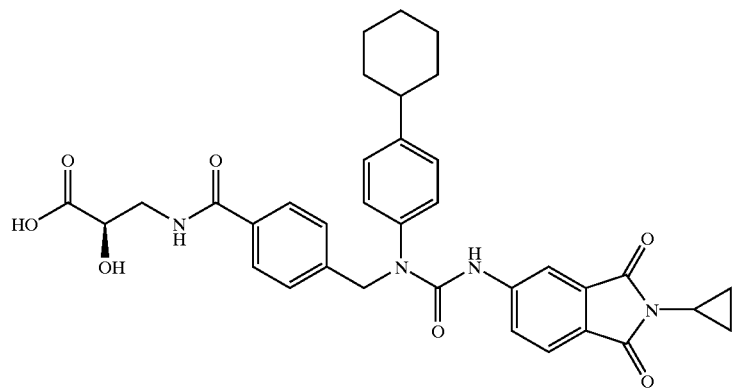
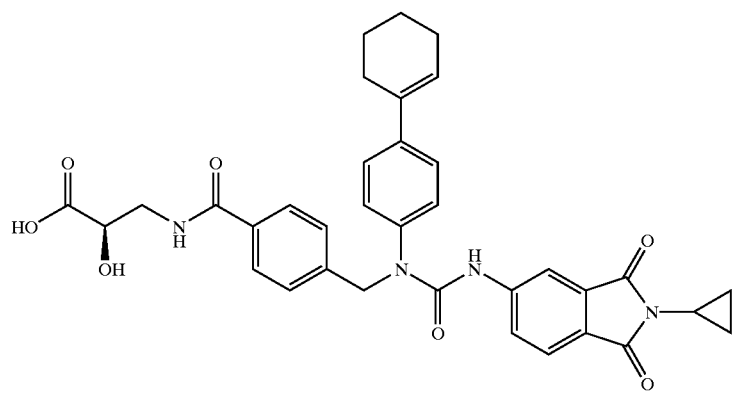

-continued
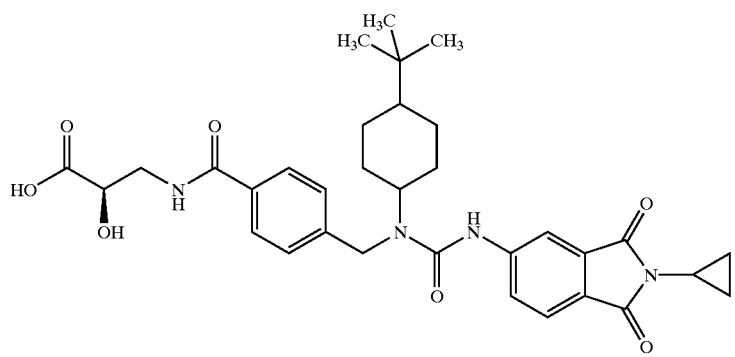
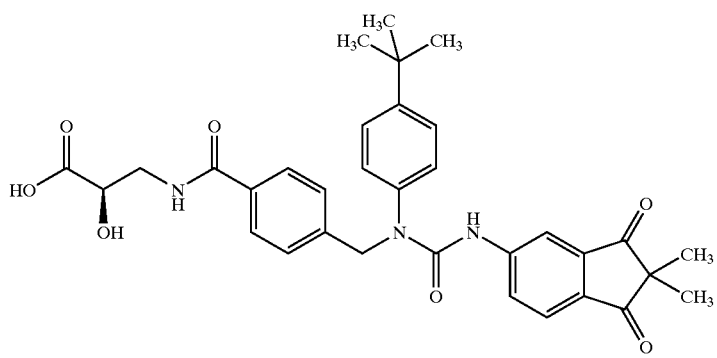
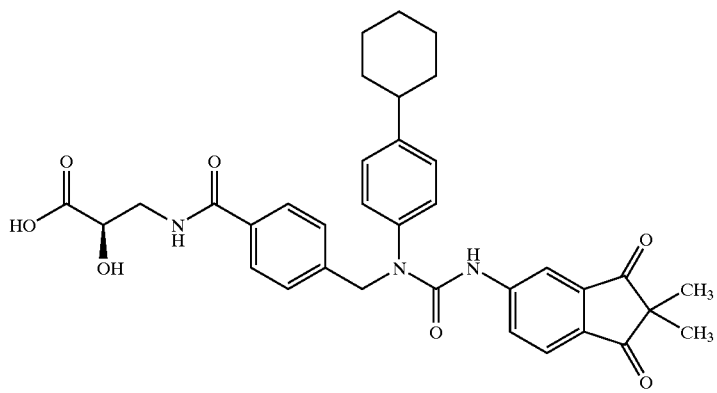
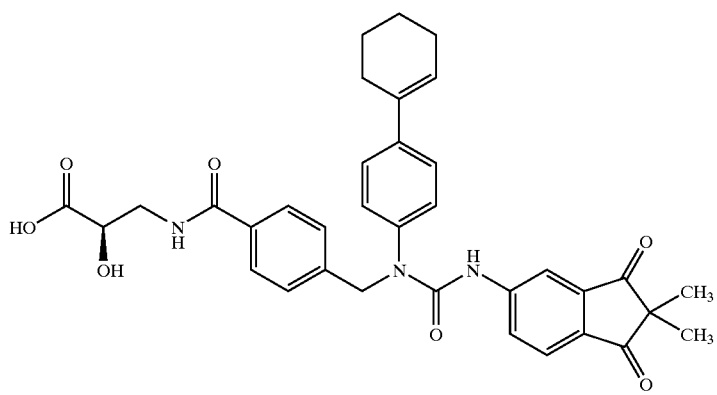

-continued
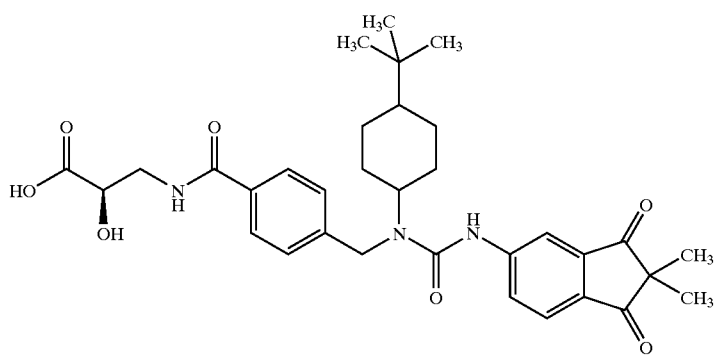
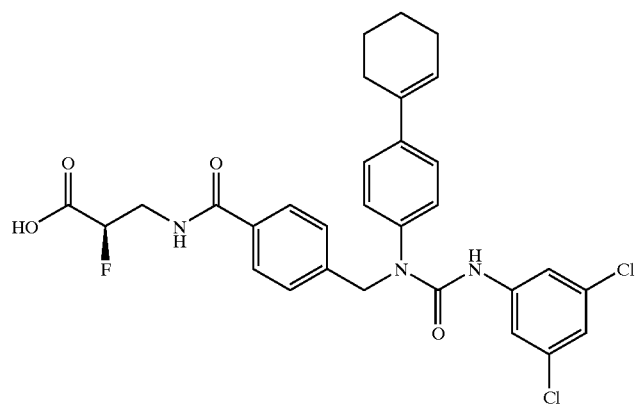
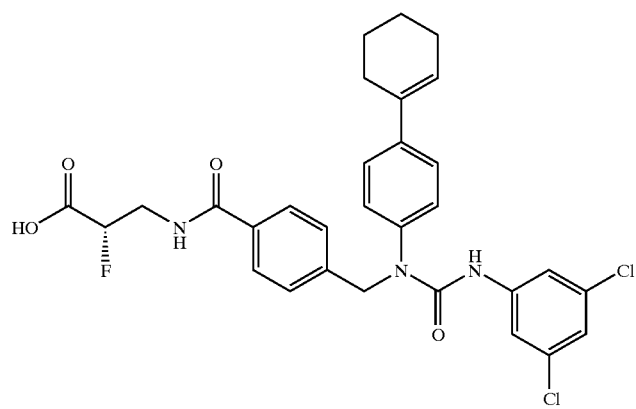
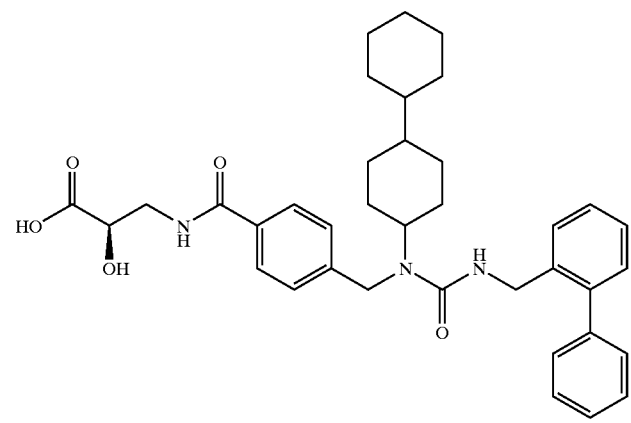

-continued
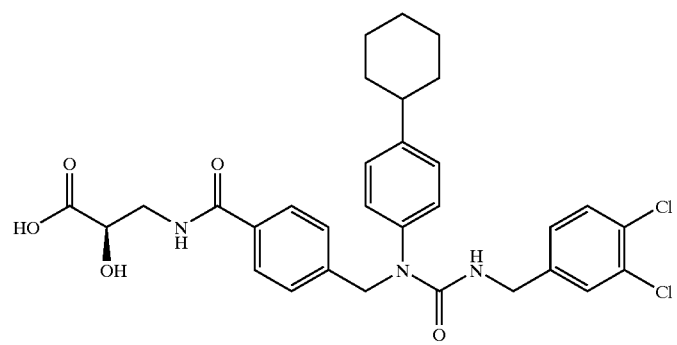
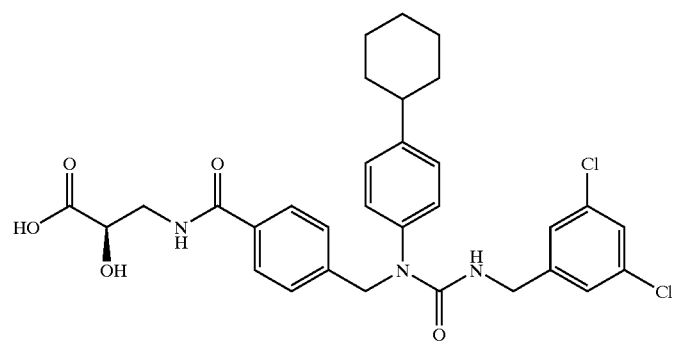
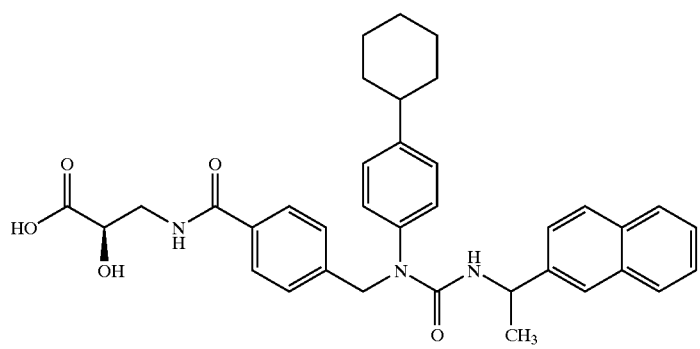
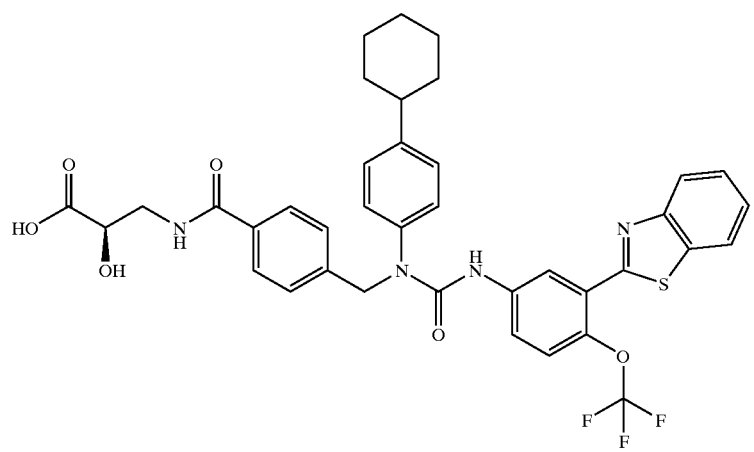

-continued
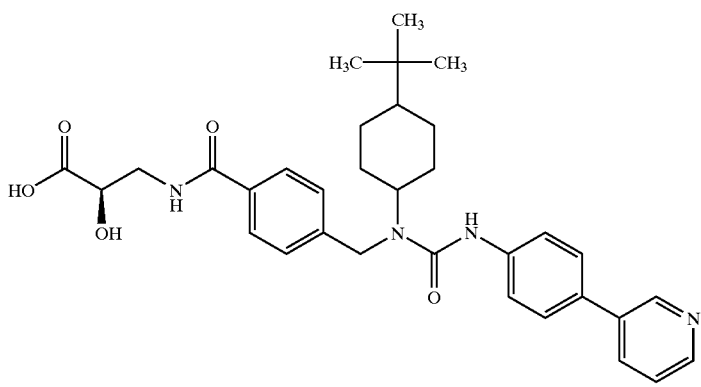
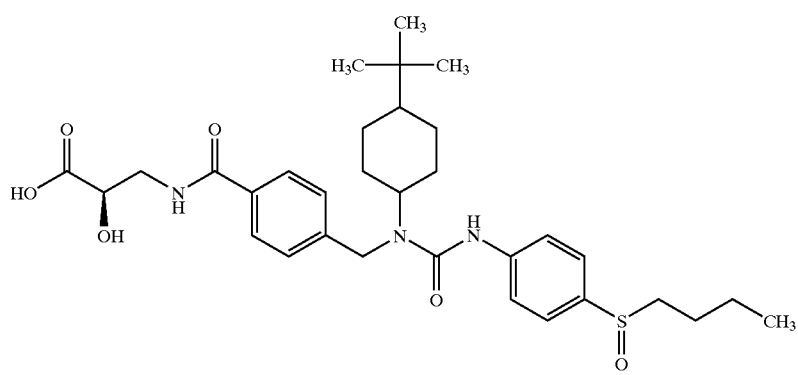
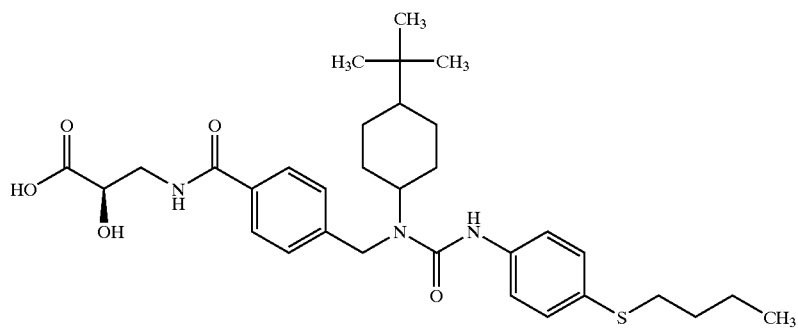
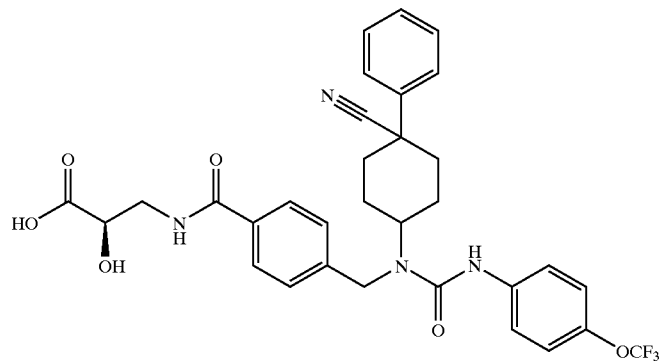

-continued
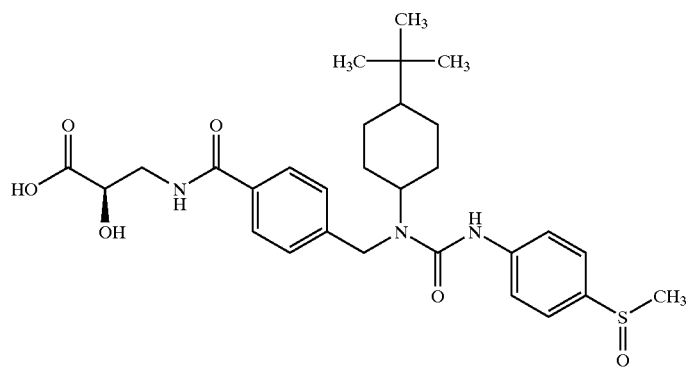
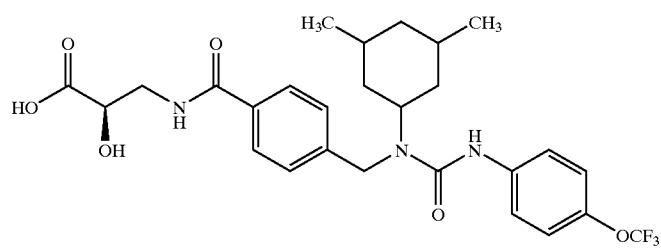
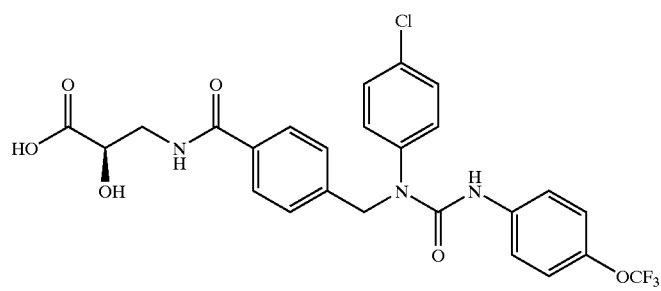
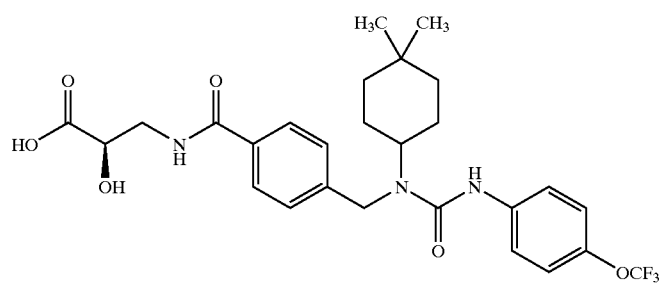
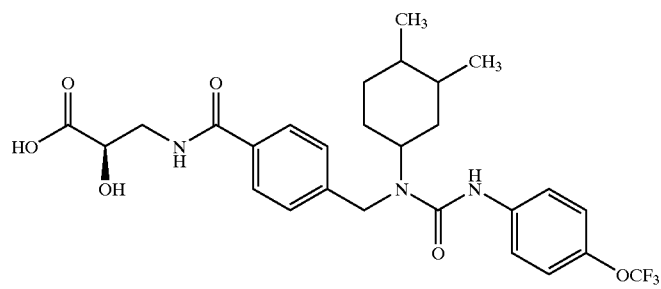

-continued
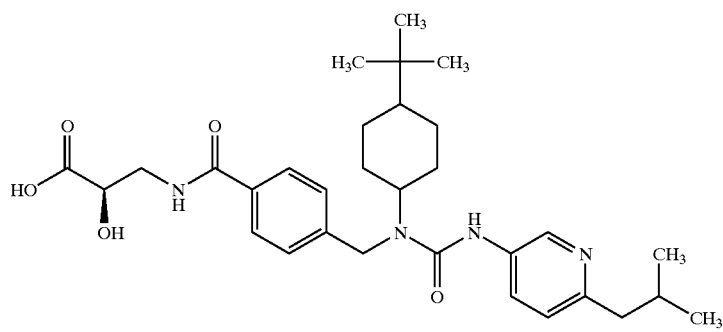
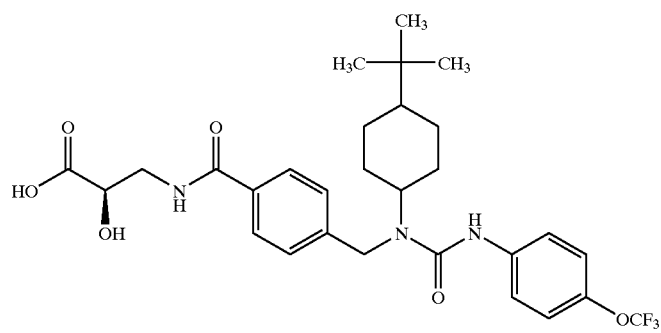
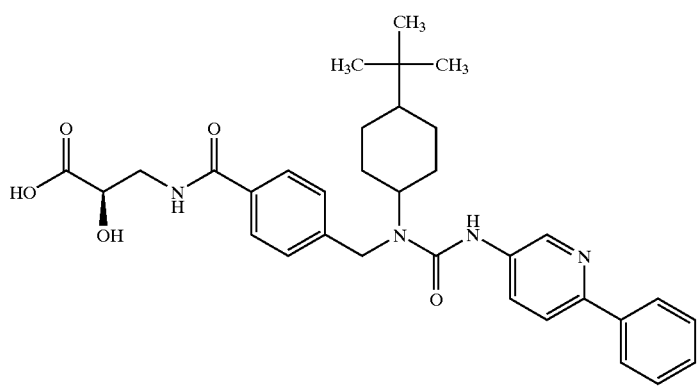
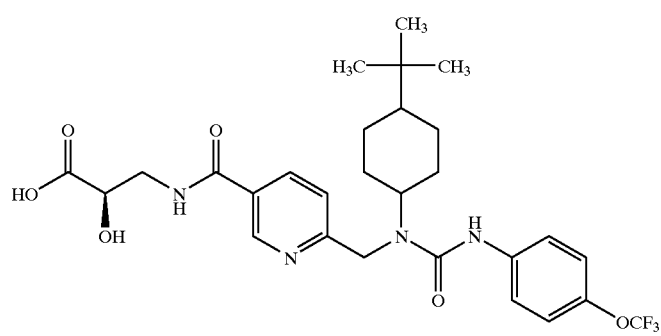

-continued
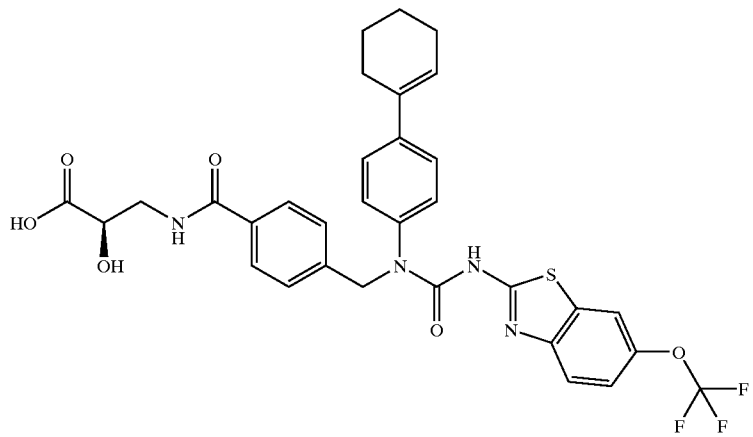
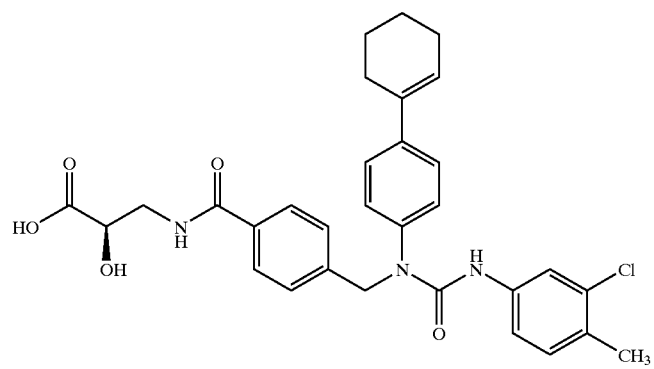
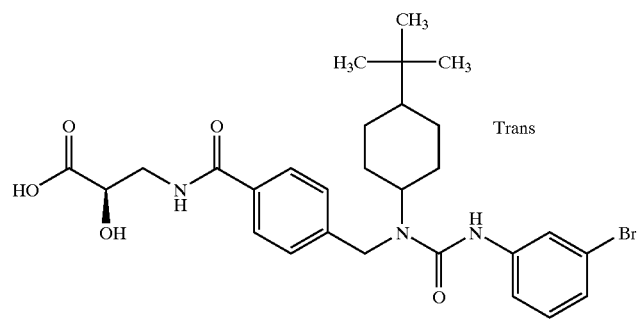
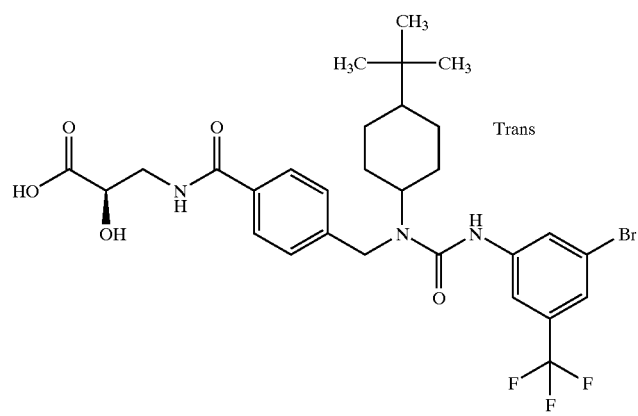

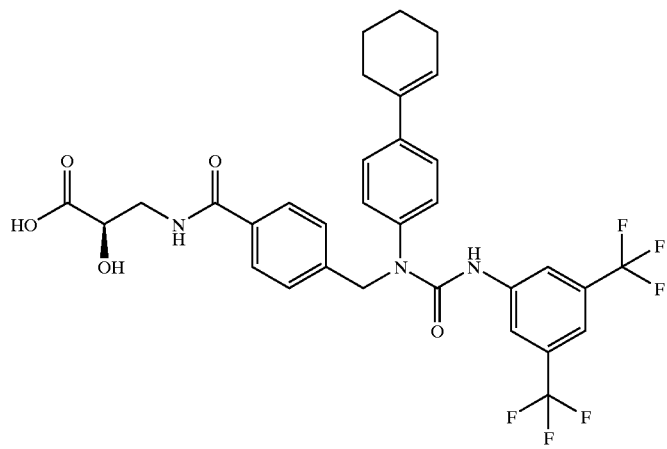
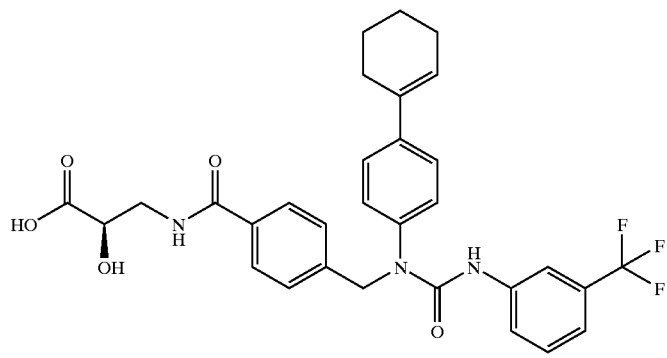
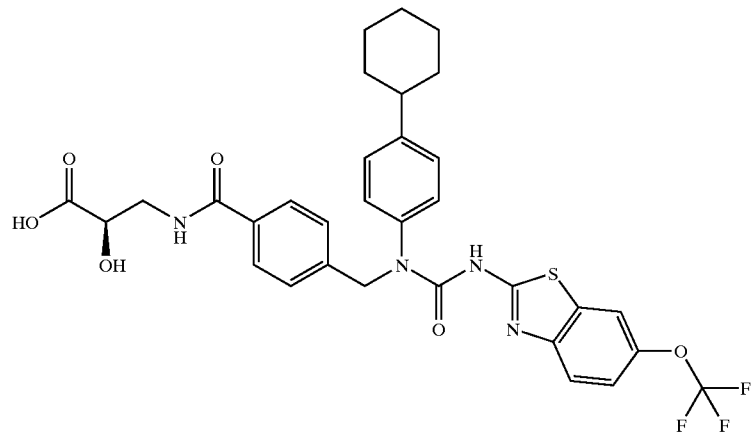

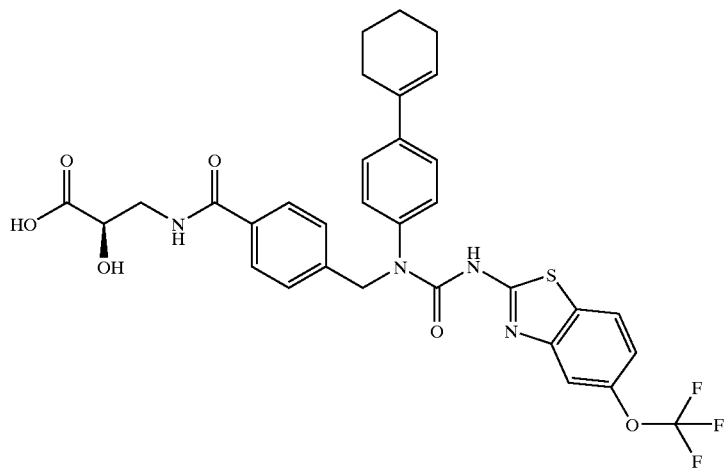
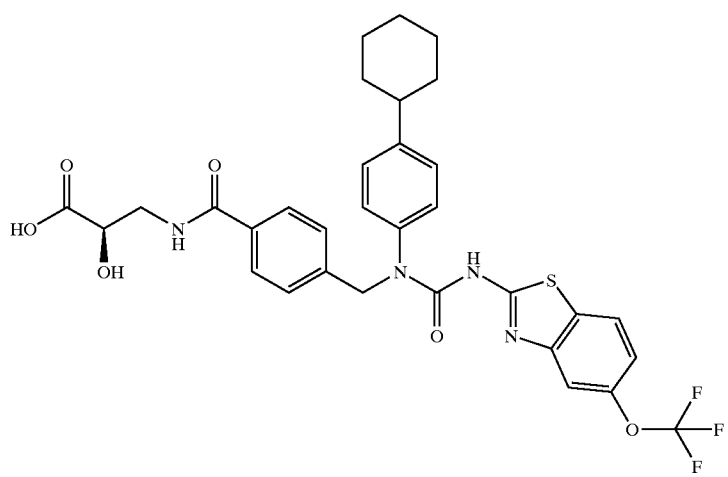
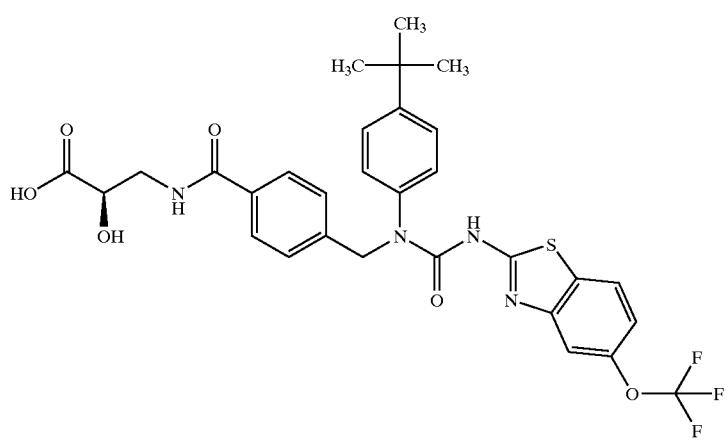

-continued
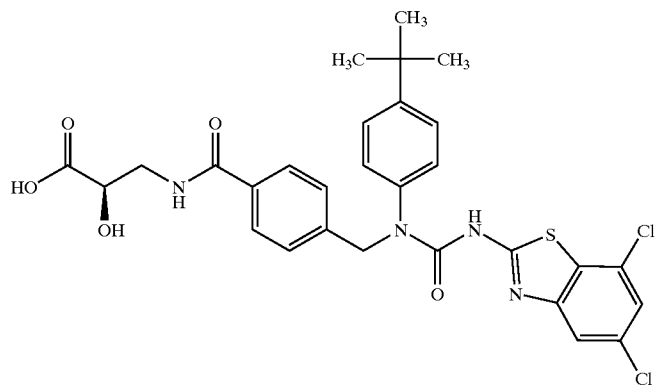
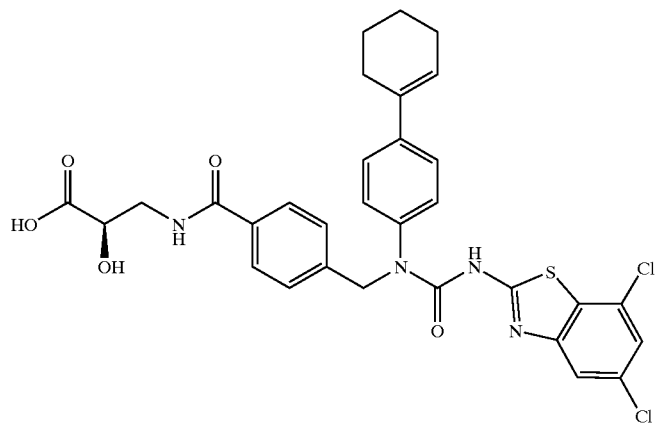
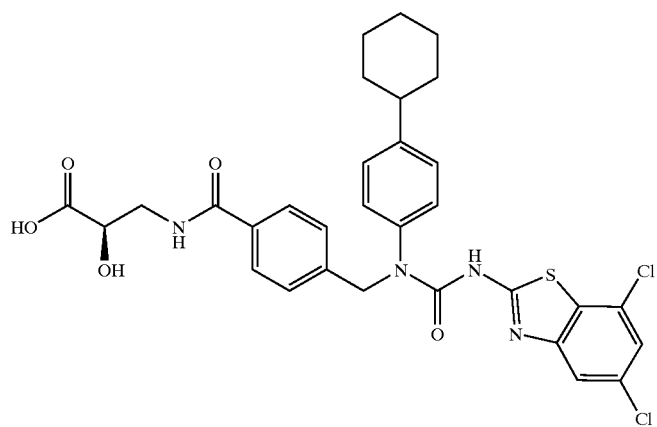

-continued
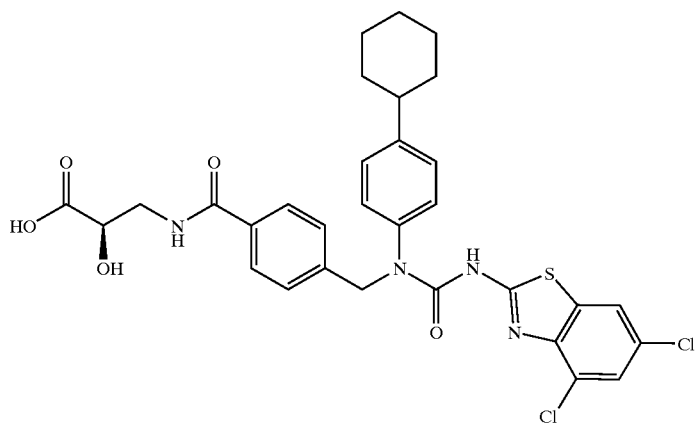
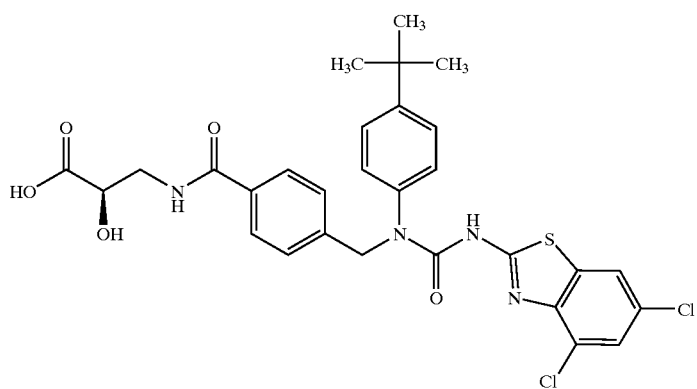
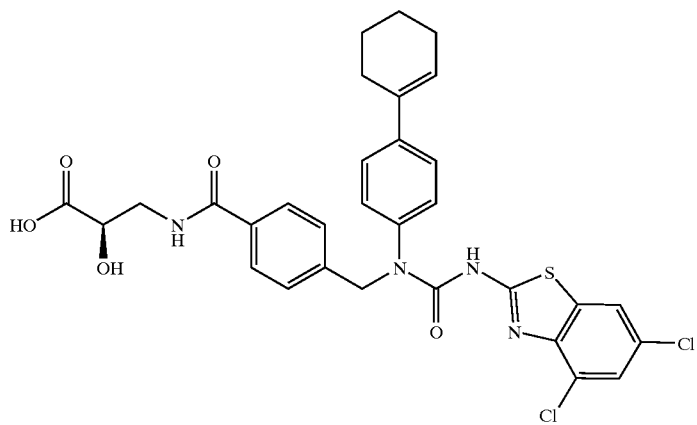

-continued
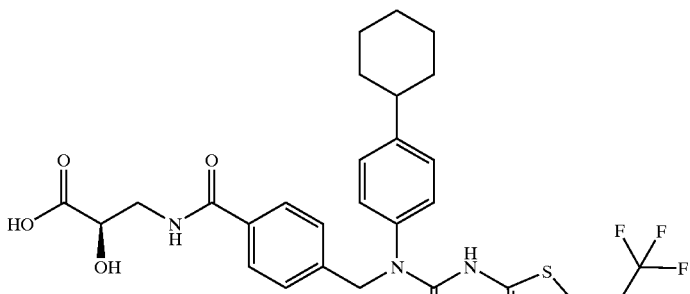
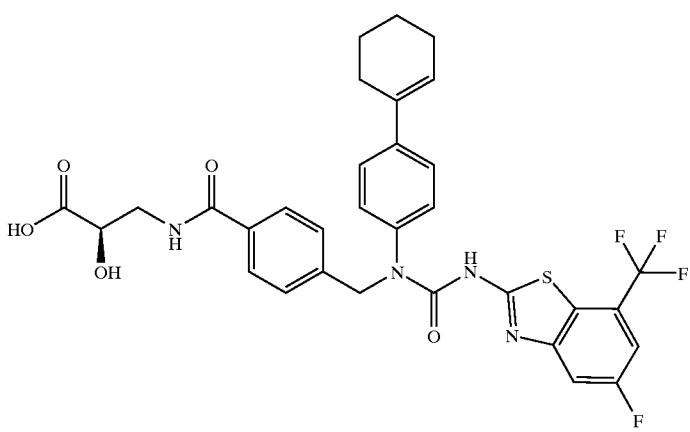
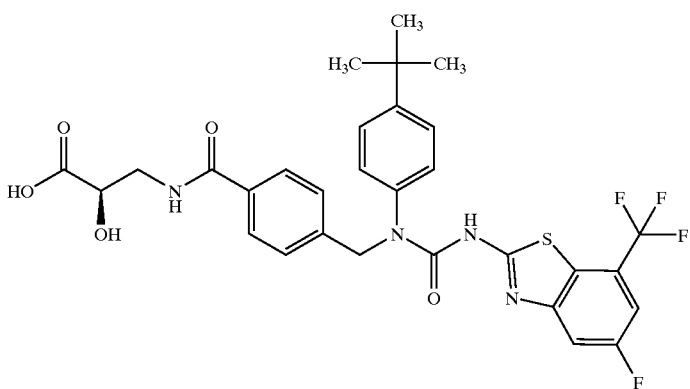
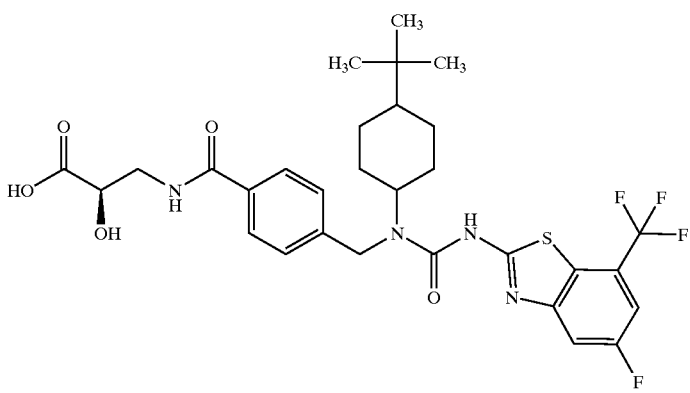

(R) and (S) diastereomers of
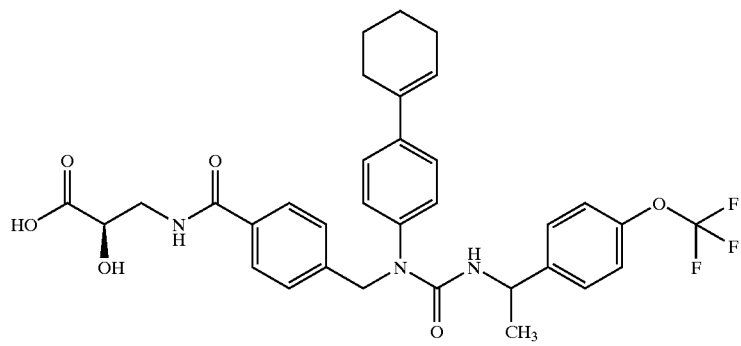
(R) and (S) diastereomers of
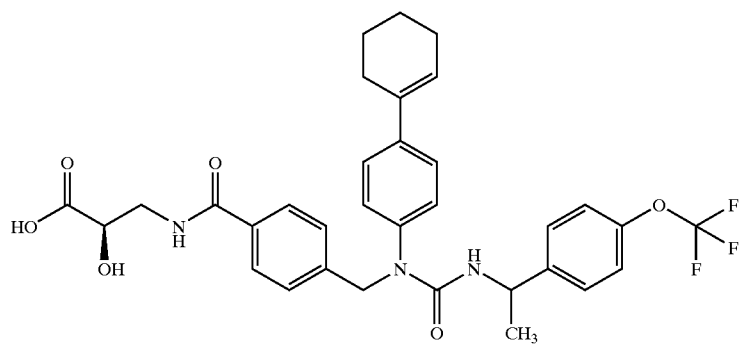
(R) and (S) diastereomers of
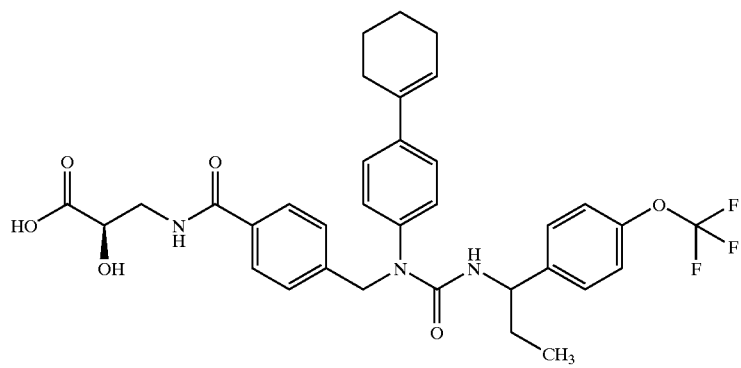
(R) and (S) diastereomers of
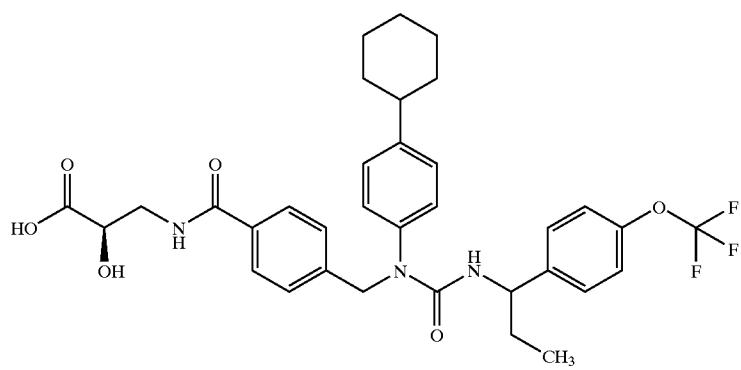

(R) and (S) diastereomers of
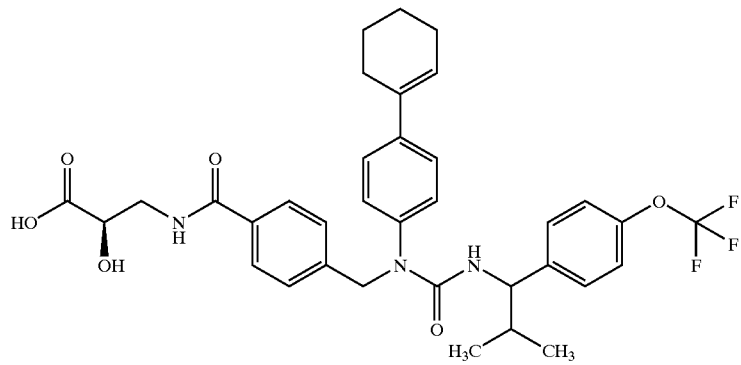
(R) and (S) diastereomers of
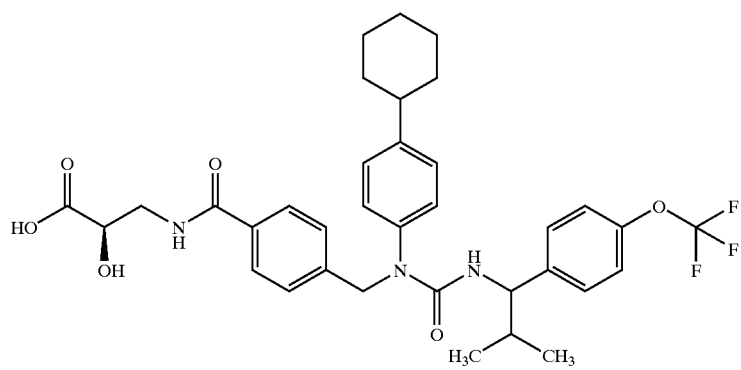
(R) and (S) diastereomers of
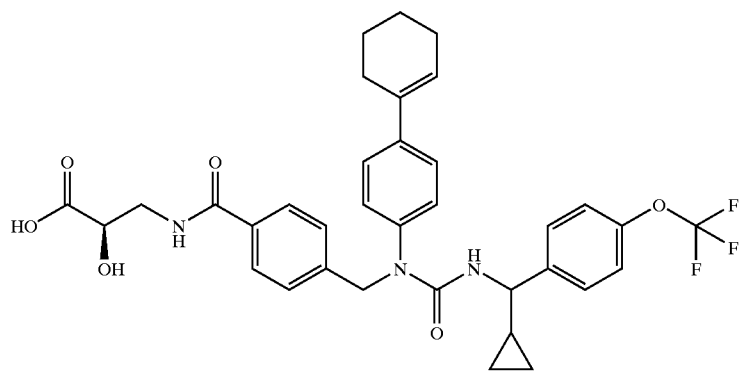

(R) and (S) diastereomers of
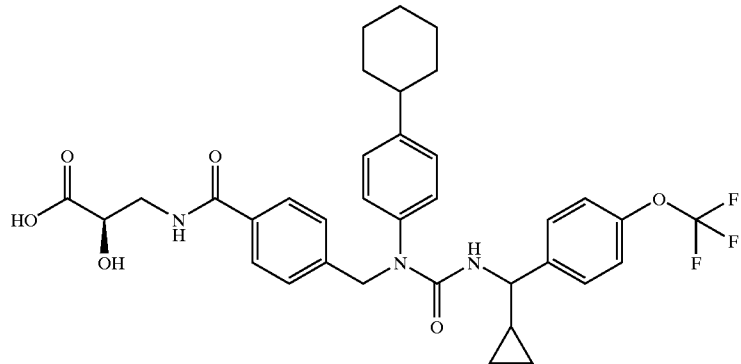
(R) and (S) diastereomers of
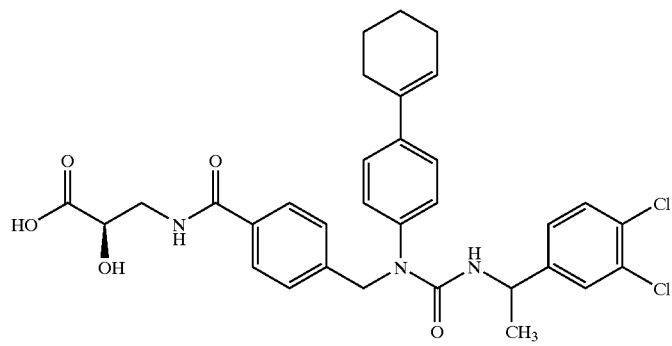
(R) and (S) diastereomers of
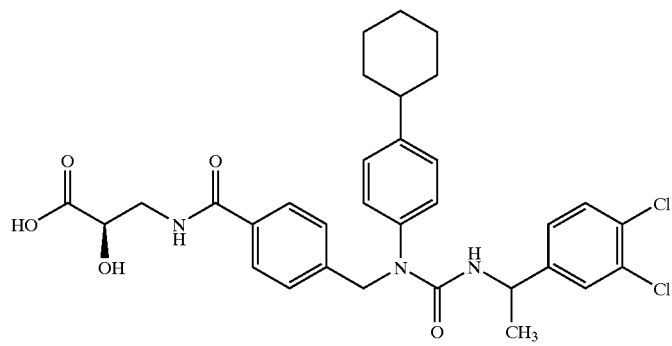

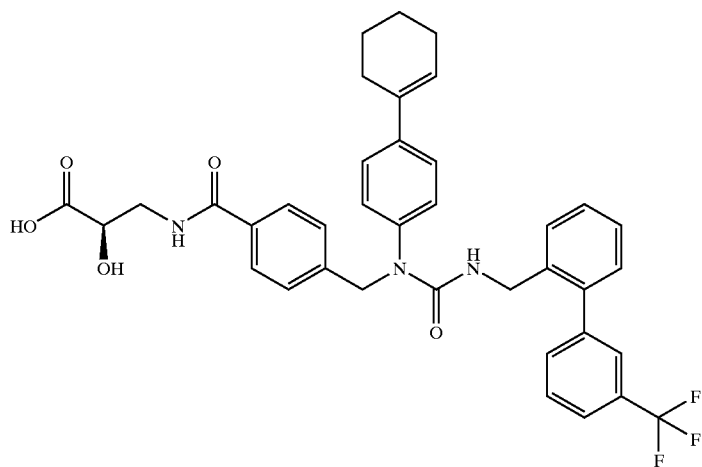
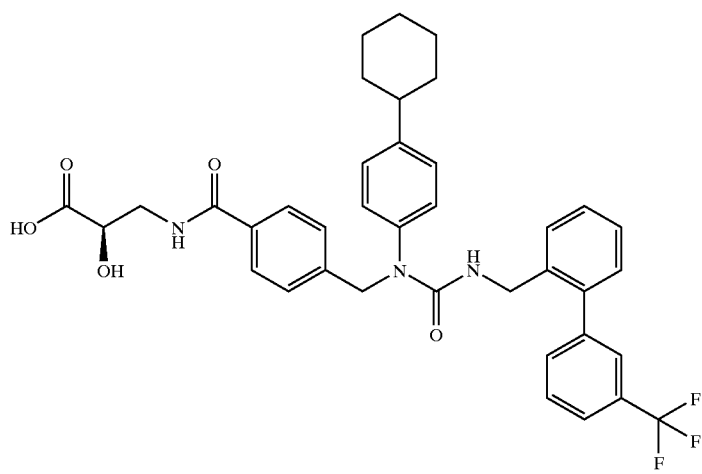
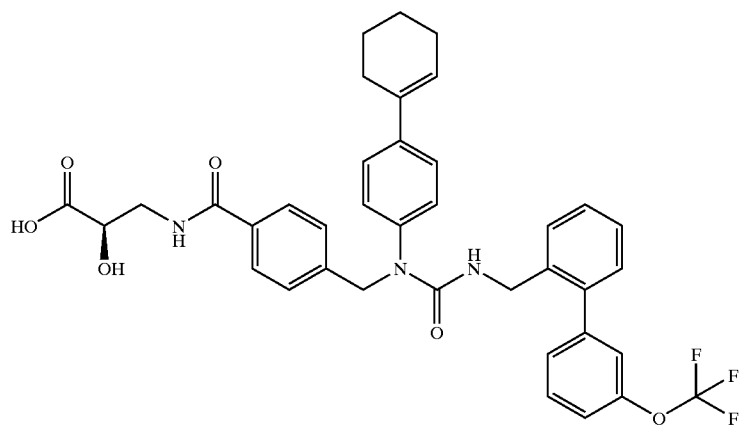

-continued
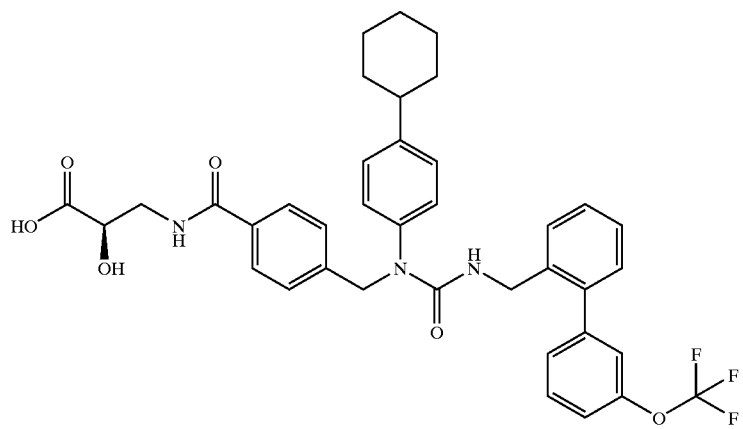
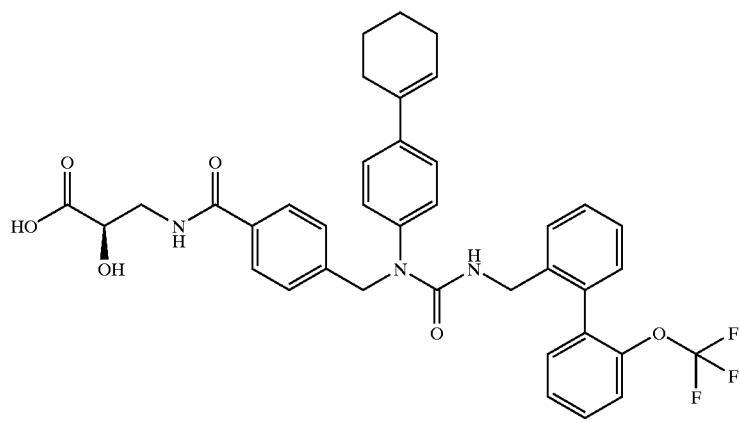
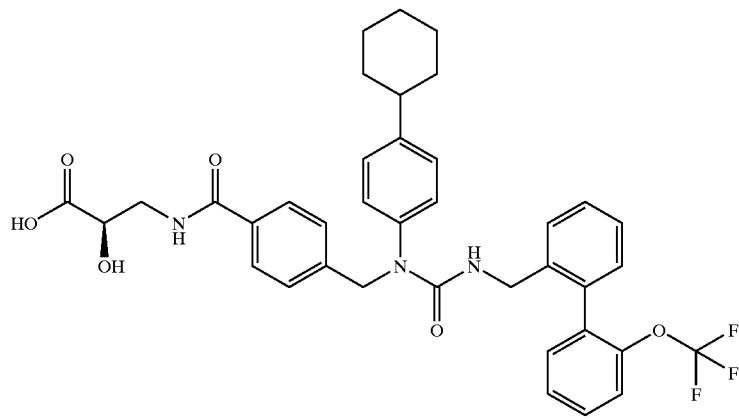

(R) and (S) diastereomers of
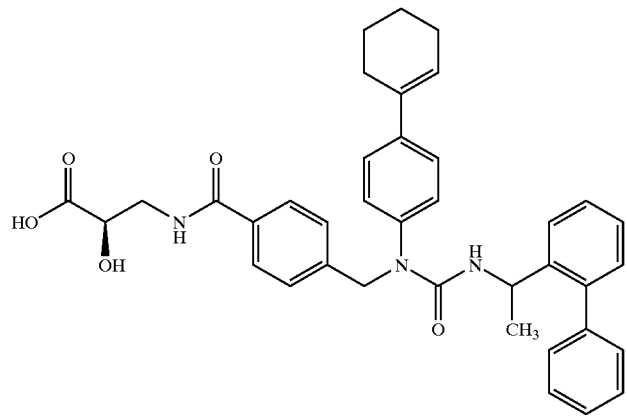
(R) and (S) diastereomers of
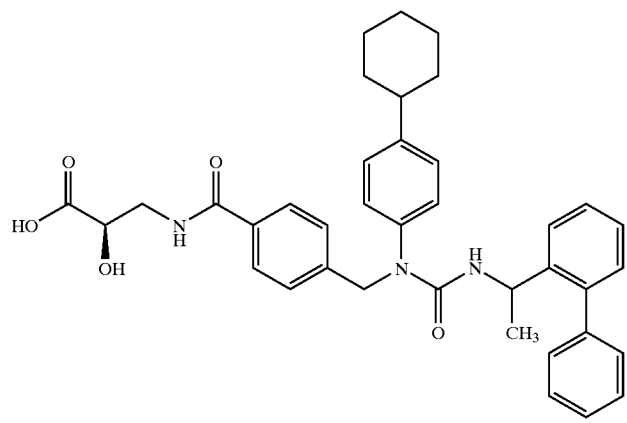
(R) and (S) diastereomers of
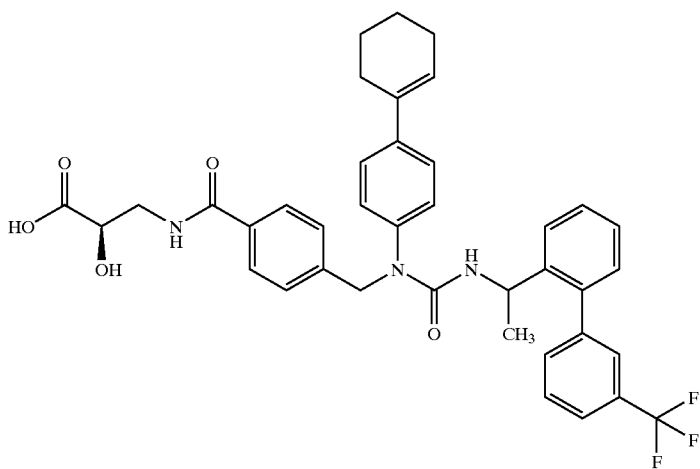

(R) and (S) diastereomers of
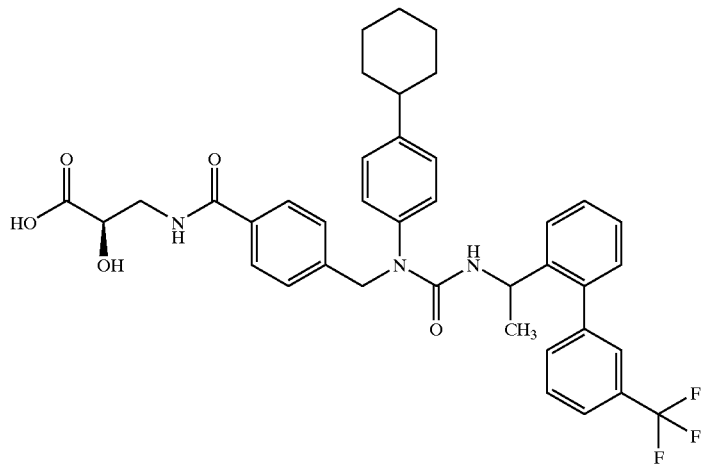
(R) and (S) diastereomers of
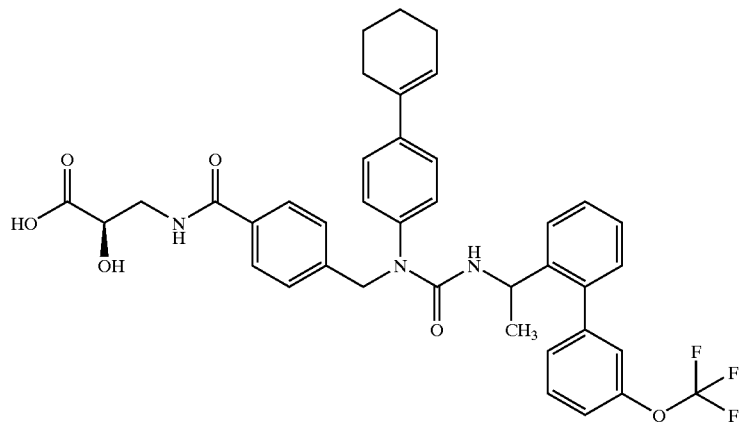
(R) and (S) diastereomers of
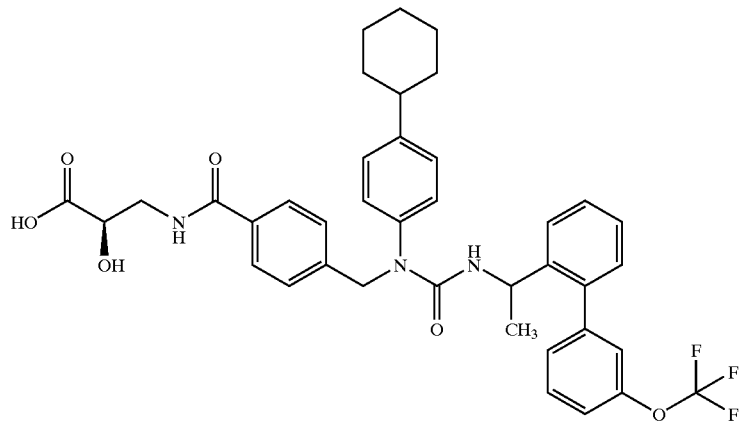

(R) and (S) diastereomers of
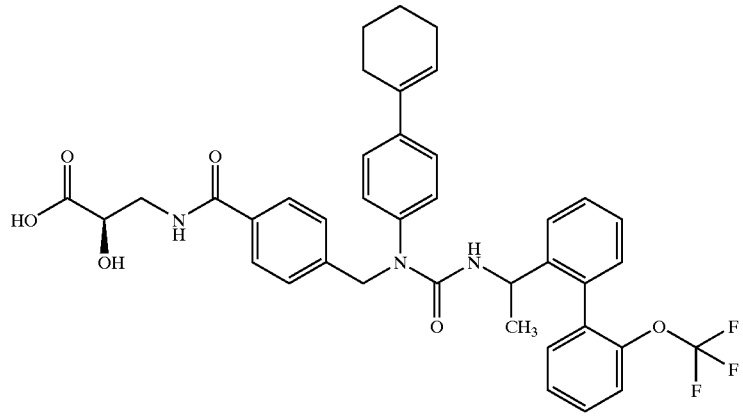
(R) and (S) diastereomers of
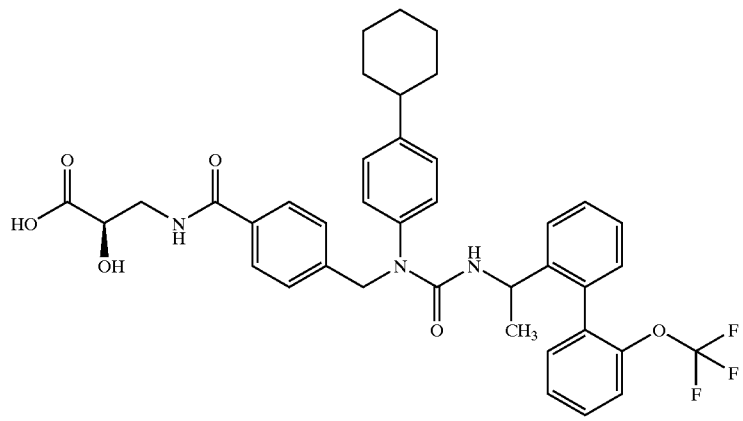
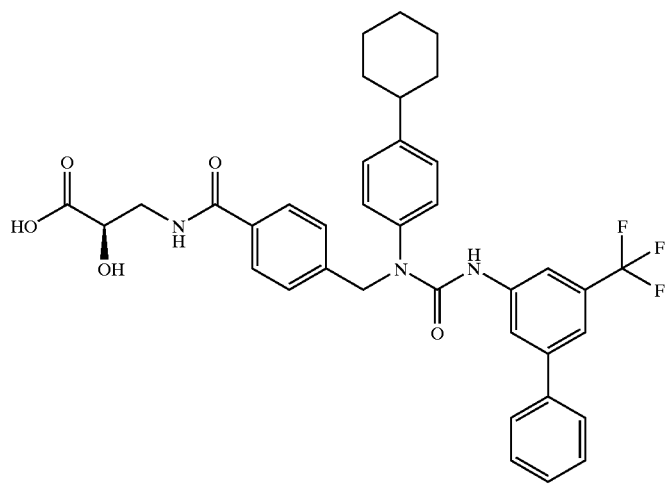

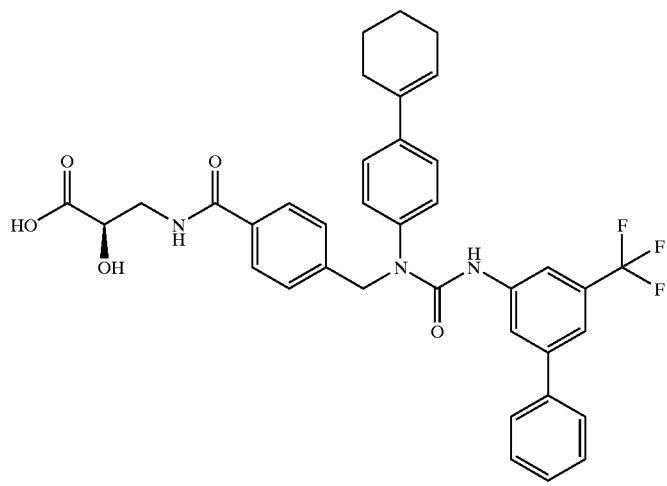
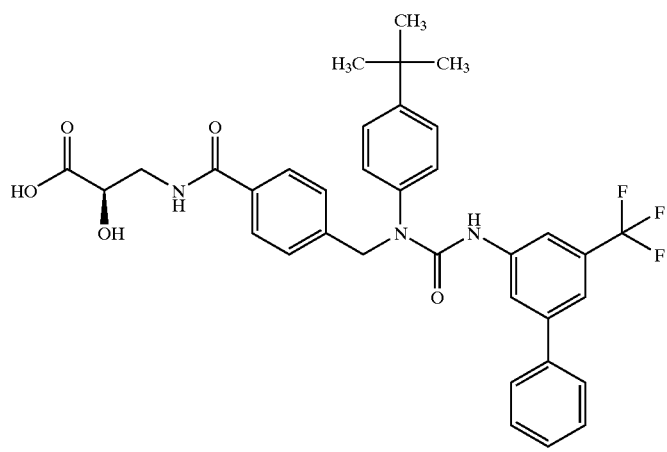
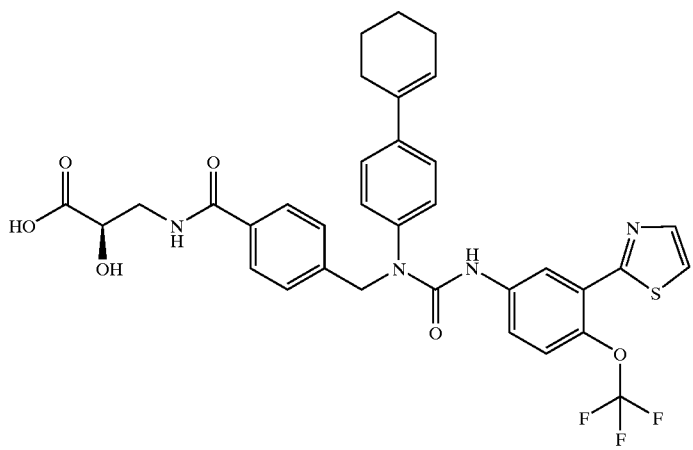

-continued
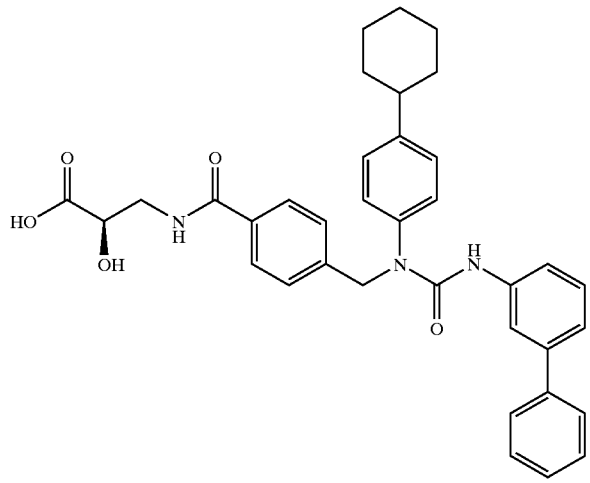
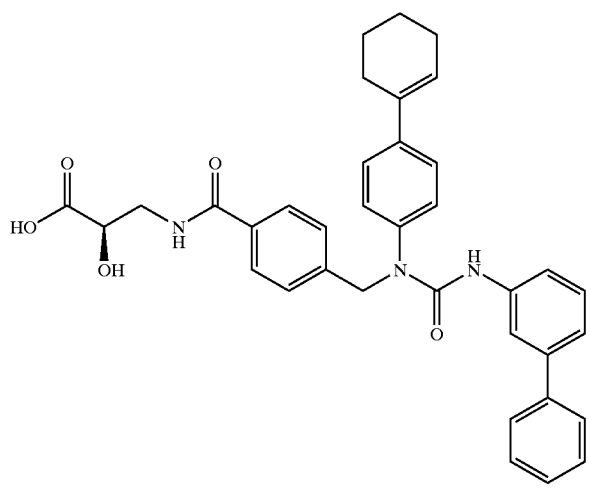
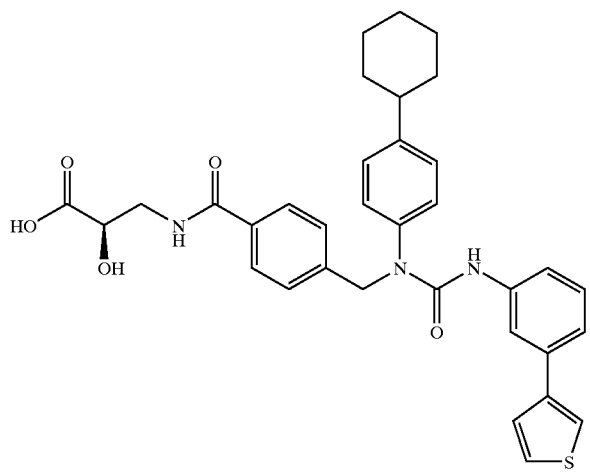

-continued
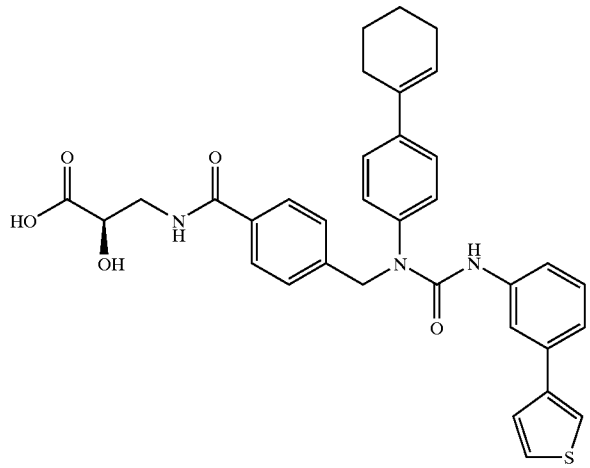
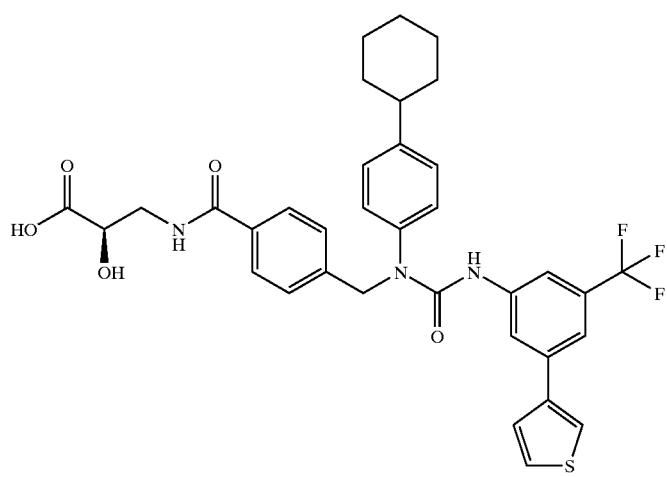
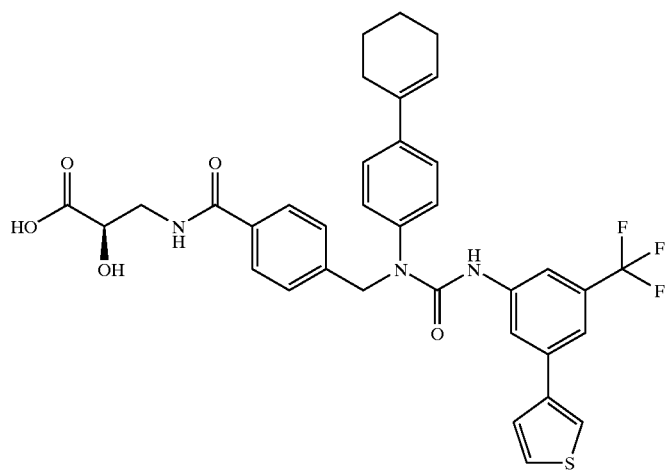

-continued
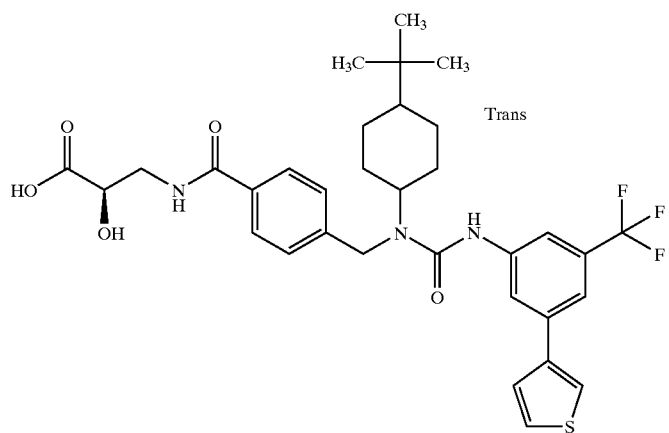
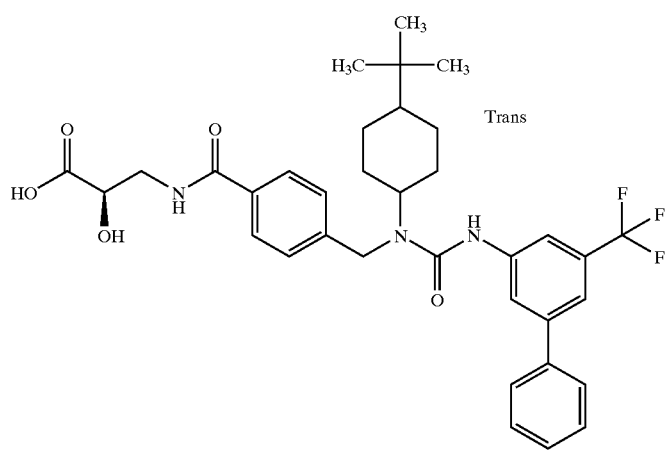
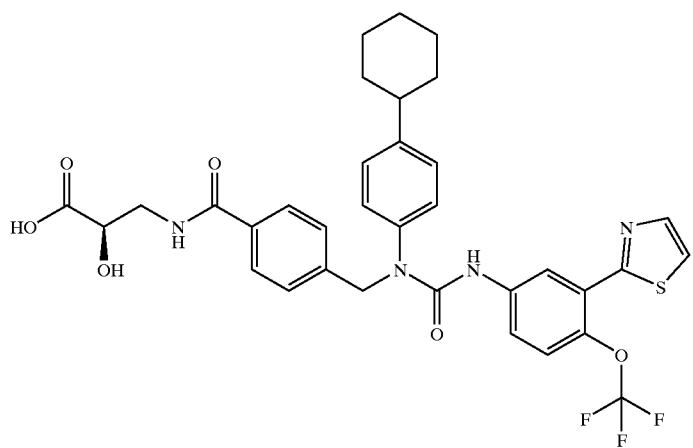

-continued
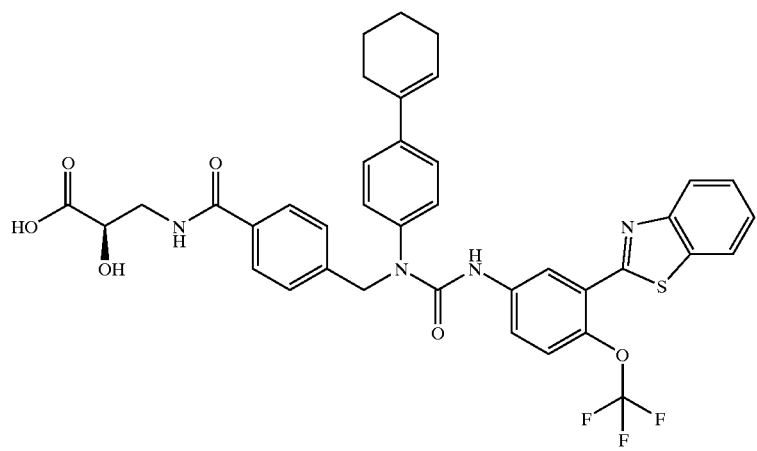
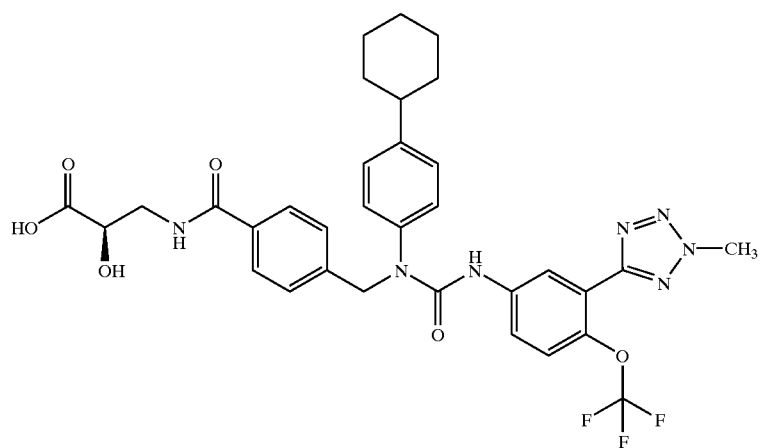
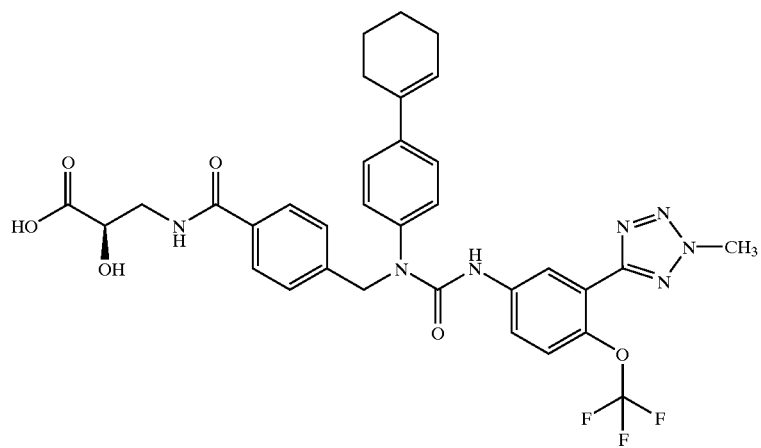

-continued
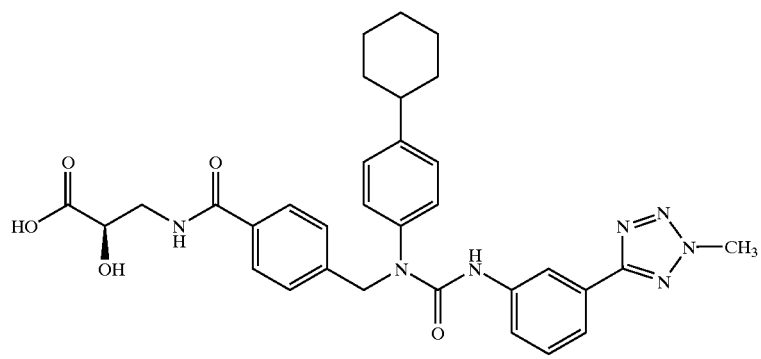
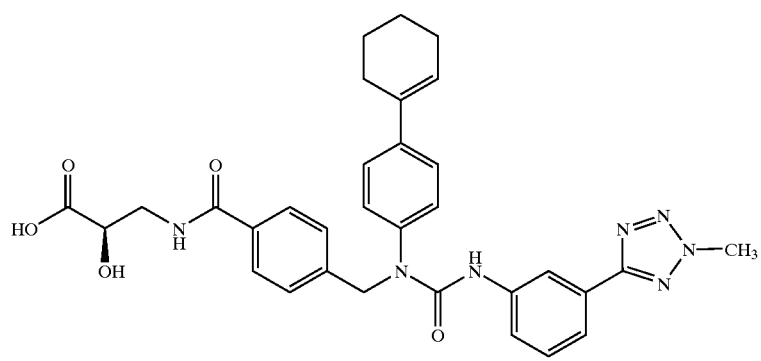
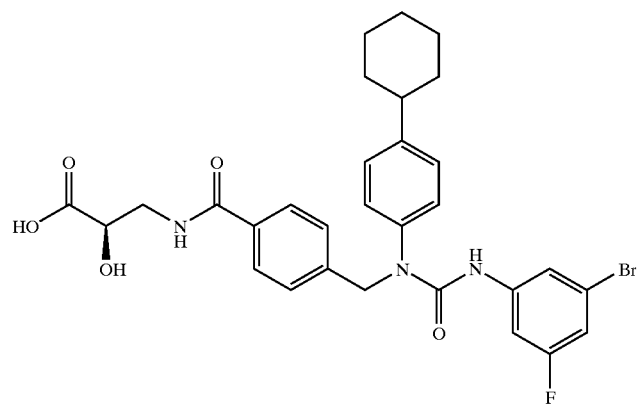
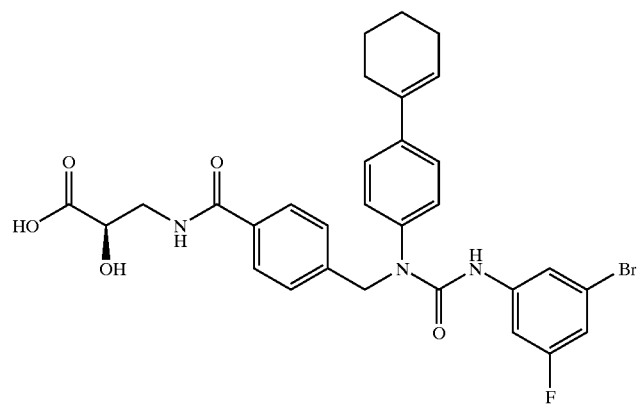

-continued
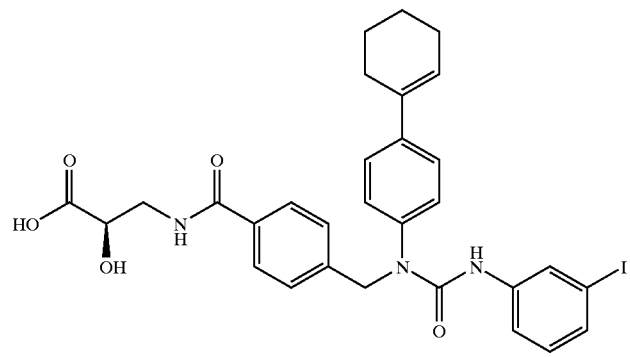
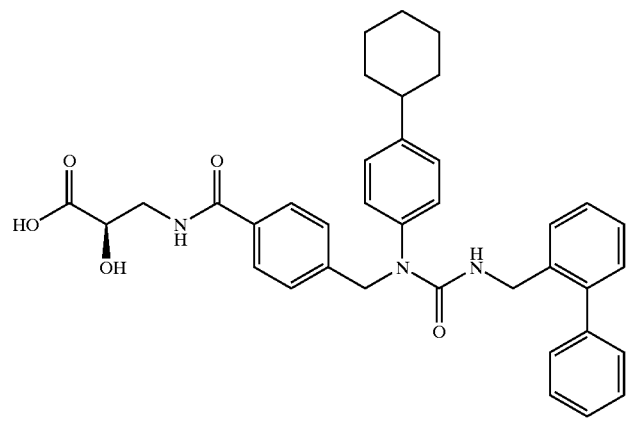
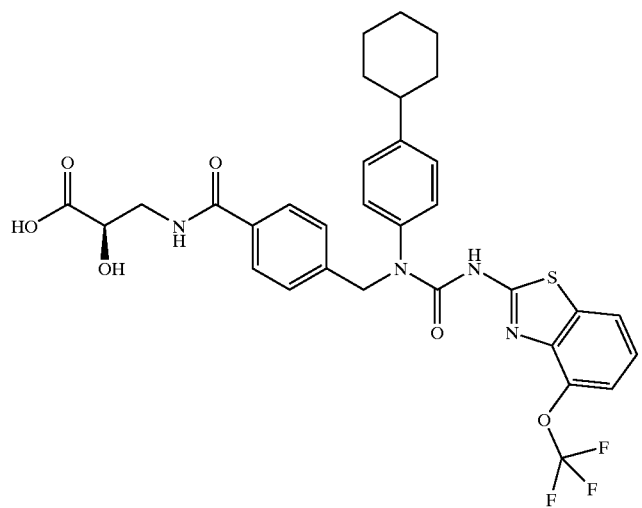

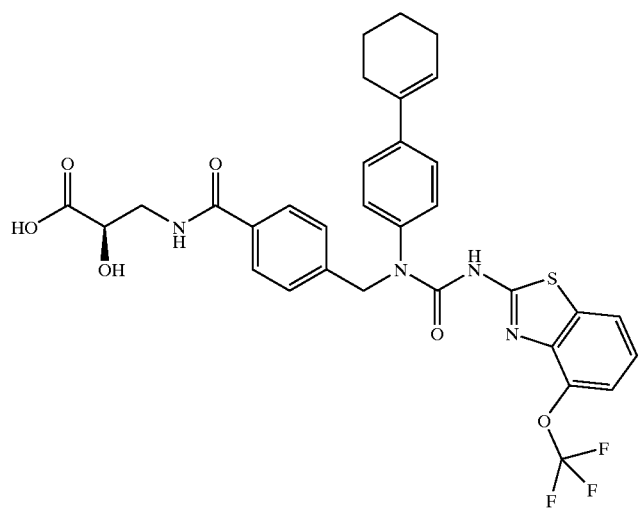
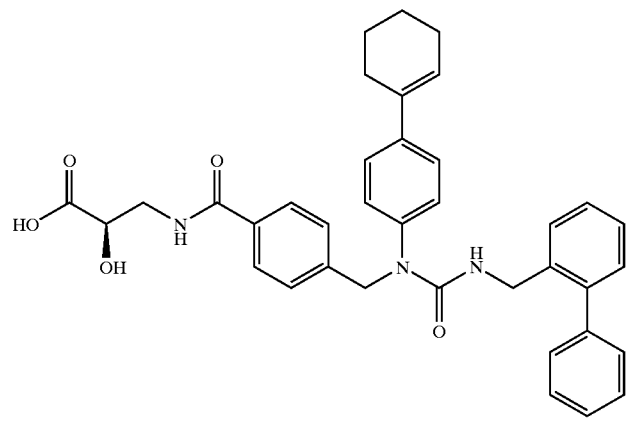
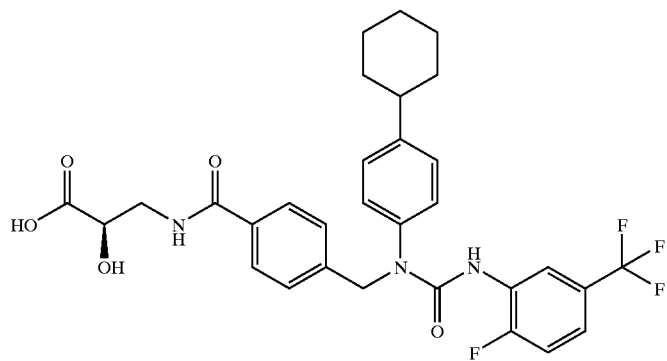

-continued
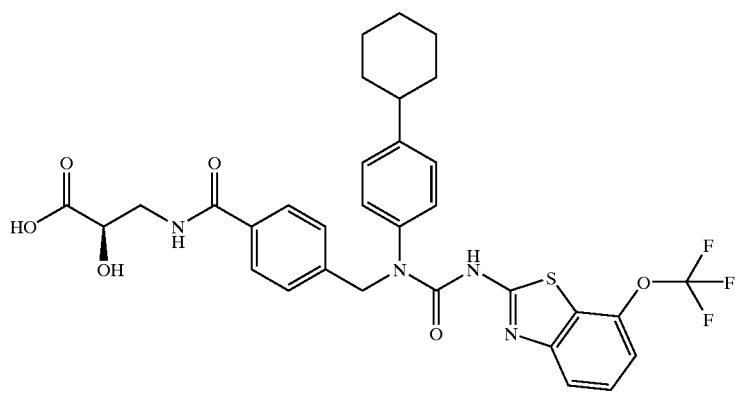
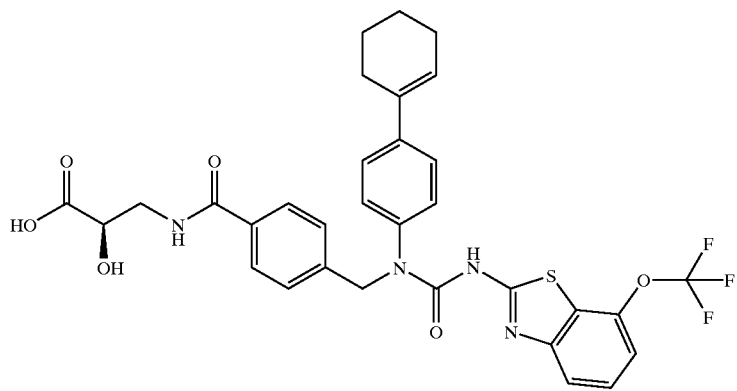
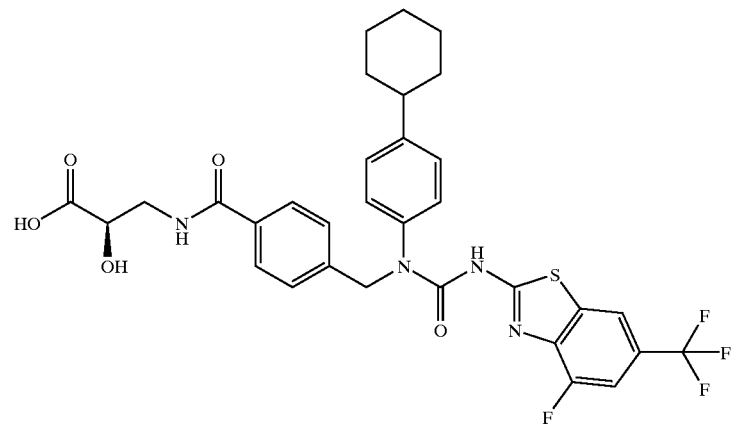

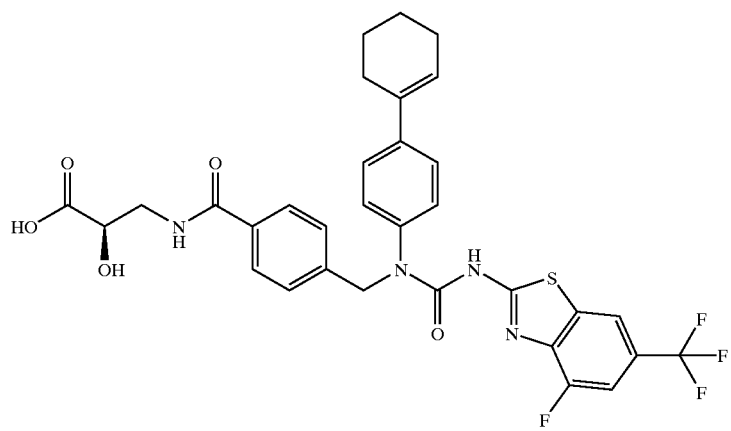
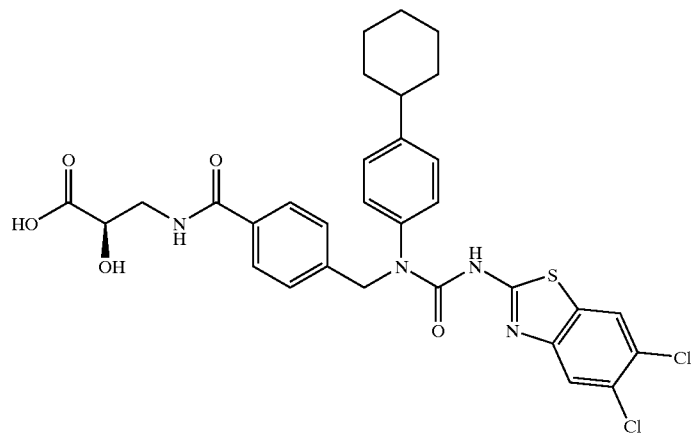
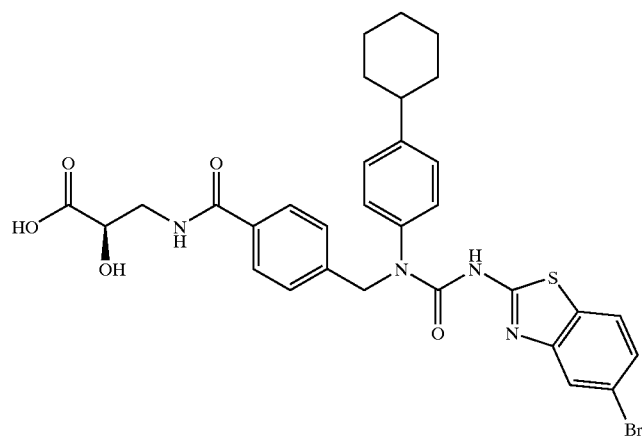

-continued
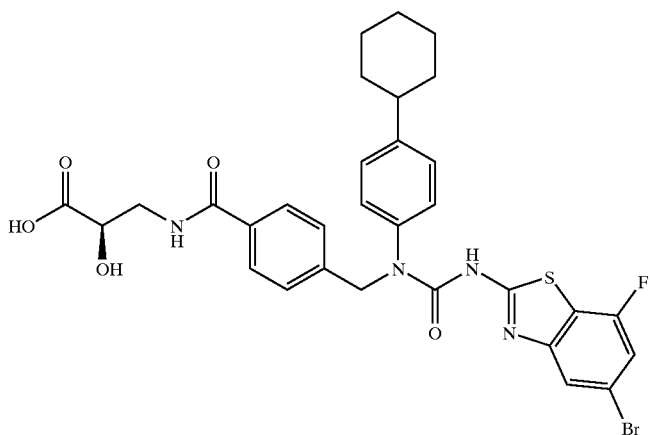
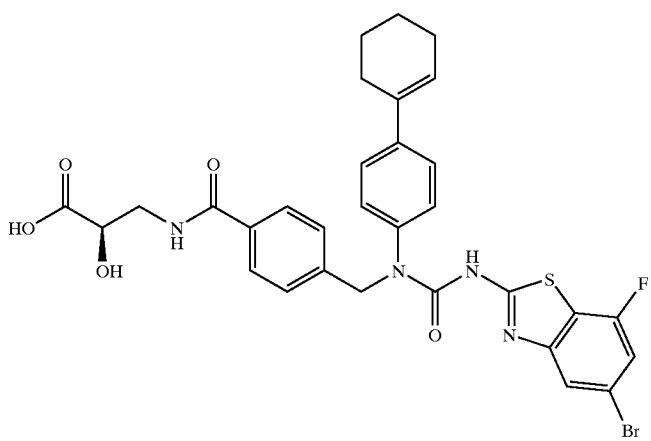
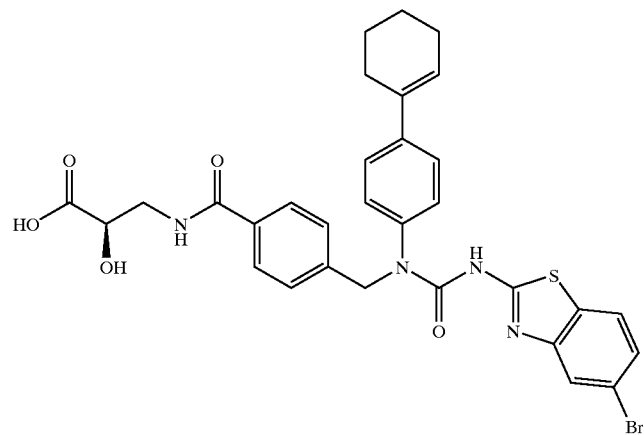

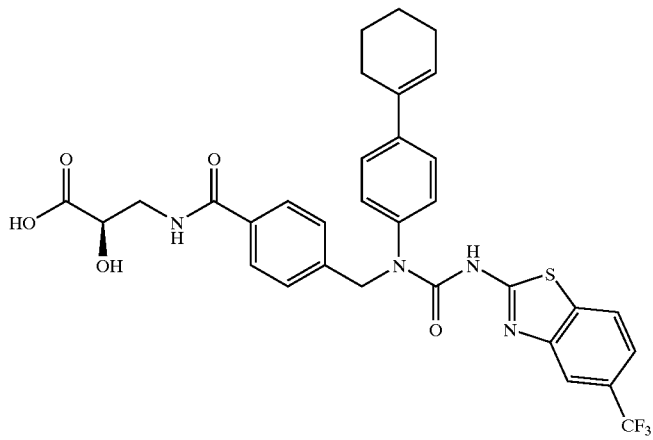
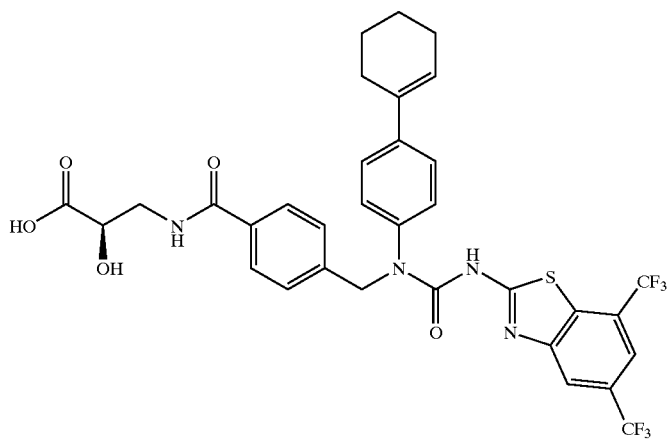
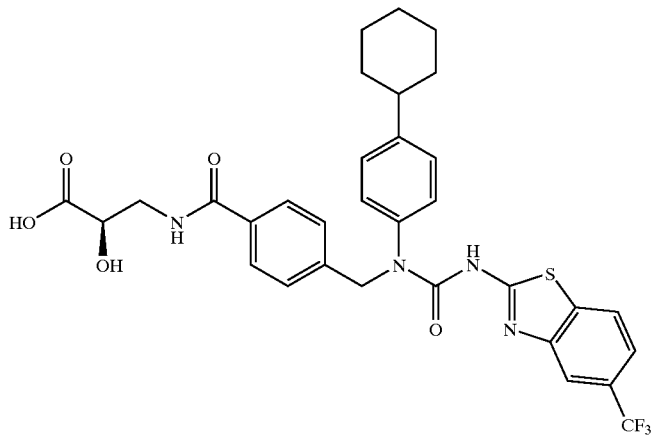

-continued
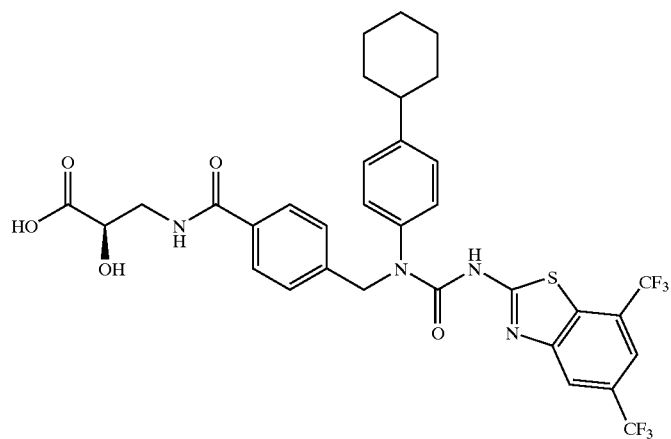
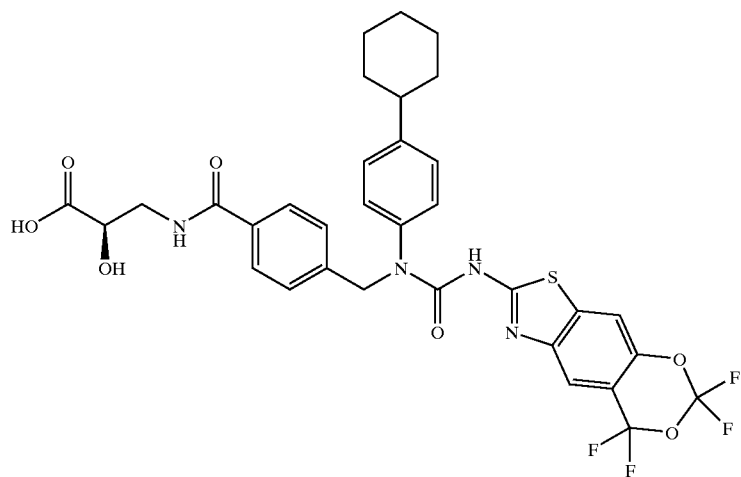
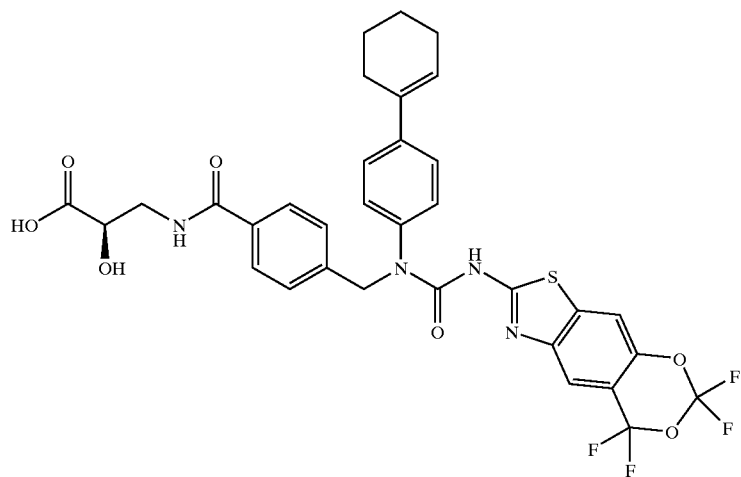

-continued
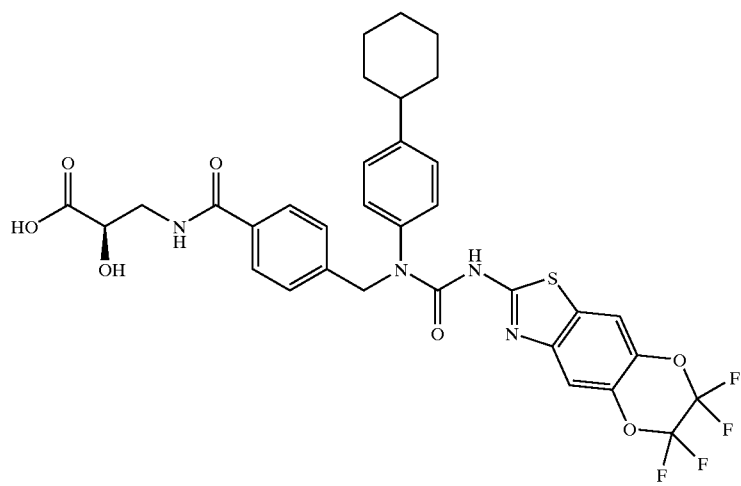
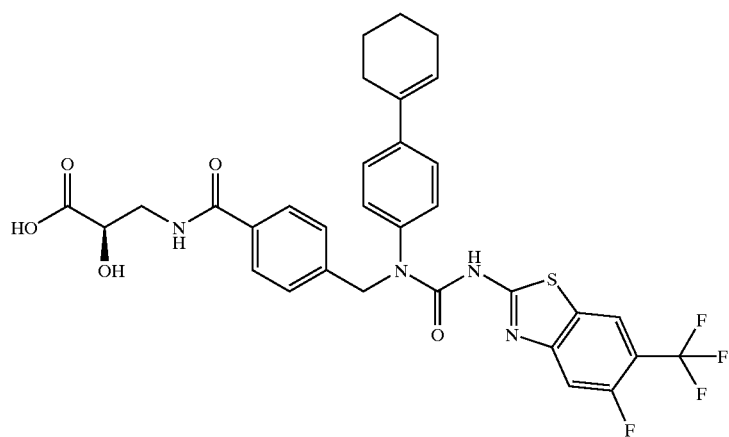
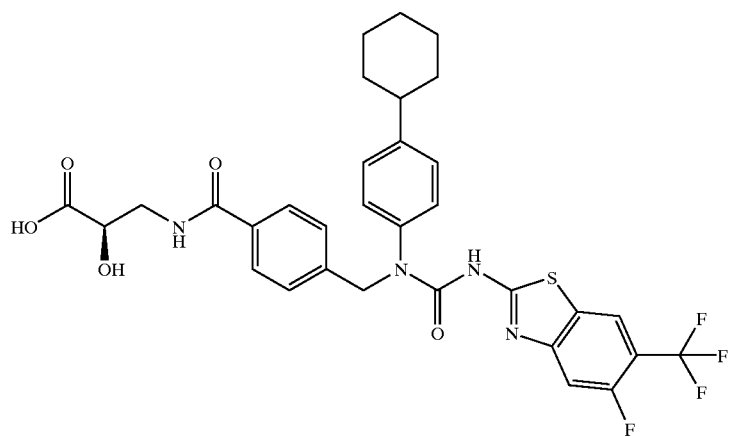

-continued
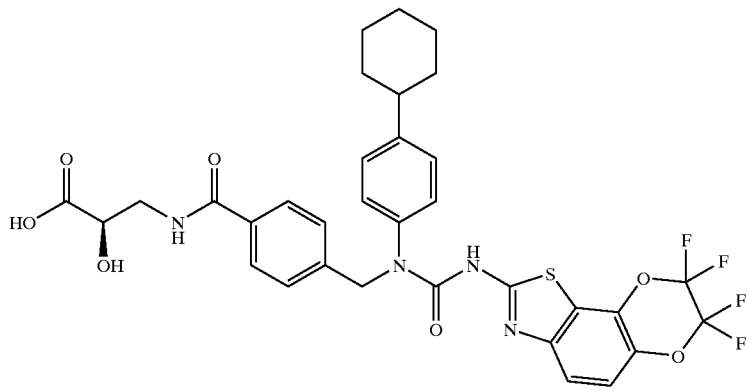
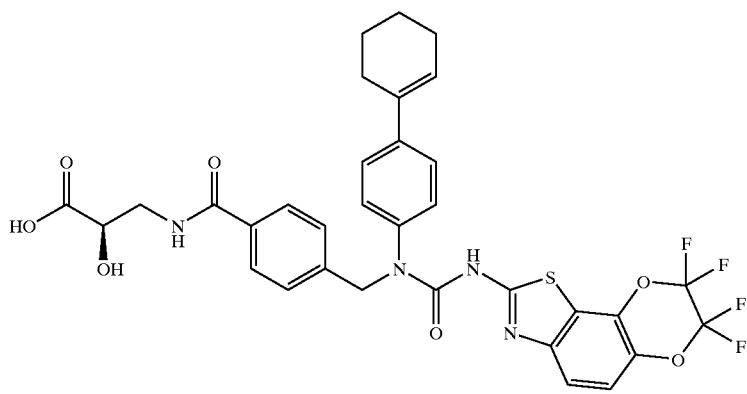
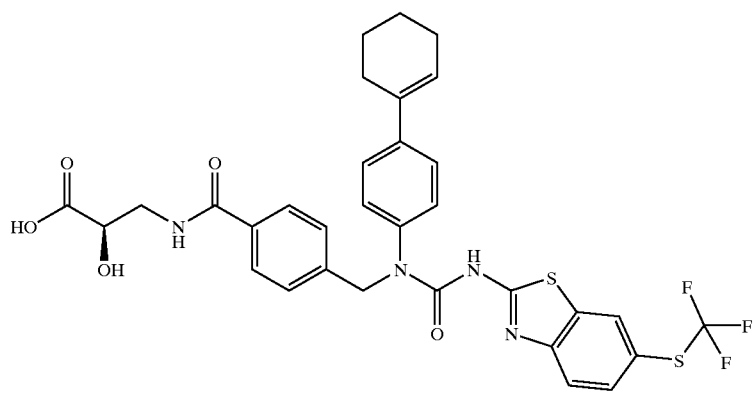
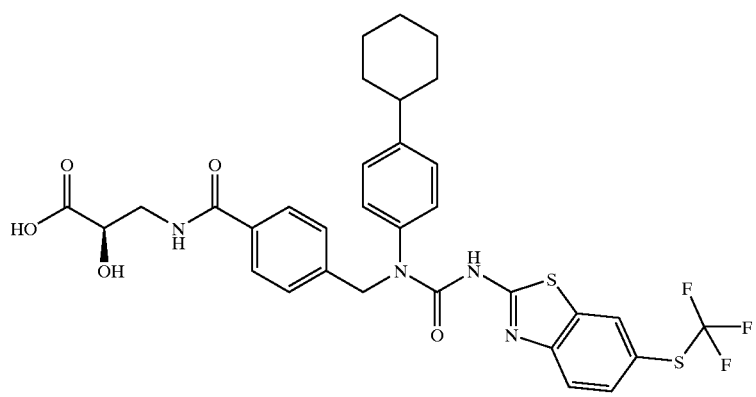

-continued
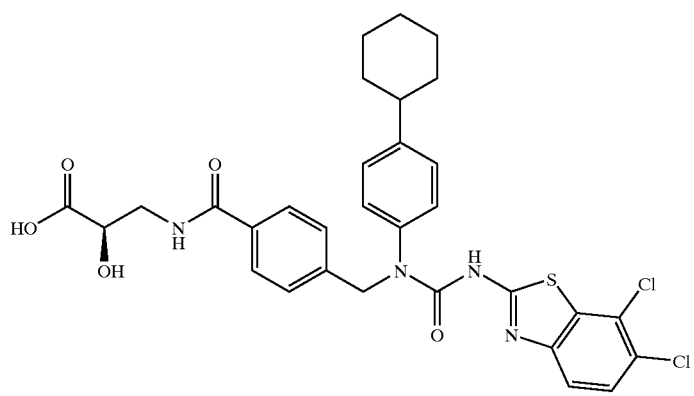
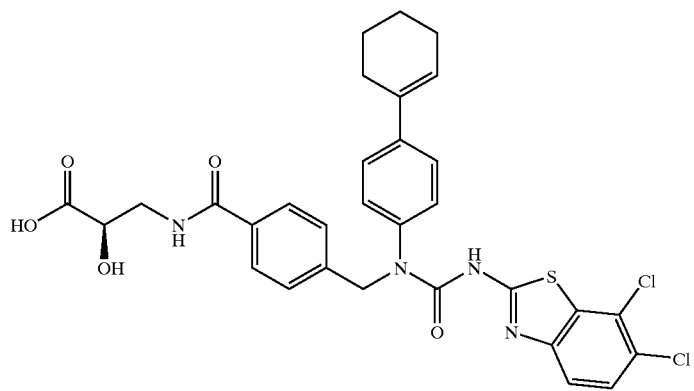
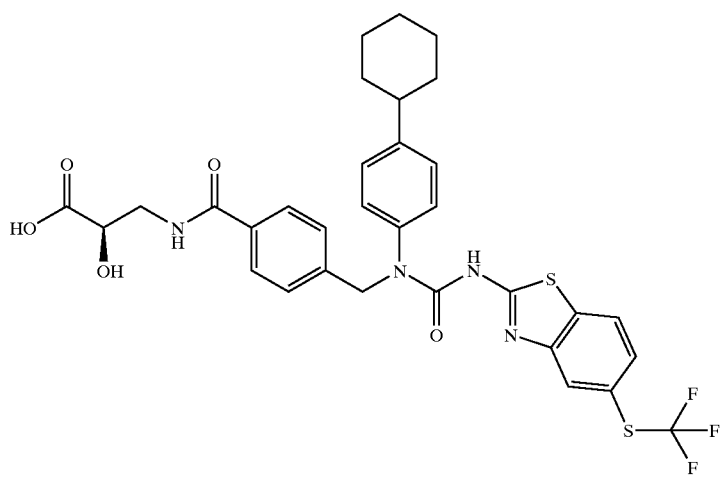

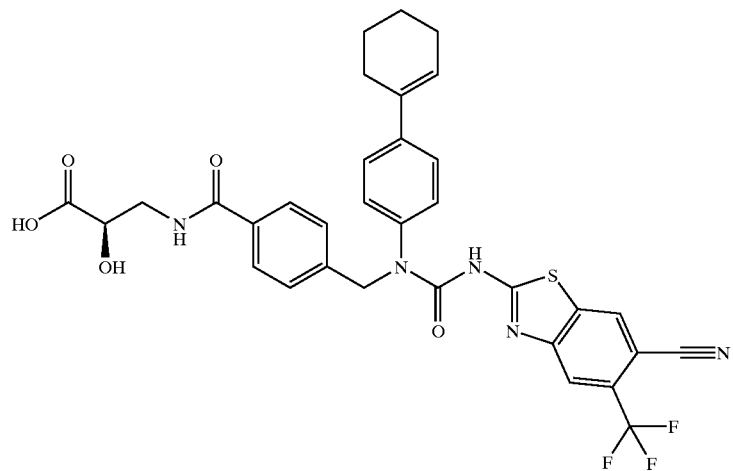
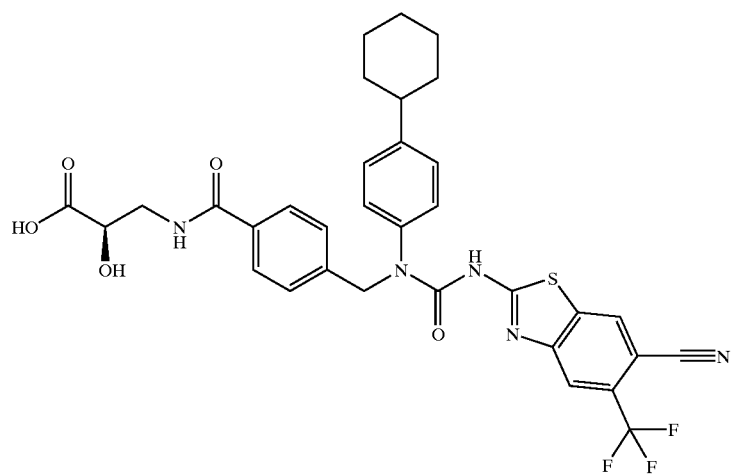
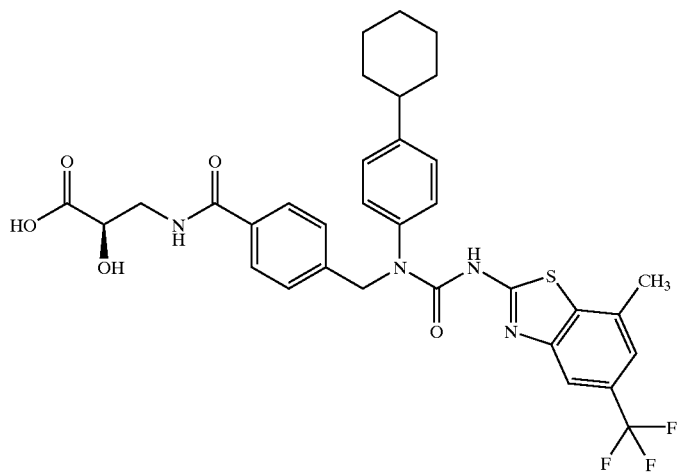

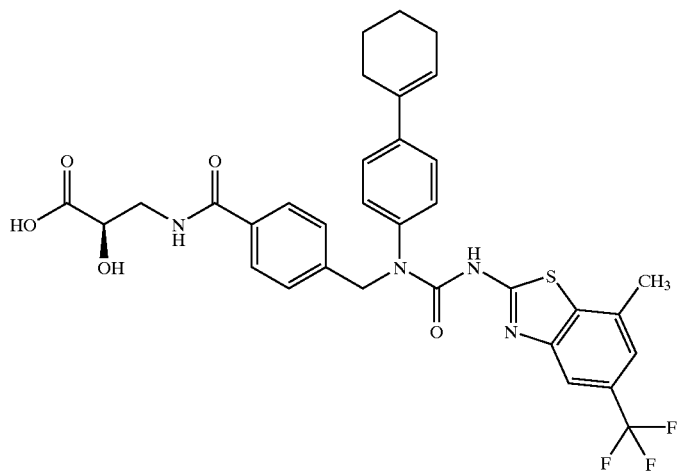
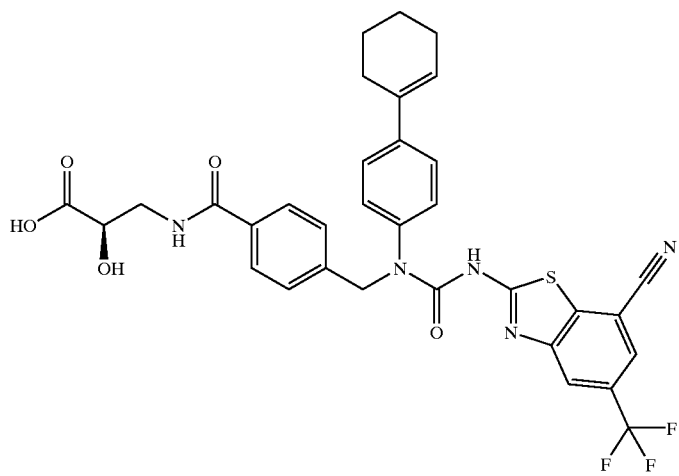
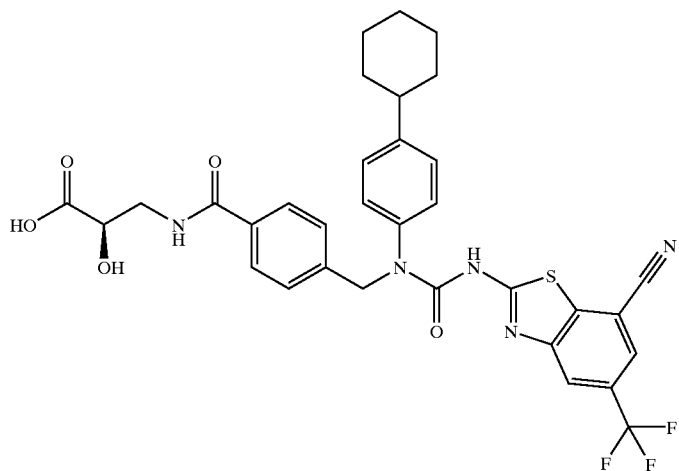

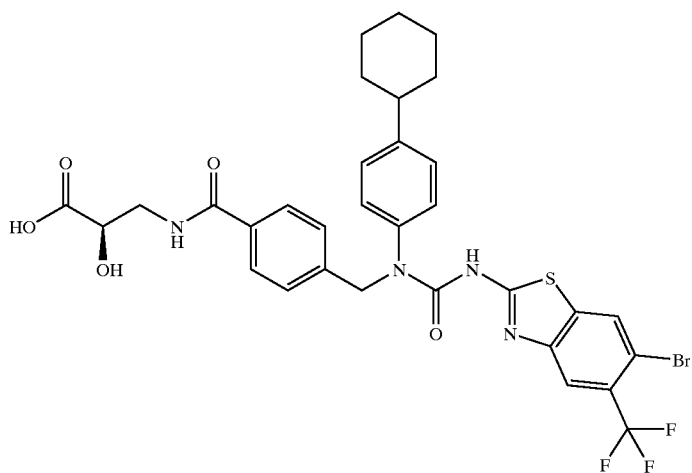
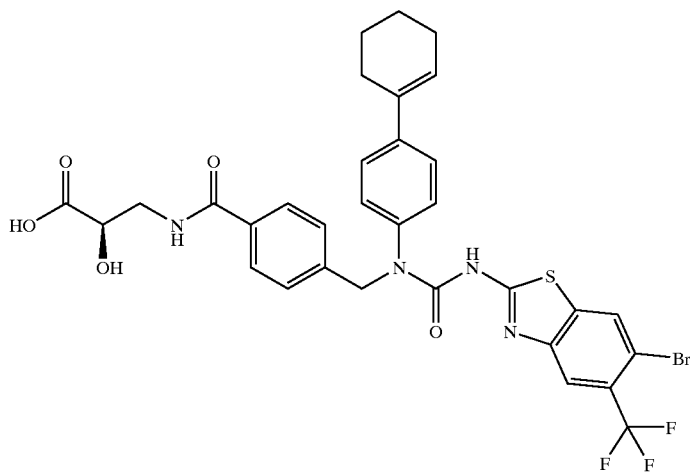
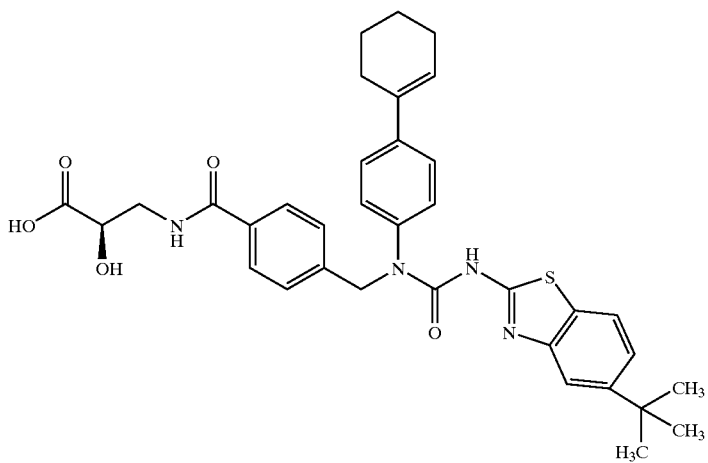

-continued
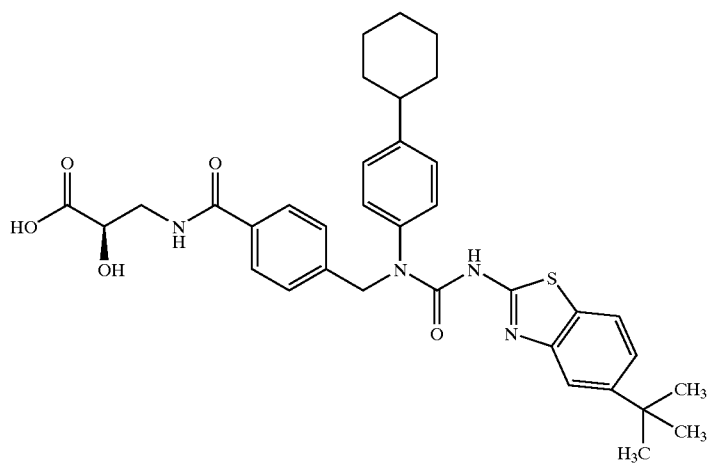
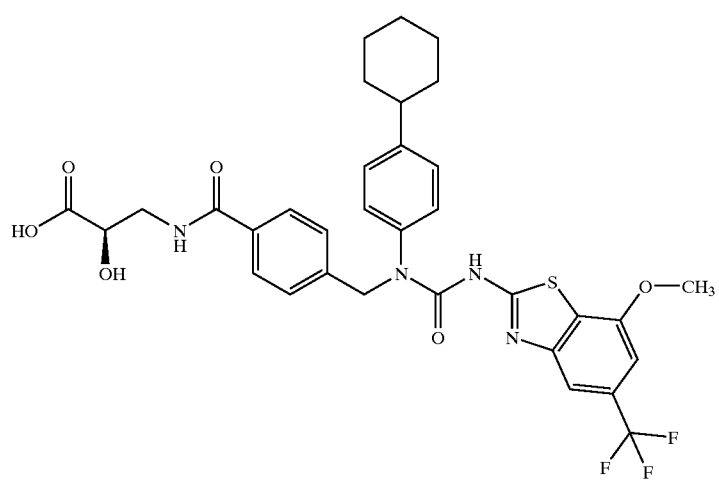
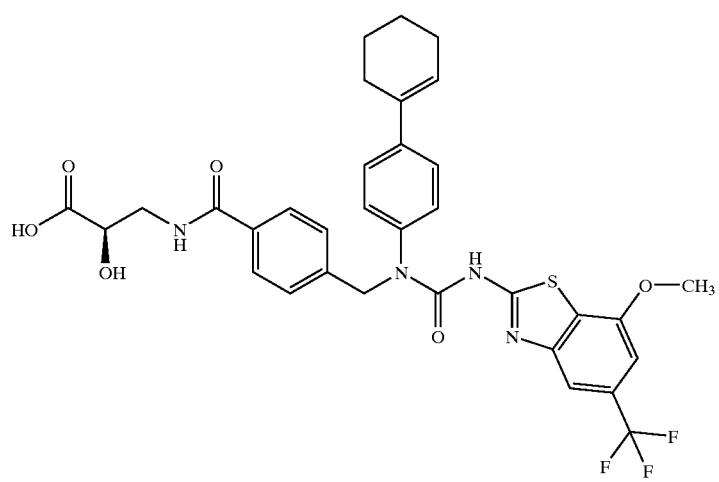

-continued
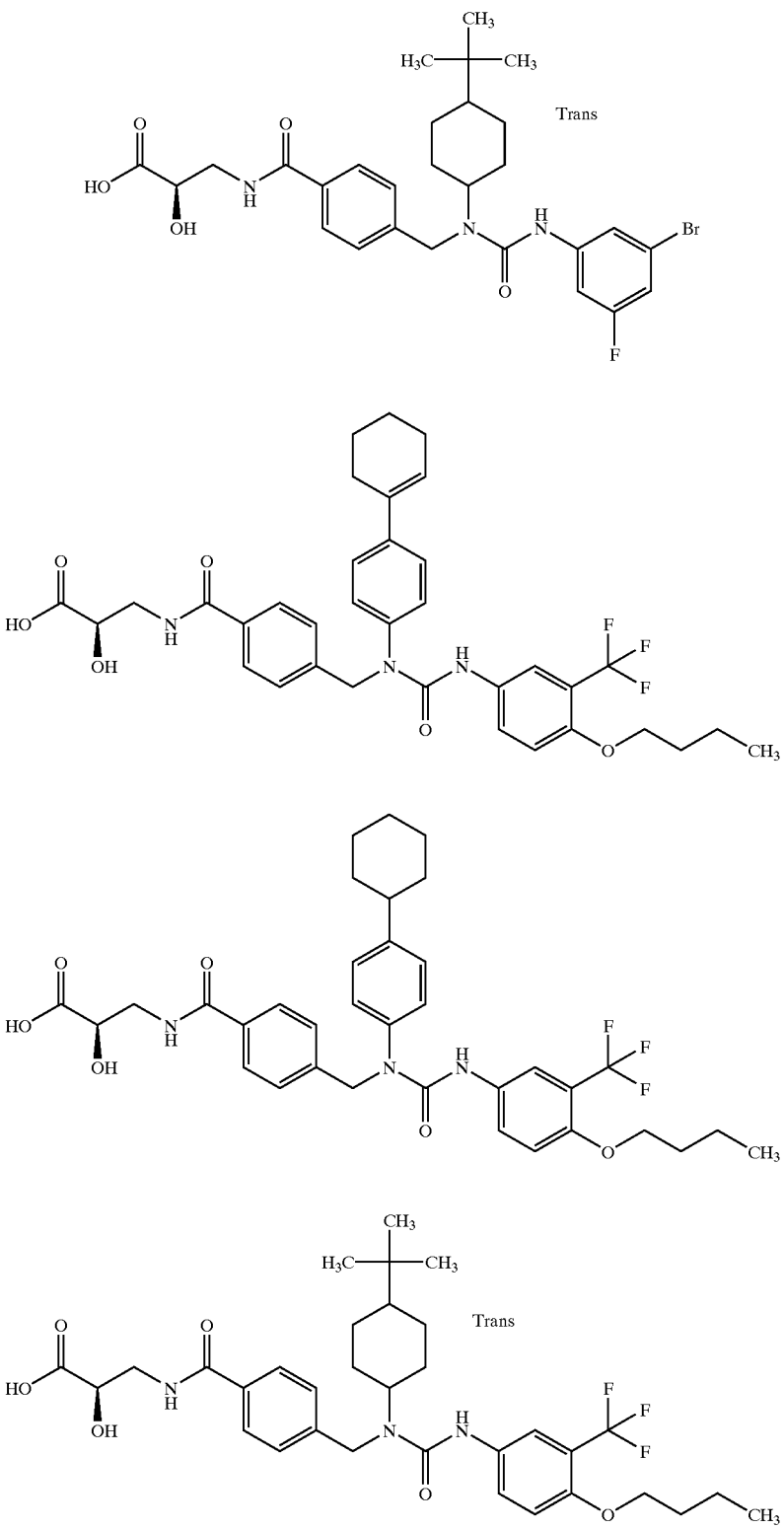

-continued
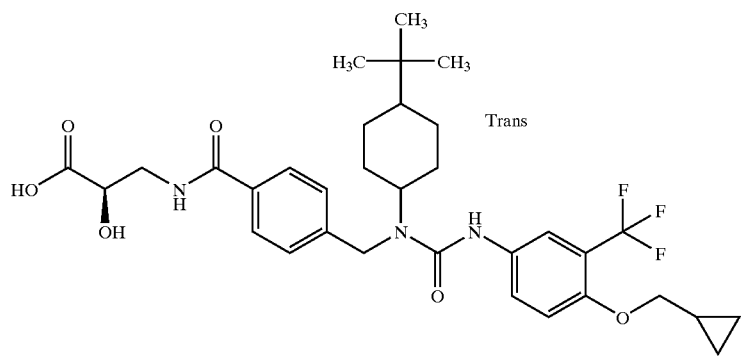
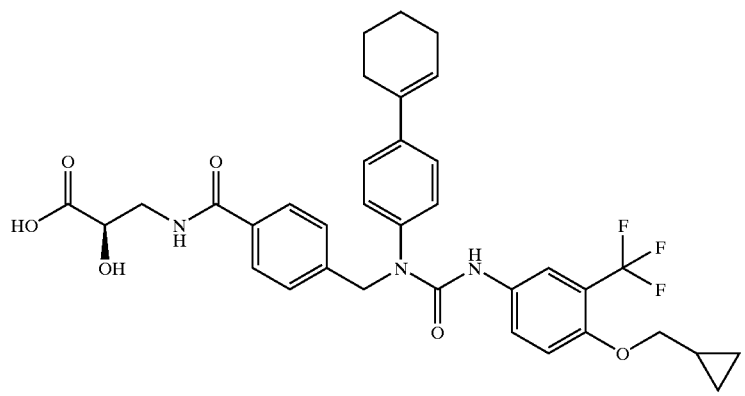
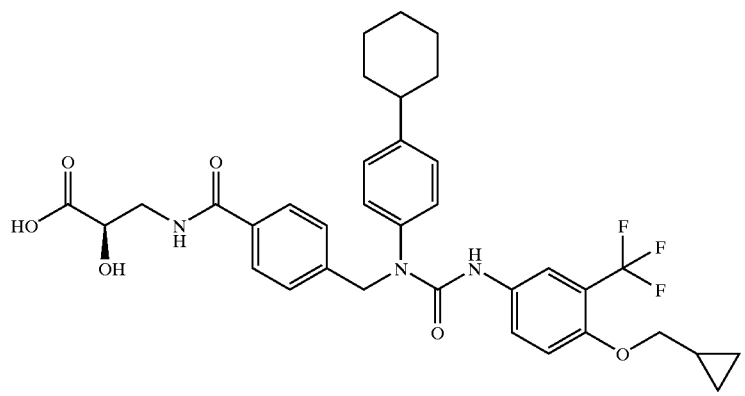
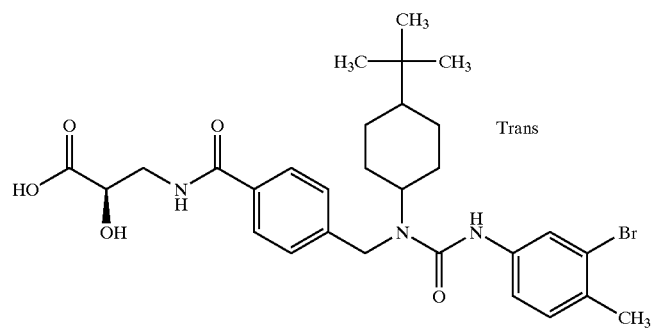

-continued
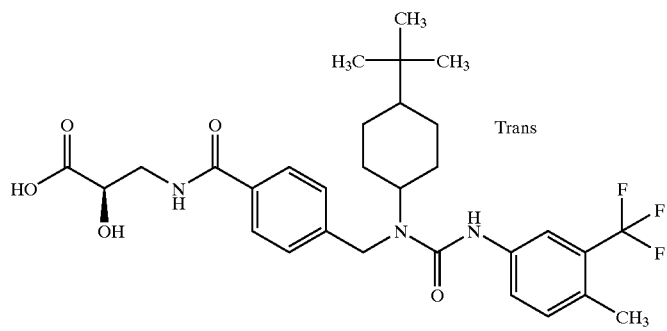
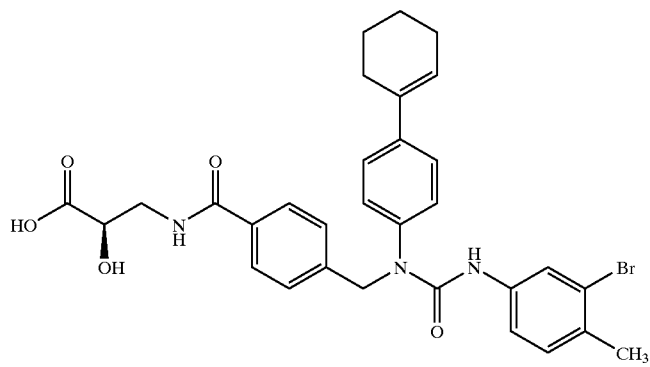
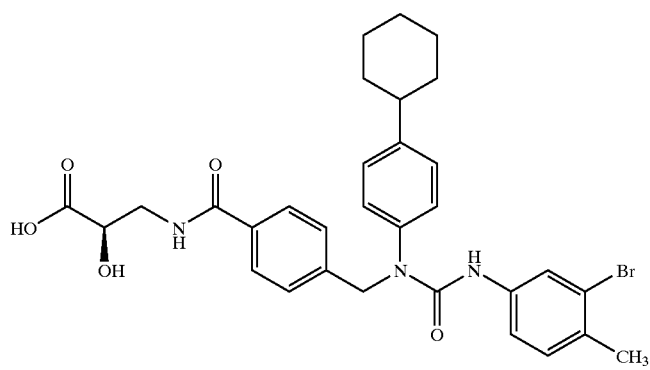
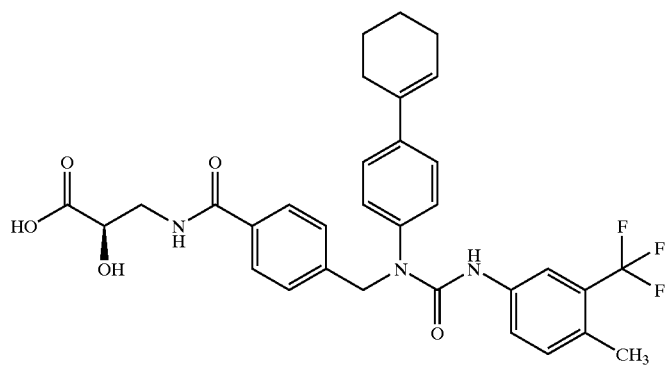

-continued
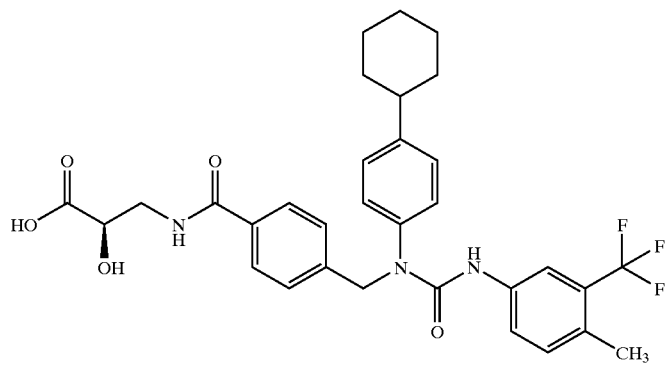
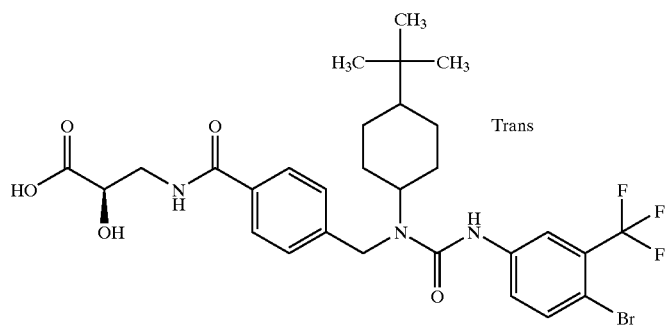
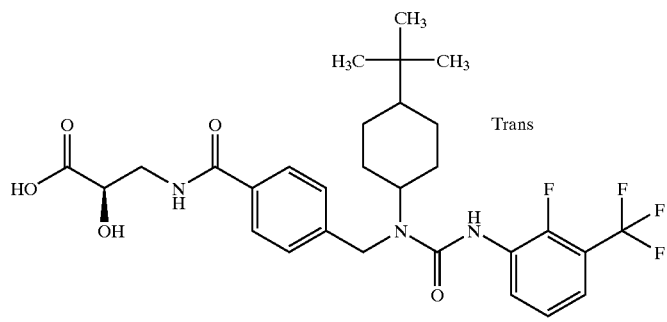
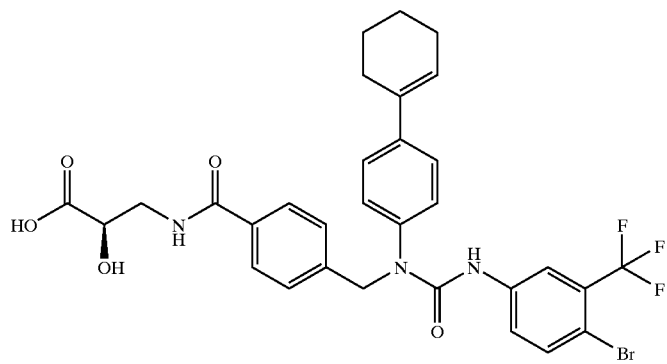

-continued
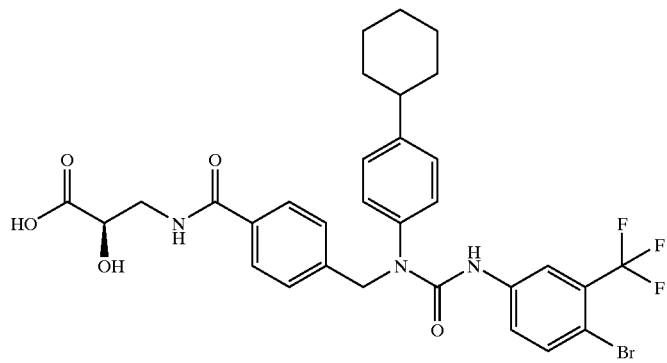
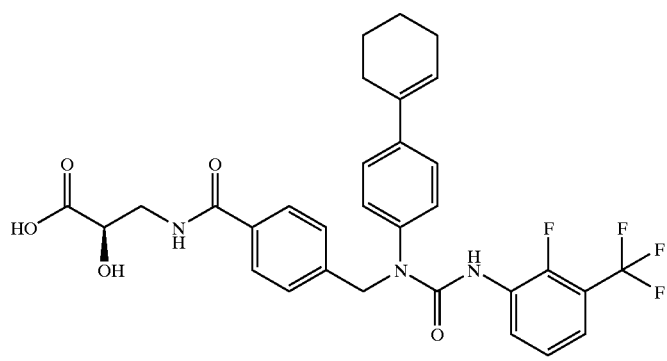
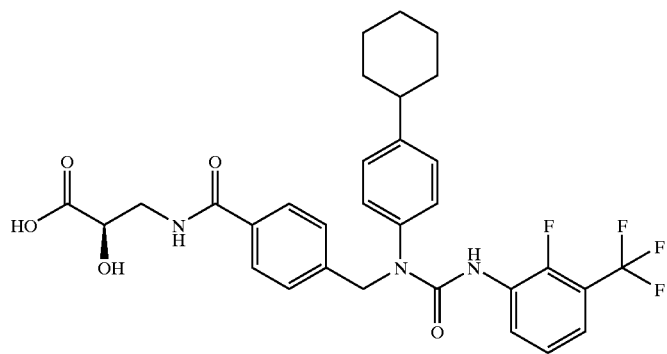
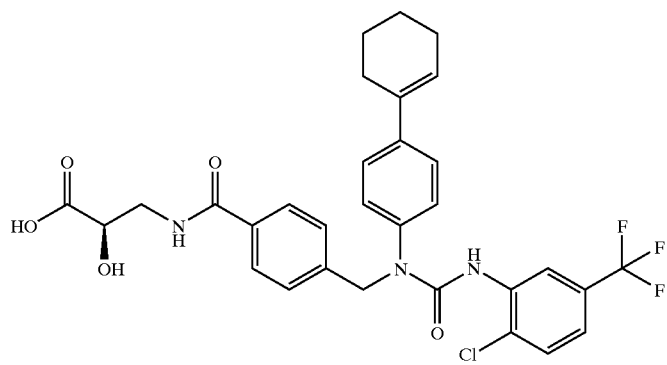

-continued
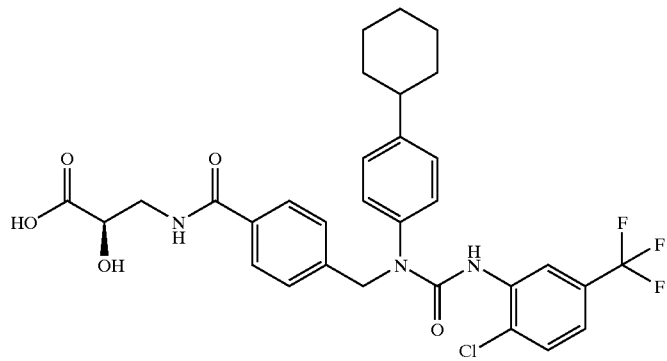
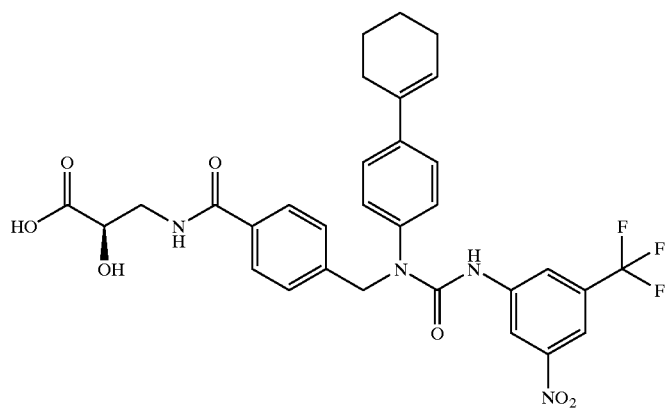
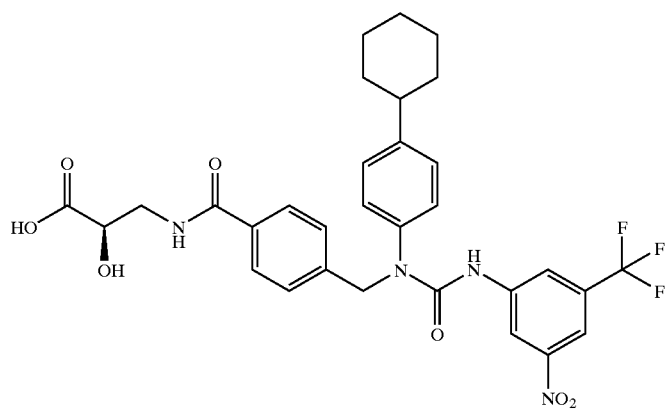
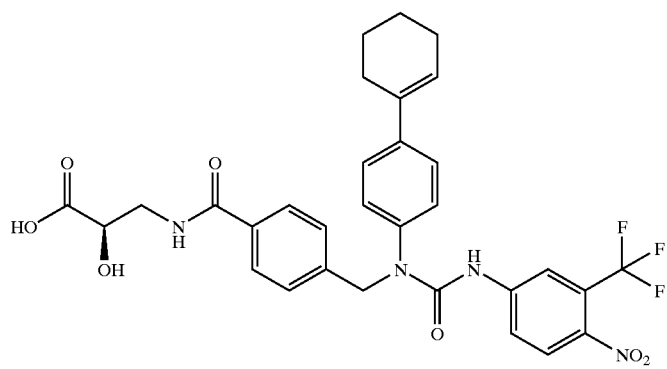

-continued
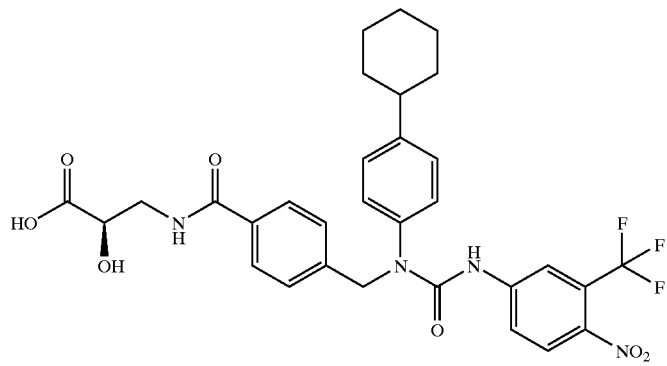
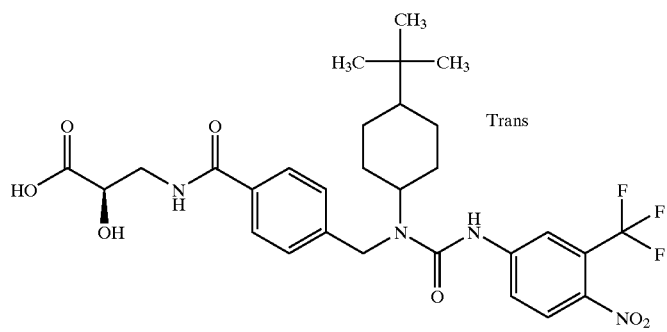
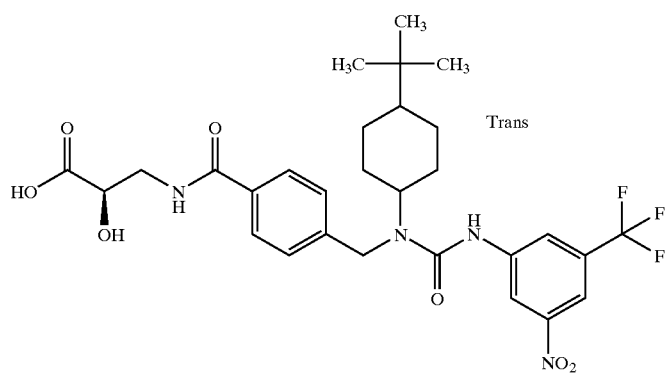
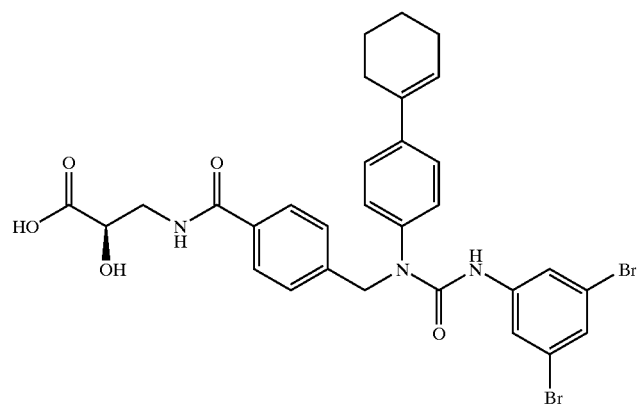

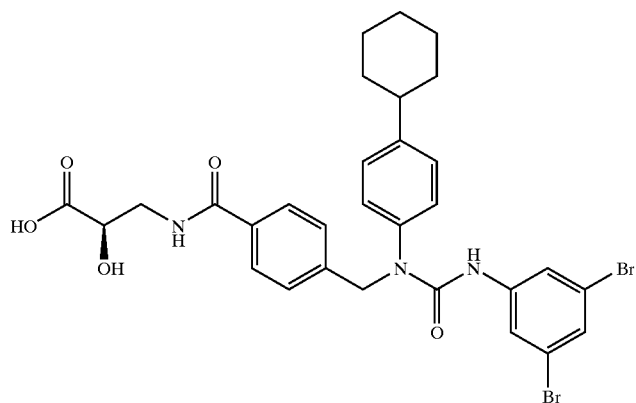
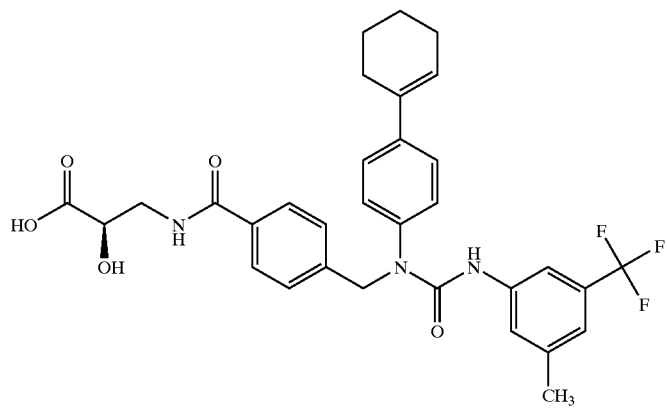
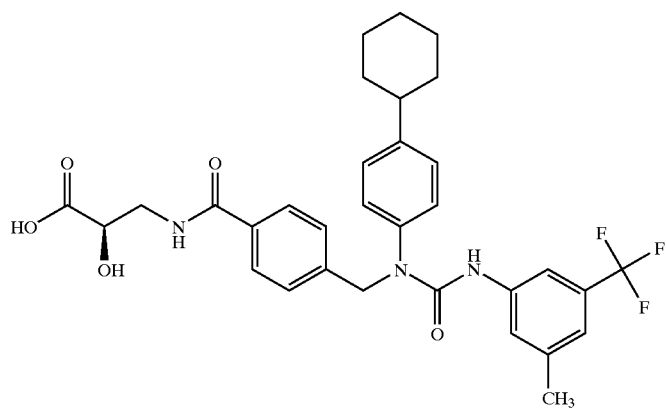

-continued
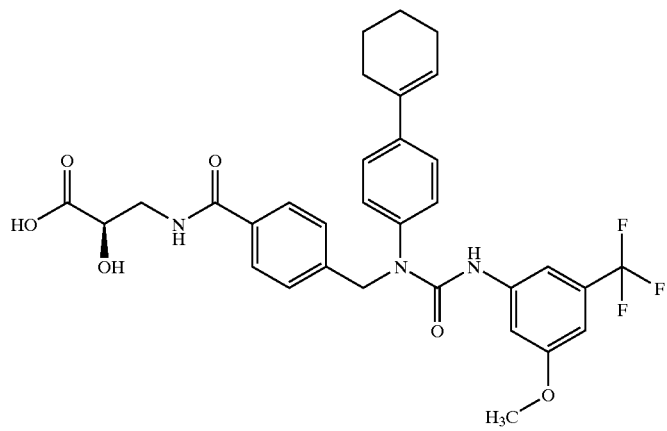
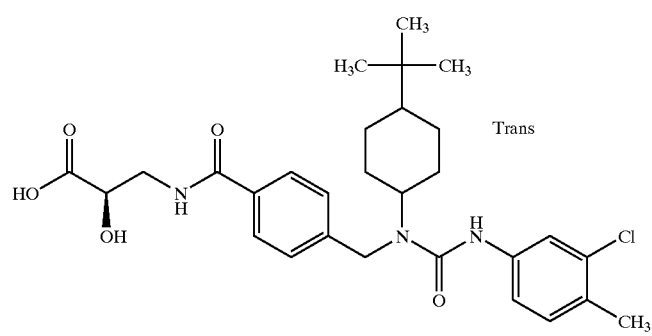
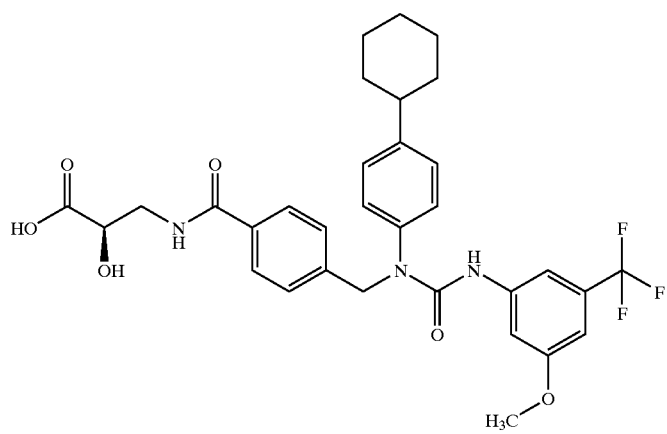
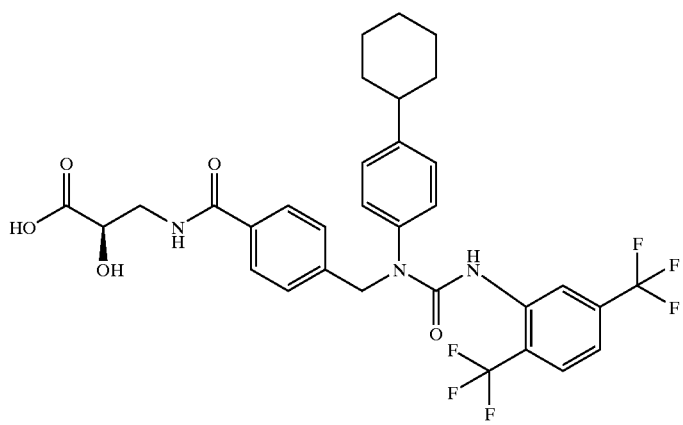

-continued
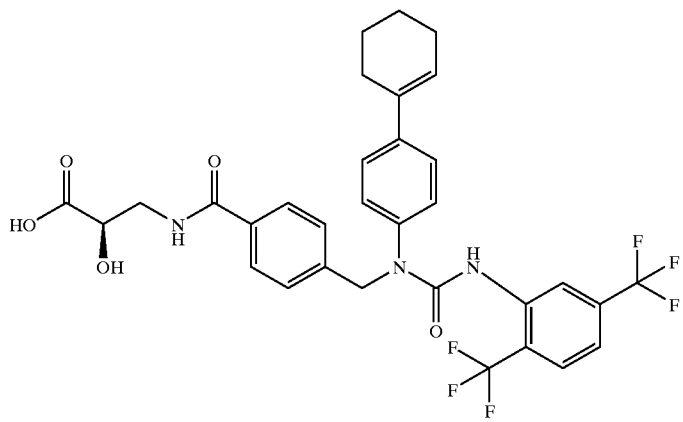
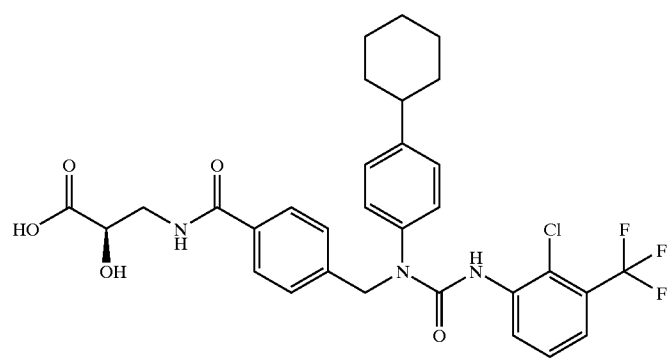
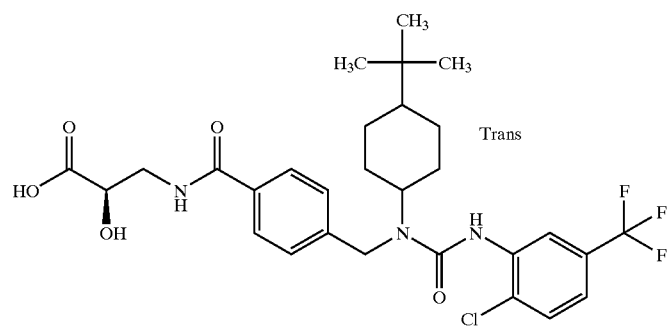
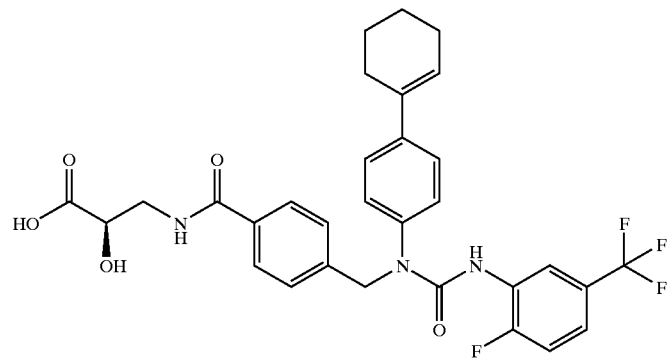

-continued
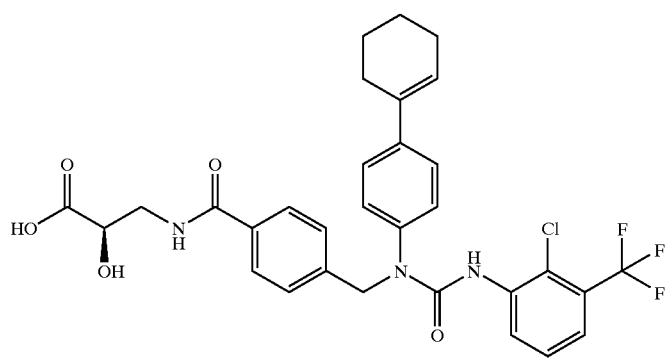
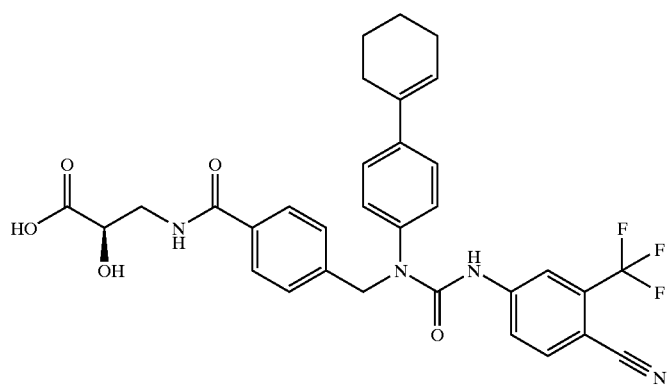
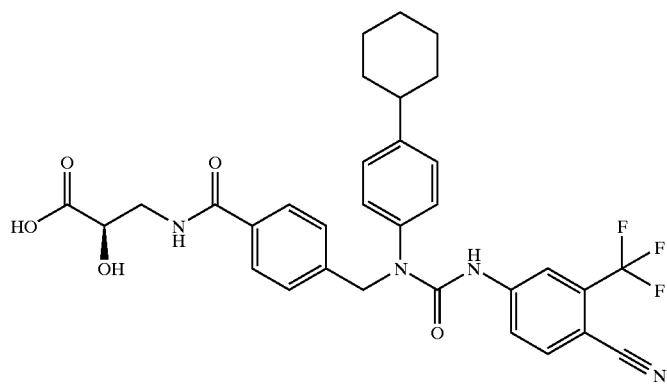
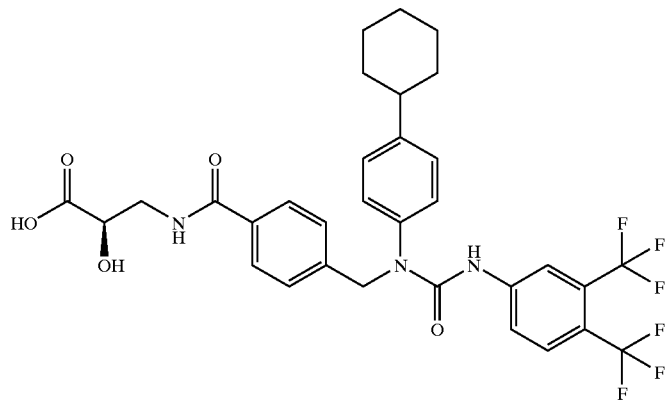

-continued
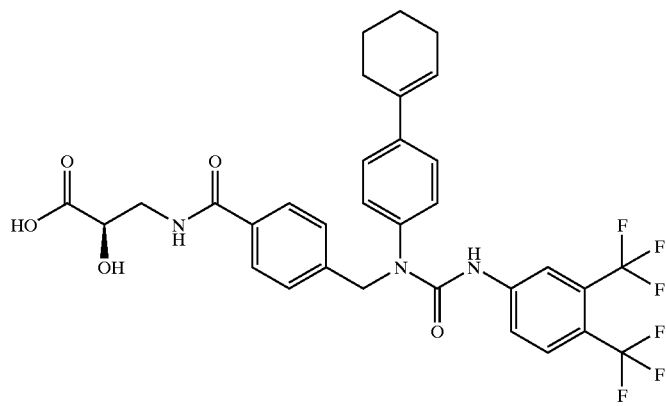
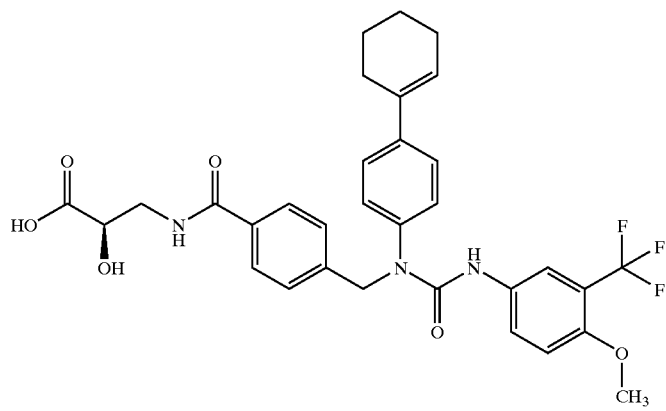
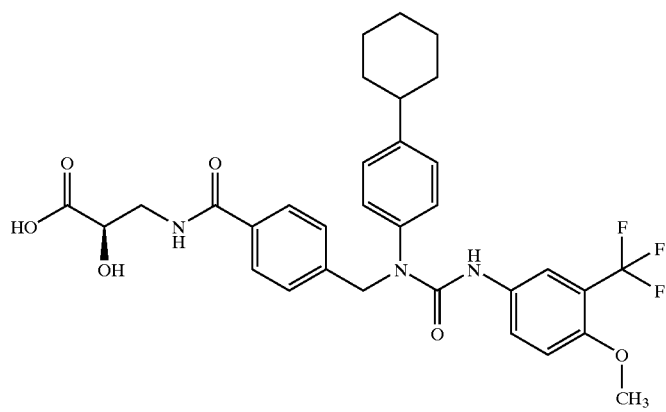
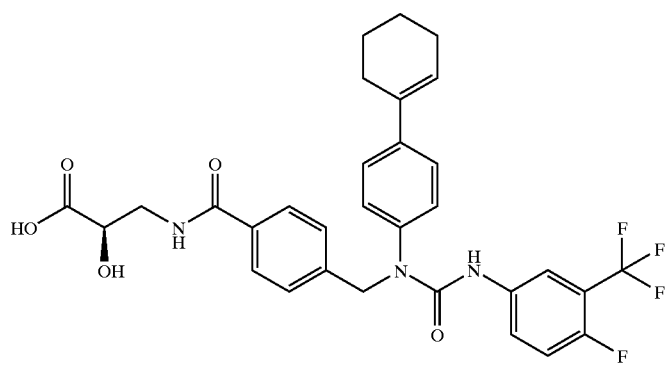

-continued
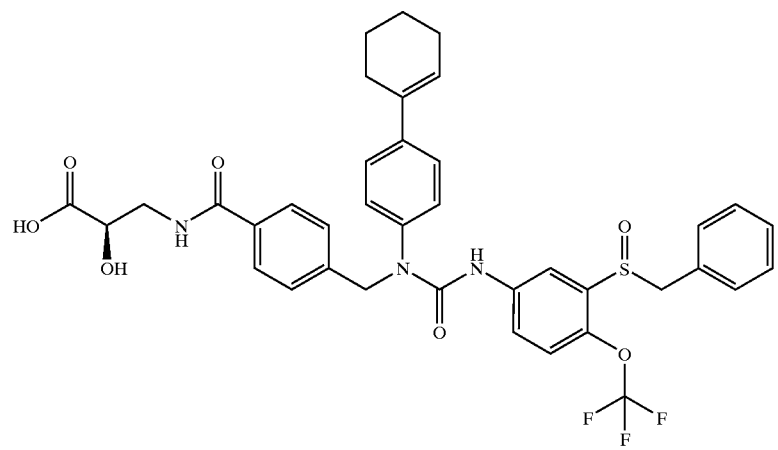
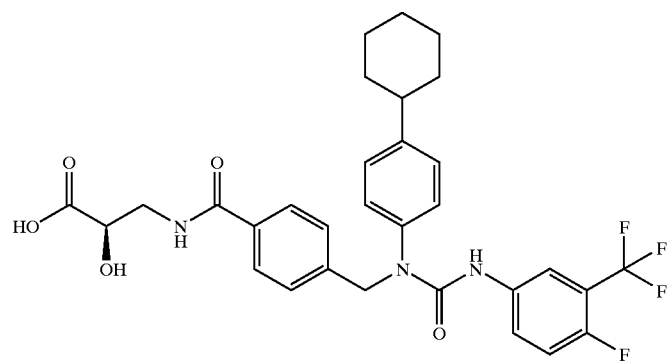
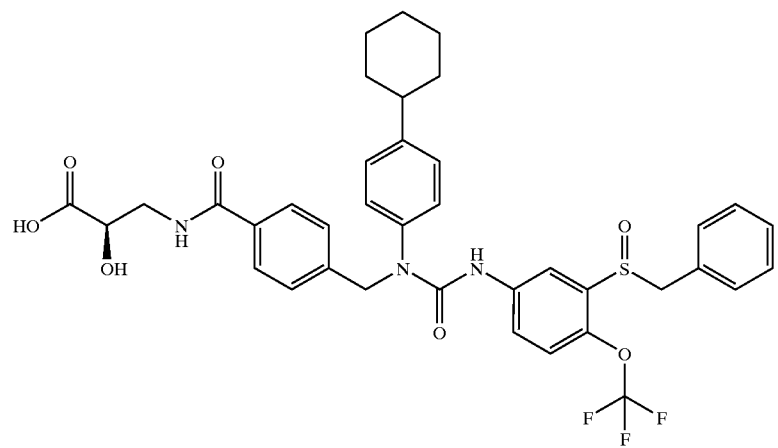

-continued
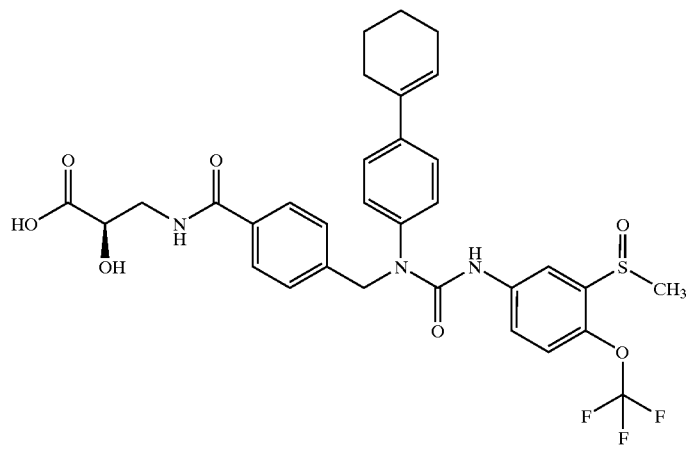
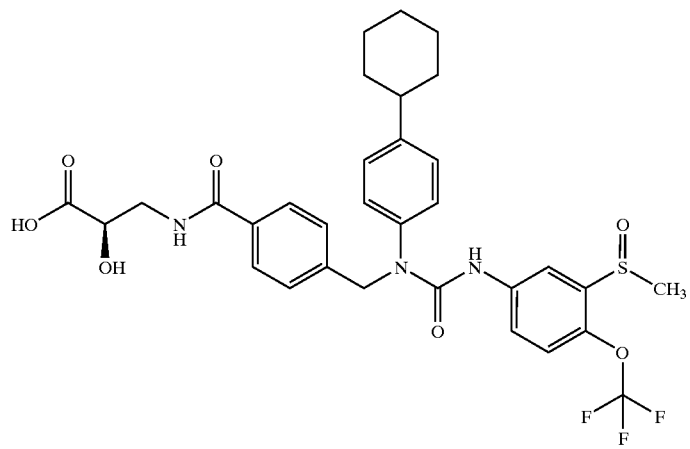
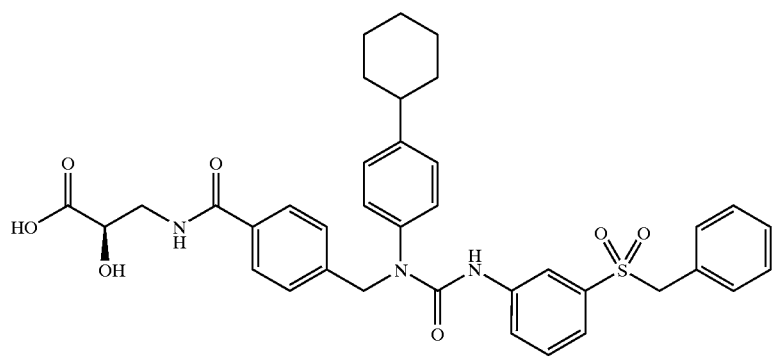
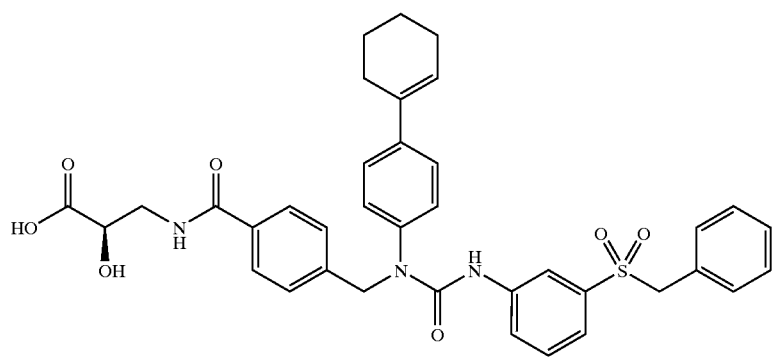

-continued
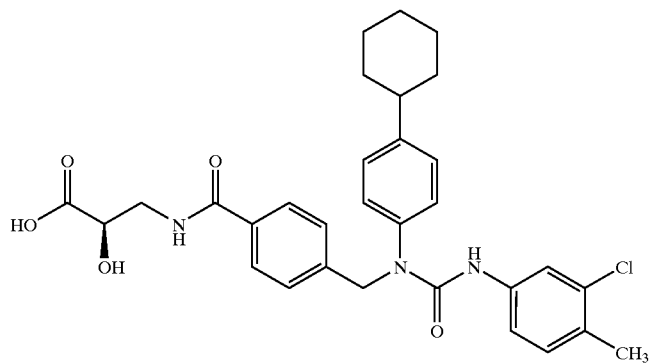
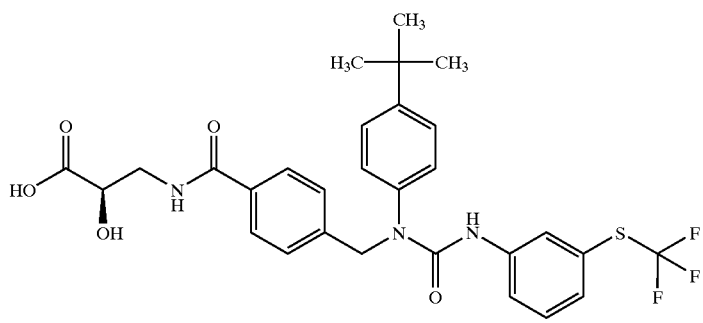
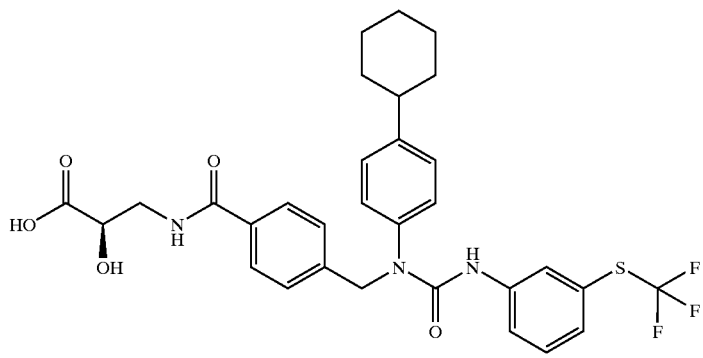
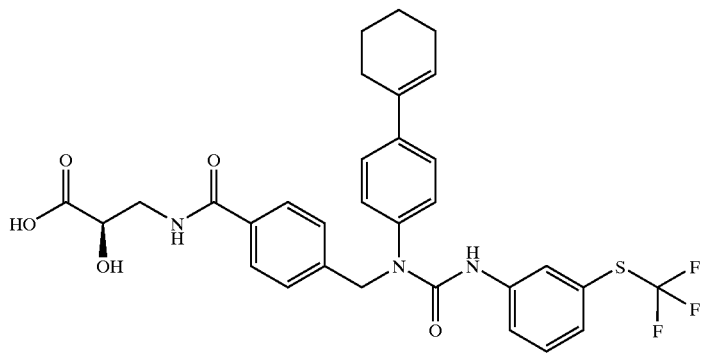

-continued
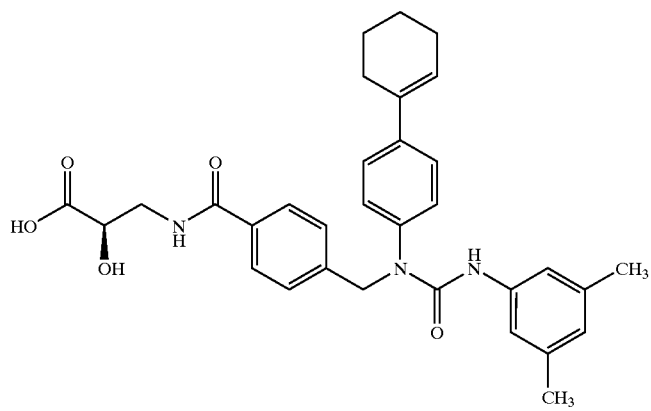
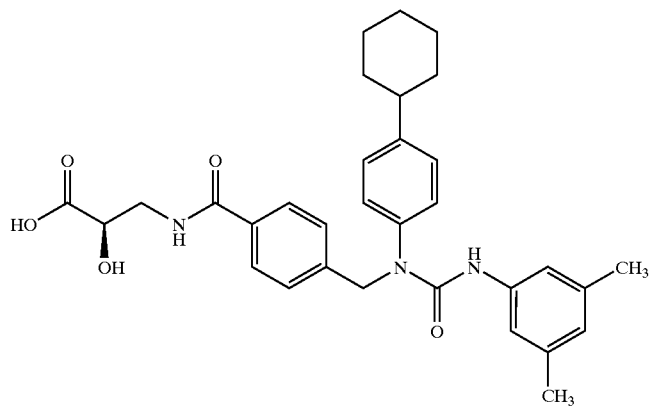
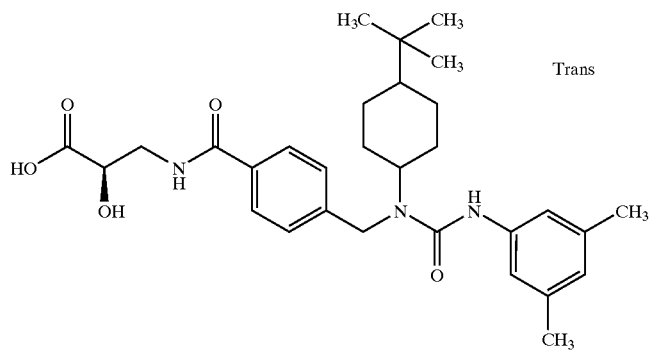
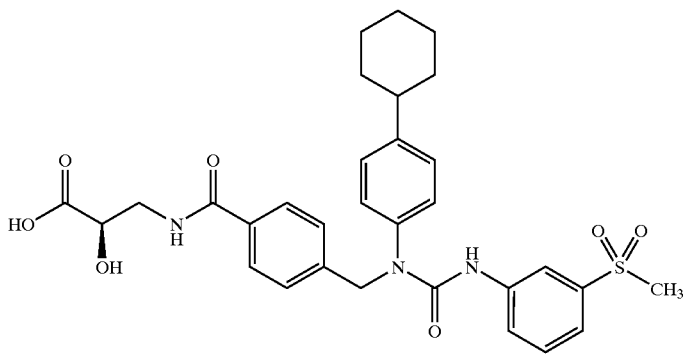

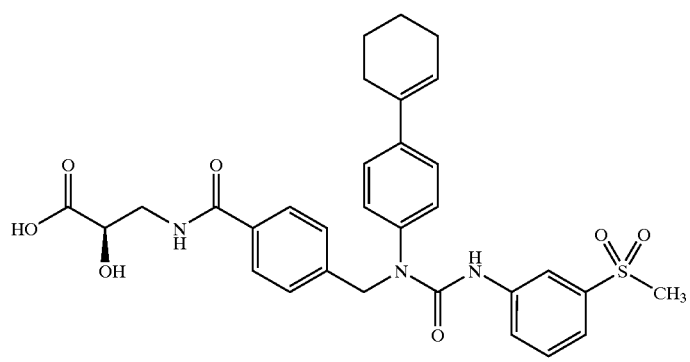
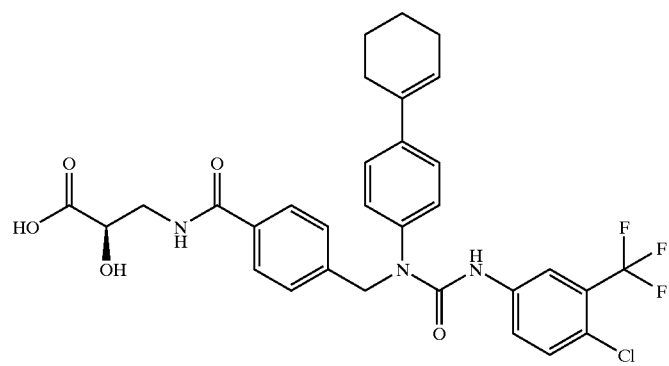
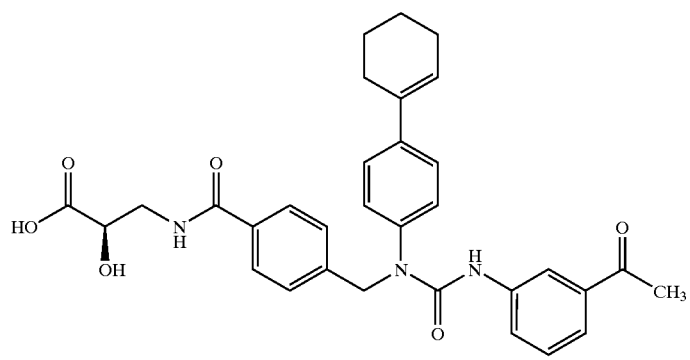
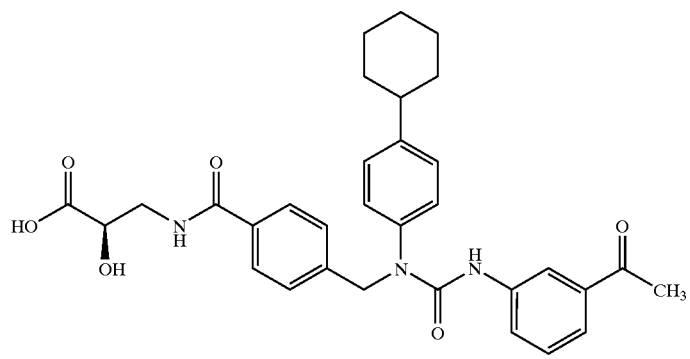

-continued
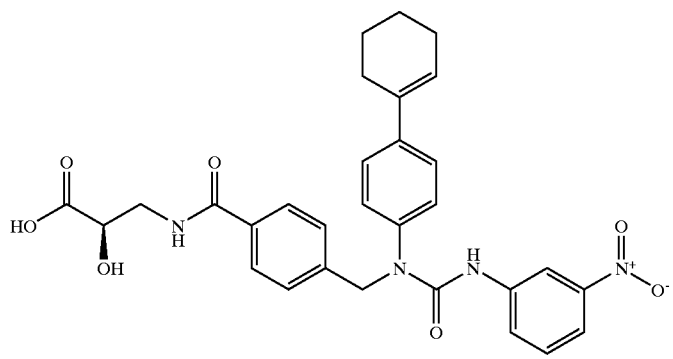
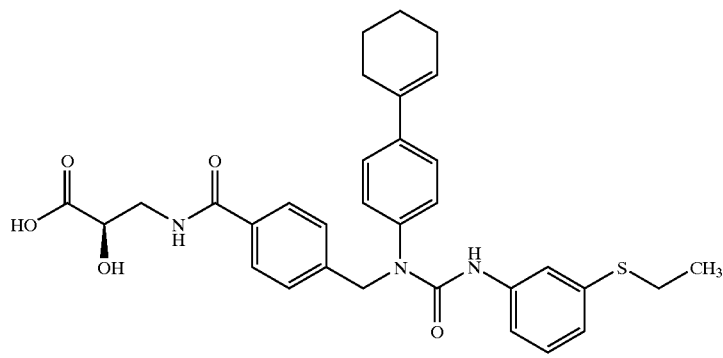
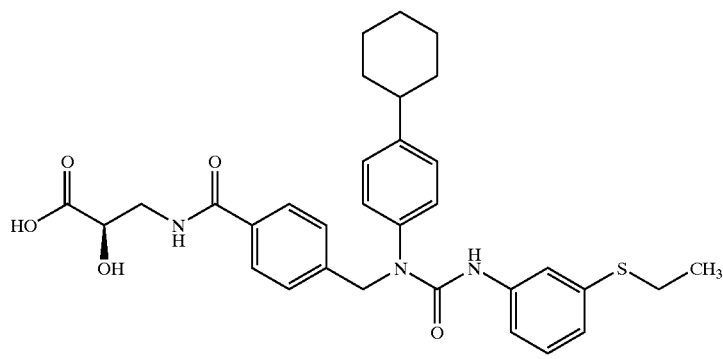
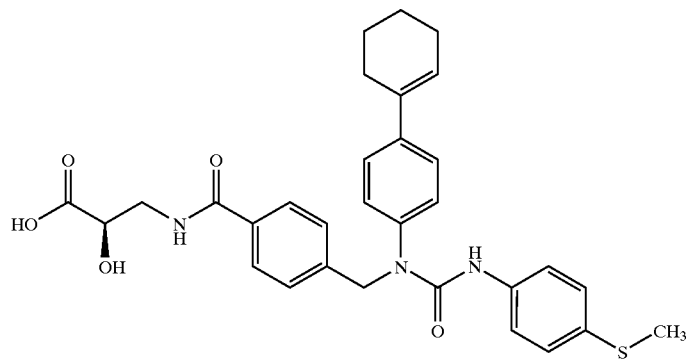

-continued
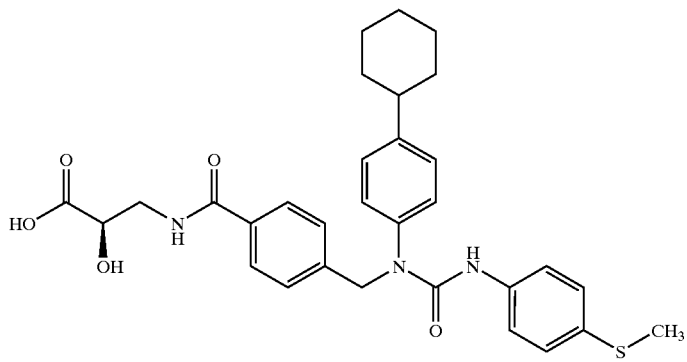
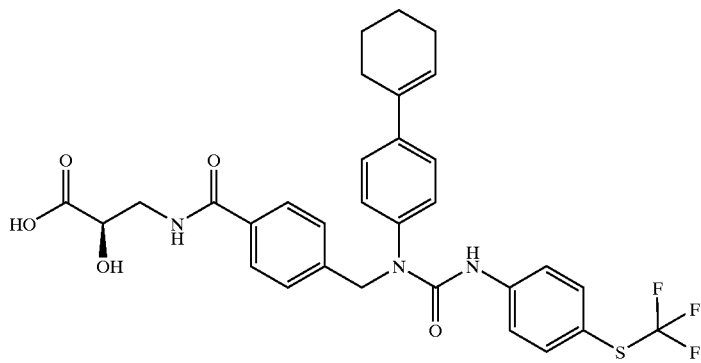
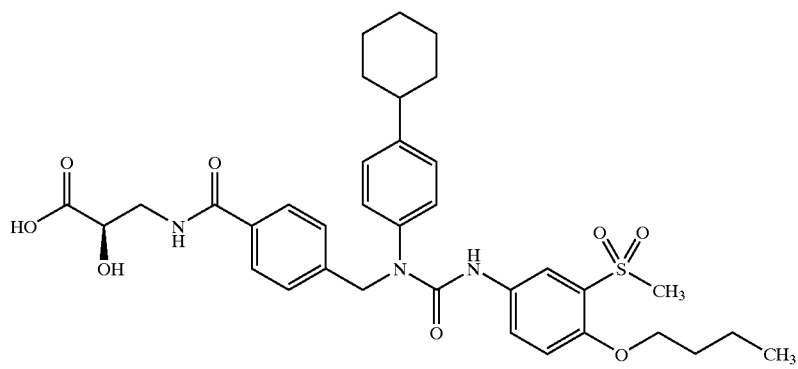
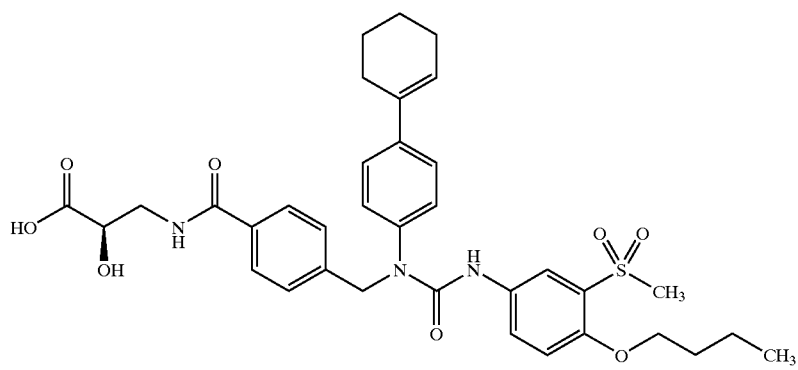

-continued
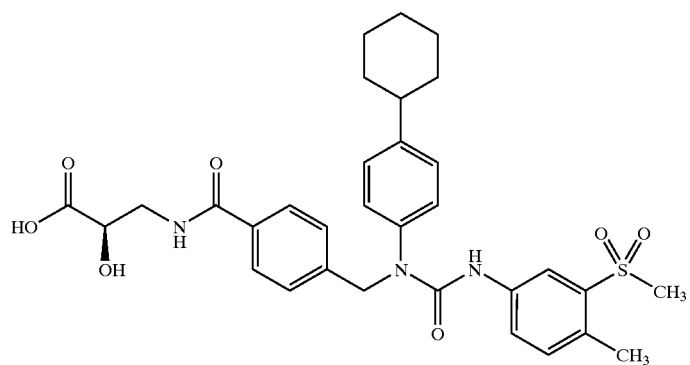
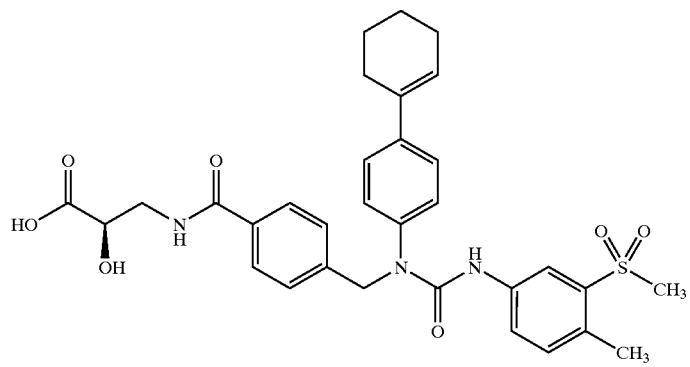
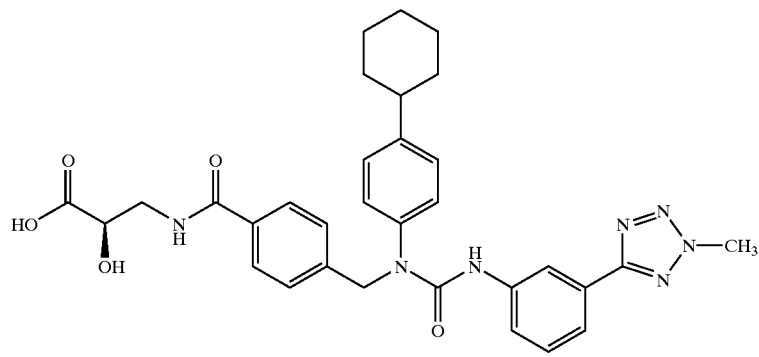
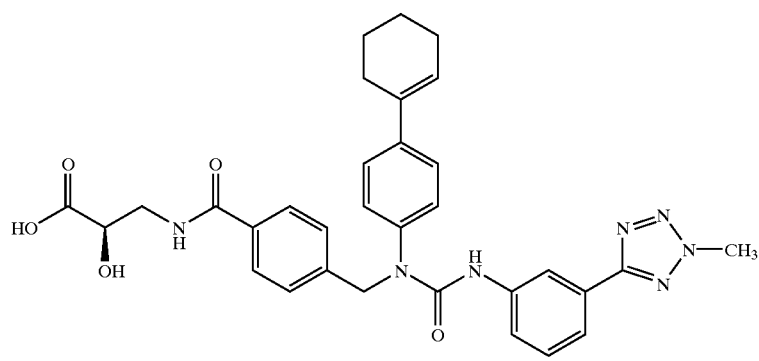

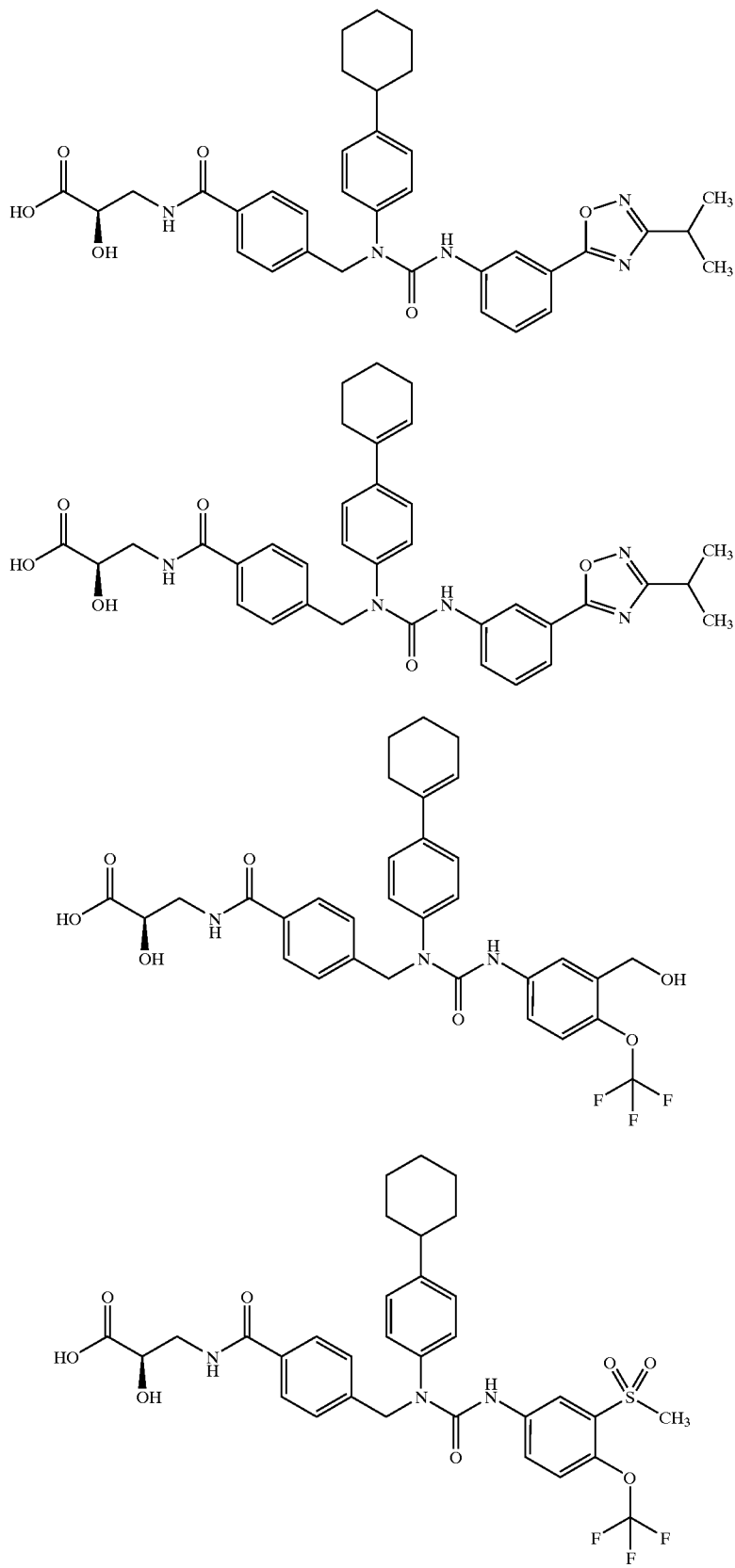

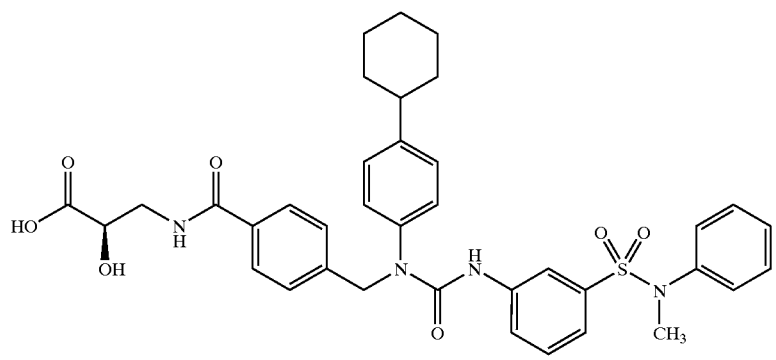
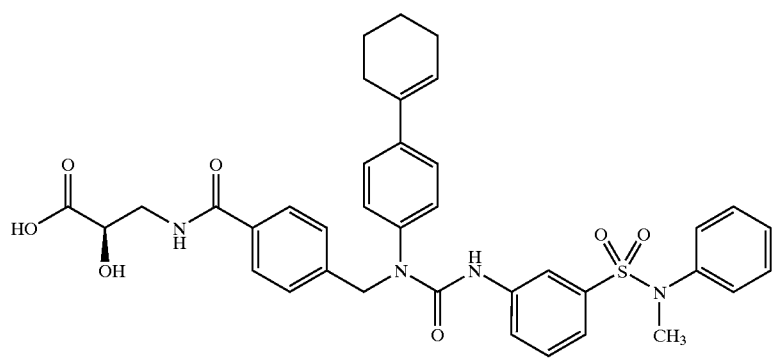
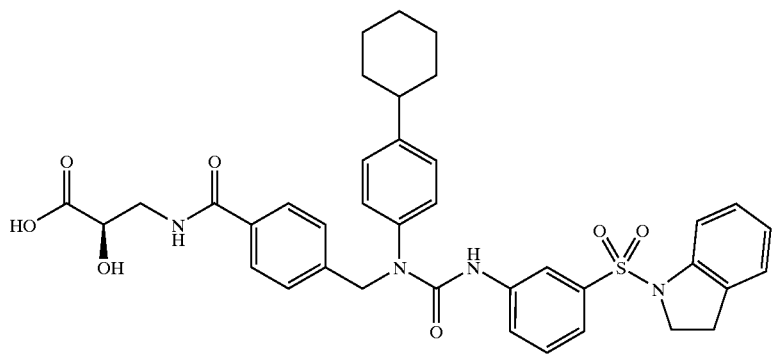
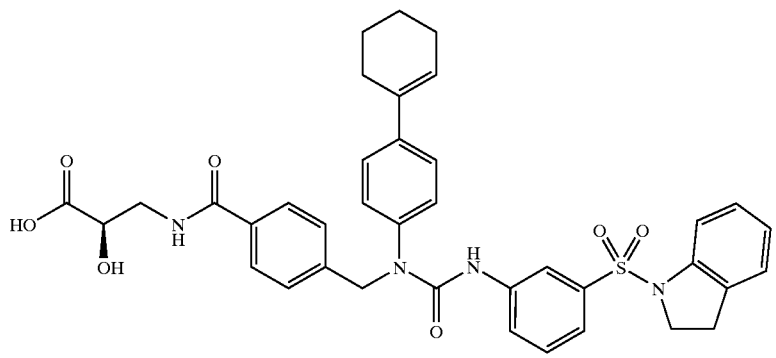

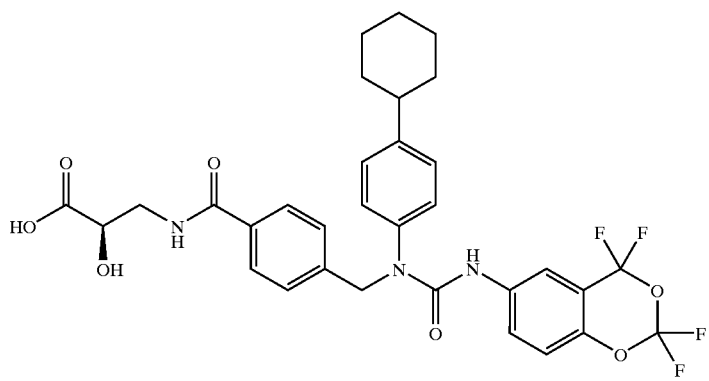
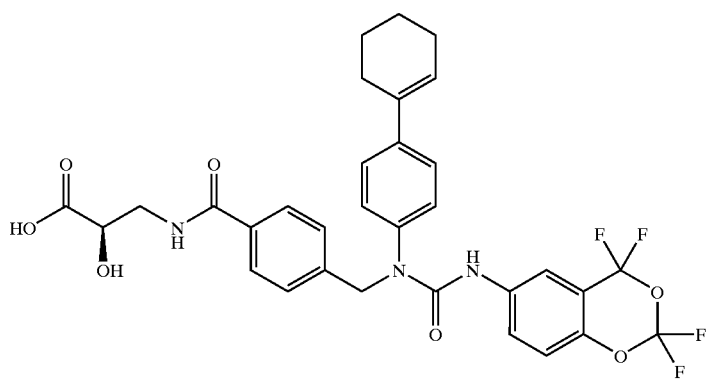
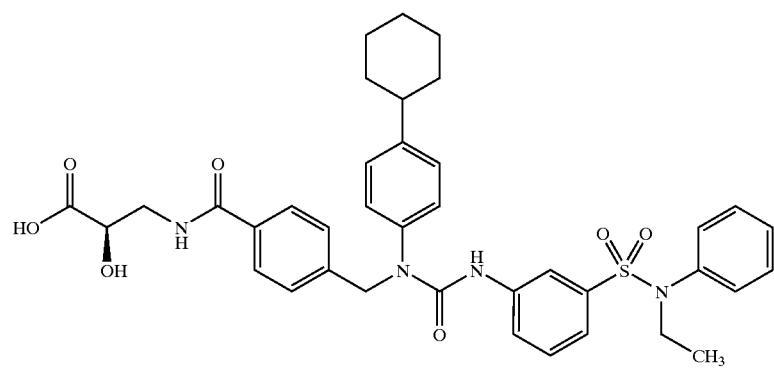
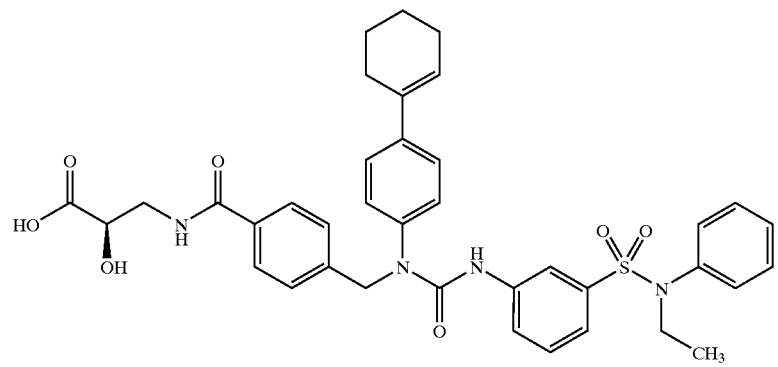

-continued
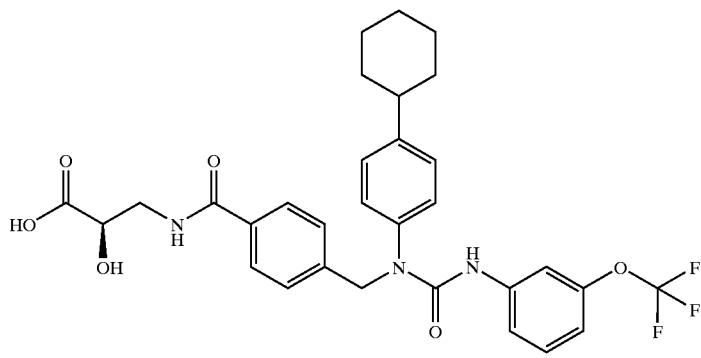
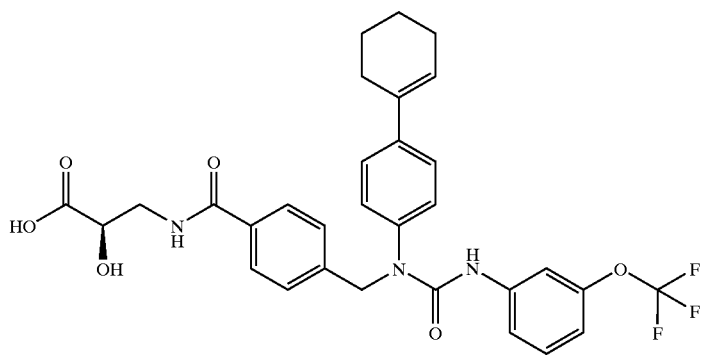
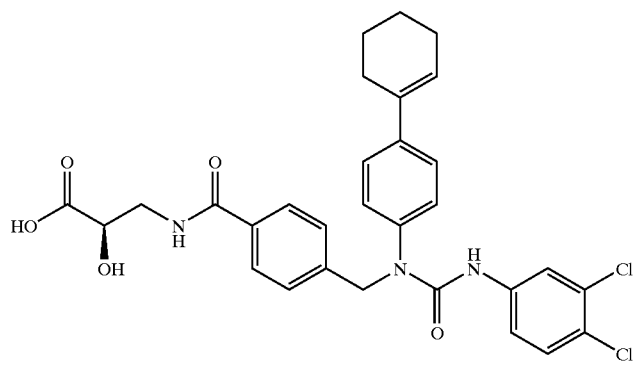
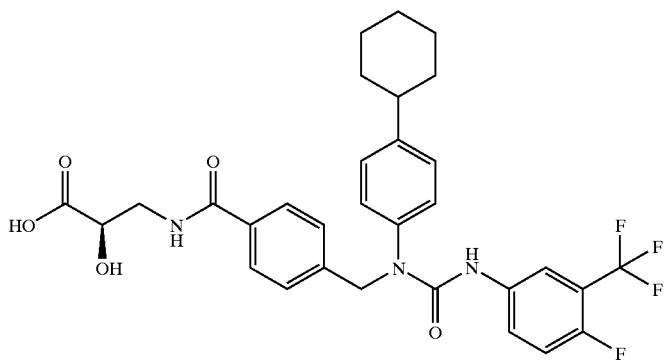

-continued
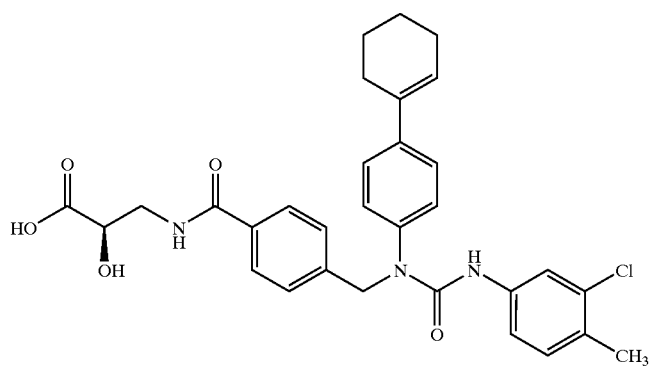
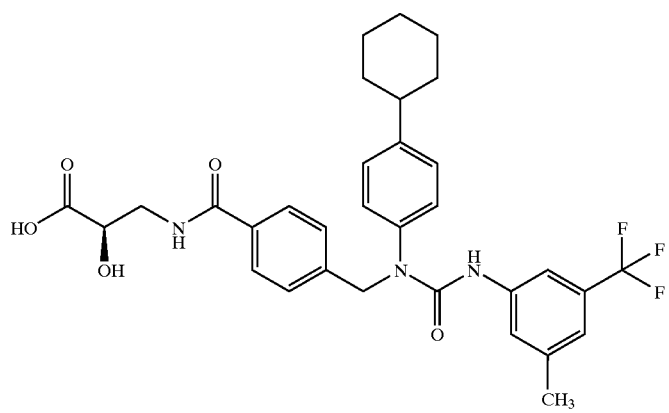
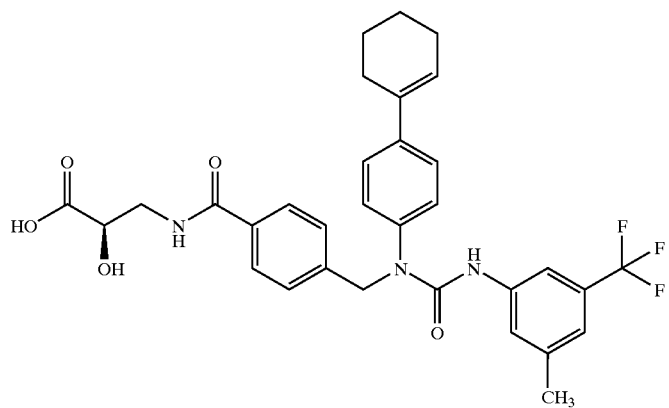

-continued
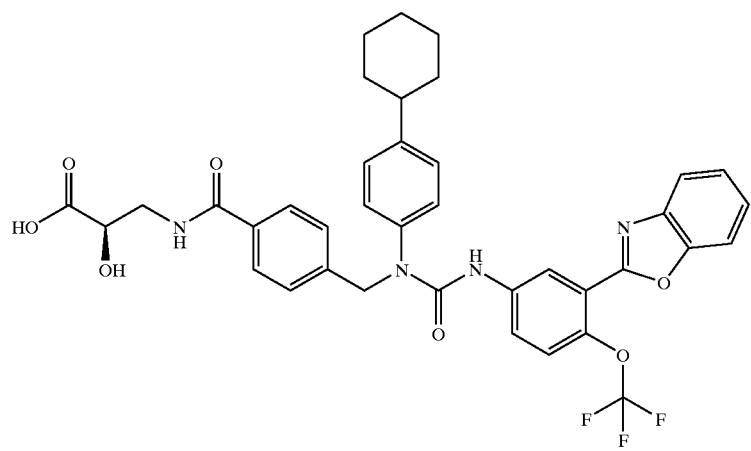
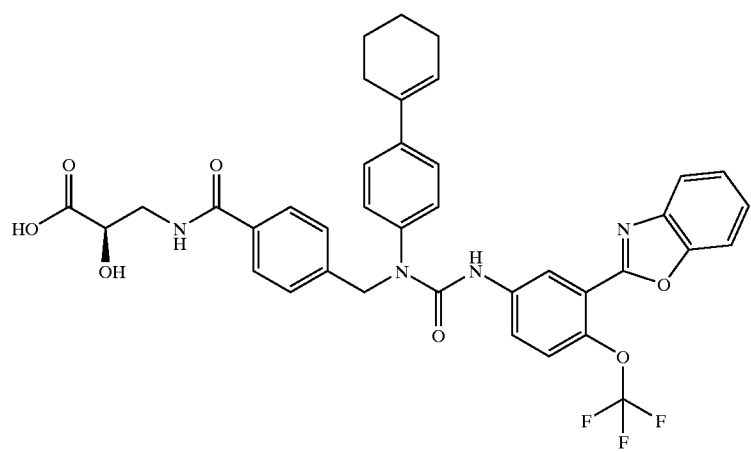
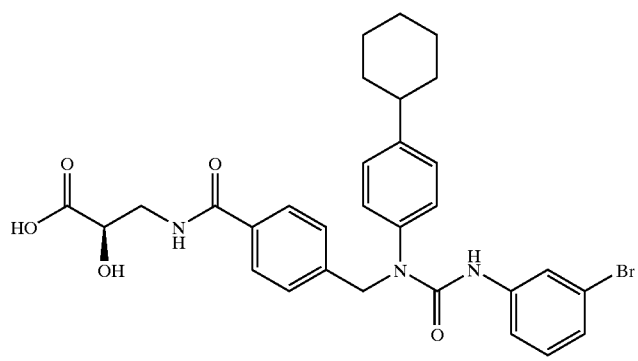
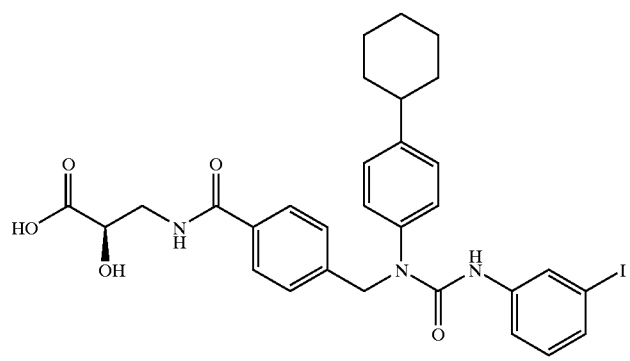

-continued
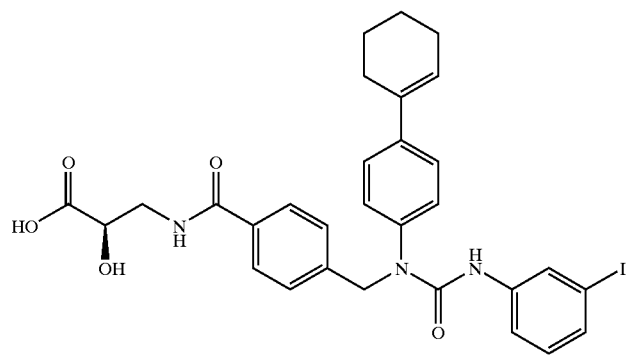
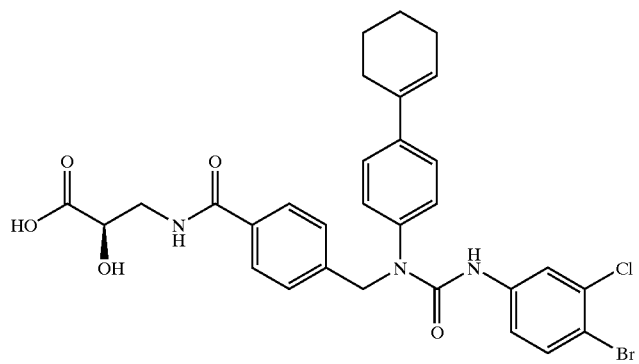
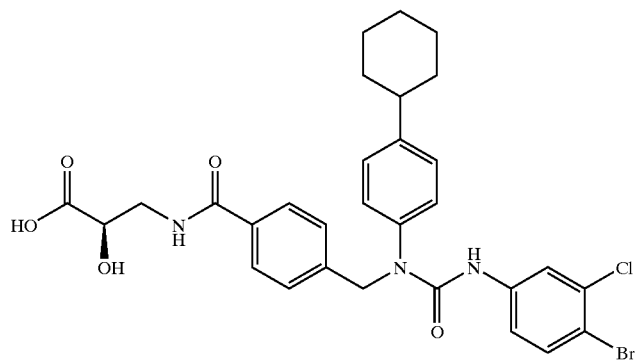
Furthermore, the following preferred compounds (as pure enantiomers of either (R) or (S) configuration or mixtures thereof, including racemates) are within the scope of the invention and may be prepared according to the procedures set forth in the foregoing description:

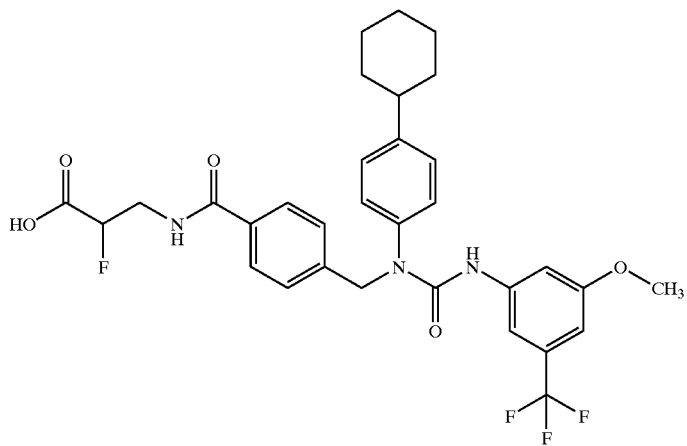
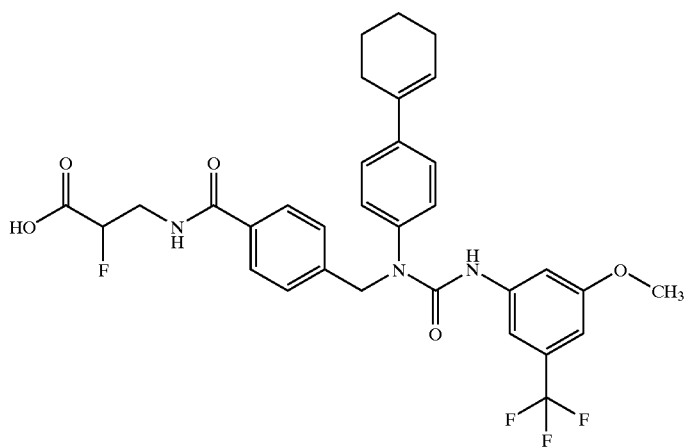
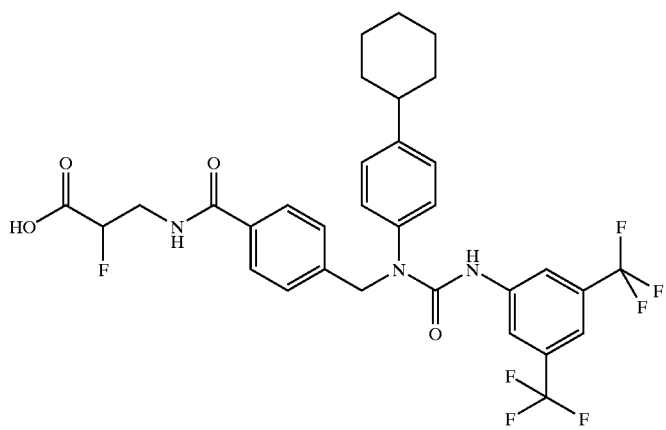

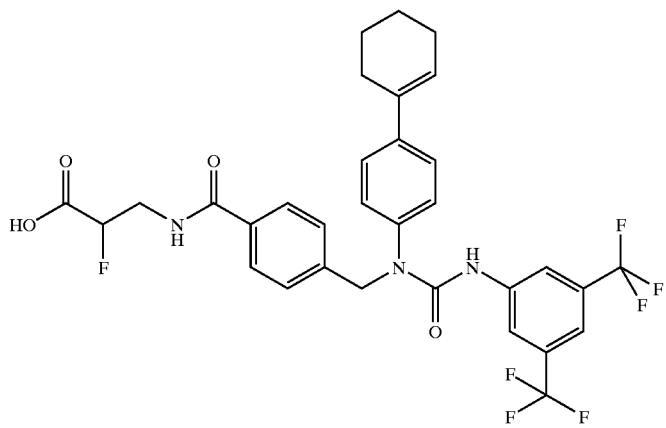
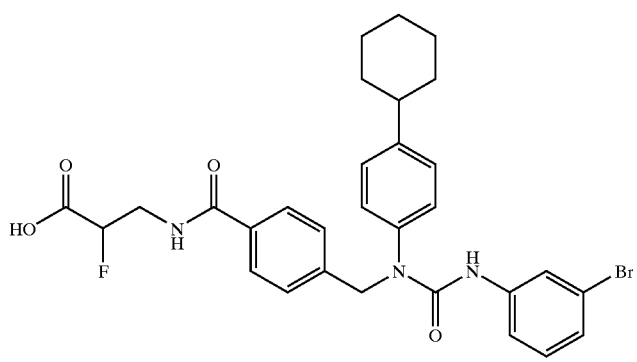
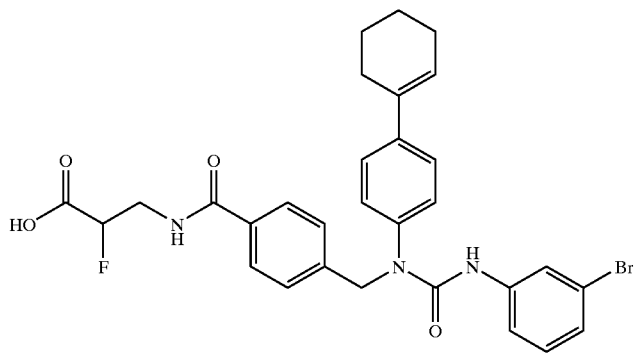
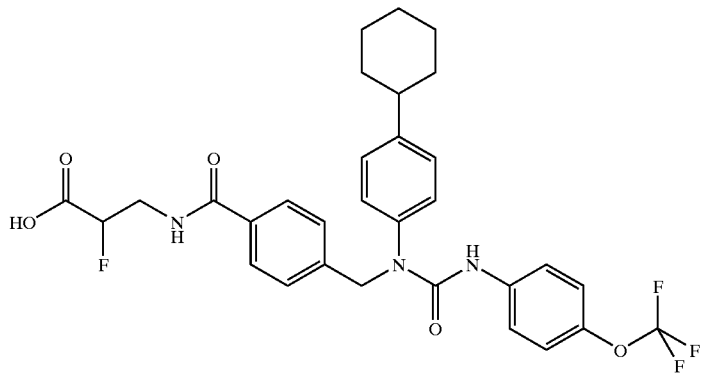

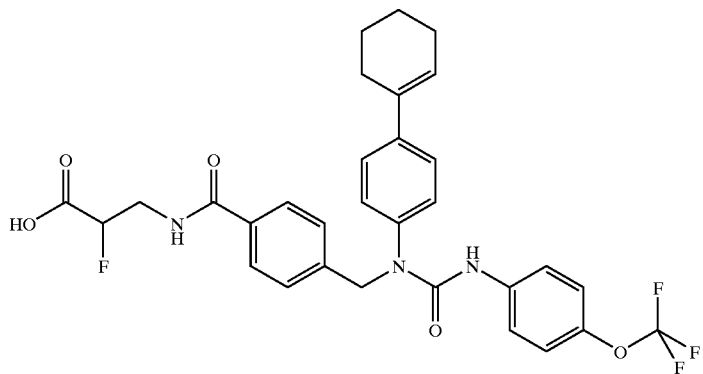
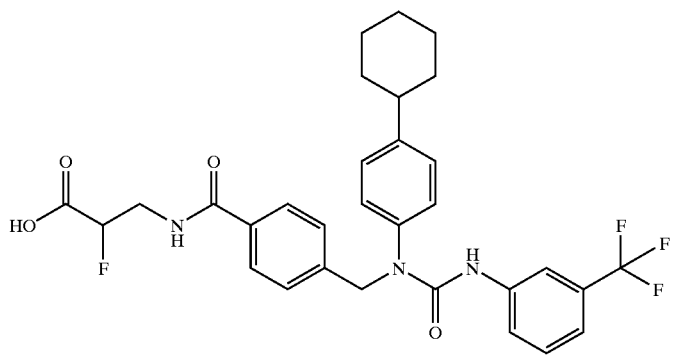
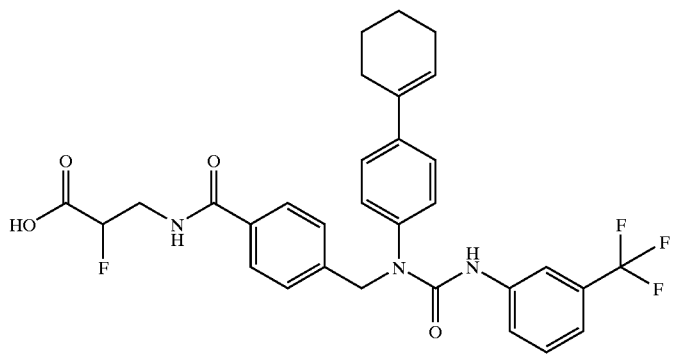
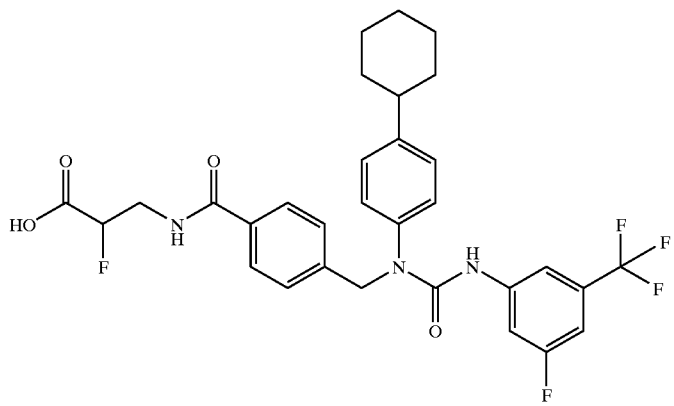

-continued
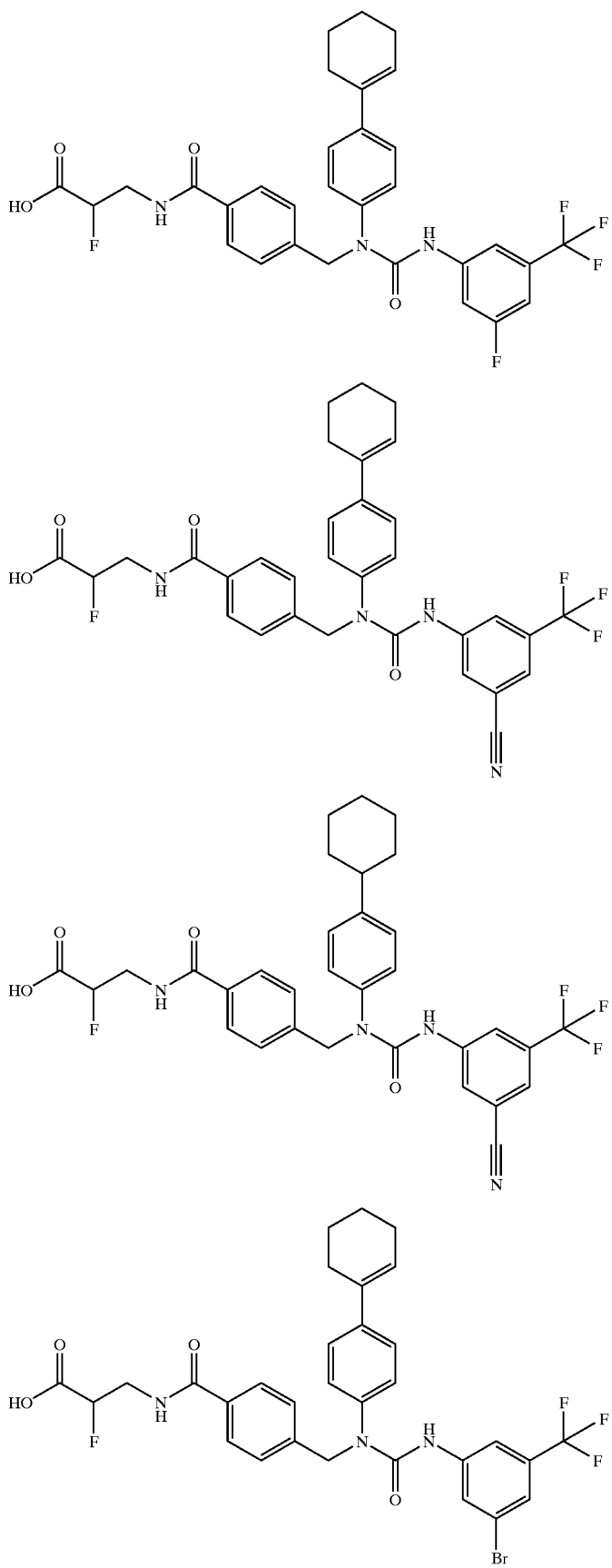

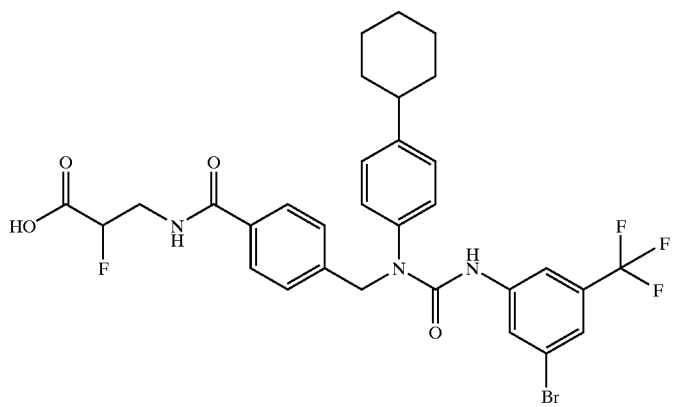
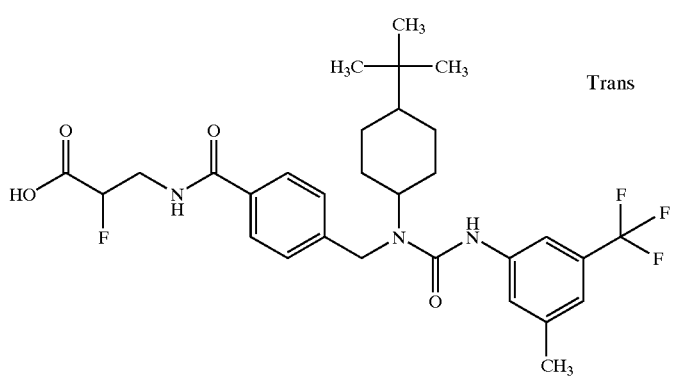
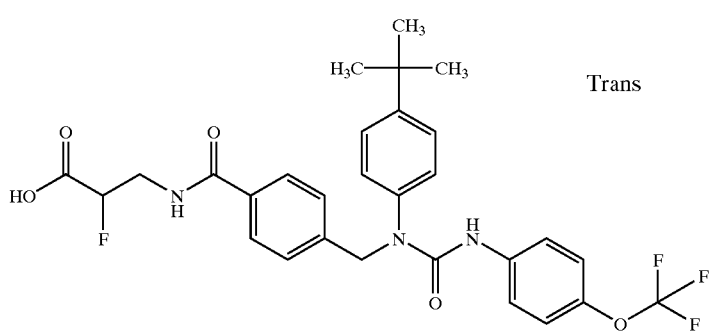
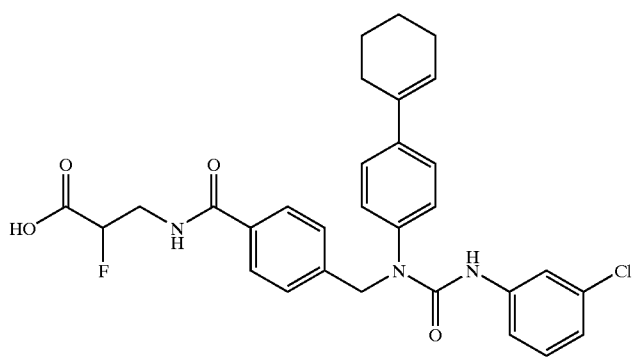

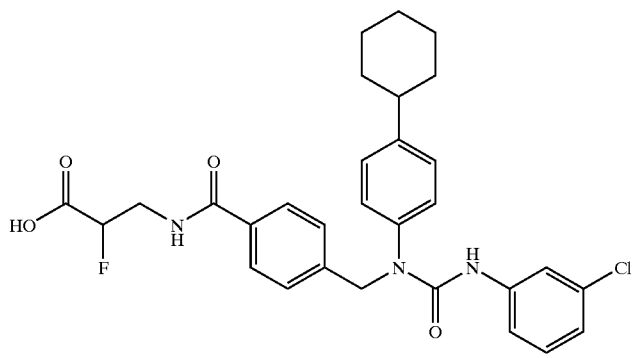
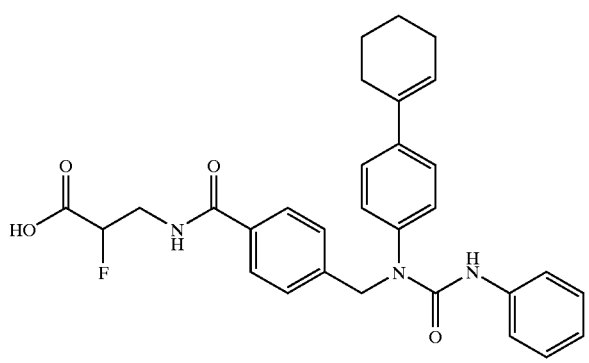
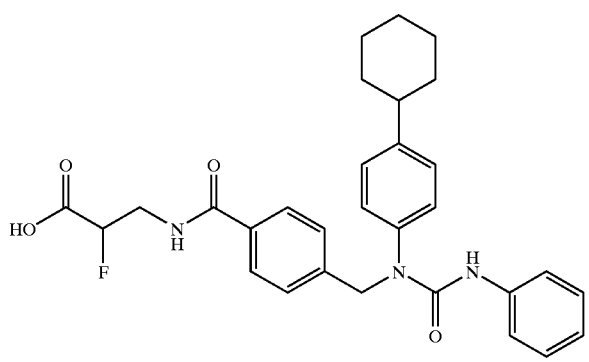
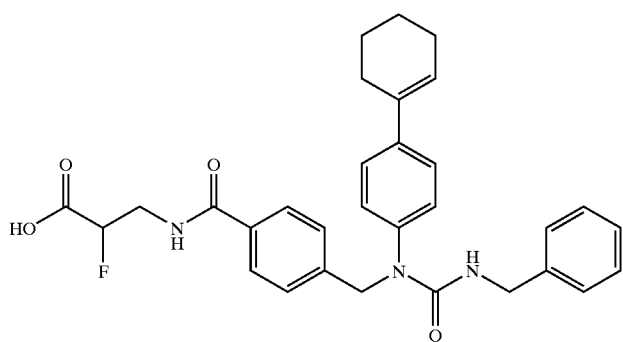

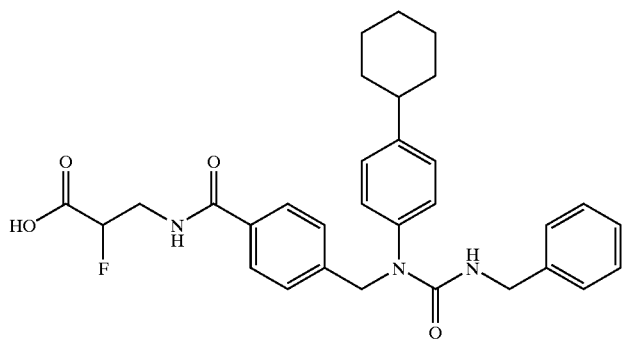
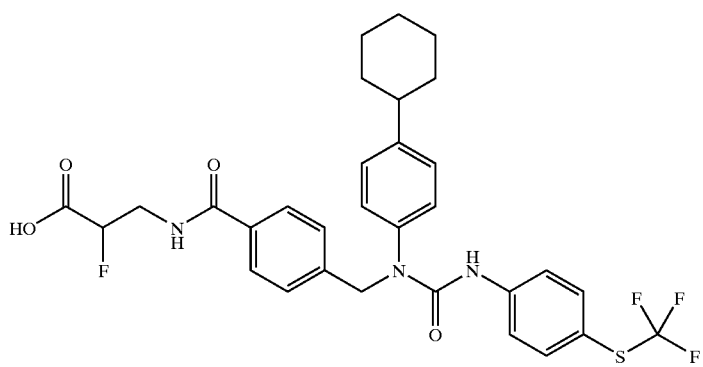
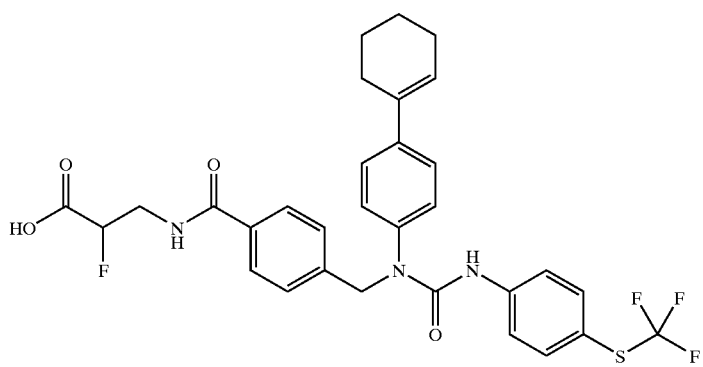
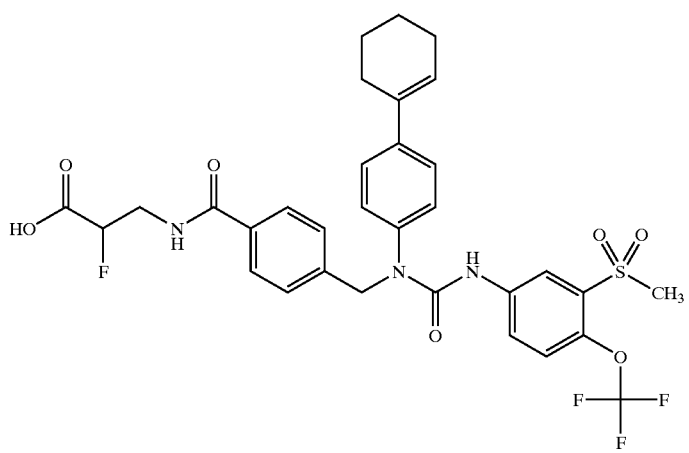

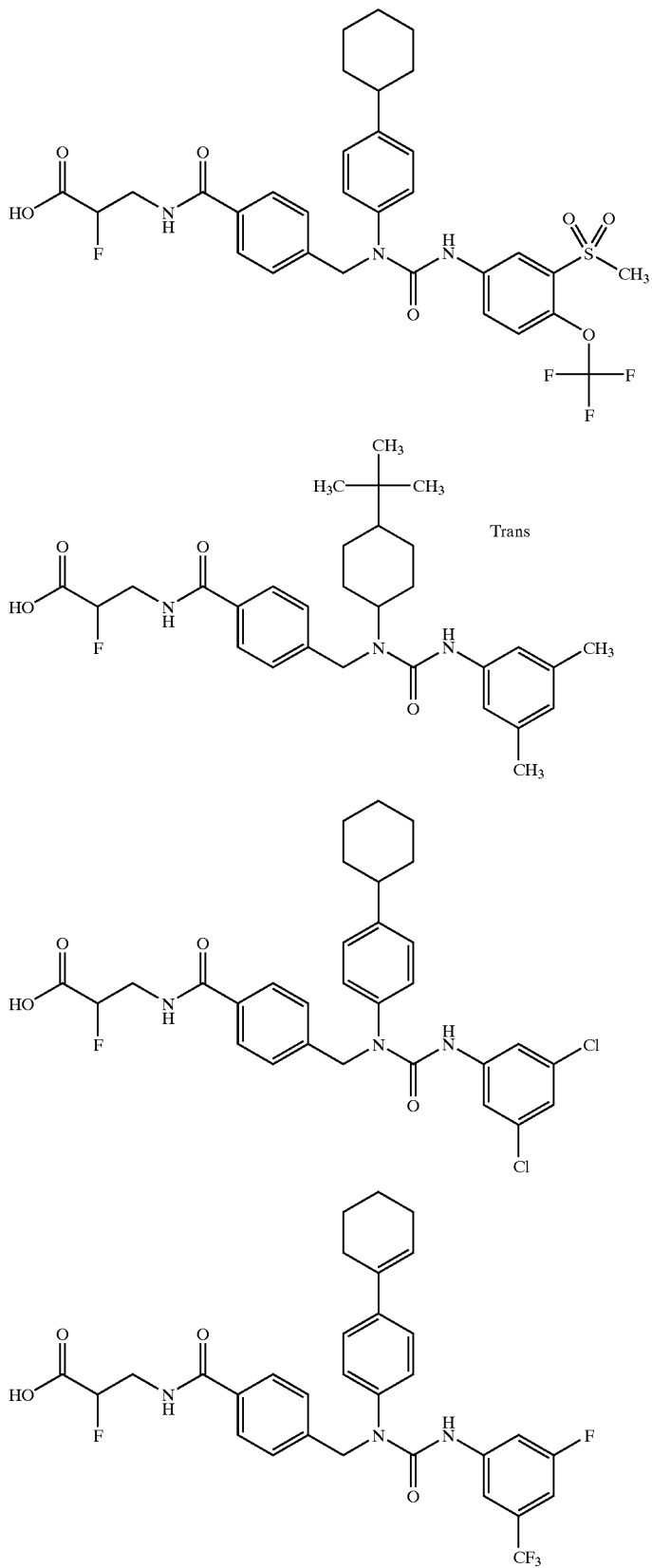

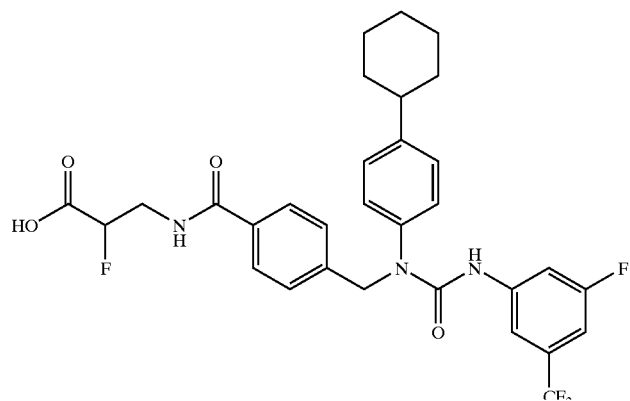
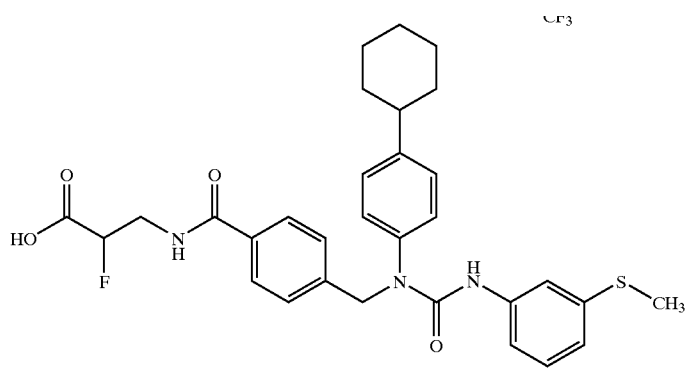
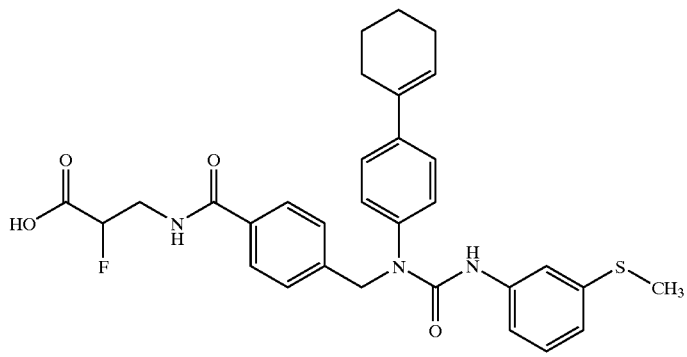
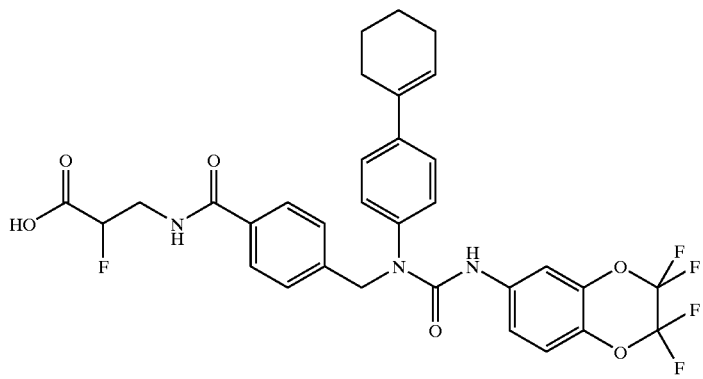

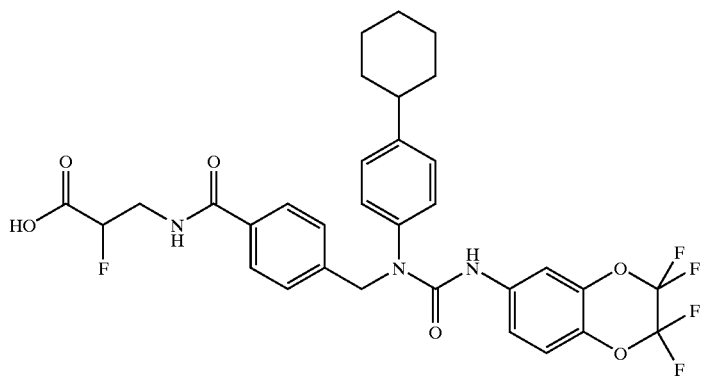
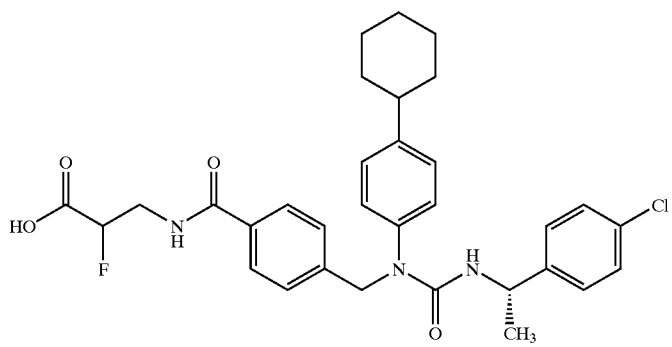
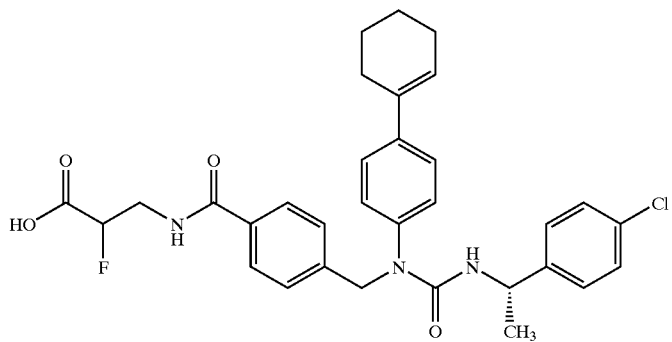
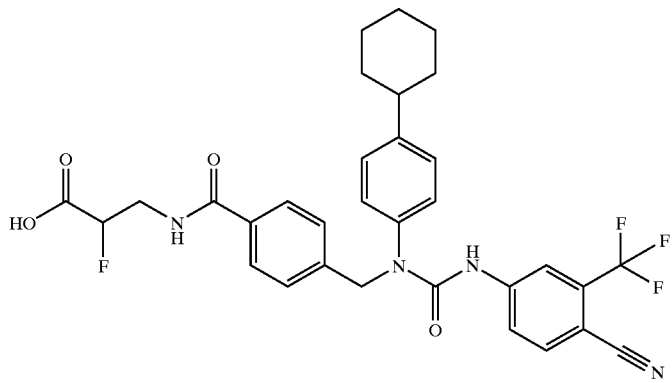

-continued
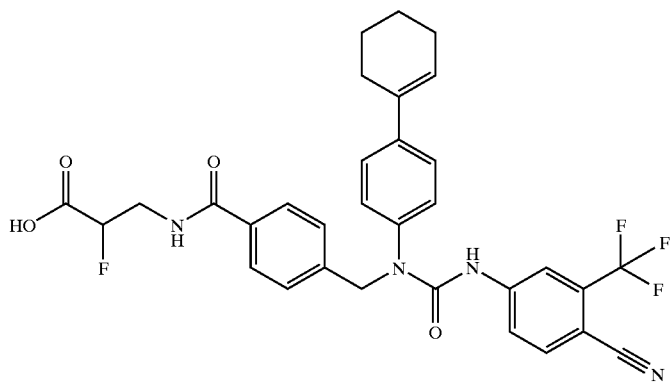
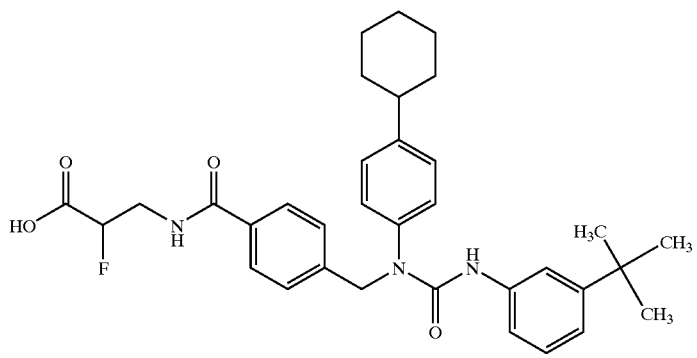
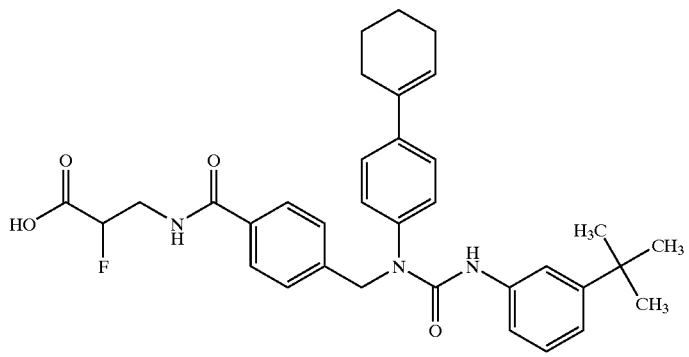
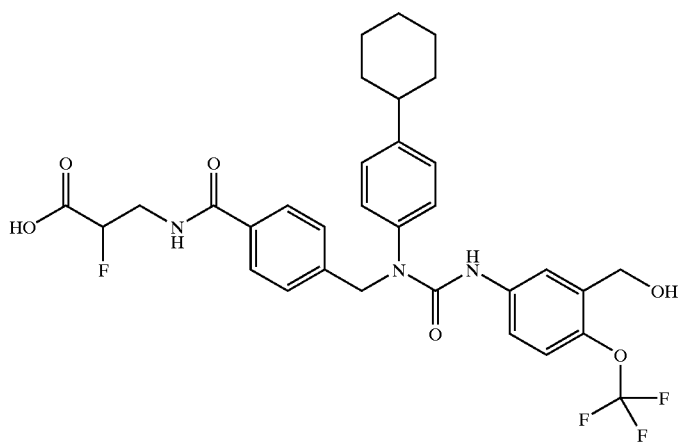

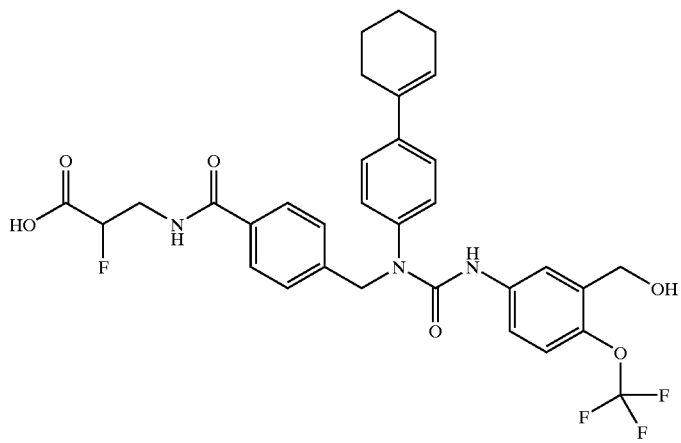
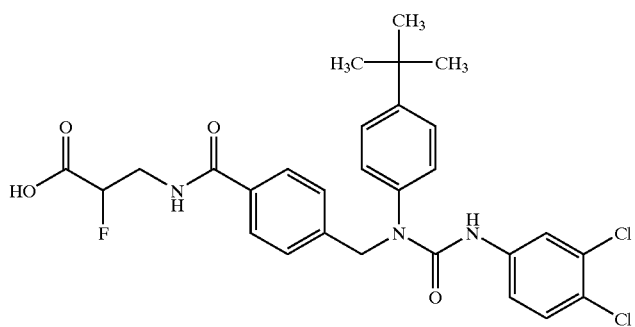
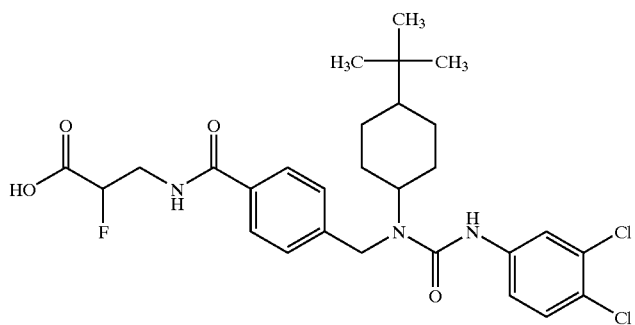
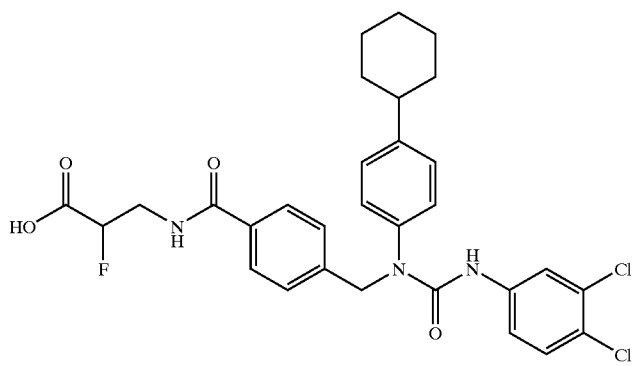

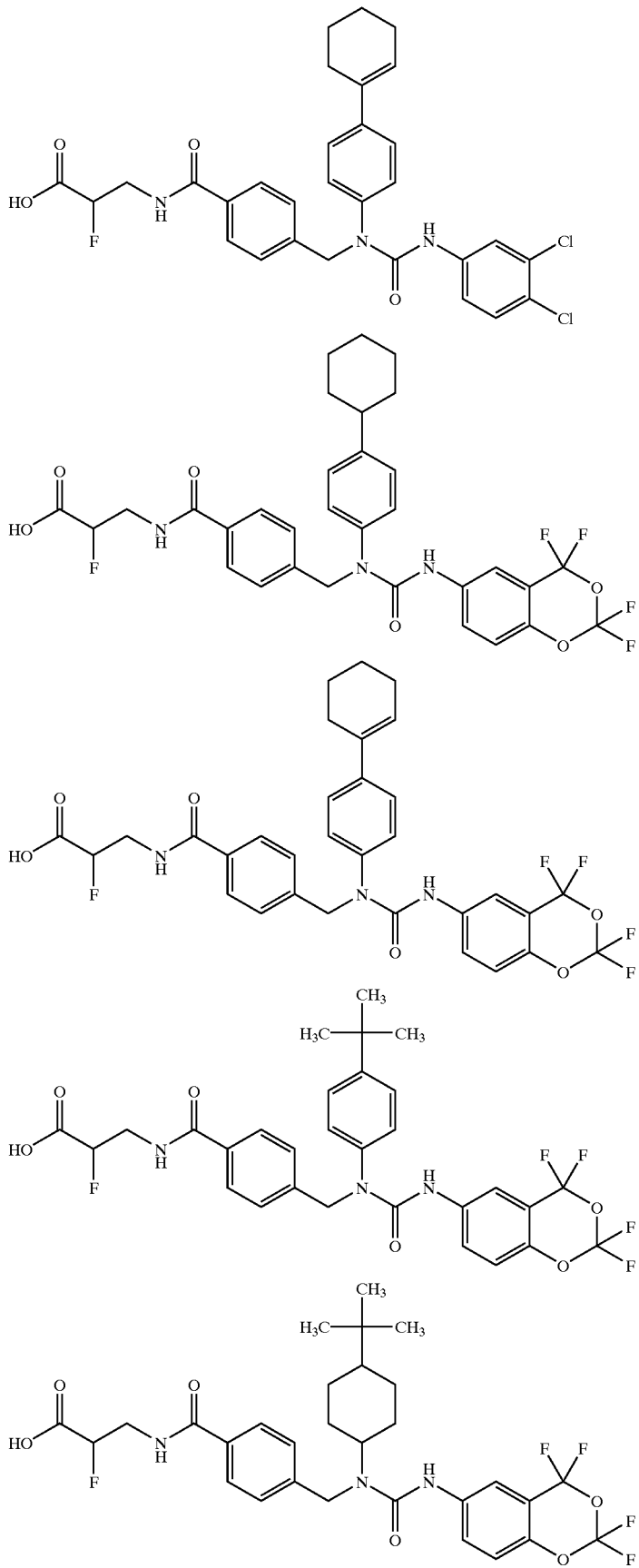

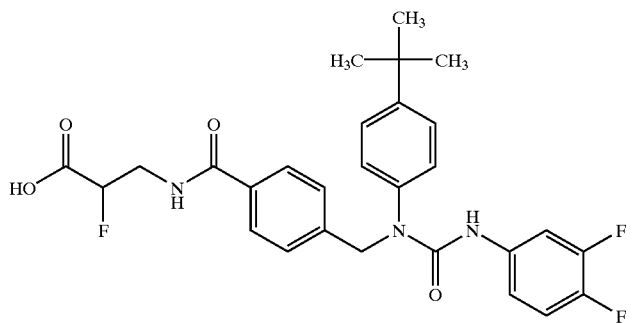
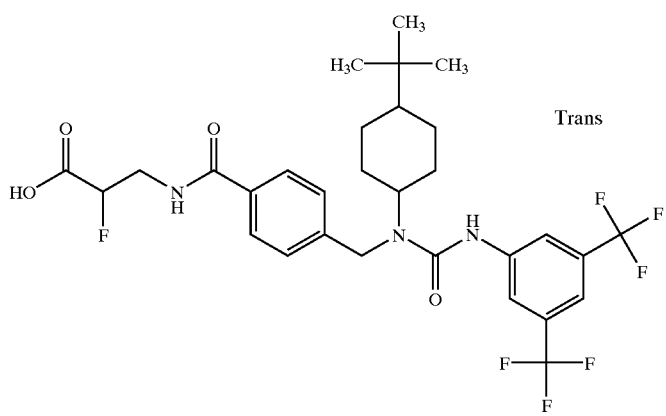
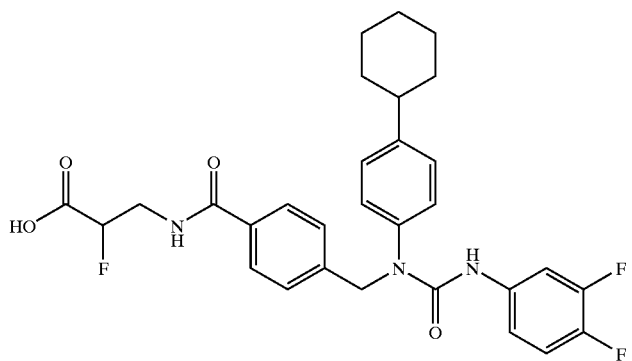
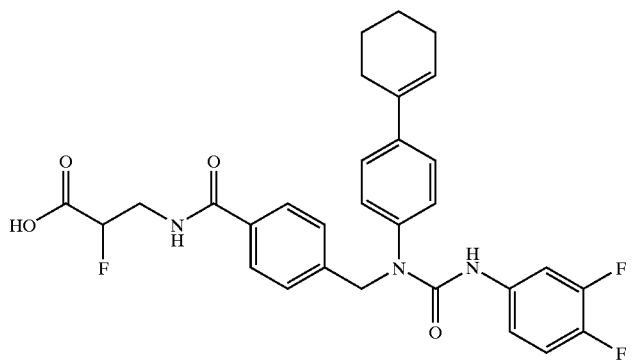

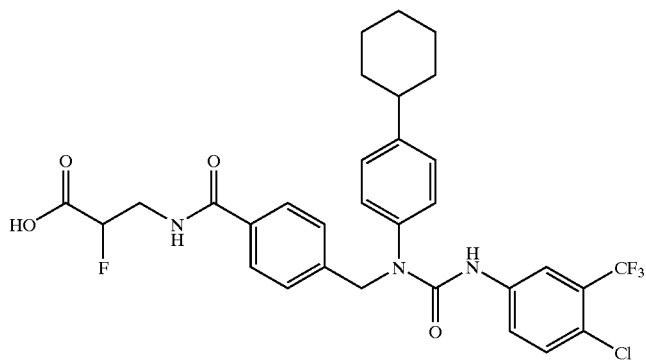
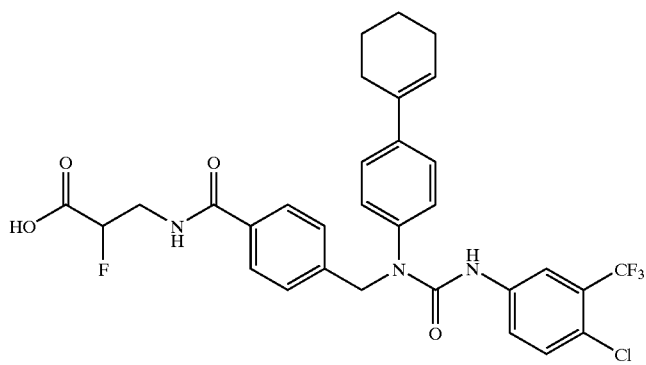
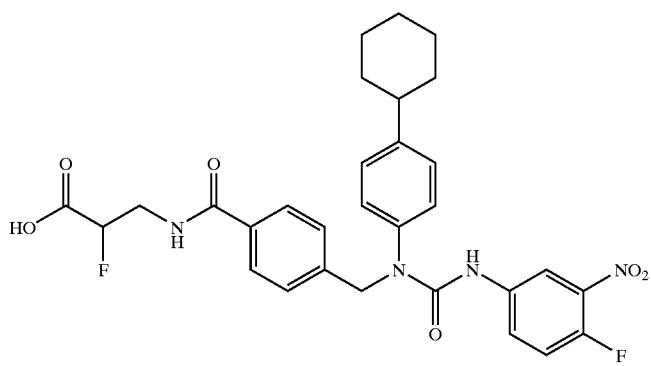
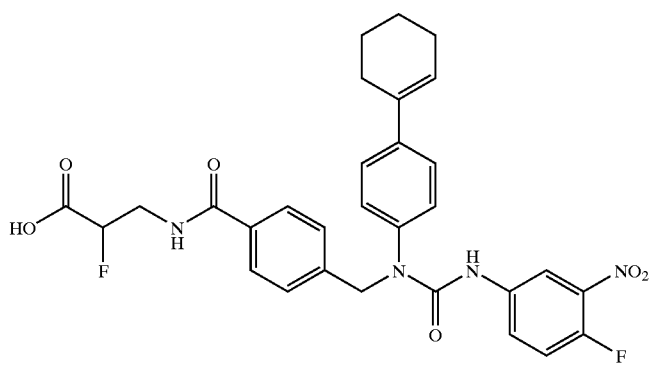

-continued
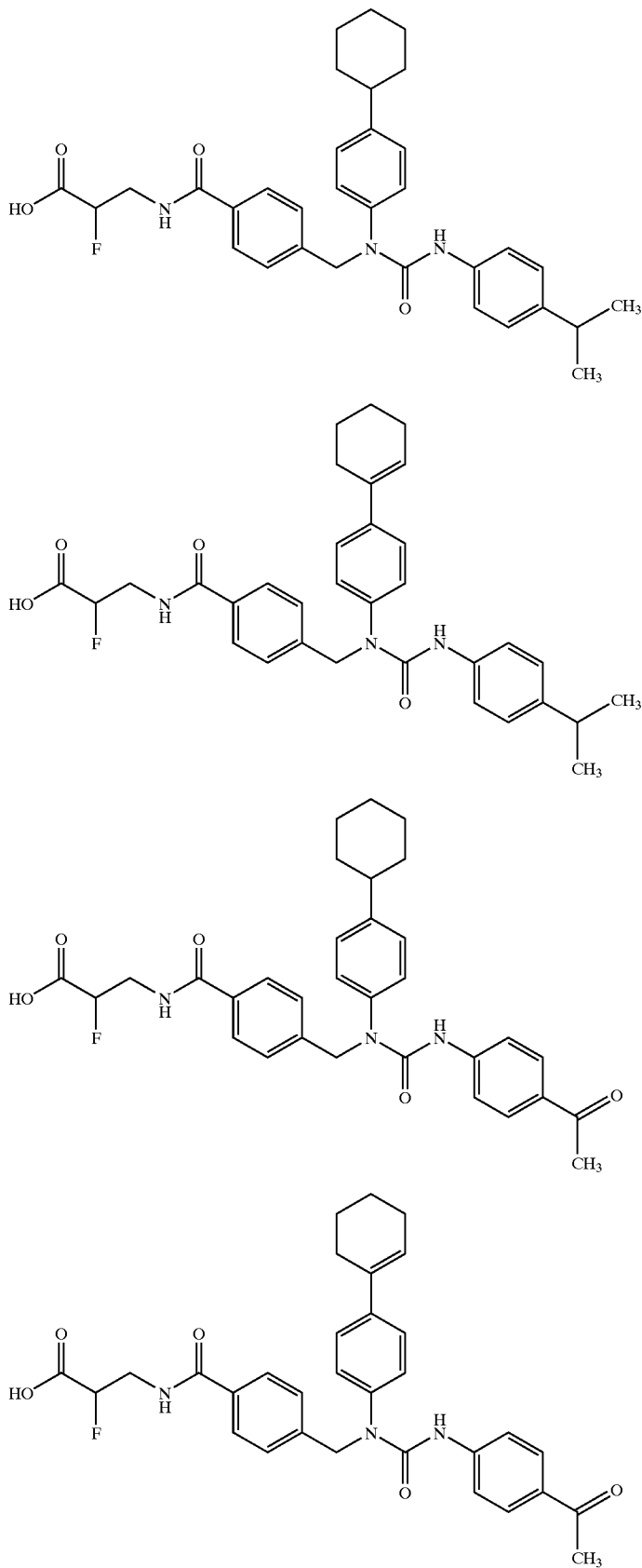

-continued
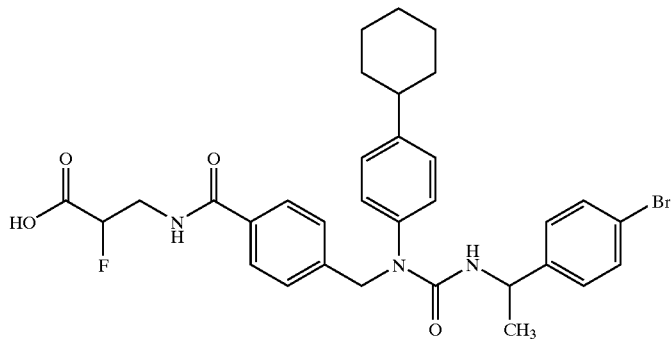
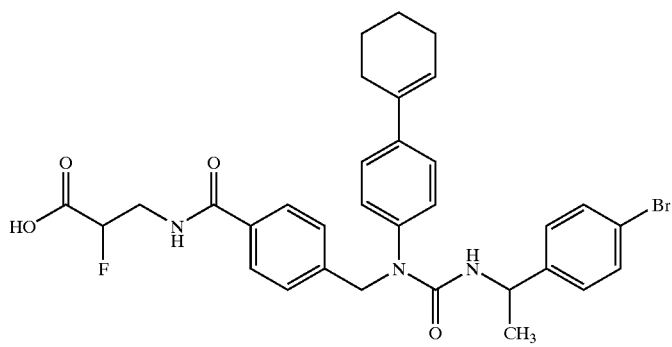
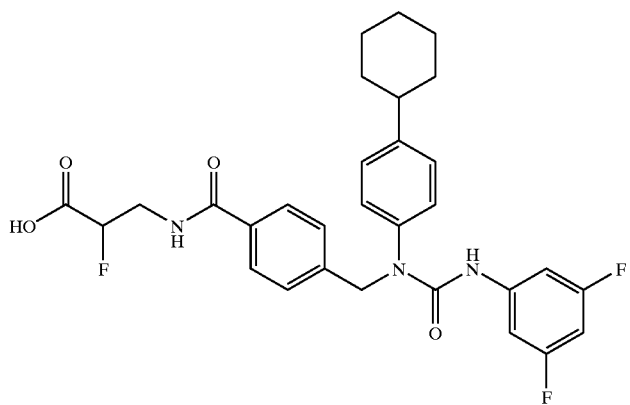
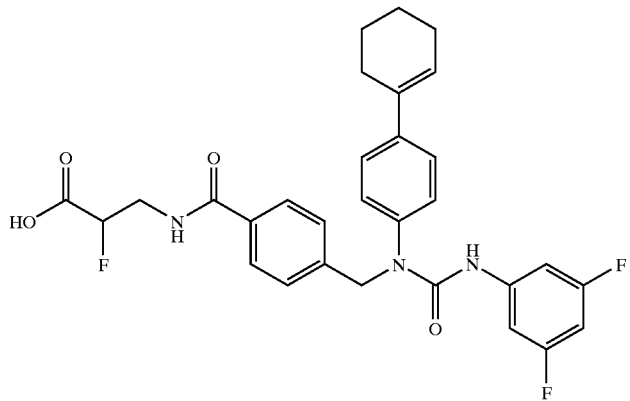

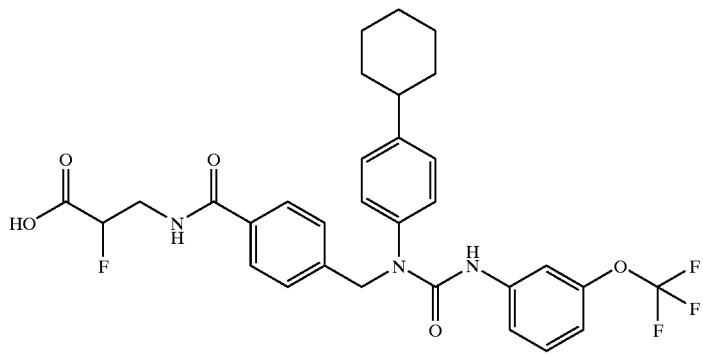
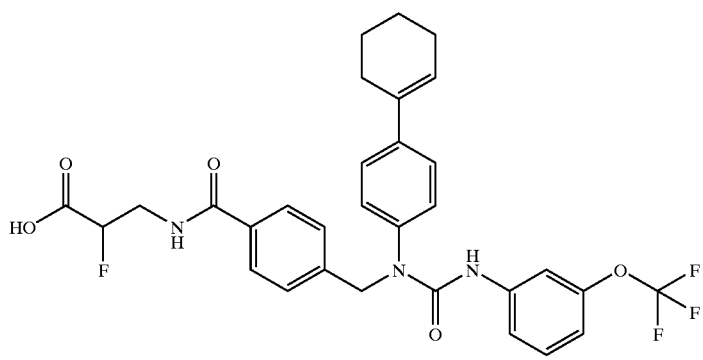
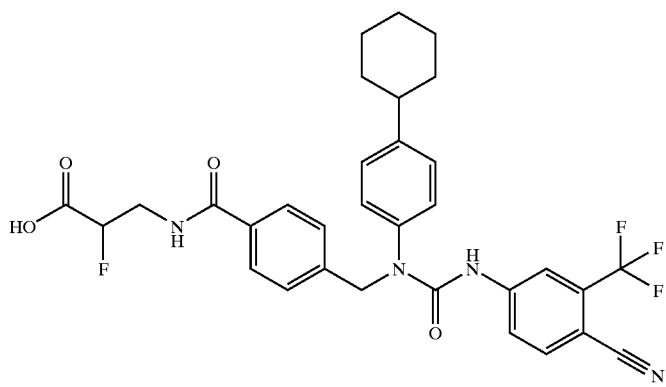
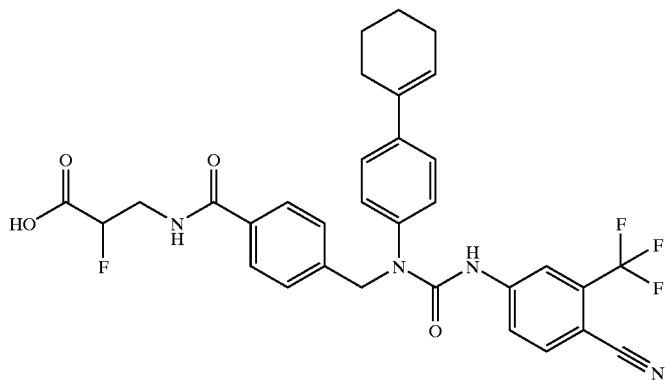

-continued
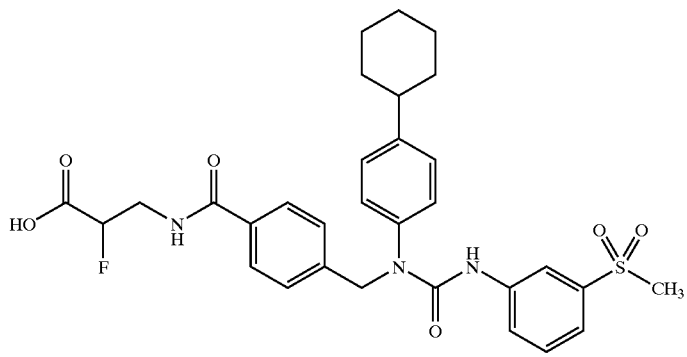
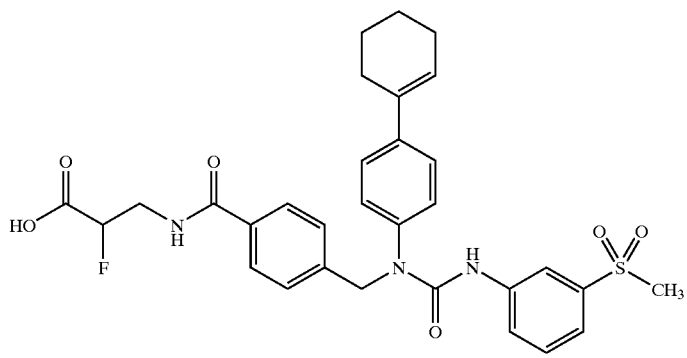
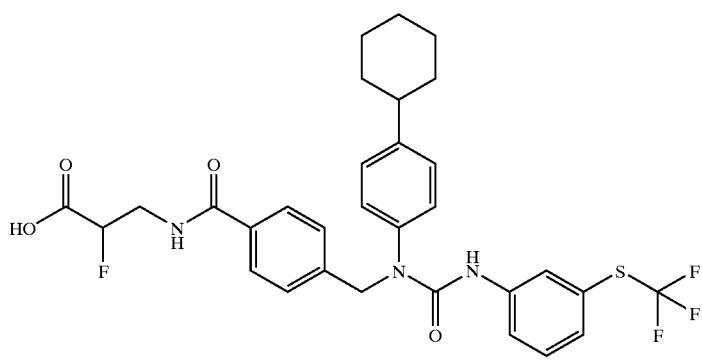
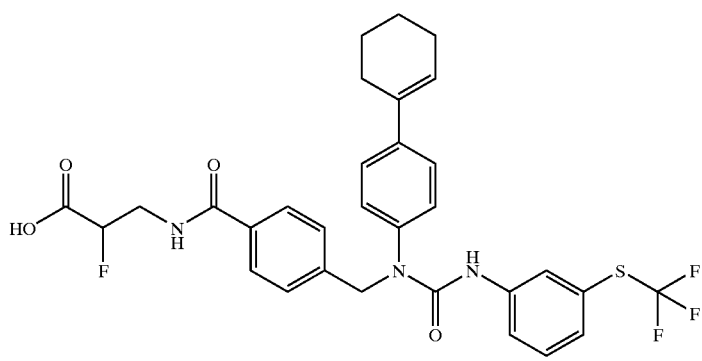

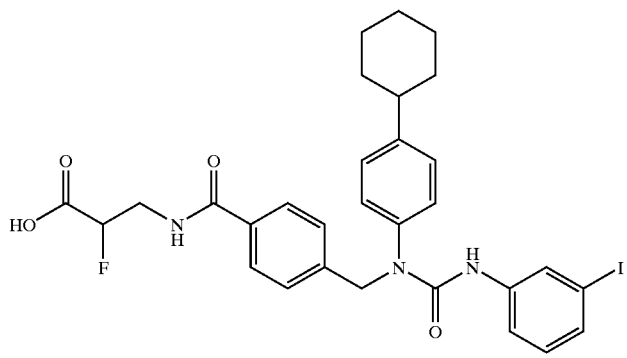
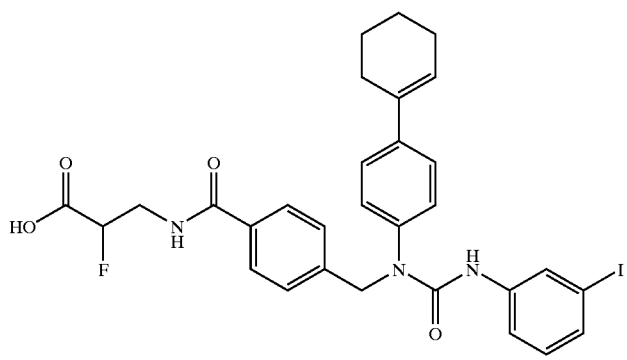
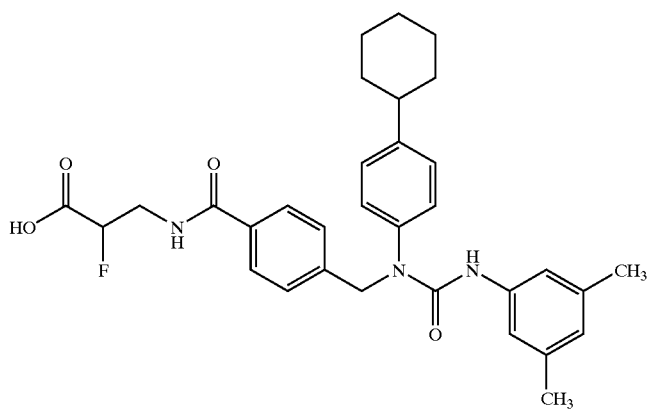
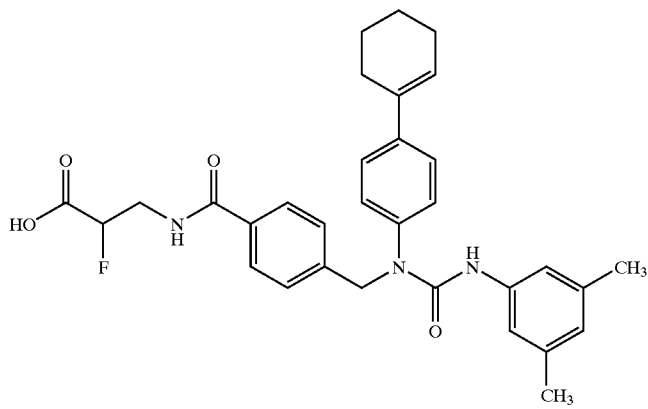

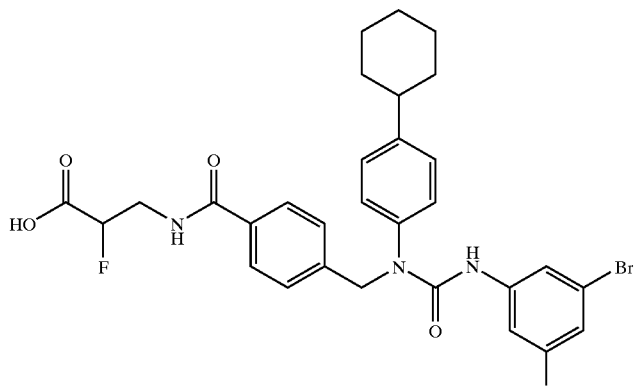
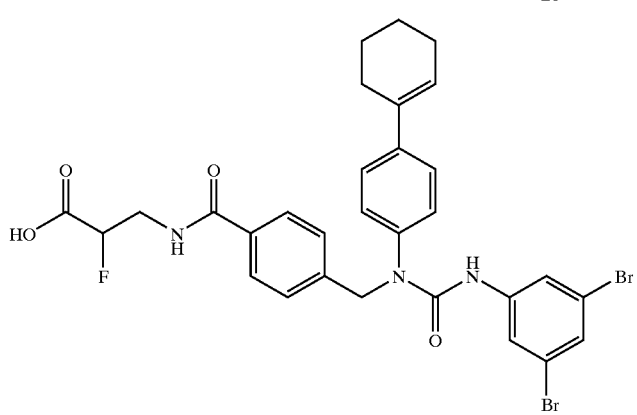
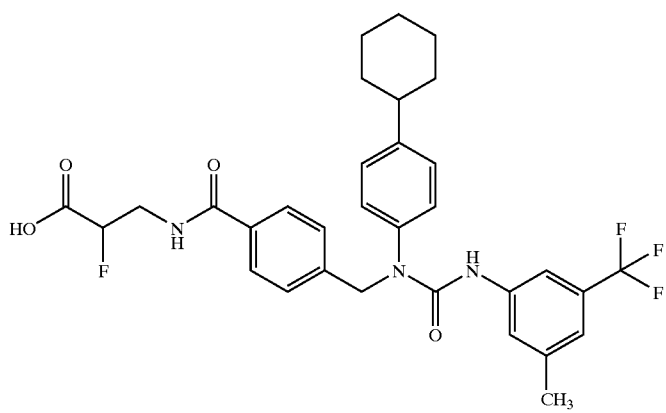
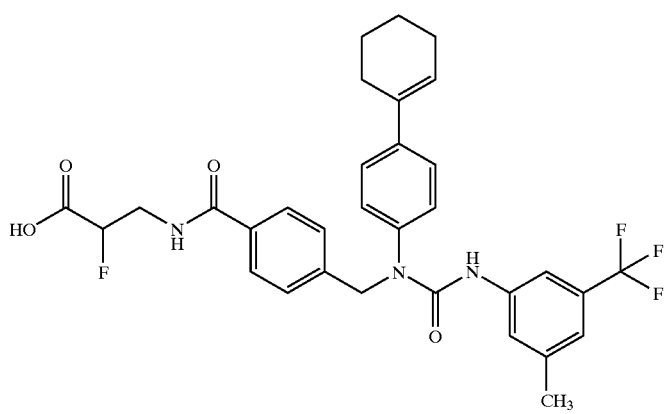

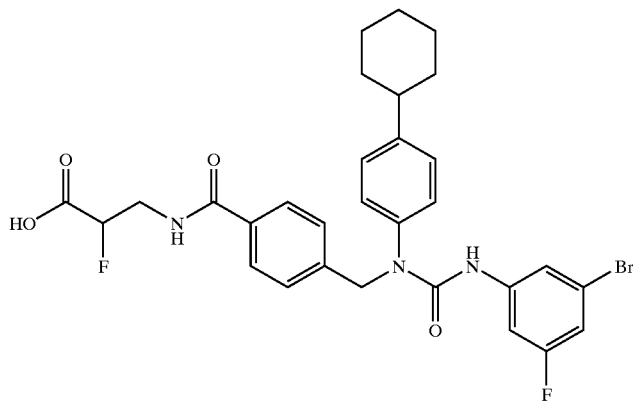
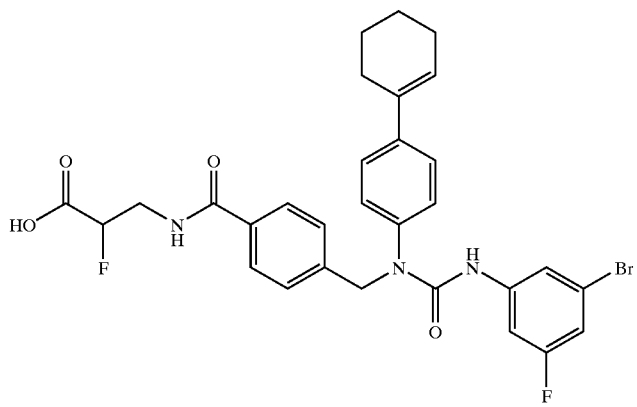
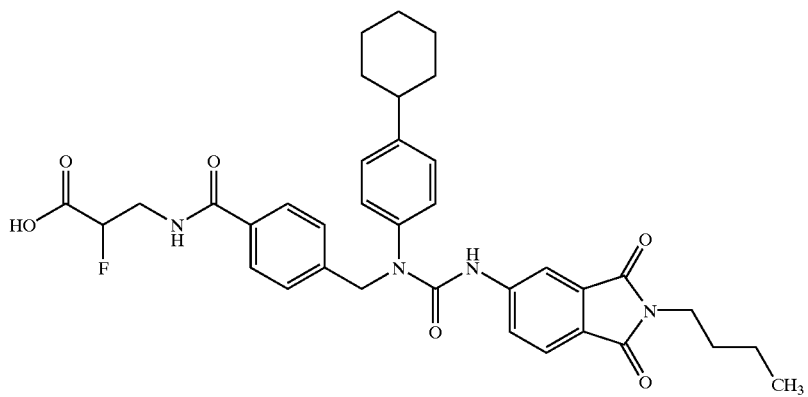
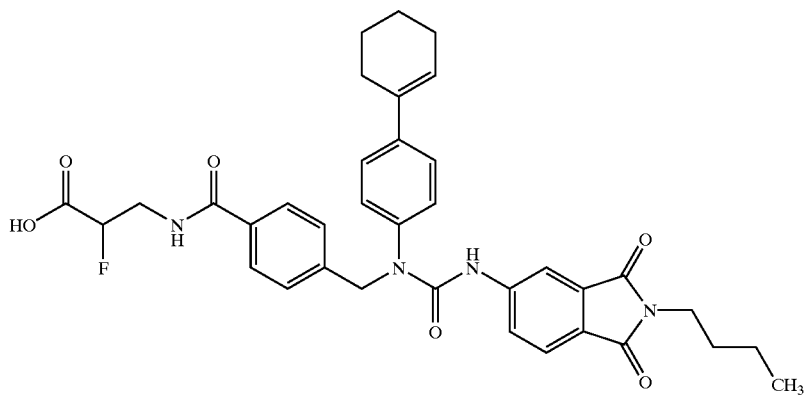

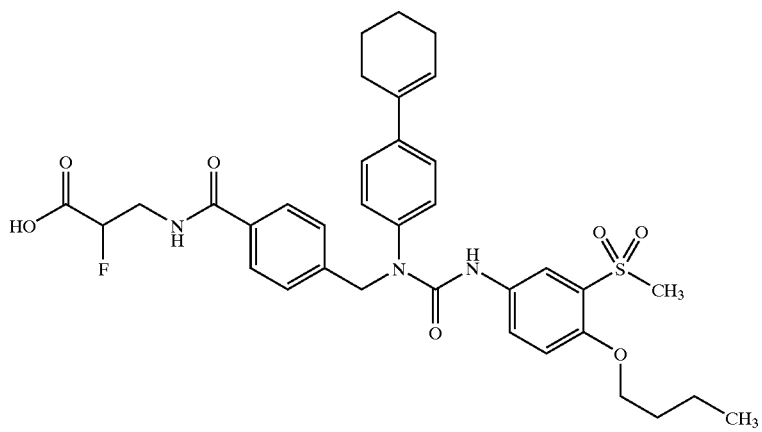
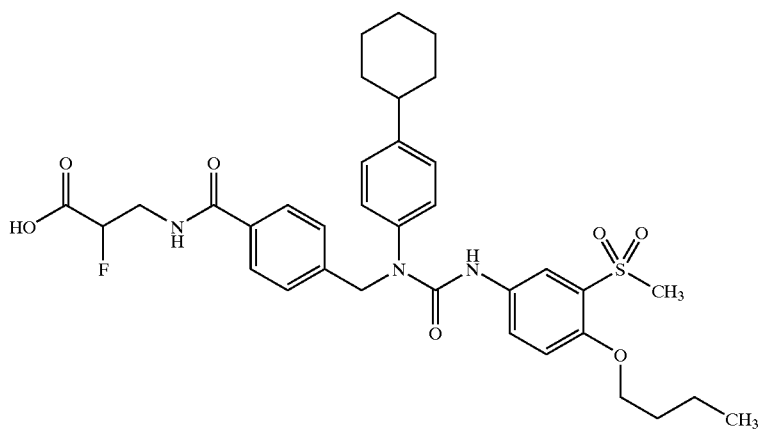
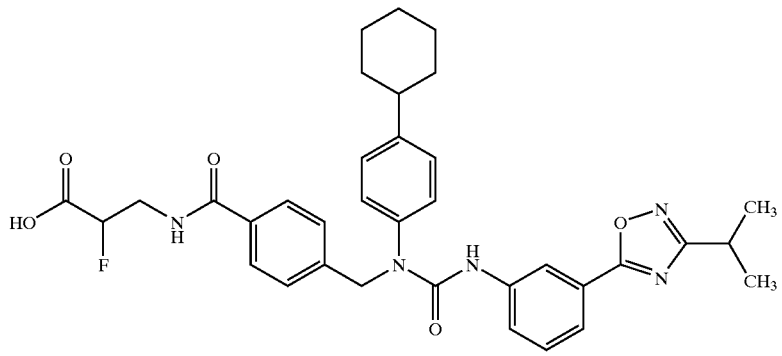
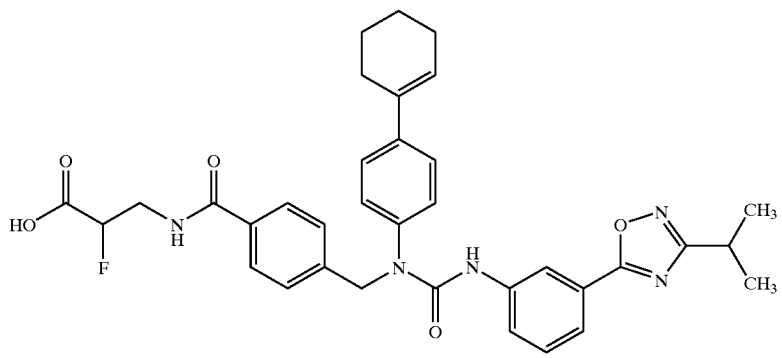

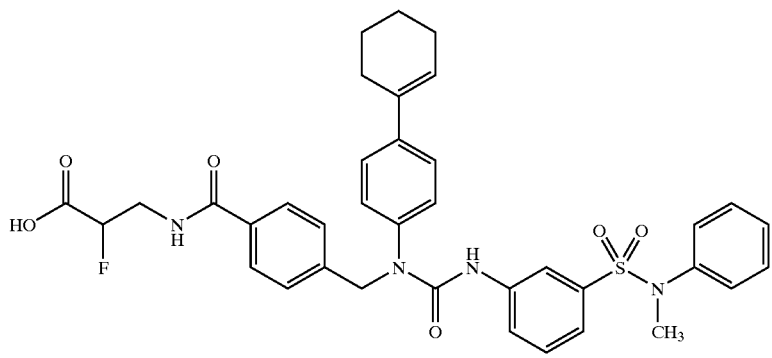
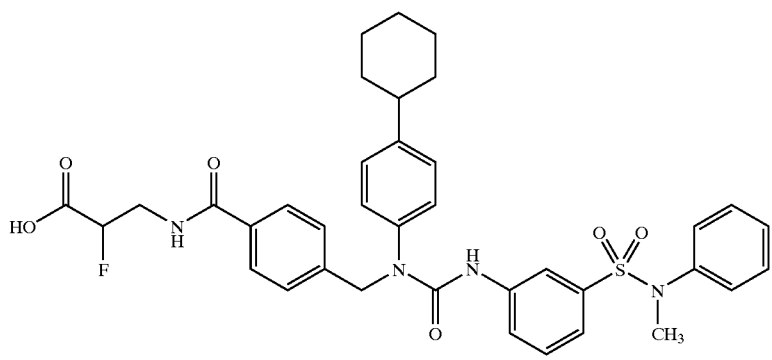
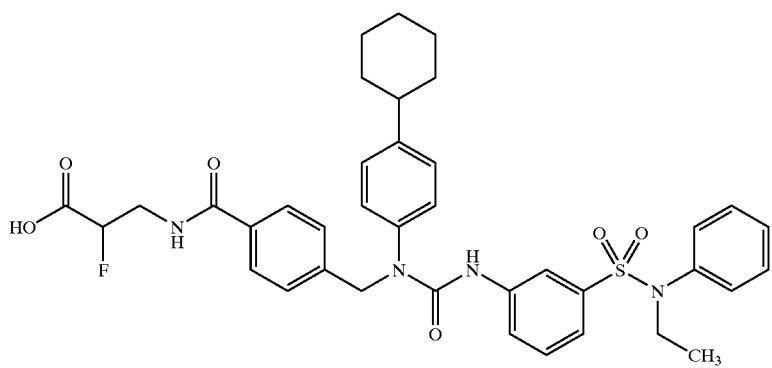
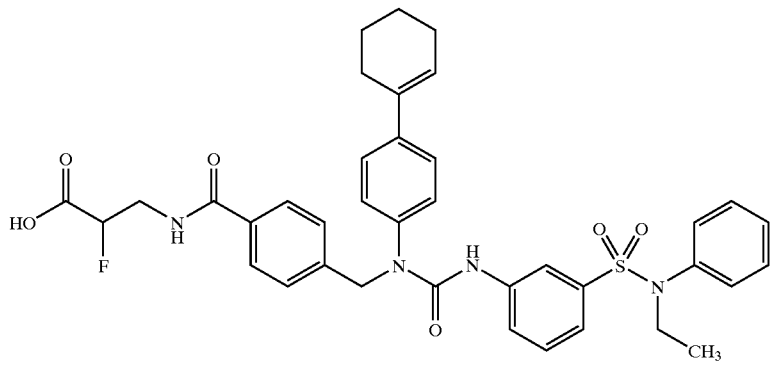

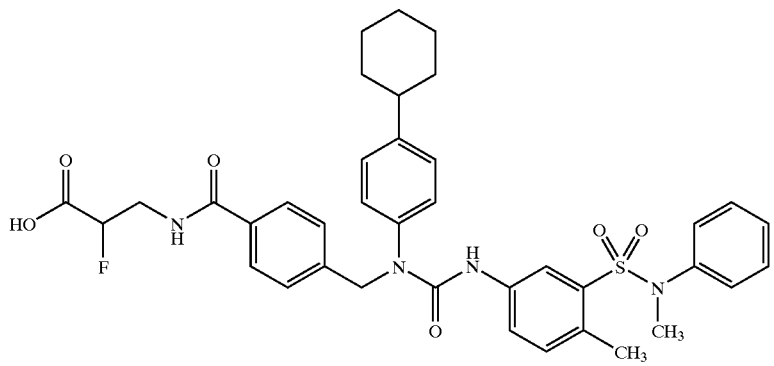
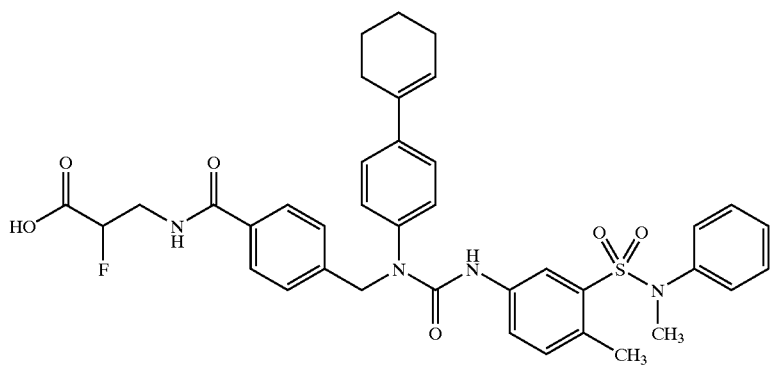
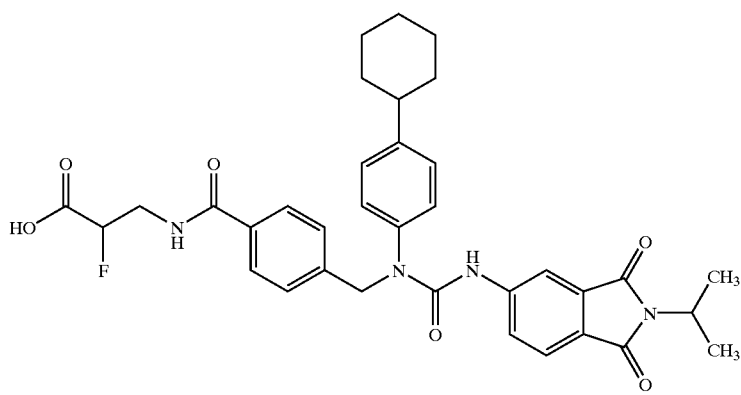
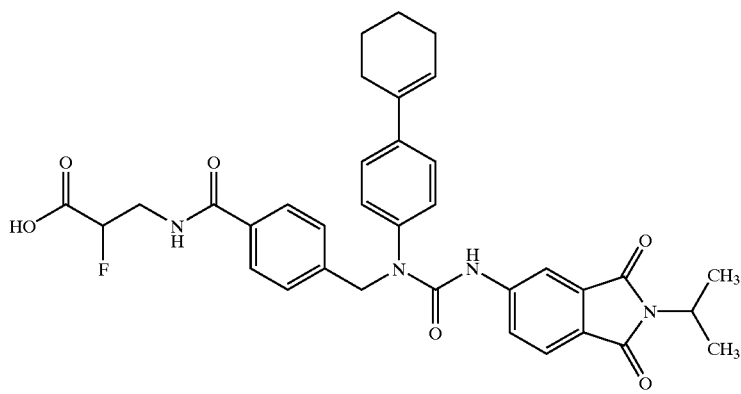

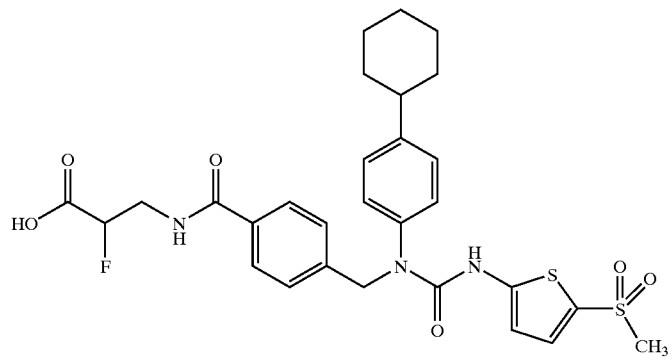
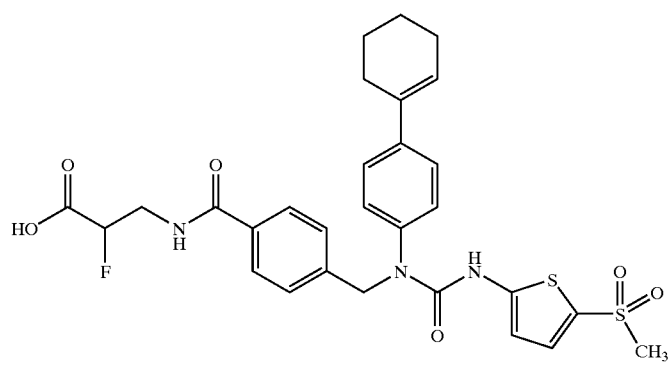
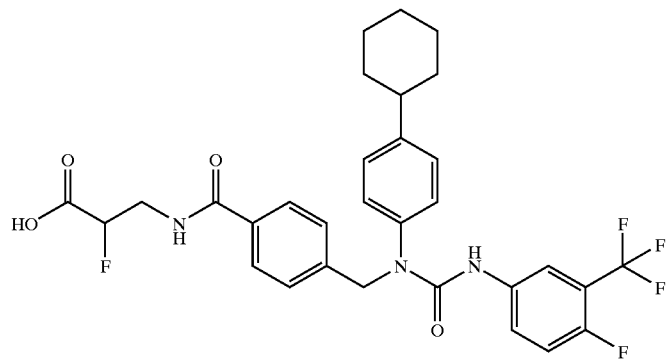
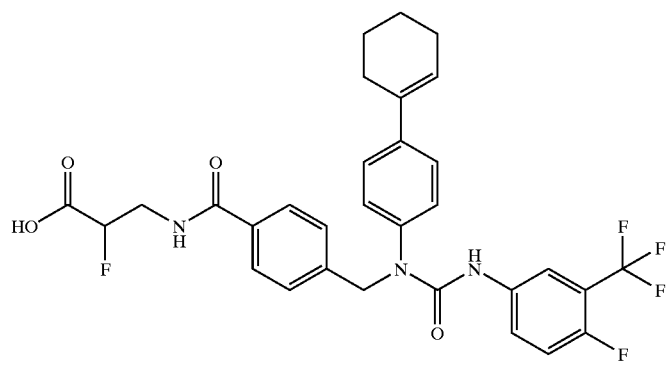

-continued
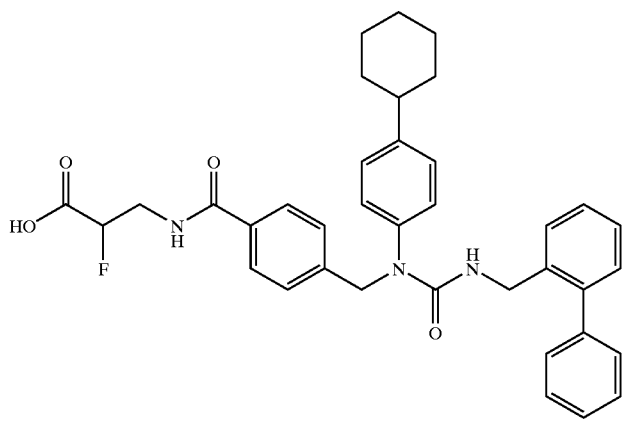
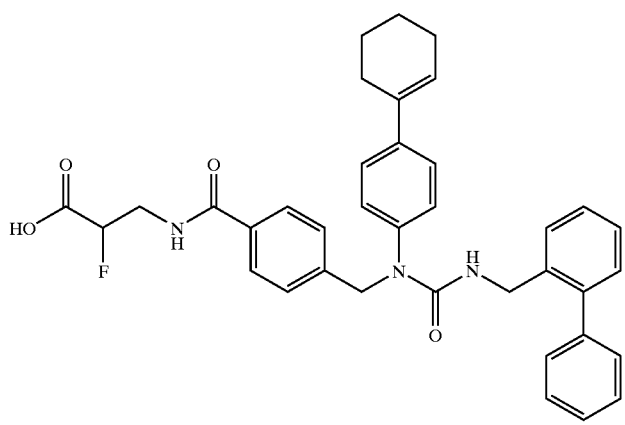
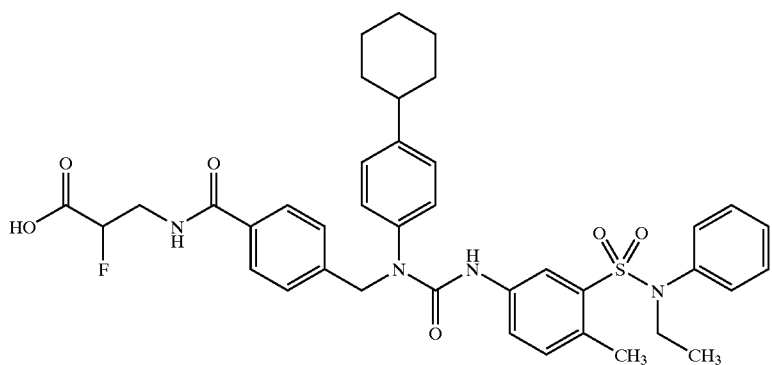
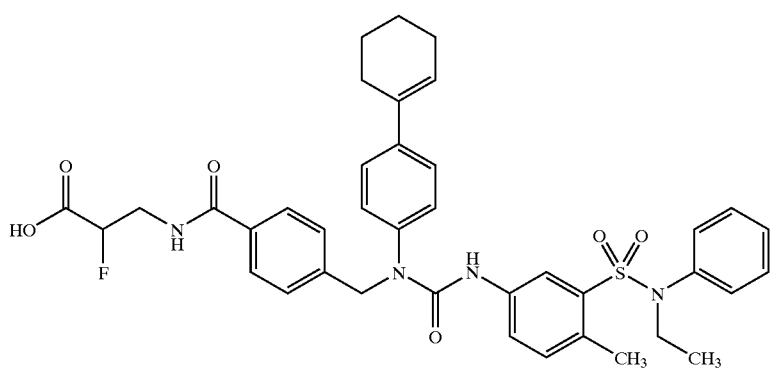

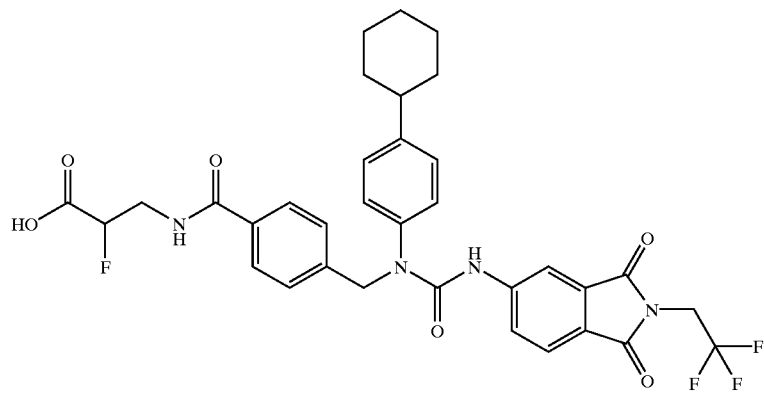
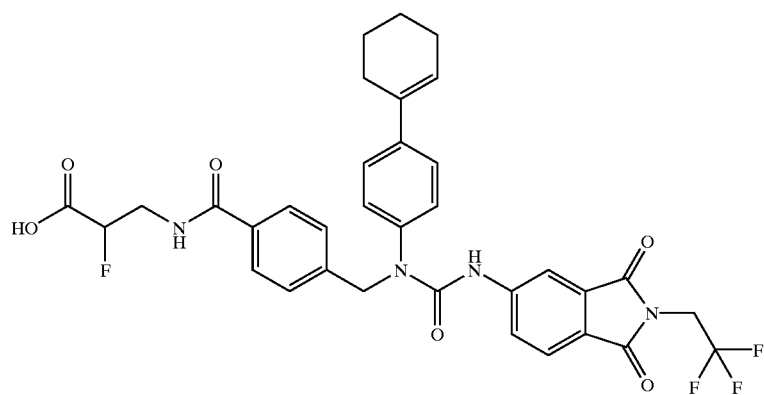
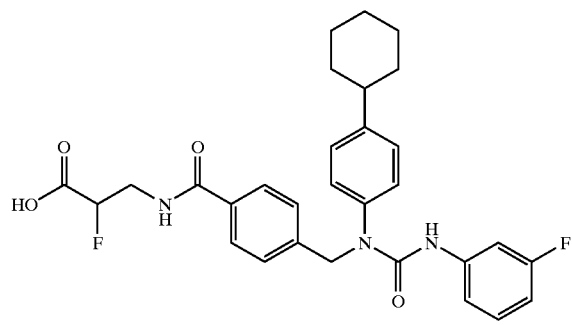
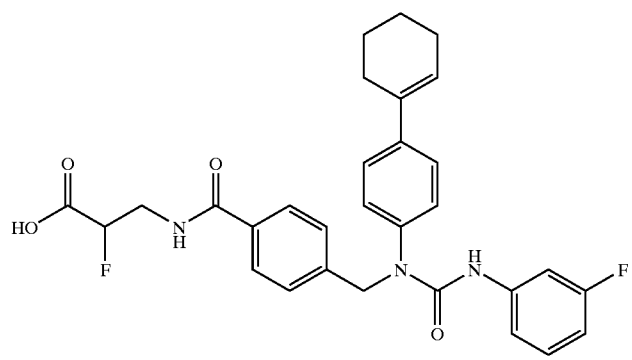

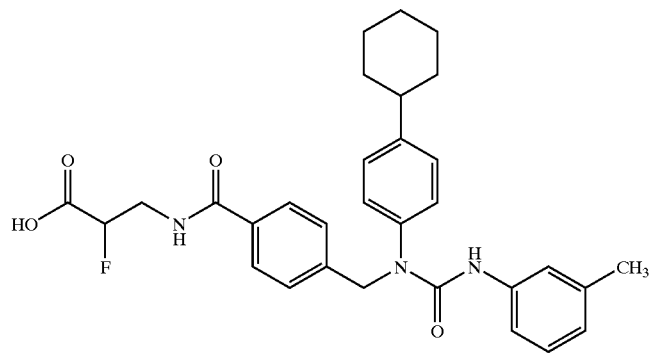
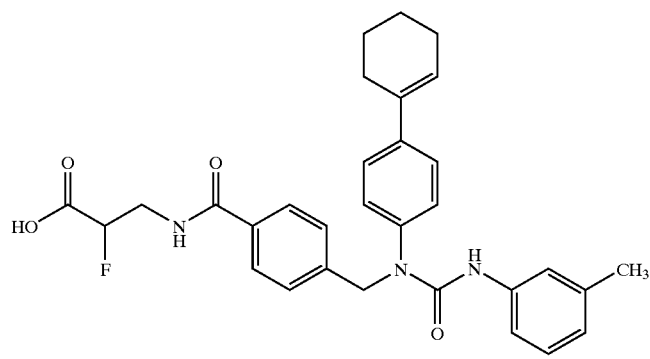
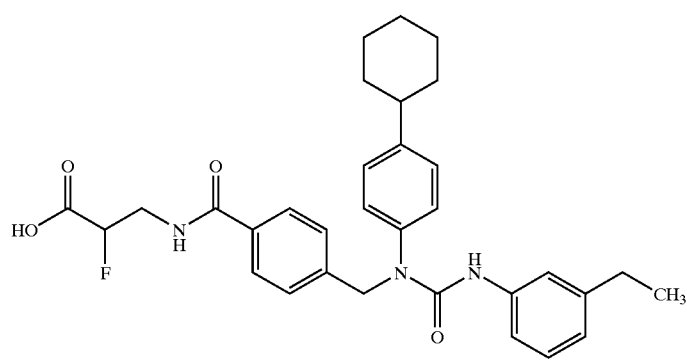
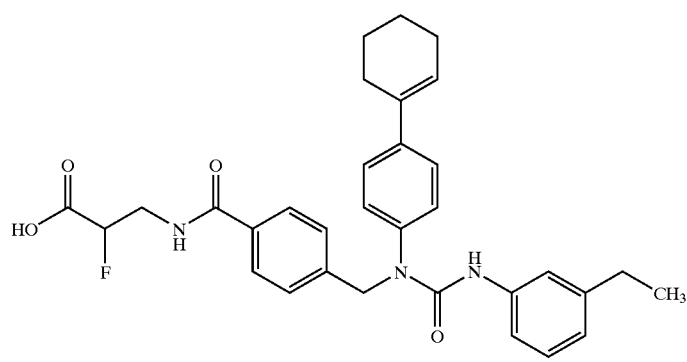

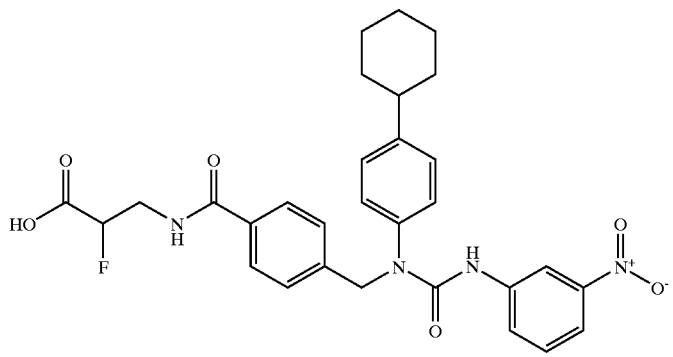
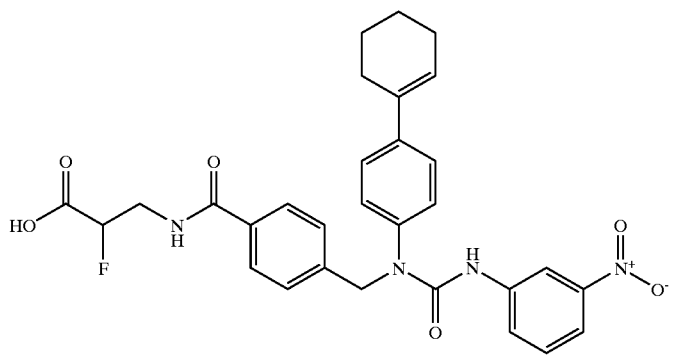
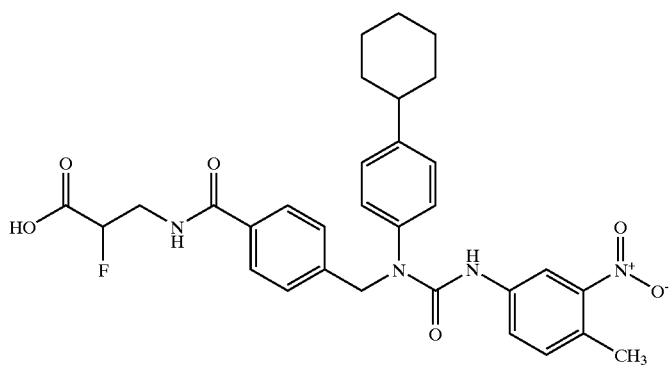
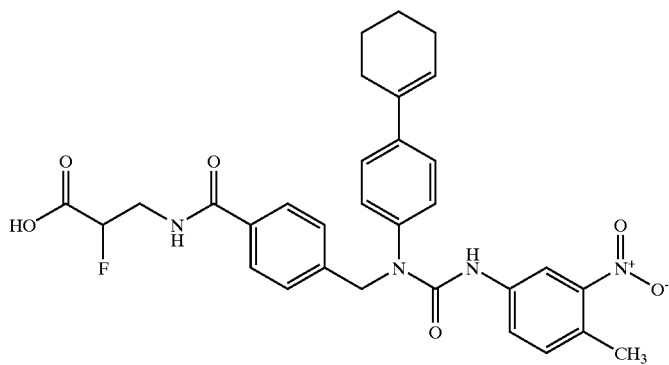

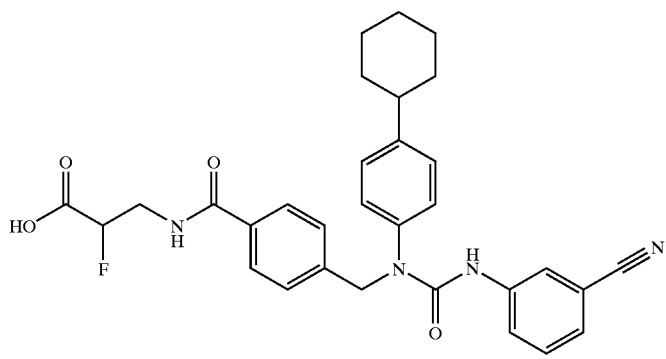
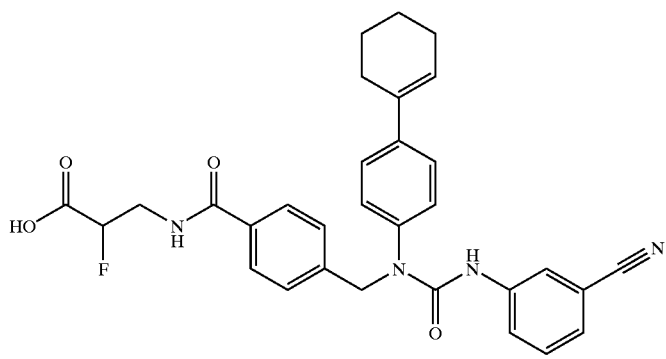
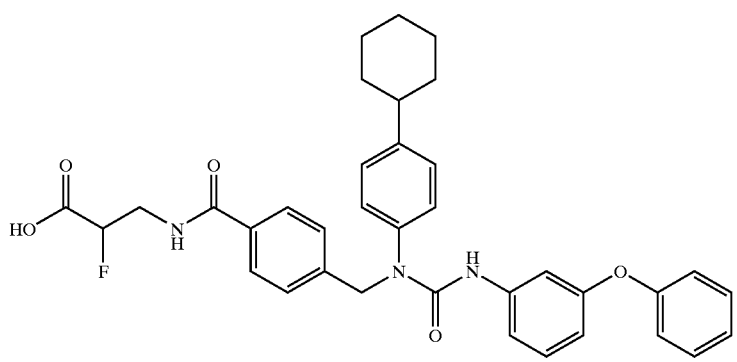
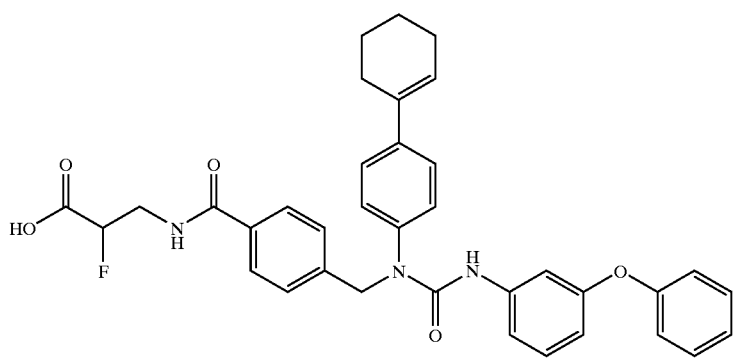

-continued

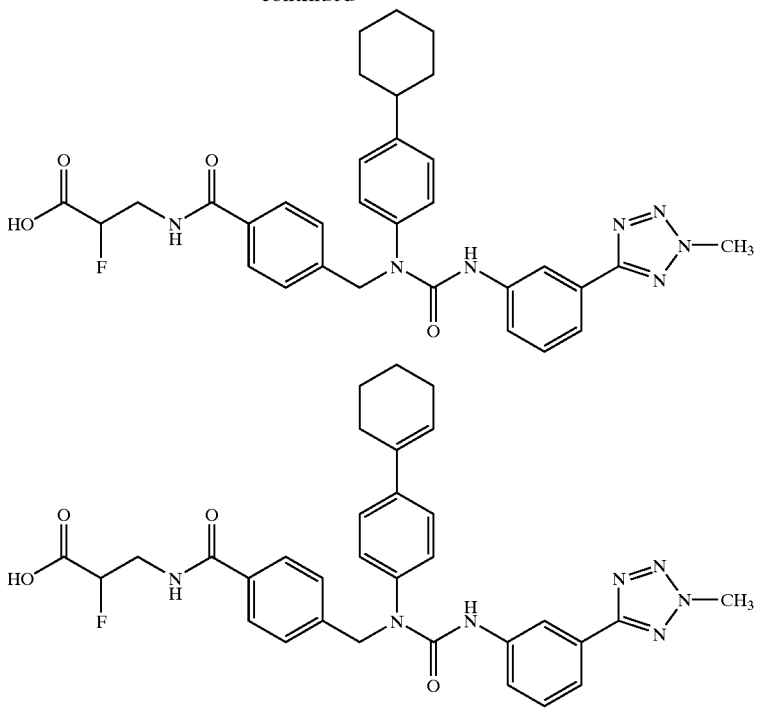

Pharmacological Methods

In the following section binding assays as well as functional assays useful for evaluating the efficiency of the compounds of the invention are described.

Binding of compounds to the glucagon receptor may be determined in a competition binding assay using the cloned human glucagon receptor.

Antagonism may be determined as the ability of the compounds to inhibit the amount of cAMP formed in the presence of 5 nM glucagon.

Glucagon Binding Assay (I)

Receptor binding are assayed using cloned human receptor (Lok et al., Gene 140, 203–209 (1994)). The receptor inserted in the pLJ6' expression vector using EcoRI/SSt1 restriction sites (Lok et al.) is expressed in a baby hamster kidney cell line (A3 BHK 570–25). Clones are selected in the presence of 0.5 mg/mL G-418 and are shown to be stable for more than 40 passages. The $K_d$ is shown to be 0.1 nM.

Plasma membranes are prepared by growing cells to confluence, detaching them from the surface and resuspending the cells in cold buffer (10 mM tris/HCl, pH 7.4 containing 30 mM NaCl, 1 mM dithiothreitol, 5 mg/L leupeptin (Sigma), 5 mg/L pepstatin (Sigma), 100 mg/L bacitracin (Sigma) and 15 mg/L recombinant aprotinin (Novo Nordisk A/S)), homogenization by two 10-s bursts using a Polytron PT 10–35 homogenizer (Kinematica), and centrifugation upon a layer of 41 w/v % sucrose at 95.000×g for 75 min. The white band located between the two layers is diluted in buffer and centrifuged at 40.000×g for 45 min. The precipitate containing the plasma membranes is suspended in buffer and stored at −80° C. until use.

Glucagon is iodinated according to the chloramine T method (Hunter and Greenwood, Nature 194, 495 (1962)) and purified using anion exchange chromatography (Jørgensen et al., Hormone and Metab. Res. 4, 223–224 (1972). The specific activity is 460 pCi/μg on the day of iodination. Tracer is stored at −18° C in aliquots and used immediately after thawing.

Binding assays are carried out in triplicate in filter microtiter plates (MADV N65, Millipore). The buffer is 50 mM HEPES, 5 mM EGTA, 5 mM $MgCl_2$, 0.005% tween 20, pH 7.4. Glucagon is dissolved in 0.05 M HCl, added an equal amount (w/w) of human serum albumin and freeze-dried. On the day of use, it is dissolved in water and diluted in buffer to the desired concentrations.

Test compounds are dissolved and diluted in DMSO. 140 μL buffer, 25 μL glucagon or buffer, and 10 μL DMSO or test compound are added to each well. Tracer (50.000 cpm) is diluted in buffer and 25 μL is added to each well. 1–4 μg freshly thawed plasma membrane protein diluted in buffer is then added in aliquots of 25 μL to each well. Plates are incubated at 30° C. for 2 hours. Non-specific binding is determined with $10^{-6}$ M of glucagon. Bound tracer and unbound tracer are then separated by vacuum filtration (Millipore vacuum manifold). The plates are washed with 2×100 μL buffer/well. The plates are air dried for a couple of hours, whereupon the filters are separated from the plates using a Millipore Puncher. The filters are counted in a gamma counter.

Functional Assay (I)

The functional assay was carried out in 96 well microtiter plates (tissue culture plates, Nunc). The resulting buffer concentrations in the assay are 50 mM tris/HCl, 1 mM EGTA, 1.5 mM $MgSO_4$, 1.7 mM ATP, 20 FM GTP, 2 mM IBMX, 0.02% tween-20 and 0.1% human serum albumin. pH was 7.4. Glucagon and proposed antagonist are added in aliquots of 35 μL diluted in 50 mM tris/HCl, 1 mM EGTA, 1.85 mM $MgSO_4$, 0.0222% tween-20 and 0.111% human serum albumin, pH 7.4.20 μL of 50 mM tris/HCl, 1 mM EGTA, 1.5 mM $MgSO_4$, 11.8 mM ATP, 0.14 mM GTP, 14 mM IBMX and 0.1% human serum albumin, pH 7.4 was added. GTP was dissolved immediately before the assay.

50 μL containing 5 μg of plasma membrane protein was added in a tris/HCl, EGTA, MgSO$_4$, human serum albumin buffer (the actual concentrations are dependent upon the concentration of protein in the stored plasma membranes). The total assay volume is 140 μL. The plates are incubated for 2 hours at 37° C. with continuous shaking. Reaction is terminated by addition of 25 μL 0.5 N HCl. cAMP is measured by the use of a scintillation proximity kit (Amersham).

Glucagon Binding Assay (II)

BHK (baby hamster kidney cell line) cells are transfected with the human glucagon receptor and a membrane preparation of the cells is prepared. Wheat Germ Agglutinin derivatized SPA beads containing a scintillant (WGA beads) (Amersham) bound the membranes. $^{125}$I-glucagon bound to human glucagon receptor in the membranes and excited the scintillant in the WGA beads to light emission. Glucagon or samples binding to the receptor competed with $^{125}$I-glucagon.

All steps in the membrane preparation are kept on ice or performed at 4° C. BHK cells are harvested and centrifuged. The pellet is resuspended in homogenisation buffer (25 mM HEPES, pH=7.4, 2.5 mM CaCl$_2$, 1.0 mM MgCl$_2$, 250 mg/L bacitracin, 0.1 mM Pefabloc), homogenised 2×10 sec using Polytron 10–35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM CaCl$_2$, 1.0 mM MgCl$_2$) and homogenised 2×10 sec. (Polytron). The protein concentration is normally around 1.75 mg/mL. Stabilisation buffer (25 mM HEPES, pH=7.4, 2.5 mM CaCl$_2$, 1.0 mM MgCl$_2$, 1% bovine serum albumin, 500 mg/L bacitracin, 2.5 M sucrose) is added and the membrane preparation is stored at-80° C. The glucagon binding assay is carried out in opti plates (Polystyrene Microplates, Packard). 50 μL assay buffer (25 mM HEPES, pH=7.5, 2.5 mM CaCl$_2$, 1.0 mM MgCl$_2$, 0.003% Tween-20, 0.005% bacitracin, 0.05% sodium azide) and 5 μL glucagon or test compound (in DMSO) are added to each well. 50 μL tracer ($^{125}$I-porcine glucagon, 50.000 cpm) and 50 μL membranes (7.5 g) containing the human glucagon receptor are then added to the wells. Finally 50 μL WGA beads containing 1 mg beads are transferred to the well. The opti plates are incubated for 4 hours on a shaker and then settled for 8–48 hours. The opti plates are counted in a Topcounter. Non-specific binding is determined with 500 nM of glucagon.

GIP Binding Assay

BHK (baby hamster kidney cell line) cells are transfected with the human GIP receptor and a membrane preparation of the cells is prepared. Wheat Germ Agglutinin derivatized SPA beads containing a scintillant (WGA beads) (Amersham) bound the membranes. $^{125}$I-GIP bound to human GIP receptor in the membranes and excited the scintillant in the WGA beads to light emission. GIP or samples binding to the receptor competed with $^{125}$I-GIP.

All steps in the membrane preparation are kept on ice or performed at 4° C. BHK cells are harvested and centrifuged. The pellet is resuspended in homogenisation buffer (25 mM HEPES, pH=7.4, 2.5 mM CaCl$_2$, 1.0 mM MgCl$_2$, 250 mg/L bacitracin, 0.1 mM Pefabloc), homogenised 2×10 sec using Polytron 10–35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM CaCl$_2$, 1.0 mM MgCl$_2$) and homogenised 2×10 sec. (Polytron). The protein concentration is normally around 1.75 mg/mL. Stabilisation buffer (25 mM HEPES, pH=7.4, 2.5 mM CaCl$_2$, 1.0 mM MgCl$_2$, 1% bovine serum albumin, 500 mg/L bacitracin, 2.5 M sucrose) is added and the membrane preparation is stored at −80° C.

The GIP binding assay is carried out in opti plates (Polystyrene Microplates, Packard). 50 μL assay buffer (25 mM HEPES, pH=7.5, 2.5 mM CaCl$_2$, 1.0 mM MgCl$_2$, 0.003% Tween-20, 0.005% bacitracin, 0.05% sodium azide) and 5 μL GIP or test compound (in DMSO) are added to each well. 50 μL tracer ($^{125}$I-porcine GIP, 50.000 cpm) and 50 μL membranes (20 μg) containing the human GIP receptor are then added to the wells. Finally 50 μL WGA beads containing 1 mg beads are transferred to the well. The opti plates are incubated for 3.5 hours on a shaker and then settled for 8–48 hours. The opti plates are counted in a Top-counter. Non-specific binding is determined with 500 nM of GIP.

The following table shows activity data for the above examples according to the invention:

| Example No | Glu Bd Assay (II) IC$_{50}$ (nM) | GIP Bd Assay IC$_{50}$ (nM) |
| --- | --- | --- |
| 1 | 29 | 701 |
| 2 | 12 | 269 |
| 3 | 18 | 653 |
| 4 | 23 | 124 |
| 5 | 26 | 519 |
| 6 | 10 | 294 |
| 7 | 26 | 292 |
| 8 | 14 | 316 |
| 9 | 11 | 285 |
| 10 | 19 | 294 |
| 11 | 41 | 914 |
| 12 | 10 | 204 |
| 13 | 228 | 700 |
| 14 | 19 | 274 |
| 15 | 35 | 395 |
| 16 | 61 | 205 |
| 17 | 22 | 448 |
| 18 | 177 | >1500 |
| 19 | 15 | 916 |
| 20 | 52 | 693 |
| 21 | 293 | 1258 |
| 22 | 354 | 2268 |
| 23 | 40 | 516 |
| 24 | 4.4 | 37 |
| 25 | 10 | 465 |
| 26 | 92 | 703 |
| 27 | 9.7 | 258 |
| 28 | 19 | 364 |
| 29 | 24 | 623 |
| 30 | 13 | 217 |
| 31 | 917 | 3000 |
| 32 | 20 | 439 |
| 33 | 12 | 189 |
| 34 | 20 | 400 |
| 35 | 40 | 432 |
| 36 | 14 | 284 |
| 37 | 19 | 520 |
| 38 | 33 | 221 |

-continued

| Example No | Glu Bd Assay (II) IC$_{50}$ (nM) | GIP Bd Assay IC$_{50}$ (nM) |
|---|---|---|
| 39 | 18 | 357 |
| 40 | 107 | 800 |
| 41 | 133 | 1588 |
| 42 | 41 | 340 |
| 43 | 17 | 226 |
| 44 | 39 | 291 |
| 45 | 61 | 373 |
| 46 | 507 | 1175 |
| 47 | 64 | 665 |
| 48 | 182 | >3000 |
| 49 | 25 | 160 |
| 50 | 119 | >3000 |
| 51 | 88 | 831 |
| 52 | 47 | 341 |
| 53 | 390 | >3000 |
| 54 | 390 | >3000 |
| 55 | 50 | 427 |
| 56 | 228 | 1374 |
| 57 | 439 | >3000 |
| 58 | 957 | >3000 |
| 59 | 594 | >3000 |
| 60 | 1021 | >3000 |
| 61 | 754 | >3000 |
| 62 | 757 | >3000 |
| 63 | 336 | >3000 |
| 64 | 514 | >3000 |
| 65 | 520 | >3000 |
| 66 | 325 | >3000 |
| 67 | 520 | >3000 |
| 68 | 528 | >3000 |
| 69 | 430 | >3000 |
| 70 | 740 | >3000 |
| 71 | 886 | >3000 |
| 72 | 542 | >3000 |
| 73 | 680 | >3000 |

What is claimed is:

1. A compound of formula (I):

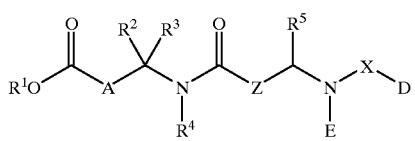

(I)

wherein $R^1$, $R^2$, $R^3$, $R^4$ and $R^5$ independently are hydrogen or $C_{1-6}$-alkyl, A is —C(O)—, —CH(OR$^6$)— or —CHF—, wherein $R^6$ is hydrogen or $C_{1-6}$-alkyl, Z is arylene or a divalent radical derived from a 5 or 6 membered heteroaromatic ring containing 1 or 2 heteroatoms selected from nitrogen, oxygen and sulfur, which may optionally be substituted with one or two groups $R^7$ and $R^8$ selected from halogen, —CN, —CF$_3$, —OCF$_3$, —NO$_2$, —OR$^9$, —NR$^9$R$^{10}$ and $C_{1-6}$alkyl, wherein $R^9$ and $R^{10}$ independently are hydrogen or $C_{1-6}$-alkyl, X is

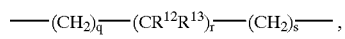

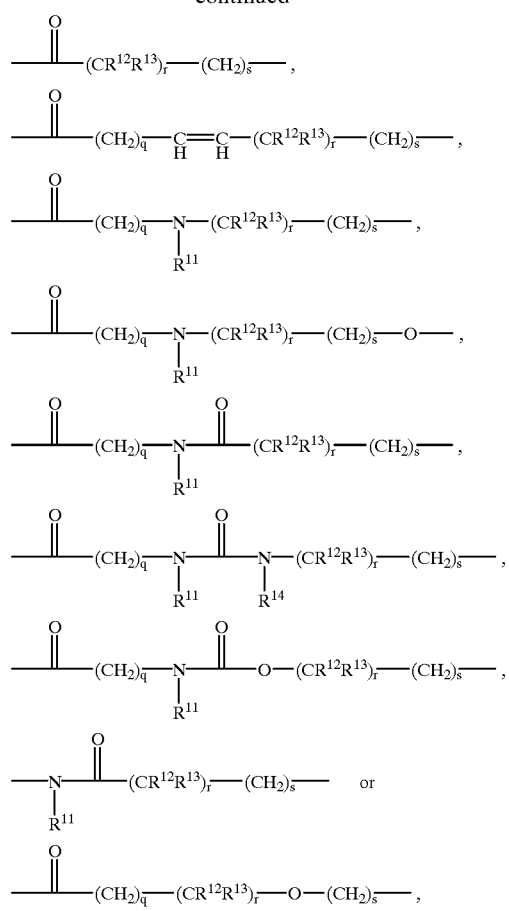

wherein r is 0 or 1, q and s independently are 0, 1, 2 or 3, $R^{11}$, $R^{12}$, $R^{13}$ and $R^{14}$ independently are hydrogen, $C_{1-6}$-alkyl or $C_{3-8}$-cycloalkyl, D is

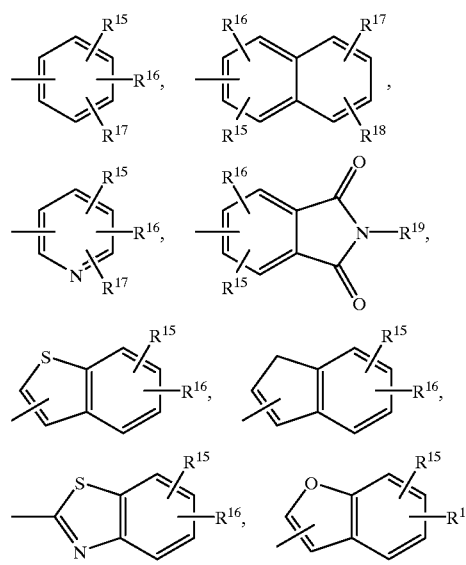

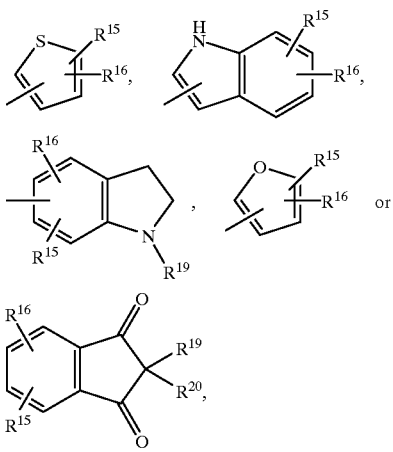

wherein
R$^{15}$, R$^{16}$, R$^{17}$ and R$^{18}$ independently are
hydrogen, halogen, —CN, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —OC(O)R$^{21}$, —C(O)R$^{21}$ or —C(O)OR$^{21}$, C$_{1-6}$-alkyl, C$_{2-6}$-alkenyl or C$_{2-6}$-alkynyl,
which may optionally be substituted with one or more substituents selected from halogen, —CN, —CF$_3$, —OCF$_3$, —NO$_2$, —OR$^{21}$, —NR$^{21}$R$^{22}$ and C$_{1-6}$-alkyl, C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{1-6}$-alkoxy, C$_{3-8}$-cycloalkyloxy, C$_{3-8}$-cycloalkyl-C$_{1-6}$-alkylthio, C$_{3-8}$-cycloalkylthio, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aryloxycarbonyl, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl,
of which the cyclic moieties optionally may be substituted with one or more substituents selected from halogen, —C(O)OR$^{21}$, —CN, —CF$_3$, —OCF$_3$, —NO$_2$, —OR$^{21}$, —NR$^{21}$R$^{22}$ and C$_{1-6}$-alkyl, wherein R$^{21}$ and R$^{22}$ independently are hydrogen, C$_{1-6}$-alkyl, aryl-C$_{1-6}$-alkyl or aryl,
or R$^{21}$ and R$_{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups R$^{15}$ to R$^{18}$ when placed in adjacent positions together may form a bridge —(CR$^{23}$R$^{24}$)$_a$—O—(CR$^{25}$R$^{26}$)$_c$—O, wherein
a is 0, 1 or 2,
c is 1 or 2,
R$^{23}$, R$^{24}$, R$^{25}$ and R$^{26}$ independently are hydrogen, C$_{1-6}$-alkyl or fluorine, R$^{19}$ and R$^{20}$ independently are hydrogen, C$_{1-6}$-alkyl, C$_{3-8}$-cycloalkyl or C$_{3-8}$-cycloalkyl-C$_{1-6}$-alkyl, E is

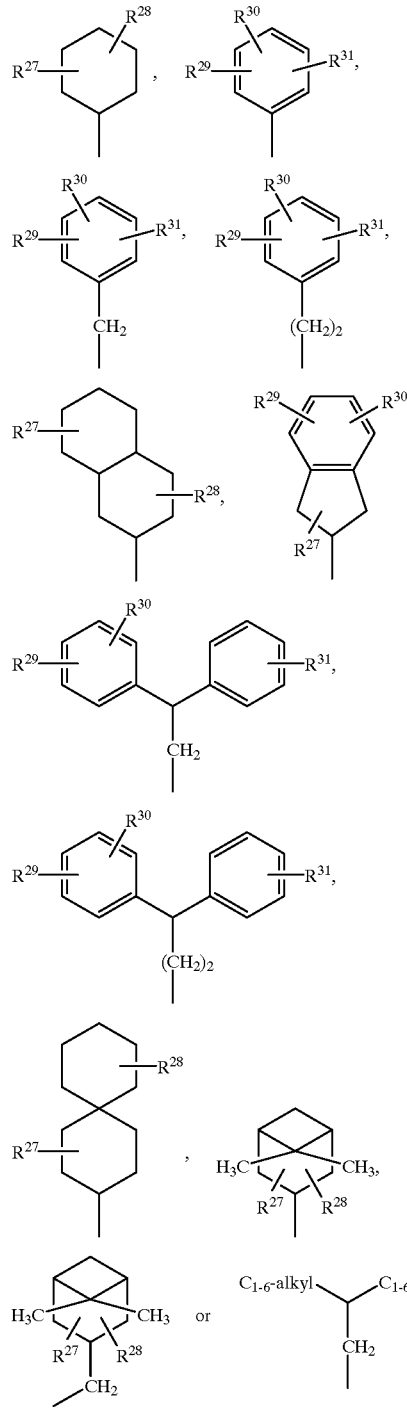

wherein
R$^{27}$ and R$^{28}$ independently are
hydrogen, halogen, —CN, —CF$_3$, —OR$^{32}$, —NR$^{32}$R$^{33}$, C$_{1-6}$-alkyl, C$_{3-8}$-cycloalkyl, C$_{4-8}$-cycloalkenyl or aryl,
wherein the aryl group optionally may be substituted with one or more substituents selected from halogen, —CN, —CF$_3$, —NO$_2$, —OR$^{32}$, —NR$^{32}$R$^{33}$ and C$_{1-6}$-alkyl, wherein $R^{32}$ and $R^{33}$ independently are hydrogen or $C_{1-6}$-alkyl, or $R^{32}$ and $R^{33}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, $R^{29}$, $R^{30}$ and $R^{31}$ independently are hydrogen, halogen, $-CHF_2$, $-CF_3$, $-OCF_3$, $-OCHF_2$, $-OCH_2CF_3$, $-OCF_2CHF_2$, $-SCF_3$, $-OR^{34}$, $-NR^{34}R^{35}$, $-SR^{34}$, $-S(O)R^{34}$, $-S(O)_2R^{34}$, $-C(O)NR^{34}R^{35}$, $-OC(O)NR^{34}R^{35}$, $-NR^{34}C(O)R^{35}$, $-OCH_2C(O)NR^{34}R^{35}$, $-C(O)R^{34}$ or $-C(O)OR^{34}$, $C_{1-6}$-alkyl, $C_{2-6}$-alkenyl or $C_{2-6}$-alkynyl,
which may optionally be substituted with one or more substituents selected from halogen, $-CN$, $-CF_3$, $-OCF_3$, $-NO_2$, $-OR^{34}$, $-NR^{34}R^{35}$ and $C_{1-6}$-alkyl, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl,
of which the cyclic moieties optionally may be substituted with one or more substituents selected from halogen, $-CN$, $-CF_3$, $-OCF_3$, $-NO_2$, $-OR^{34}$, $-NR^{34}R^{35}$ and $C_{1-6}$-alkyl,
wherein $R^{34}$ and $R^{35}$ independently are hydrogen, $C_{1-6}$-alkyl or aryl,
or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{29}$, $R^{30}$ and $R^{31}$ when attached to the same ring carbon atom or different ring carbon atoms together may form a radical $-O-(CH_2)_t-CR^{36}R^{37}-(CH_2)_l-O-$, or $-S-(CH_2)_t-CR^{36}R^{37}-(CH_2)_l-S-$, wherein t and l independently are 0, 1, 2, 3, 4 or 5, $R^{36}$ and $R^{37}$ independently are hydrogen or $C_{1-6}$-alkyl, as well as any optical or geometric isomer or tautomeric form thereof including mixtures of these or a pharmaceutically acceptable salt thereof.

2. A compound according to claim 1, wherein $R^1$, $R^2$, $R^3$, $R^4$ and $R^5$ are hydrogen.

3. A compound according to claim 1, wherein A is $-CHF-$.

4. A compound according to claim 1, wherein A is $-CH(OR^6)-$, wherein $R^6$ is as defined in claim 1.

5. A compound according to claim 4, wherein A is $-CH(OH)-$.

6. A compound according to claim 1, wherein Z is

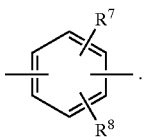

7. A compound according to claim 6, wherein Z is

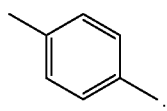

8. A compound according to claim 1, wherein X is

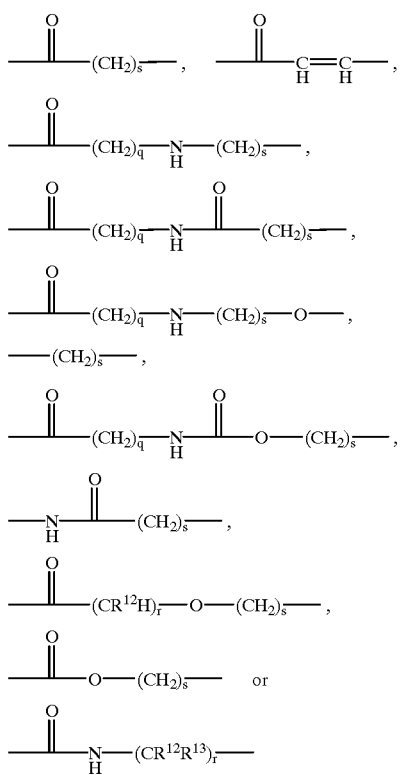

wherein q is 0 or 1, r is 0 or 1, s is 0, 1 or 2, and $R^{12}$ and $R^{13}$ independently are hydrogen or $C_{1-6}$-alkyl.

9. A compound according to claim 8, wherein X is $-C(O)NH-$, $-C(O)NHCH_2-$, $-C(O)NHCH(CH_3)-$, $-C(O)NHC(CH_3)_2-$, $-C(O)NHCH_2CH_2-$, $-C(O)CH_2-$, $-C(O)CH_2CH_2-$, $-C(O)CH=CH-$, $-(CH_2)_s-$, $-C(O)-$, $-C(O)O-$ or $-NHC(O)-$, wherein s is 0 or 1.

10. A compound according to claim 9, wherein X is $-C(O)NH-$, $-C(O)NHCH_2-$, $-C(O)NHCH(CH_3)-$, $-C(O)NHCH_2CH_2-$, $-C(O)CH_2-$, $-C(O)CH=CH-$, $-(CH_2)_s-$, $-C(O)-$, $-C(O)O-$ or $-NHC(O)-$, wherein s is 0 or 1.

11. A compound according to claim 10, wherein X is $-C(O)NH-$, $-C(O)NHCH_2-$, $-C(O)NHCH(CH_3)-$, $-C(O)NHCH_2CH_2-$, $-C(O)CH_2-$, $-CH_2-$, $-C(O)-$ or $-NHC(O)-$.

12. A compound according to claim 11, wherein X is $-C(O)NH-$, $-C(O)NHCH_2-$, $-C(O)NHCH(CH_3)-$, $-C(O)CH_2-$ or $-C(O)-$.

13. A compound according to claim 12, wherein X is —C(O)NH—.

14. A compound according to claim 1, wherein D is

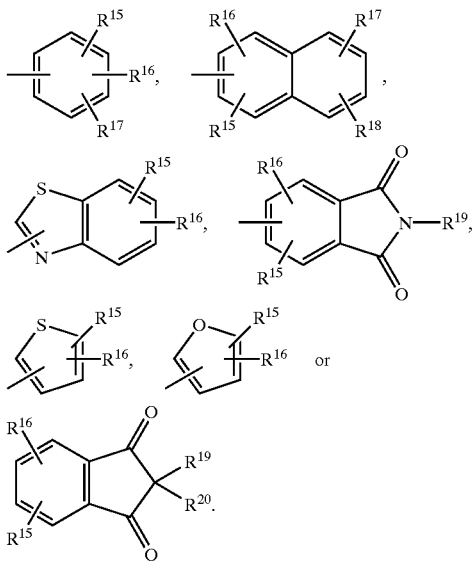

15. A compound according to claim 14, wherein D is

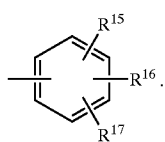

16. A compound according to claim 14, wherein $R^{15}$, $R^{16}$ and $R^{17}$ independently are hydrogen, halogen, —CN, —NO$_2$, —CF$_3$, —OCF$_3$, —SCF$_3$, C$_{1-6}$-alkyl, C$_{1-6}$-alkoxy, —S—C$_{1-6}$-alkyl, —C(O)OR$^{21}$, —C(O)R$^{21}$, —CH$_2$OR$^{21}$, C(O)NR$^{21}$R$^{22}$, —S(O)R$_{21}$, —S(O)$_2$R$^{21}$, —S(O)$_2$CF$_3$, —S(O)$_2$NR$^{21}$R$^{22}$, C$_{3-8}$-cycloalkyl, C$_{3-8}$-cycloalkyl-C$_{1-6}$-alkoxy or C$_{3-8}$-cycloalkyl-C$_{1-6}$-thioalkyl, or aryl, heteroaryl or aryloxy, which may optionally be substituted with —CF$_3$, —OCF$_3$, C$_{1-6}$-alkyl, halogen or —C(O)OR$^{21}$, or two of the groups $R^{15}$, $R^{16}$ and $R^{17}$ when placed in adjacent positions together form a bridge —(CR$^{23}$R$^{24}$)$_a$—O—(CR$^{25}$R$^{26}$)$_c$—O—, and wherein $R^{21}$ and $R^{22}$ independently are hydrogen or C$_{1-6}$-alkyl.

17. A compound according to claim 16, wherein $R^{15}$, $R^{16}$ and $R^{17}$ independently are hydrogen, halogen, —CN, —CF$_3$, —OCF$_3$ or C$_{1-6}$-alkoxy or wherein $R^{15}$ and $R^{16}$ together form a bridge —CF$_2$O —CF$_2$—O— and $R^{17}$ is hydrogen.

18. A compound according to claim 17, wherein $R^{15}$, $R^{16}$ and $R^{17}$ independently are hydrogen, halogen, —CN, —CF$_3$, —OCF$_3$ or C$_{1-6}$-alkoxy.

19. A compound according to claim 14, wherein D is

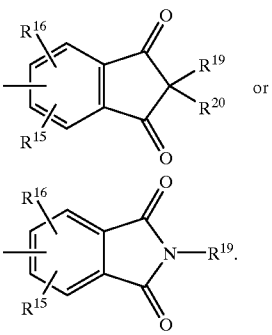

20. A compound according to claim 19, wherein D is

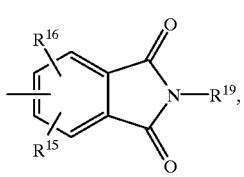

wherein $R^{15}$ and $R^{16}$ are both hydrogen and $R^{19}$ is C$_{1-6}$-alkyl, C$_{3-8}$-cycloalkyl or C$_{3-8}$-cycloalkyl-C$_{1-6}$-alkyl.

21. A compound according to claim 19, wherein D is

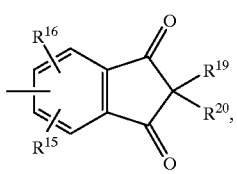

wherein $R^{15}$ and $R^{16}$ are both hydrogen and $R^{19}$ and $R^{20}$ are both C$_{1-6}$-alkyl.

22. A compound according to claim 1, wherein E is

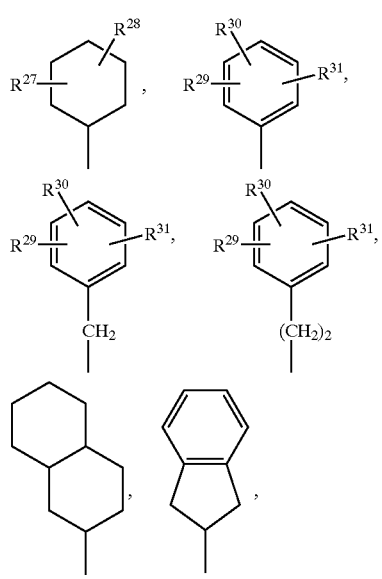

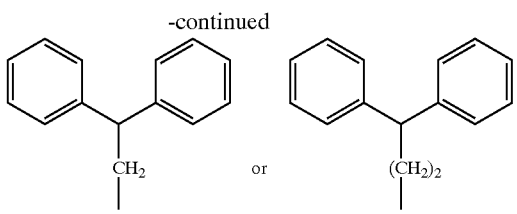

23. A compound according to claim 22, wherein E is

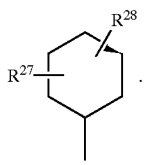

24. A compound according to claim 23, wherein F is

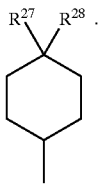

25. A compound according to claim 23, wherein $R^{27}$ and $R^{28}$ independently are hydrogen, $C_{1-6}$-alkyl, $C_{3-8}$-cycloalkyl, $C_{4-8}$-cycloalkenyl or aryl, wherein the aryl group is optionally substituted with one or more substituents selected from halogen, —CN, —CF$_3$, —NO$_2$, —OR$^{32}$, —NR$^{32}$R$^{33}$ and $C_{1-6}$-alkyl.

26. A compound according to claim 25, wherein $R^{27}$ and $R^{28}$ independently are hydrogen, $C_{1-6}$-alkyl, $C_{3-8}$-cycloalkyl or $C_{4-8}$-cycloalkenyl.

27. A compound according to claim 26, wherein $R^{27}$ is hydrogen and $R^{28}$ is $C_{1-6}$-alkyl, $C_{3-8}$-cycloalkyl or $C_{4-8}$-cycloalkenyl.

28. A compound according to claim 27, wherein $R^{27}$ is hydrogen and $R^{28}$ is $C_{1-6}$-alkyl or $C_{3-8}$-cycloalkyl.

29. A compound according to claim 22, wherein E is

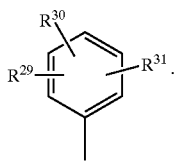

30. A compound according to claim 29, wherein E is

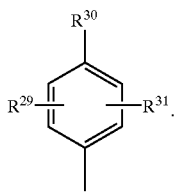

31. A compound according to claim 29, wherein $R^{29}$, $R^{30}$ and $R^{31}$ independently are
hydrogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$,
$C_{1-6}$-alkyl, $C_{2-6}$-alkenyl or $C_{2-6}$-alkynyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl,
$C_{3-8}$-cycloalkyl or $C_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl,
wherein $R^{34}$ and $R^{35}$ independently are hydrogen, $C_{1-6}$-alkyl or aryl, or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

32. A compound according to claim 31, wherein $R^{29}$, $R^{30}$ and $R^{31}$ independently are hydrogen, $C_{1-6}$-alkoxy, halogen, —CF$_3$, —OCF$_3$ or —NR$^{34}$R$^{35}$, or $C_{1-6}$-alkyl, $C_{3-8}$-cycloalkyl or $C_{4-8}$-cycloalkenyl, which are optionally substituted with one or more substituents selected from halogen, —CN, —CF$_3$, —OCF$_3$, —NO$_2$, —OR$^{34}$, —NR$^{34}$R$^{35}$ and $C_{1-6}$-alkyl.

33. A compound according to claim 32, wherein $R^{29}$, $R^{30}$ and $R^{31}$ independently are hydrogen or $C_{1-6}$-alkyl, $C_{3-8}$-cycloalkyl or $C_{4-8}$-cycloalkenyl, which are optionally substituted as defined in claim 32.

34. A compound according to claim 32, wherein $R^{29}$, $R^{30}$ and $R^{31}$ independently are
hydrogen or
$C_{1-6}$-alkyl, $C_{3-8}$-cycloalkyl or $C_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl,
wherein $R^{34}$ and $R^{35}$ independently are hydrogen, $C_{1-6}$-alkyl or aryl,
or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

35. A compound according to claim 34, wherein $R^{29}$ and $R^{31}$ are both hydrogen, and $R^{30}$ is different from hydrogen.

36. A compound according to claim 34, wherein $R^{29}$ and $R^{31}$ are both hydrogen, and $R^{30}$ is $C_{3-8}$-cycloalkyl or $C_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl,
wherein $R^{34}$ and $R^{35}$ independently are hydrogen, $C_{1-6}$-alkyl or aryl,
or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

37. A compound according to claim 36, wherein $R^{29}$ and $R^{31}$ are both hydrogen, and $R^{30}$ is $C_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl wherein $R^{34}$ and $R^{35}$ independently are hydrogen, $C_{1-6}$-alkyl or aryl, or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

38. A compound according to claim 37, wherein $R^{29}$ and $R^{31}$ are both hydrogen, and $R^{30}$ is cyclohexenyl, which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl, wherein $R^{34}$ and $R^{35}$ independently are hydrogen, $C_16$-alkyl or aryl, or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

39. A compound according to claim 37, wherein $R^{30}$ is substituted with one $C_{1-6}$-alkyl substituent.

40. A compound according to claim 33, wherein $R^{29}$, $R^{30}$ and $R^{31}$ independently are hydrogen, $C_{1-6}$-alkyl, $C_{3-8}$-cycloalkyl or $C_{4-8}$-cycloalkenyl.

41. A compound according to claim 40, wherein $R^{29}$ and $R^{31}$ are both hydrogen and $R^{30}$ is $C_{1-6}$-alkyl, $C_{3-8}$-cycloalkyl or C4-8-cycloalkenyl.

42. A compound according to claim 1 of formula (I$_1$):

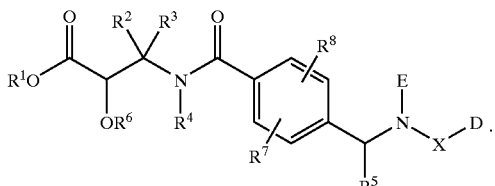

43. A compound according to claim 1 of formula (I$_2$):

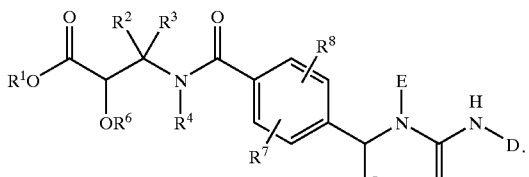

44. A compound according to claim 1 of formula (I$_3$):

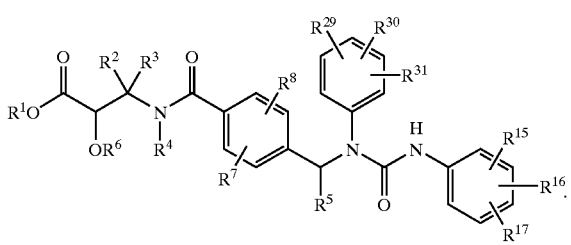

45. A compound according to claim 42, wherein $R^1$, $R^2$, $R^3$, $R^4$, $R^5$, $R^6$, $R^7$ and $R^8$ are hydrogen.

46. A compound according to claim 1 of formula (I$_4$):

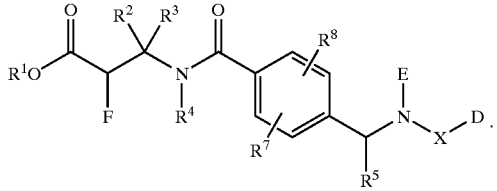

47. A compound according to claim 1 of formula (I$_5$):

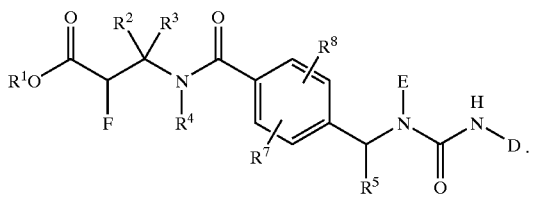

48. A compound according to claim 46, wherein $R^1$, $R^2$, $R^3$, $R^4$, $R^5$, $R^7$ and $R^8$ are hydrogen.

49. A compound according to claim 1, which has an IC$_{50}$ value of no greater than 5 $\mu$M as determined by Glucagon Binding Assay (I) or Glucagon Binding Assay (II).

50. A compound according to claim 49, which has an IC$_{50}$ value of less than 1 $\mu$M as determined by Glucagon Binding Assay (I) or Glucagon Binding Assay (II).

51. A compound according to claim 1, which is an agent useful for the treatment and/or prevention of an indication selected from the group consisting of hyperglycemia, impaired glucose tolerance (IGT), Type 2 diabetes, Type 1 diabetes, dyslipidemia and obesity.

52. A method for the treatment and/or prevention of disorders or diseases, wherein a glucagon antagonistic action is beneficial, the method comprising administering to a subject in need thereof an effective amount of a compound according to claim 1.

53. The method according to claim 52, wherein the effective amount of the compound is in the range of from about 0.05 mg to about 2000 mg per day.

54. A compound according to claim 49, which has an IC$_{50}$ value of less than 500 nM as determined by Glucagon Binding Assay (I) or Glucagon Binding Assay (II).

55. A compound according to claim 49, which has an IC$_{50}$ value of less than 100 nM as determined by Glucagon Binding Assay (I) or Glucagon Binding Assay (II).

56. The method according to claim 52, wherein the effective amount of the compound is in the range of from about 0.1 mg to about 1000 mg per day.

57. The method according to claim 52, wherein the effective amount of the compound is in the range of from about 0.5 mg to about 500 mg per day.

58. A compound according to claim 1, wherein said compound is selected from the group consisting of:

(R)-3-{4-[1-(4-Cyclohexylphenyl)-3-(3-methoxy-5-trifluoromethylphenyl)ureidomethyl]-benzoylamino}-2-hydroxypropionic acid, (R)-3-{4-[3-(3,5-Bis(trifluoromethyl)phenyl)-1-(4-cyclohexylphenyl)ureidomethyl]-benzoylamino}-2-hydroxypropionic acid, (R)-3-{4-[3-(3-Bromophenyl)-1-(4-cyclohexylphenyl)ureidomethyl]benzoylamino}-2-hydroxypropionic acid, (R)-3-{4-[1-(4-Cyclohexylphenyl)-3-(4-trifluoromethoxyphenyl)ureidomethyl]benzoylamino}-2-hydroxypropionic acid,
(R)-3-{4-[1-(4-Cyclohexylphenyl)-3-(3-trifluoromethylphenyl)ureidomethyl]benzoylamino}-2-hydroxypropionic acid
(R)-3-{4-[1-(4-Cyclohexylphenyl)-3-(3-fluoro-5-trifluoromethylphenyl)ureidomethyl]benzoylamino}-2-hydroxypropionic acid,
(R)-3-{4-[3-(3-Cyano-5-trifluoromethylphenyl)-1-(4-cyclohex-1-enylphenyl)ureidomethyl]benzoylamino}-2-hydroxypropionic acid,
(R)-3-{4-[3-(3-Cyano-5-trifluoromethylphenyl)-1-(4-cyclohexylphenyl)ureidomethyl]benzoylamino}-2-hydroxypropionic acid,
(R)-3-{4-[3-(3-Bromo-5-trifluoromethylphenyl)-1-(4-cyclohex-1-enylphenyl)ureidomethyl]-benzoylamino}-2-hydroxypropionic acid,
(R)-3-{4-[1-(4-Cyclohex-1-enylphenyl)-3-(3-methoxy-5-trifluoromethylphenyl)ureidomethyl]benzoylamino}-2-hydroxypropionic acid,
(R)-3-{4-[3-(3-Bromophenyl)-1-(4-cyclohex-1-enylphenyl)ureidomethyl]benzoylamino}-2-hydroxypropionic acid,
(R)-3-{4-[3-(3-Bromo-5-trifluoromethylphenyl)-1-(4-cyclohexylphenyl)ureidomethyl]-benzoylamino}-2-hydroxypropionic acid,
(S)-Trans-3-{4-[3-(3,5-Bis(trifluoromethyl)phenyl)-1-(4-tert-butylcyclohexyl)ureidomethyl]benzoylamino}-2-hydroxypropionic acid,
(R)-Trans-3-{4-[3-(3,5-bis(trifluoromethyl)phenyl)-1-(4-tert-butylcyclohexyl)ureidomethyl]benzoylamino}-2-hydroxypropionic acid,
Trans-(R)-3-{4-[3-(3-methyl-5-trifluoromethylphenyl)-1-(4-tert-butylcyclohexyl)-ureidomethyl]benzoylamino}-2-hydroxypropionic acid,
(RS)-3-{4-[1-(4-tert-Butylphenyl)-3-(4-trifluoromethoxyphenyl)ureidomethyl]benzoylamino}-2-hydroxypropionic acid,
(RS)-3-{4-[1-(4-Cyclohex-1-enylphenyl)-3-(3,5-dichlorophenyl)ureidomethyl]benzoylamino}-2-hydroxypropionic acid,
(S)-3-{4-[1-(4-Cyclohex-1-enylphenyl)-3-(3,5-dichlorophenyl)ureidomethyl]benzoylamino}-2-hydroxypropionic acid,
(R)-3-{4-[1-(4-Cyclohex-1-enylphenyl)-3-(3,5-dichlorophenyl)ureidomethyl]benzoylamino}-2-hydroxypropionic acid,
(R)-3-{4-[3-(3-Chlorophenyl)-1-(4-cyclohex-1-enylphenyl)ureidomethyl]benzoylamino}-2-hydroxypropionic acid,
(R)-3-{4-[1-(4-Cyclohex-1-enylphenyl)-3-phenylureidomethyl]benzoylamino}-2-hydroxypropionic acid,
(R)-3-{4-[3-Benzyl-1-(4-cyclohex-1-enylphenyl)ureidomethyl]benzoylamino}-2-hydroxypropionic acid,
(RS)-3-{4-[1-(4-Cyclohex-1-enylphenyl)3-(3,5-dichlorophenyl)ureidomethyl]benzoylamino}-2-fluoropropionic acid,
(R)-3-{4-[1-(4-Cyclohexylphenyl)-3-(4-trifluoromethylsulfanylphenyl)ureidomethyl]benzoylamino}-2-hydroxypropionic acid,
(R)-3-{4-[1-(4-Cyclohexen-1-ylphenyl)-3-(3-methanesulfonyl-4-trifluoromethoxyphenyl)ureidomethyl]benzoylamino}-2-hydroxypropionic acid,
Trans-(R)-3-{4-[-3-(3,5-bis(methyl)phenyl)-1-(4-tert-butylcyclohexyl)ureidomethyl]benzoylamino}-2-hydroxypropionic acid,
(R)-3-{4-[1-(4-Cyclohexylphenyl)-3-(3,5-dichlorophenyl)ureidomethyl]benzoylamino}-2-hydroxypropionic acid,
(R)-(3-{4-[1-(4-Cyclohex-1-enylphenyl)-3-(3-fluoro-5-trifluoromethylphenyl)ureidomethyl]benzoylamino}-2-hydroxypropionic acid,
(R)-3-{4-[1-(4-Cyclohexylphenyl)-3-(3-methylsulfanylphenyl)ureidomethyl]benzoylamino}-2-hydroxypropionic acid,
(R)-3-{4-[1-(4-Cyclohex-1-enylphenyl)-3-(2,2,4,4-tetrafluoro-4-H-benzo[1,3]dioxin-6-yl) ureidomethyl]benzoylamino}-2-hydroxypropionic acid,
3-{4-[1-(4-Cyclohex-1-enylphenyl)-3-(3,5-dichlorophenyl)ureidomethyl]benzoylamino}-2(R)-methoxypropionic acid,
3-(4-{3-(3,5-Dichlorophenyl)-1-[4-(2-methylcyclohex-1-enyl)phenyl]ureidomethyl}benzoylamino)-2-(R)-hydroxypropionic acid and (R,S)-3-(4-{3-(3,5-dichlorophenyl)-1-[4-(6-methylcyclohex-1-enyl)phenyl]ureidomethyl}benzoylamino)2(R)-hydroxypropionic acid,
3-{4-[1-[4-(4-tert-Butylcyclohex-1-enyl)phenyl]-3-(3,5-dichlorophenyl)ureidomethyl]-benzoylamino}-2-(R)-hydroxypropionic acid,
(R,S)-3-(4-(3-(3,5-Dichlorophenyl)-1-(4-(5-methylcyclohex-1-enyl)phenyl)ureidomethyl)benzoylamino)-2-hydroxypropionic acid and (R,S)-3-(4-(3-(3,5-dichlorophenyl)-1-(4-(3-methylcyclohex-1-enyl)phenyl)ureidomethyl)benzoylamino)-2-hydroxypropionic acid,
3-{4-[3-[1(S)-(4-Chlorophenyl)ethyl]-(4-cyclohexylphenyl)ureidomethyl]benzoylamino}-2(R)-hydroxypropionic acid
3-{4-[3-Biphenyl-2-ylmethyl-1-(4-cyclohexylphenyl)ureidomethyl]benzoylamino}-2(R) hydroxypropionic acid,
(R)-3-{4-[3-(4-Cyano-3-trifluoromethylphenyl)-1-(4-cyclohexylphenyl)ureidomethyl]benzoylamino}-2-hydroxypropionic acid,
(R)-3-{4-[3-(3-tert-Butylphenyl)-1-(4-cyclohexylphenyl)ureidomethyl]benzoylamino}-2 hydroxypropionic acid,
(R)-3-{4-[1-(4-Cyclohexylphenyl)-3-(3-hydroxymethyl-4-trifluoromethoxyphenyl)ureidomethyl]benzoylamino}-2-hydroxypropionic acid,
(R)-3-{4-[1-(4-tert-Butylphenyl)-3-(3,4-dichlorophenyl)ureidomethyl]benzoylamino}-2-hydroxypropionic acid,
(R)-3-{4-[1-(4-tert-Butylcyclohexyl)-3-(3,4-dichlorophenyl)ureidomethyl]benzoylamino}-2-hydroxypropionic acid,
(R)-3-{4-[1-(4-Cyclohexylphenyl)-3-(3,4-dichlorophenyl)ureidomethyl]benzoylamino}-2-hydroxypropionic acid,
(R)-3-{4-[1-(4-Cyclohexylphenyl)-3-(2,2,4,4-tetrafluoro-4H-benzo[1,3]dioxin-6-yl)ureido methyl]benzoylamino}-2-hydroxypropionic acid,
(R)-3-{4-[1-(4-tert-Butylphenyl)-3-(2,2,4,4-tetrafluoro-4H-benzo[1,3]dioxin-6-yl)ureidomethyl]benzoylamino}-2-hydroxypropionic acid,
(R)-3-{4-[1-(4-tert-Butylcyclohexyl)-3-(2,2,4,4-tetrafluoro-4H-benzo[1,3]dioxin-6-yl)ureidomethyl]benzoylamino}-2-hydroxypropionic acid,
(R)-3-{4-[1-(4-tert-Butylphenyl)-3-(3,4-difluorophenyl)ureidomethyl]benzoylamino}-2-hydroxypropionic acid,
(R)-3-{4-[1-(4-Cyclohexylphenyl)-3-(3,4-difluorophenyl)ureidomethyl]benzoylamino}-2-hydroxypropionic acid,
(R)-3-{4-[1-(4-Cyclohex-1-enylphenyl)-3-(3,4-difluorophenyl)ureidomethyl]benzoylamino}-2-hydroxypropionic acid,
(R)-3-{4-[3-(4-Chloro-3-trifluoromethylphenyl)-1-(4-cyclohexylphenyl)ureidomethyl]benzoylamino}-2-hydroxypropionic acid, (R)-3-{4-[1-(4-Cyclohexylphenyl)-3-(4-fluoro-3-nitrophenyl)ureidomethyl]benzoylamino}-2-hydroxypropionic acid, (R)-3-{4-[1-(4-Cyclohexylphenyl)-3-(4-isopropylphenyl)ureidomethyl]benzoylamino}-2-hydroxypropionic acid, (R)-3-{4-[1-(4-Cyclohex-1-enylphenyl)-3-(3,4-dichlorophenyl)ureidomethyl]benzoylamino}-2-hydroxypropionic acid, (R)-3-{4-[3-(4-Acetylphenyl)-1-(4-cyclohexylphenyl)ureidomethyl]benzoylamino}-2-hydroxypropionic acid, 3-{4-[3-[1(RS)-(4-Bromophenyl)ethyl]-1-(4-cyclohexylphenyl)ureidomethyl]benzoylamino}-2(R)-hydroxypropionic acid, (R)-3-{4-[1-(4-Cyclohexylphenyl)-3-(3, 5-difluorophenyl)ureidomethyl]benzoylamino}-2 hydroxypropionic acid, (R)-3-[4-({(4-tert-Butylcyclohexyl)-[2-(4-trifluoromethoxyphenyl)acetyl]amino}-methyl)benzoylamino]-2-hydroxypropionic acid, (R)-3-[4-({(4-tert-Butylcyclohexyl)-[2-(3-fluoro-5-trifluoromethylphenyl)acetyl]amino}-methyl)benzoylamino]-2-hydroxypropionic acid, (R)-3-[4-({(2-2-Diphenylethyl)-[2-(3-fluoro-5-trifluoromethylphenyl)acetyl]amino}methyl)benzoylamino)-2-hydroxypropionic acid, (R)-3-(4-{[(5-Chlorobenzo[b]thiophene-3-carbonyl)-(2,2-diphenylethyl)amino]methyl}-benzoylamino)-2-hydroxypropionic acid, (R)-3-[4-({(2-2-Diphenylethyl)-[2-(4-trifluoromethoxyphenyl)acetyl]amino}methyl)benzoylamino]-2-hydroxypropionic acid, (R)-3-(4-{[(4-tert-Butylcyclohexyl)-(5-chlorobenzo[b]thiophene-3-carbonyl)amino]methyl}-benzoylamino)-2-hydroxypropionic acid, (R)-3-(4-{[(2,2-Diphenylethyl)-(5-trifluoromethoxy-1H-indole-2-carbonyl)amino]methyl}-benzoylamino)-2-hydroxypropionic acid, (R)-3-[4-({(4-Cyclohexylphenyl)-[(4-trifluoromethoxyphenyl)acetyl]amino}methyl)benzoylamino]-2-hydroxypropionic acid, (R)-3-[4-({(4-Cyclohexylphenyl)-[(3-trifluoromethoxyphenyl)acetyl]amino}methyl)benzoylamino]-2-hydroxypropionic acid, (R)-3-[4-({(4-Cyclohexylphenyl)-[(3-fluoro-5-trifluoromethylphenyl)acetyl]amino}methyl)benzoylamino]-2-hydroxypropionic acid, (R)-3-(4-{([(3,5-Bis(trifluoromethyl)phenyl)acetyl]-(4-cyclohexylphenyl)amino)methyl}-benzoylamino)-2-hydroxypropionic acid, (R)-3-[4-({(4-Cyclohexylphenyl)-[(3-trifluoromethylphenyl)acetyl]amino}methyl)benzoylamino]-2-hydroxypropionic acid, (R)-3-[4-({(4-Cyclohexylphenyl)-[(3,4-dichlorophenyl)acetyl]amino}methyl)benzoylamino]-2-hydroxypropionic acid, (R)-3-(4-{[[(3-Bromophenyl)acetyl]-(4-cyclohexylphenyl)amino]methyl}benzoylamino)-2-hydroxypropionic acid, (R)-3-(4-{[(Biphenyl-4-ylacetyl)-(4-cyclohexylphenyl)amino]methyl}benzoylamino)-2-hydroxypropionic acid, (R)-3-(4-{[(4-Cyclohexylphenyl)-(2-naphthylacetyl)amino]methyl}benzoylamino)-2-hydroxypropionic acid, (R)-3-(4-{[(3-(3,5-Bis(trifluoromethyl)phenyl)propionyl)-(4-cyclohexylphenyl)amino]methyl}benzoylamino)-2-hydroxypropionic acid, and (R)-3-[4-({(4-Cyclohexylphenyl)-[3-(3-nitrophenyl)propionyl]amino}methyl)benzoylamino]-2-hydroxypropionic acid.

59. A method for the treatment and/or prevention of disorders or diseases, wherein a glucagon antagonistic action is beneficial, the method comprising administering to a subject in need thereof an effective amount of a compound according to claim 58.

60. The method according to claim 59, wherein the effective amount of the compound is in the range of from about 0.05 mg to about 2000 mg per day.

61. The method according to claim 59, wherein the effective amount of the compound is in the range of from about 0.1 mg to about 1000 mg per day.

62. The method according to claim 59, wherein the effective amount of the compound is in the range of from about 0.5 mg to about 500 mg per day.

63. A pharmaceutical composition comprising, as an active ingredient, a compound according to claim 1 together with one or more pharmaceutically acceptable carriers or excipients.

64. The pharmaceutical composition according to claim 63 in unit dosage form, said composition comprising from about 0.05 mg to about 1000 mg, of the compound.

65. The pharmaceutical composition according to claim 63 in unit dosage form, said composition comprising from about about 0.1 mg to about 500 mg of the compound.

66. A pharmaceutical composition according to claim 63 in unit dosage form, said composition comprising from about 0.5 mg to about 200 mg of the compound.

67. A pharmaceutical composition comprising, as an active ingredient, a compound according to claim 58 together with one or more pharmaceutically acceptable carriers or excipients.

68. The pharmaceutical composition according to claim 67 in unit dosage form, said composition comprising from about 0.05 mg to about 1000 mg, of the compound.

69. The pharmaceutical composition according to claim 67 in unit dosage form, said composition comprising from about about 0.1 mg to about 500 mg of the compound.

70. A pharmaceutical composition according to claim 67 in unit dosage form, said composition comprising from about 0.5 mg to about 200 mg of the compound.

* * * * *